(12) United States Patent
Sakanaka et al.

(10) Patent No.: US 7,235,267 B1
(45) Date of Patent: Jun. 26, 2007

(54) BRAIN CELL OR NERVE CELL-PROTECTING AGENTS COMPRISING MEDICINAL GINSENG

(75) Inventors: Masahiro Sakanaka, Ehime (JP); Nobuji Maeda, Ehime (JP); Junya Tanaka, Ehime (JP); Kimihiko Nakata, Ehime (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/070,209

(22) PCT Filed: Jun. 22, 2000

(86) PCT No.: PCT/JP00/04102

§ 371 (c)(1),
(2), (4) Date: Jul. 12, 2002

(87) PCT Pub. No.: WO01/15717

PCT Pub. Date: Mar. 8, 2001

(30) Foreign Application Priority Data

Aug. 30, 1999 (JP) .................................. 11-243378

(51) Int. Cl.
*A61K 36/258* (2006.01)
*A61K 36/00* (2006.01)
(52) U.S. Cl. ...................................... 424/728; 424/725
(58) Field of Classification Search ................ 424/725, 424/728
See application file for complete search history.

(56) References Cited

U.S. PATENT DOCUMENTS 4,966,893 A 10/1990 Pang et al.

FOREIGN PATENT DOCUMENTS

EP 1 170 012 A1 1/2002
FR 2648046 A1 * 12/1990

(Continued)

OTHER PUBLICATIONS

Sakanaka et al. Ginseng Root's Ability to Prevent Learning Disability and Neuronal Loss in Normothermic Gerbils With 5-Min Forebrain Ischemia; Jpn. J. PHarmacol. (1995) 67, Suppl. I, 299P (One page English Abstract provided).*

(Continued)

*Primary Examiner*—Patricia Leith
(74) *Attorney, Agent, or Firm*—Peter F. Corless, Esq.; Gregory B. Butler, Esq.; Edwards Angell Palmer & Dodge, LLP

(57) ABSTRACT

The present invention provides medicinal or pharmaceutical compositions and preparations for administration, which are useful as cytoprotective agents and a remedy for neurotrauma, comprising ginseng, its extract, ginseng components, metabolites thereof or salts thereof (for example, red ginseng powder or components thereof). More particularly, the present invention provides medicinal or pharmaceutical compositions for inhibiting apoptosis or apoptosis-like cell death, medicinal or pharmaceutical compositions for promoting the expression of a cell death-suppressing gene product Bcl-$x_L$, or preparations for oral or intravenous administration, comprising ginseng, its extracts, ginseng components, metabolites thereof or salts thereof preferably at low concentrations. These medicinal or pharmaceutical compositions and/or preparations for administration are characterized by containing, as the active ingredient(s), ginseng, its extracts, ginseng components, metabolites thereof or salts thereof at low concentrations. These drugs are useful for therapy, prevention or treatment of brain and nervous diseases, heart diseases, etc.

4 Claims, 33 Drawing Sheets

* $P<0.05$  ** $P<0.01$

FOREIGN PATENT DOCUMENTS

| | | |
|---|---|---|
| JP | 02 152926 | 6/1990 |
| JP | 4-504414 | 8/1992 |
| JP | 6-316527 | 11/1994 |
| JP | 2000-159793 | 6/2000 |
| WO | WO 99/09837 | 3/1999 |
| WO | WO 00/04912 | 2/2000 |

OTHER PUBLICATIONS

Masahiro, H. Preventive Effects of a Medicinal Carrot Component on Nerve Cell Death and Learning Behavior Disorder After Cerebral Ischemia; Mod. Phys. (1995) vol. 15, No. 3, pp. 384-388 (One page English Abstract provided).*

Tamiko et al. Clinical Studies of Red Ginseng Powder on Cerebrovascular Disease; Wakan Iyakugaku Zasshi (Journal of Traditional Medicines) (1994) vol. 11, No. 4, pp. 352-353 (One page English Abstract provided).*

Lin et al., "Transformation of ginsenosides Rg1 and Rb1, and crude Sanchi saponins by human intestinal microflora," *Journal of the Chinese Chemical Society* 48(1) (2001) (Abstract Only) Database Accession No. 2001:204459. (XP-002276421).

Zhang et al, "Influences of ginsenosides $Rb_1$ and $Rg_1$ on reversible focal brain ischemia in rats," *Acta Pharmacologica Sinica* 17:1 pp. 44-48 (1996). (XP002926090).

Sakanaka et al. "Ginseng Root's Ability to Prevent Learning Diability and Neuronal Loss in Normothermic Gerbils with 5-min Forebrain Ischemia," *Japanese Journal of Pharmacology* 67:1 (1995) (Abstract Only) (XP-001059689).

Gong et al., "Stroke therapy in traditional Chinese medicine (TCM): prospects for drug discovery and development," *Trends in Pharmacological Sciences, Elsevier Trends Journal* 20(5):pp. 191-196 (1999).

Database WPI, Section Ch, Week 199725 *Derwent Publications Ltd.* (Abstract Only) (XP-002276423).

Choi et al., "Inhibitory Effects of *Panax ginseng* Saponin Fractions on Dexamethasone-induced Thymus Apoptosis," *Symposium on Current Topics in Pharmacology and Toxicology Catholic Research Institutes of Medical Science* pp. 162 (1997) (Abstract Only) (XP-001180904).

Kim et al., "*Panax ginseng* blocks morphine-induced thymic apoptosis by lowering plasma corticosterone level," *General Pharmacology* 32(6):647-652 (1999).

Chen et al., "Cardiovascular Protection by Ginsenosides and Their Nitric Oxide Releasing Action," *Clinical and Experimental Pharmacology and Physiology* 23:728-732 (1996).

Gonzalez-Garcia et al., "*bcl-x* is expressed in embryonic and postnatal neural tissues and functions to prevent neuronal cell death," *Proc. Natl. Acad. Sci USA* 92:4304-4308 (1995).

Wen et al., "Ginseng root prevents learning disability and neuronal loss in gerbils with 5-minute forebrain ischemia," *Acta Neuropathol.* 91:15-22 (1996).

Kim Young, "Ginsenosides Rb1 and Rg3 protect cultured rat cortical cells from glutamate-induced neurodegeneration," Database Biosis Accession No. PREV199800408338 (Abstract).

Li et al., "Study on the Anit-Apoptotic Mechanism of Ginsenoside Rg1 In Cultured Cortical Neurons," *Acta Pharmaceutica Sinica*, 32(6):406-410 (1997).

Kim et al., "Radioprotective Effect of Red Ginseng in Irradiated Mice with High and Low Dose of Radiation," *Korean J. Ginseng Sci.*, 22(1):66-72 (1998).

Zhang et al., "Influences of ginsenosides $Rb_1$ and $Rg_1$ on reversible focal brain ischemia in rats," *Acta Pharmaceutica Sinica*, 17(1):44-48 (1996).

Lim et al., "Protection of ischemic hippocampal neurons by ginsenoside $Rb_1$, a main ingredient of ginseng root," *Neuroscience Research*, 28:191-200 (1997).

Liu et al., "Protective Effects of Ginsenoside $Rb_1$ and $Rg_1$ on Cultured Hippocampal Neurons," *Acta Pharmaceutica Sinica*, 30(9):674-678 (1995).

Zhang et al., "Protective effects of total saponins of *Panax ginseng* on ischemia-reperfusion injury in rat brains," *Chinese Journal of Pharmacology an Toxicology*, 8(1):7-12 (1994).

Chu et al., "Protective effect of ginsenosides on acute cerebral ischemia/reperfusion injury of rats," *Chinese Journal of Pharmacology and Toxicology*, 3(1):18-23 (1989).

Jiang er al., "Influences of ginsenosides $Rb_1$, $Rg_2$, and $Rb_3$ on electric and contractile activities of normal and damages cultured myocadiocytes," *Acta Pharmaceutica Sinica*, 13(5):403-406 (1992).

Li et al., "Effects of berbamine on isolated myocardium in guinea pigs and humans," *Acta Pharmaceutica Sinica*, 7(3)222-226 (1986).

Chen, "Cardiovascular Protection by Ginsenosides and Their Nitric Oxide Releasing Action," *Clinical and Experimental Pharmacology and Physiology*, 23:728-732 (1996).

Li et al., "The Protective Effect of Ginsenosides and its Components on Myocytes Anoxia/Reoxygenation and Myocardial Reperfusion Injury," *Acta Pharmaceutica Sinica*, 22(1):1-5 (1987).

Kondo et al., "Studies on the Constituents of Himalayan Ginseng, *Panax pseudoginseng*. I. The Structures of the Saponins," *Chemical and Pharmaceutical Bulletin*, 21(13):2702-2711 (1973).

Kanaoka et al., "Studies on the Enzyme Immunoassay of Bio-active Constituents in Oriental Medicinal drugs. VI. Enzyme Immunoassay of Ginsenoside $Rb_1$ from *Panax ginseng*," *Chemical and Pharmaceutical Bulletin*, 40(2):314-317 (1992).

* cited by examiner

*P<0.05  **P<0.01

*P<0.05  **P<0.01

*P<0.05

* P<0.05

A

Bcl-x$_L$ protein

Distilled Water     Red Ginseng Powder

B

*P<0.05    N=4

A

Bcl-x$_L$ protein

Distilled Water      Red Ginseng Powder

B

\* $P<0.05$    $N=4$ (20S)-Ginsenoside-Rg₃

Ginsenoside-Rb₃

Ginsenoside-Rd    R=H
Malonylginsenoside-Rd R=CH₂CO-COOH

** $p<0.01$  * $p<0.05$

** $p<0.01$ * $p<0.05$ vs Rb1=0

BRAIN CELL OR NERVE CELL-PROTECTING AGENTS COMPRISING MEDICINAL GINSENG

This is a 371 of International Application Number PCT/JP00/04102, filed Jun. 22, 2000, which international application claims priority from JP 11-243378, filed in Japan on Aug. 30, 1999.

TECHNICAL FIELD

The present invention relates to medicinal ginseng, extracts thereof, ginseng components or metabolites thereof useful as cell-protecting agents. More particularly, the present invention relates to medicinal or pharmaceutical compositions for suppressing apoptosis or apoptosis-like cell death or for promoting the expression of a cell death-suppressing gene product Bcl-$x_L$ comprising ginseng, its extracts, ginseng components, metabolites thereof or salts thereof.

Further, the present invention relates to a medicinal or pharmaceutical composition(s) for protecting cells comprising ginsenoside $Rb_1$, metabolites thereof or salts thereof. More particularly, the present invention relates to a medicinal or pharmaceutical composition(s) for preventing, treating or curing brain edema, brain and nervous tissue edema or spinal cord tissue edema comprising ginsenoside $Rb_1$, metabolites thereof or salts thereof; a medicinal or pharmaceutical composition(s) for preventing, treating or curing bedsores caused by spinal cord injuries comprising ginsenoside $Rb_1$, metabolites thereof or salts thereof; a medicinal composition(s) for promoting the expression of a cell death-suppressing gene product Bcl-$x_L$ in the nervous tissues, comprising ginsenoside $Rb_1$, metabolites thereof or salts thereof; a medicinal or pharmaceutical composition(s) for promoting the expression of a cell death-suppressing gene product Bcl-$x_L$ in oligodendrocytes comprising ginsenoside $Rb_1$, metabolites thereof or salts thereof; a protective agent(s) for oligodendrocytes comprising ginsenoside $Rb_1$, metabolites thereof or salts thereof; a medicinal or pharmaceutical composition(s) for promoting the expression of a cell death-suppressing gene product Bcl-$x_L$ in myocardial cells comprising ginsenoside $Rb_1$, metabolites thereof or salts thereof; and a medicinal or pharmaceutical composition(s) for suppressing apoptosis or apoptosis-like cell death of myocardial cells comprising ginsenoside $Rb_1$, metabolites thereof or salts thereof.

Further, the present invention relates to a preparation(s) for intravenous administration comprising medicinal ginseng, its extract, ginseng components, metabolites thereof or salts thereof. More particularly, the present invention relates to the preparation(s) for intravenous administration at low concentrations and low doses.

Further, the present invention relates to the use of components of medicinal ginseng or metabolites thereof as leading compounds for exploring novel active compounds for preventing, curing or treating the diseases or lesions hereinbefore, or for exploring brain cell-protective agents or neuroprotective agents.

Further, the present invention also relates to a novel chemical derivative prepared from ginsenoside $Rb_1$ as a leading compound, namely dihydroginsenoside $Rb_1$ which is useful as a cell protective agent or cytoprotective agent. Further, the present invention relates to a medicinal or pharmaceutical composition(s) for prevention, therapy or treatment of cerebral infarction or cerebral apoplexy, or a medicinal or pharmaceutical composition(s) for suppressing necrosis, apoptosis or apoptosis-like cell death of nerve cells or neurons, comprising dihydroginsenoside $Rb_1$, metabolites thereof or salts thereof. The present invention further relates to a medicinal or pharmaceutical composition(s) in a preparation(s) for intravenous administration comprising dihydroginsenoside $Rb_1$, metabolites thereof or salts thereof, namely, the medicinal or pharmaceutical composition(s) comprising the preparation(s) for repetitive or continuous intravenous administrations or the preparation(s) for a single intravenous infusion at low concentrations and low doses.

BACKGROUND ART

In intractable nervous diseases such as cerebral apoplexy and neurodegenerative diseases, brain cell death or nerve cell death commonly occurs. As a result, irreversible higher nervous functional disorders are developed. Once such functional disorders occur, the improvement, therapy and treatment of the diseases are very difficult and the QOL (quality of life) of patients is damaged for a long term. Consequently, although excellent preparations for oral administration which could prevent damage to these nerve cells are highly desirable for use prior to brain cell death or nerve cell death, such medicinal or pharmaceutical compositions have not been invented up to the present time.

Among the various ginsengs, red ginseng powder is frequently used in Chinese medical prescriptions, and it is positioned as one of the galenicals having various drug effects such as circulation improvement action and activation of the autonomic nervous system—endocrine system. It has also been reported that oral administration of red ginseng powder to patients with cerebrovascular disorder at chronic stage leads to improvement in cold flush or numbness in the lesioned extremities, as well as increased deep skin temperature. The effect is thought to be caused by the circulation-improving action of red ginseng powder (Yamaguchi, Takenori, Effect of medicinal ginseng on sequela of cerebrovascular disorder, in Ginseng '95, pp. 6-18, Kumagaya, Akira Ed., Kyoritsu Publishing Co.). However, if the red ginseng powder is administered orally to patients with cerebrovascular disorder at chronic stage (e.g. cerebral apoplexy patients at chronic stage), no improvement in cerebral apoplectic lesion itself is found. Further, it is not known whether the red ginseng powder is used for the prevention, therapy and/or treatment of cerebrovascular disorders at acute stage (e.g. acute cerebral apoplexy) in common clinical practice. Further, there is no known experimental medical basis for the use of red ginseng powder to treat other neurodegenerative diseases accompanied by nerve cell death, head injury or spinal cord injury in clinical medicine.

One of the inventors of the present invention (Sakanaka) has proved that when red ginseng powder at a dose of 0.9 g/kg/day or 1.5 g/kg/day, was administered to gerbils orally once a day for 7 days prior to a 5-minute transient forebrain ischemia, the learning disability after ischemia was significantly improved. This treatment also significantly prevented nerve cell death in the hippocampal CA1 area (Wen et al., Acta Neuropathol. 91, 15-22, 1996). Gerbils with forebrain ischemia are thought to be an animal model for transient ischemic attack in human. However, when red ginseng powder was administered orally at the same dose for one week after the 5-minute forebrain ischemia, the nerve cell death in the hippocampal CA1 area of gerbils was not suppressed; and the neuroprotective effect of oral administration of red ginseng powder was not so strong. Consequently, application of red ginseng powder to patients with more severe brain infarction than transient ischemic attack, e.g. to patients with permanent cerebrovascular occlusion), was thought to be unreasonable. Furthermore, the mechanism by which the oral administration of red ginseng powder suppresses the delayed neuronal death in the hippocampal CA1 area has not been elucidated. If such a mechanism of action is elucidated, it will be expected that new effects and improved efficacy of red ginseng powder will be discovered.

Originally, the methods for treatment of cerebral apoplexy (cerebral vascular diseases) have been different among cerebral infarction, cerebral embolism, cerebral hemorrhage, transient brain ischemic attack and subarachnoid hemorrhage; and strictly speaking, no effective countermeasures can be taken unless a cerebral CT inspection is performed. For example, thrombolytic agents can be used only for the treatment of cerebral infarction and brain embolism, and they are regarded as a contraindication for the treatment of cerebral hemorrhages. However, cerebral apoplexy is a serious disease resulting in a permanent disorder in higher functional activities, and threatening the survival of patients if no treatment is performed to protect the nerve cells or neurons at the lesion site at the earliest possible opportunity. Consequently, treatment or therapy should be initiated without a moment's delay. Even the period of time required for the CT inspection of the brain is, to put it strongly, a factor in reducing the possibility of recovery for patients with cerebral apoplexy. Surely, the treatment or therapy of acute phase cerebral apoplexy is a struggle against, not only the cerebral apoplectic lesion, but also the time after its onset. Quite unfortunately, at present, whatever is the disease type of cerebral apoplexy (cerebral infarction, cerebral hemorrhage, cerebral embolism, subarachnoidal hemorrhage or transient ischemic attack), the actual situation is that very few drugs are known which show a potent effect, even if they are administered immediately after the onset of cerebral apoplexy.

Ginsenoside $Rb_1$ is a compound having the following chemical structure:

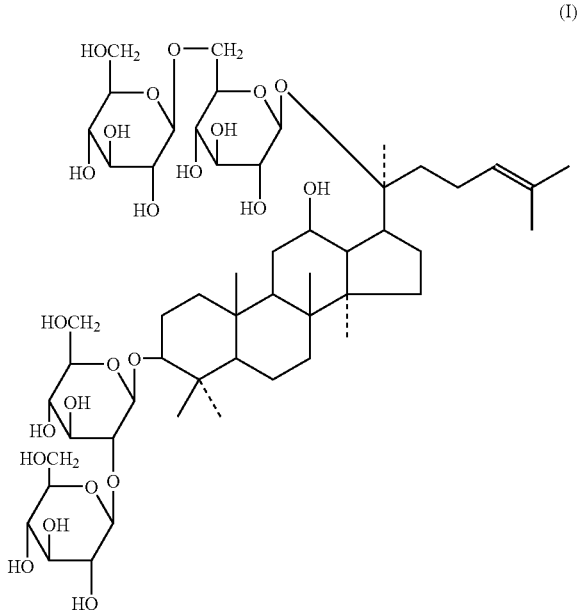

(I)

Ginsenoside $Rb_1$ is a known compound described in the reference by Shibata et al. (Shibata et al., Economic and medicinal plant research, World Scientific, Philadelphia, pp. 217-284, 1985).

Intraperitoneal administration of ginsenoside $Rb_1$ has been reported to show a tranquilizing action on the brain (Yoshimura H. et al., Eur. J. Pharmacol., 146, 291-197, 1988), but no mechanism of action has been elucidated. The possibility has been raised that a mixture of ginsenoside $Rb_1$ and ginsenoside $Rg_1$, or ginsenoside $Rb_1$ or ginsenoside $Rg_1$ at extracellular concentrations from $10^{-6}M$ to $10^{-7}$ M is active in the central nervous system and shows some effect against Alzheimer's disease. This effect is the result of activating the liberation of acetylcholine from acetylcholine-containing nerve cells (U.S. Pat. No. 5,137,878: Composition and method for treatment of senile dementia). However, since it can not be said that the main cause of Alzheimer's disease is a functional disturbance of the acetylcholine-containing nerve cells, this hypothesis has many remaining problems to be solved. Further, the above US patent did not disclose problems whether ginsenoside $Rb_1$ could extend the survival of acetylcholine-containing nerve cells, particularly whether it prevents the death of acetylcholine-containing cells or not.

In addition, the nerve cell-protective or neuroprotective action resulting from a single use of ginsenoside $Rb_1$ has been hardly elucidated until we initiated the studies on ginsenoside $Rb_1$. Using the transient forebrain ischemia model in gerbils, we have previously studied how the protective action of ginsenoside $Rb_1$ is exerted for cells other than acetylcholine-containing nerve cells. It has been proved that in this forebrain ischemia animal model, occlusion of the bilateral common carotid arteries for 3 to 5 minutes while maintaining the brain temperature at 37° C. results in neuronal loss of hippocampal CA1 pyramidal cells (containing no acetylcholine). This occurs within one week after ischemia, depending on the occlusion time (this event is called delayed neuronal death). It is also noted that the learning behavioral function of the ischemic animals deteriorates (Wen T.-C. et al., Acta Neuropathol., 91, 15-22, 1996). These facts mean that the transient forebrain ischemia model of gerbils reflects the human pathologic condition which results from a transient ischemic attack (TIA).

One of the inventors of the present invention (Sakanaka) has proved that administering ginsenoside $Rb_1$ (10 mg/kg or 20 mg/kg) into the peritoneal cavity of gerbils, once a day for one week in advance, can significantly prevent delayed neuronal death and the learning disability resulting from occlusion of the common carotid arteries for 5 minutes (Wen T.-C. et al., Acta Neuropathol., 91, 15-22, 1996). However, intraperitoneal administration of ginsenoside $Rb_1$ immediately after a 3- or 5-minute occlusion of the common carotid arteries, produced no effect (Wen T.-C. et al., Acta Neuropathol., 91, 15-22, 1996; Lim J.-H. et al., Neurosci. Res., 28, 191-200, 1997). Consequently, since both the transition rate and the transportation rate of peripherally (intraperitoneally) administered ginsenoside $Rb_1$ to the brain are thought to be very low, no clinical application of ginsenoside $Rb_1$ was considered at that time.

One of the inventors of the present invention (Sakanaka) reported that intracerebroventricular infusion of ginsenoside $Rb_1$ starting immediately after occlusion of the common carotid arteries for 3 or 3.5 minutes in stead of the above peripheral (intraperitoneal) administration suppressed the delayed neuronal death and learning disability (Lim J.-H. et al., Neurosci. Res., 28, 191-200, 1997). Further, the inventors of the present invention (Sakanaka, Tanaka and Maeda)

proved that in spontaneous hypertensive stroke-prone (SH-SP) rats, with permanent occlusion of the cortical branch of the middle cerebral artery (MCA) (the cerebral infarction model of rats), intracerebroventricular infusion of ginsenoside $Rb_1$ immediately after permanent occlusion of the MCA caused a significant reduction in the infarcted area in the cerebral cortex and ameliorated the ischemia-induced place navigation disability of the animals (Zhang B. et al., J. Stroke Cerebrovasc. Dis., 7, 1-9, 1998).

Even though ginsenoside $Rb_1$ is effective in direct intracerebroventricular infusion, it appears impossible, however, to apply ginsenoside $Rb_1$ to human transient cerebral ischemic attack (TIA) and cerebral infarction due to problems in the route of administration. These are similar to problems with other peptide growth factors (Sakanaka, M. et al. Proc. Natl. Acad. Sci. USA, 95, 4635-4640, 1998; Wen T.-C. et al. J. Exp. Med., 188, 635-649, 1998).

In order to identify compounds useful for treating, preventing or curing cerebral infarction, the methods for screening candidate substances for preventing, treating or curing cerebral infarction with the use of the cerebral ischemia/reperfusion model in gerbils or rats, have recently been frequently employed. However, it is important to note that the cerebral ischemia/reperfusion model using gerbils or rats does not always reflect, as explained later, the pathologic condition involved in human cerebral infarction. As described earlier, one of the inventors of the present invention (Sakanaka) has reported that in the cerebral ischemia/reperfusion model using gerbils, intraperitoneal administration of ginsenoside $Rb_1$ at a dose of 10 mg/kg/day or 20 mg/kg/day, before cerebral ischemia, rescued approximately 30% of the nerve cells in the hippocampal CA1 area. (Wen T.-C. et al., Acta Neuropathol., 91, 15-22, 1996). Zhang, Y. G and Liu, T. P. reported that a single intravenous administration of ginsenoside $Rb_1$ at doses of 10-40 mg/kg before ischemia, (using the ischemia/reperfusion model of the middle cerebral arteries of rats) reduced the infarction size approximately 20%-49% as compared with the control groups. Such an administration also reduced the infarction size approximately 12%-35% as compared with the control group when it was conducted after the reperfusion (Zhang, Y. G. and Liu, T. P., Chung Kuo Yao Li Hsuech Pao, Chinese Pharmacol. J., 17, 44-48, 1996). However, this effect can not always be said to be superior to the candidate substances of drugs (for example, glutamate antagonists and free radical scavengers) so far developed for treatment of cerebral ischemia/reperfusion, rather it may be inferior (Slusher, B. S. et al., Nature Med., 5, 1396-1402, 1999). Furthermore, the intravenous administration of ginsenoside $Rb_1$ at the dose of 40 mg/kg, which produced a comparatively good effect and high efficacy for the prevention and treatment of cerebral ischemia/reperfusion injuries, as reported earlier by Zhang, Y. G. and Liu, T. P., can be said to be too high in dose. Consequently, we can not deny the possibility of side effects or ill effects appearing following the single intravenous administration of ginsenoside $Rb_1$. This is true when we consider that the LD50 of the intravenously administered ginsenoside $Rb_1$ is approximately 448 mg/kg (Saito, H., et al., Shoyakugaku Zasshi, J. Galenicals, 34, 177-181, 1980). For a single intravenous administration, such a high dose of ginsenoside $Rb_1$ is critical, and intravenous administration on consecutive days (or continuous intravenous administration) may be difficult.

In case of actual human cerebral infarction (cerebral thrombosis or cerebral embolism), except for a few cases in which the thrombolytic therapy is performed after catheterization in the area of the obstructed cerebral artery for recanalization, there are many cases of permanent cerebrovascular occlusion. Consequently, a truly useful remedy for cerebral infarction is that it can be administered after permanent occlusion of a part of the cerebral arteries (for example, the middle cerebral artery), and the drugs which can protect specifically cerebral cells and nerve cells located in the ischemic penumbra until one month after the onset of cerebral infarction are needed. At this point, the cerebral infarct (cerebral thrombosis and cerebral embolism) lesion has entered a stable stage, and hopefully the broken cerebral vascular networks are recovered and reconstructed. It should be noted that the pharmacological analysis of drug candidates for the treatment or therapy of cerebral infarction should be performed by using animals with completely obstructed cerebral arteries. According to the earlier report by Zhang, Y. G and Liu, T. P., intravenous administration of ginsenoside $Rb_1$ at a dose of 10 mg/kg to rats before permanent occlusion of the middle cerebral artery, resulted in absolutely no effect. However, only when ginsenoside $Rb_1$ at a dose of 40 mg/kg was administered intravenously before but not after permanent occlusion of the middle cerebral artery, the size of the infarction was reduced about 14% as compared with the control group. Consequently, even if a single intravenous administration of ginsenoside $Rb_1$ at the high dose (40 mg/kg) was performed earlier in rats with a permanently occluded middle cerebral artery, it produced an obviously weak effect as compared with results obtained from an intravenous administration of ginsenoside $Rb_1$ into rats with ischemia and reperfusion of the middle cerebral artery. Furthermore, when the high dose (40 mg/kg) of ginsenoside $Rb_1$ is administered to rats with permanent occlusion of the middle cerebral artery before cerebral infarction occurs, it produces a very weak effect. If we consider that the LD50 of ginsenoside $Rb_1$ for intravenous administration is approximately 448 mg/kg, then such a high dose (40 mg/kg) of ginsenoside $Rb_1$ for intravenous administration every day (or consecutive days) is thought to be impossible. Based on the experience of the inventors of the present invention, a single or one more intravenous administration of a drug candidate for the treatment or therapy of cerebral infarction into experimental animals with a permanently occluded part of the cerebral arteries (for example middle cerebral artery) may show an effect for 1-2 days after the onset of cerebral infarction. However, if the same drug candidate is not administered on consecutive days thereafter, the cerebral infarct lesion will surely expand, and eventually in one month after the permanent cerebrovascular occlusion (namely, when the cerebral infarct lesion enters the almost stable stage), almost no effect is observed. Consequently, an important qualification for drugs for the treatment or therapy of cerebral infarction is that the compound can be administered intravenously for a long term or intravenously every day. However, based on the previous report of Zhang, Y. G. and Liu, T. P., it was thought to be practically impossible to apply intravenous administration of the high doses of ginsenoside $Rb_1$ in a repeated or continuous manner for treating, preventing or curing cerebral infarction or cerebral apoplexy.

The invention to counteract the previous idea that it was almost impossible to utilize ginsenoside $Rb_1$ for the therapy, prevention or treatment of cerebral infarction, was developed by the inventors of the present invention (Sakanaka and Tanaka). Details are described in the specification of Japanese Patent Application No. Hei 10-365560, PCT/JP99/02550 (Brain cell- or nerve cell-protective agents comprising ginsenoside $Rb_1$) and Japanese Patent Application No. Hei 11-340850, PCT/JP99/06804 (Cerebrovascular regeneration/reconstruction promoters and nerve tissue secondary degeneration inhibitors comprising ginsenoside $Rb_1$). In particular, we have found in the prior patent application that when repetitive or continuous intravenous infusion of ginsenoside $Rb_1$ was conducted at a dose of 60 μg/day or 6 μg/day for 28 days after the middle cerebral artery (MCA) of spontaneous hypertensive stroke-prone (SH-SP) rats was permanently occluded, the volume of the cerebral infarct (cerebral embolism) lesion was reduced to about ¼ as compared to what occurred in a group of cerebral infarction infused with physiological saline (vehicle). That is to say, repetitive or continuous intravenous administration of low doses of ginsenoside $Rb_1$, after permanent occlusion of the MCA, resulted in about a 75% reduction of the volume of the cerebral infarct lesions as compared with those in the control group. Moreover, it was found that even with repetitive or continuous intravenous infusions of such small amounts of ginsenoside $Rb_1$ for 28 days, cerebral vessels which had been destroyed after MCA permanent occlusion were regenerated and reconstructed. This occurred even if the intravenous administration of ginsenoside $Rb_1$ was subsequently terminated, and thereafter the cerebral infarct lesion had no longer deteriorated. Since the body weight of the SH-SP rats used by us (Sakanaka and Tanaka) is about 300 g, the daily dose of ginsenoside $Rb_1$ is about 200 μg/kg or 20 μg/kg. Consequently, when this is compared with the single intravenous administration of ginsenoside $Rb_1$ at a dose of 40 mg/kg that was used in the report by Zhang, Y. G. and Liu, T. P. (Chung Kuo Yao Li Hsuech Pao, Chinese Pharmacol. J., 17, 44-48, 1996), the daily dose to our SH-SP rats is 1/200 or 1/2000 of theirs. In the Japanese Patent Application No. Hei 10-365560, PCT/JP99/02550 and Japanese Patent Application No. Hei 11-340850, PCT/JP99/06804, the inventors of the present invention (Sakanaka and Tanaka) invented an excellent method for treating or curing cerebral infarction (cerebral thrombosis or cerebral embolisms), and for the treatment or therapy of cerebral apoplexy and cerebrovascular disorders. This method involved the long-term intravenous repetitive or continuous administration of small amounts of ginsenoside $Rb_1$. Small amounts of ginsenoside $Rb_1$ can be administered as a single intravenous infusion every day, or as a small amount of ginsenoside $Rb_1$ mixed with the other compositions or components for drip infusion so that the intravenous infusion can be performed constantly throughout the day or throughout a certain period. Further the prior report by the inventors of the present invention showed that the intracranial administration or the intracerebroventricular administration of ginsenoside $Rb_1$ suppressed secondary degeneration of the ischemic nervous tissues (Wen T.-C. et al., Acta Neuropathol., 91, 15-22, 1996; Zhang, B. et al., J. Stroke Cerebrovasc. Dis., 7, 1-9, 1998). Also in the prior patent applications, the inventors of the present invention (Sakanaka and Tanaka) demonstrated that repetitive or continuous intravenous administration of small amounts of ginsenoside $Rb_1$ suppressed effectively the secondary degeneration of the nervous tissues. And finally, in the prior patent application, the present inventors (Sakanaka and Tanaka) showed that repetitive or continuous intravenous administration of small amounts of ginsenoside $Rb_1$ can be applied for prevention, therapy or treatment of neurotrauma, head injury or spinal cord injury.

In the pathologic states of cerebral apoplexy, neurotrauma, head injury, spinal cord injury, intracranial hemorrhage, cardiac arrest, hypoxic ischemic encephalopathy or encephalitis, etc., if a large invasion or damage into the brain and nervous tissues occurs, brain edema appears. As a result, the pressure on the brain is significantly increased and this frequently threatens the survival of patients. In the field of clinical medicine, in order to prevent, treat or cure herniation of the brain tissue which accompanies increases in brain edema or brain pressure (intracranial pressure), mannitol, glycerol and/or steroids are frequently used. However, problems from the rebound effect and other side effects following termination of the drug administration have not been solved. Consequently, a safe drug for the therapy or treatment of brain edema, which can be administered over a long time, may certainly be required in the future, but no such drugs are available.

Regarding a mechanism of neuroprotection by peripheral (intraperitoneal) administration of ginsenoside $Rb_1$, the inventors of the present invention have reported that when low concentrations (0.1-100 fg/ml) of ginsenoside $Rb_1$ were added in advance to the culture medium, the necrosis of nerve cells caused by the hydroxyl radical inducer (ferrous sulfate) was reduced (Lim, J.-H. et al., Neurosci. Res., 28, 191-200, 1997; Zhang, B. et al., J. Stroke Cerebrovasc. Dis., 7, 1-9, 1998). We presumed that ginsenoside $Rb_1$ eliminated the hydroxyl radicals and thus reduced the lipid peroxide of the cell membrane and thereby protected the cultured nerve cells. However, no report to prove this hypothesis has been published.

High concentrations (approximately 0.11-11 μg/ml) of ginsenoside $Rb_1$ reduced the neurotoxicity of glutamic acid and prevented nerve cell death (Kim, Y.-C., et al., J. Neurosci. Res., 53, 426-432, 1998; Liu, M. and Zhang, J. T., Acta Pharmaceutica Sinica, 30, 674-678, 1995). Also, the high concentration of ginsenoside $Rb_1$ at 500 μM (550 μg/ml) may protect against apoptosis-like death in cell culture experiments (Tanaka, Tomoaki et al., The Ginseng Review, 24, 61-65, 1998). However, according to cell culture experiments by the present inventors, the high concentration of ginsenoside $Rb_1$ did not suppress nerve cell death (Lim, J.-H. et al., Neurosci. Res., 28, 191-200, 1997; Zhang B., et al., J. Stroke Cerebrovasc. Dis., 7, 1-9, 1998).

It is very difficult to reproduce or maintain such high concentrations of ginsenoside $Rb_1$ in the in vivo lesioned tissues or in the extracellular fluid of the nervous tissues. Furthermore, considering the cost and the possibility of side (ill) effects appearing, the present inventors (Sakanaka and Tanaka) speculate that the administration of large amounts of ginsenoside $Rb_1$ in vivo is not feasible. Actually, in view of the earlier experimental results of the present inventors, it has been demonstrated that high doses of ginsenoside $Rb_1$ do not always produce preferable effects and efficacy (Zhang, B., et al., J. Stroke Cerebrovasc. Dis., 7, 1-9, 1998).

At present, the mechanism of neuroprotection by ginsenoside $Rb_1$ has not been elucidated.

In Japanese Patent Application No. Hei 10-365560, PCT/JP99/02550 (Brain cell or nerve cell-protective agents comprising ginsenoside $Rb_1$), we (Sakanaka and Tanaka) have found that ginsenoside $Rb_1$, at a markedly low concentration range never previously reported suppresses apoptosis-like nerve cell death by increasing the expression of a cell death-suppressing gene product $Bcl-x_L$. These concentrations ranged from 1 ng/ml or less, and preferably from 1 fg to 100 fg/ml. Specifically, in the previous patent application, we (Sakanaka and Tanaka) found that ginsenoside $Rb_1$ is the only non-peptidic $Bcl-x_L$ expression stimulator in the world. Although ginsenoside $Rb_1$ at a concentration of 100 fg/ml showed a slight suppressive action on the formation of lipid peroxides, no such effect was observed at the lower concentrations. Consequently, the hypothesis presented earlier in relation to the action mechanism of ginsenoside $Rb_1$, namely the hypothesis in which ginsenoside $Rb_1$ decreases cell membrane lipid peroxides as a result of erasing hydroxyl radicals to protect nerve cells, was found to be inappropriate. Further, in the previous patent application, the present inventors (Sakanaka and Tanaka) found that ginsenoside $Rb_1$ inhibited apoptosis-like cell death in vivo.

Since $Bcl-x_L$ is expressed not only in nerve cells or neurons, but also in cells of the other peripheral tissues or glial cells, the fact that ginsenoside $Rb_1$ enhances the expression of the cell death-suppressing gene product $Bcl-x_L$, suggests that ginsenoside $Rb_1$ also has the same action on the other cells. Importantly, we (Sakanaka and Tanaka) have described in the prior patent applications (Japanese Patent Application No. Hei 10-365560, PCT/JP99/02550, Brain cell or nerve cell-protective agents comprising ginsenoside $Rb_1$; Japanese Patent Application No. Hei 11-340850, PCT/JP99/06804, Cerebrovascular regeneration/reconstruction promoters and nerve tissue secondary degeneration inhibitors comprising ginsenoside $Rb_1$) the idea that since myocardial cells abundantly express $Bcl-x_L$, they are highly possible targets on which ginsenoside $Rb_1$ at low concentrations and low doses act to show effect and efficacy.

Although ginsenoside $Rb_1$ is a kind of purified saponin which is contained in medicinal ginseng, it can not be detected in the blood following a single oral administration. As a result, the pharmacological action resulting from oral administration of ginsenoside $Rb_1$ has been denied. Consequently, in the Japanese Patent Application No. Hei 10-365560, PCT/JP99/02550, Brain cell or nerve cell-protective agents comprising ginsenoside $Rb_1$ and Japanese Patent Application No. Hei 11-340850, PCT/JP99/06804, Cerebrovascular regeneration/reconstruction promoters and nerve tissue secondary degeneration inhibitors comprising ginsenoside $Rb_1$, we (Sakanaka and Tanaka) have demonstrated that intravenously administered ginsenoside $Rb_1$ at low doses have effects, efficacy and/or usages independent of those of medicinal ginseng.

In the crude saponin fraction(s) of medicinal ginseng, besides ginsenoside $Rb_1$, there are at least approximately 30 different purified saponins similar in chemical structure to ginsenoside $Rb_1$ (Shoji, Ginseng '95, pp. 251-161, Kumagai, Akira, Ed. Kyoritsu Publ. Co.). Quite naturally, as described in our prior patent application (Japanese Patent Application No. Hei 10-365560, PCT/JP99/02550, Brain cell or nerve cell-protective agents comprising ginsenoside $Rb_1$), these other purified saponins are expected to exhibit effects and efficacy similar to those obtained by intravenous administration of ginsenoside $Rb_1$ at low doses. We have also described in our prior patent application (Japanese Patent Application No. Hei 11-243378) the concept that novel useful compounds could be prepared by using components of medicinal ginseng and/or ginsenoside $Rb_1$ as the leading compounds.

As described above, we have referred to the importance of elucidating the mechanisms of action involved in oral administration of medicinal ginseng. We have also described the marked effects resulting from the continuous intravenous administration of small amounts of ginsenoside $Rb_1$, the importance of prevention, therapy and treatment of cerebral edema, the upregulation of $bcl-x_L$ expression by ginsenoside $Rb_1$, and the importance of elucidating the physiological actions of the crude saponin fractions of medicinal ginseng or components thereof. In the present invention, we have found that oral administration of red ginseng powder exhibited an unexpectedly excellent suppressive action against cerebral infarction, an ameliorating effect on cerebral edema and an improvement in place navigation disability in rats which had undergone permanent occlusion of the cortical branch of the middle cerebral artery (MCA). This damage caused by permanent MCA occlusion is more severe than the transient forebrain ischemia model of gerbils and is similar to the pathological state of human cerebral infarction. We have also found that oral administration of red ginseng powder enhanced the expression of the cell death-suppressing gene product $Bcl-x_L$ protein in the nervous tissues. Further, we have found that: the continuous intravenous administration of small or low dosages of ginsenoside $Rb_1$ suppresses the onset of cerebral edema quite effectively; that ginsenoside $Rb_1$ at concentrations of 0.01-$10^4$ fg/ml or 1-$10^4$ fg/ml enhanced the expression of $Bcl-x_L$ in myocardial cells and suppressed apoptosis or apoptosis-like cell death of myocardial cells; and that the continuous intravenous administration of small amounts of a crude saponin fraction of ginseng (red ginseng powder) exhibits therapeutic effects on spinal cord injuries. These effects were similar to those obtained by intravenous continuous administration of low dosages of ginsenoside $Rb_1$. With these findings we have completed the present invention. In addition, we have found a novel chemical derivative of ginsenoside $Rb_1$, i.e. dihydroginsenoside $Rb_1$ which exhibits excellent therapeutic effects against cerebral infarction, and thus we have completed the present invention.

DISCLOSURE OF THE INVENTION

An object of the present invention is to provide medicament exhibiting an excellent brain cell- or nerve cell-protecting effect and protecting cells by promoting expression of a cell death-suppressing gene product $Bcl-x_L$ protein. A further object of the present invention is to provide: a preparation which can be used at low dosages by intravenous administration for the prevention, therapy and/or treatment of cerebral edema, brain edema, brain and nervous tissue edema or spinal cord tissue edema; a preparation which can be used at low doses by intravenous administration for the prevention, therapy and/or treatment of bedsores (decubitus) which accompany spinal cord injuries; a preparation for intravenous administration to promote the expression of a cell death-suppressing gene product $Bcl-x_L$ in the nervous tissues; a medicinal or pharmaceutical composition to promote expression of the cell death-suppressing gene $Bcl-x_L$ in oligodendrocytes; a protective agent for oligodendrocytes; a medicinal or pharmaceutical composition to promote expression of the cell death-suppressing gene $Bcl-x_L$ in myocardial cells; and a medicinal or pharmaceutical composition to suppress apoptosis or apoptosis-like cell death in myocardial cells. A further object of the present invention is to provide a preparation for intravenous administration which can be used for the prevention, treatment or therapy of diseases caused by injury or trauma to the nervous tissues or spinal cord tissue, and to provide a medicinal or pharmaceutical composition for suppressing demyelination, apoptosis or apoptosis-like cell death of oligodendrocytes, or secondary degeneration of the nervous tissues, which are caused by injury or trauma to the nervous tissues or spinal cord tissue.

A further object of the present invention is to provide a preparation which can be used at small or low doses by continuous intravenous administration for the prevention, therapy or treatment of cerebral infarction or cerebral apoplexy; and also to provide a medicinal or pharmaceutical composition for suppressing apoptosis of nerve cells (neurons) or apoptosis-like nerve cell death. An additional object of the present invention is to demonstrate methods for preparing novel useful brain cell-protective agents, or neuroprotective agents, by utilizing components or ingredients of ginseng or metabolites thereof as leading compounds.

The present invention provides effective preparations for oral administration comprising medicinal ginseng, its extracts, components of ginseng or metabolites thereof which are useful as cytoprotective agents. More particularly, the present invention provides medicinal or pharmaceutical composition(s) for preventing apoptosis or apoptosis-like cell death comprising ginseng, its extracts, components or ingredients of ginseng or metabolites thereof. It also provides medicinal or pharmaceutical composition(s) for promoting the expression of a cell death-suppressing gene product Bcl-$x_L$ protein comprising ginseng, its extracts, components of ginseng or metabolites thereof. Further, the present invention(s) provides a preparation for oral administration which is useful for the therapy, prevention or treatment of brain or nervous diseases or cerebral edema comprising medicinal ginseng, its extracts, components of medicinal ginseng or metabolites thereof.

In addition, the present invention provides: a preparation(s) which can be used at low or small dosages by intravenous administration for the prevention, therapy or treatment of cerebral edema, brain edema, brain and nervous tissue edema or spinal cord tissue edema, comprising ginsenoside $Rb_1$, metabolites thereof or salts thereof. It also provides a preparation(s) at low doses by intravenous administration which can be used for the prevention, therapy and/or treatment of bedsores (decubitus) associated with spinal cord injuries, comprising ginsenoside $Rb_1$, metabolites thereof or salts thereof. Additionally it provides a preparation(s) for intravenous administration to promote the expression of a cell death-suppressing gene Bcl-$x_L$ in the nervous tissues, comprising ginsenoside $Rb_1$, metabolites thereof or salts thereof; a medicinal or pharmaceutical composition(s) for promoting expression of the cell death-suppressing gene Bcl-$x_L$ in oligodendrocytes, comprising ginsenoside $Rb_1$, metabolites thereof or salts thereof; a protective agent(s) for oligodendrocytes comprising ginsenoside $Rb_1$, metabolites thereof or salts thereof; a medicinal or pharmaceutical composition(s) for promoting the expression of the cell death-suppressing gene Bcl-$x_L$ in myocardial cells, comprising ginsenoside $Rb_1$, metabolites thereof or salts thereof; and a medicinal or pharmaceutical composition(s) for suppressing apoptosis or apoptosis-like cell death in myocardial cells, comprising low concentrations of ginsenoside $Rb_1$, metabolites thereof or salts thereof.

The present invention further provides a medicinal or pharmaceutical composition(s) for the prevention, treatment or therapy of diseases caused by injuries or trauma to the nervous tissues or spinal cord tissue, comprising the crude saponin fraction(s) of ginseng, any one of constitutional components thereof, metabolites thereof or salts thereof. More particularly, the present invention provides a medicinal or pharmaceutical composition(s) for prevention, treatment or therapy of the secondary degeneration of nervous tissues resulting from injuries to the nervous tissues; a medicinal or pharmaceutical composition(s) for prevention, treatment or therapy of diseases caused by spinal cord injuries, head injuries or neurotrauma; and a medicinal or pharmaceutical composition(s) for prevention, treatment or therapy of diseases caused by nervous tissue or spinal cord tissue injuries that are accompanied by demyelination. The present invention also provides a medicinal or pharmaceutical composition(s) for suppressing the apoptosis or apoptosis-like cell death of oligodendrocytes comprising the crude saponin fraction(s) of ginseng, any one of the constitutional components thereof, metabolites thereof or salts thereof. The present invention further provides the crude saponin fraction(s) of medicinal ginseng, any one of constitutional components thereof, metabolites thereof or salts thereof which are useful as suppressive agents against the secondary degeneration of nervous tissues.

The present invention provides a method for the use of components of medicinal ginseng or metabolites thereof, as leading compounds for exploring novel active compounds or ingredients for the prevention, treatment or therapy of diseases or lesions described above, and for exploring brain cell-protective agents or neuroprotective agents.

Further, the present invention provides a novel ginsenoside $Rb_1$ derivative, i.e. dihydroginsenoside $Rb_1$ which is useful as a cytoprotective agent. Dihydroginsenoside $Rb_1$ can be prepared by using ginsenoside $Rb_1$ (one of components of ginseng) as a leading compound. More particularly, the present invention provides a medicinal or pharmaceutical composition(s) for prevention, therapy or treatment of cerebral infarction or cerebral apoplexy, or a medicinal or pharmaceutical composition(s) for suppressing apoptosis or apoptosis-like nerve cell death, comprising dihydroginsenoside $Rb_1$, metabolites thereof or salts thereof. The present invention also provides a medicinal or pharmaceutical composition(s) for intravenous administration comprising dihydroginsenoside $Rb_1$, metabolites thereof or salts thereof, namely the medicinal or pharmaceutical composition(s) for repetitive or continuous intravenous administration or single intravenous infusion at low concentrations or low dosages.

As described earlier, the present invention describes experiments on the oral administration of medicinal ginseng, experiments on the repetitive or continuous intravenous administration of ginsenoside $Rb_1$ at low dosages, cell culture experiments using ginsenoside $Rb_1$, experiments on continuous intravenous administration of small amounts of the crude saponin fraction(s) of medicinal ginseng, and experiments on the intravenous administration of a novel chemical derivative of ginsenoside $Rb_1$, i.e. dihydroginsenoside $Rb_1$. In the following description, the experiments on oral administration of medicinal ginseng, which were demonstrated in the prior patent application, Japanese Patent Application No. Hei 11-243378 (Brain cell or nerve cell-protective agents comprising ginseng), will be explained. Thereafter, the experiments on the intravenous administration of the crude saponin fraction(s), the experiments on the repetitive or continuous intravenous administration of ginsenoside $Rb_1$ at low doses and the cell culture experiments using low concentrations of ginsenoside $Rb_1$ will be described. Finally, the results of the experiments using the novel chemical derivative of ginsenoside $Rb_1$, dihydroginsenoside $Rb_1$, will be explained.

BRIEF EXPLANATION OF DRAWINGS

In FIG. 1, the upper figure shows results at the 2nd week, and the lower figure shows results at the 4th week. In FIG. 1: open circles indicate distilled water-administered ischemia group; closed circles indicate sham-operated group; open squares indicate red ginseng powder (0.6 g/kg/day)-administered ischemia group; closed squares indicate red ginseng powder (0.75 g/kg/day)-administered ischemia group; open triangles indicate red ginseng powder (0.9 g/kg/day)-administered ischemia group; closed triangles indicate red ginseng powder (1.2 g/kg/day)-administered ischemia group.

In FIG. 5, the upper figure shows results at the 2nd week, and the lower figure shows results at the 4th week. In FIG. 5: open circles indicate distilled water administered ischemia group; and closed squares indicate red ginseng powder (0.9 g/kg/day)-administered ischemia group. For reference, the experimental results of sham operation used in FIG. 1 are indicated by closed circles.

FIG. 10 (B) shows graphs quantifying the results of Western blotting in FIG. 10 (A) by densitometry.

FIG. 11 (B) shows graphs quantifying the results of Western blotting in FIG. 11 (A) by densitometry.

FIG. 21 is also photographs showing the occurrence of bedsore (decubitus) in the rat administered with physiological saline after spinal cord injury. Further, FIG. 21 is also photographs showing no occurrence of bedsore in the rat administered intravenously with ginsenoside $Rb_1$ (60 μg/day) after spinal cord injury.

BEST MODE FOR CARRYING OUT THE INVENTION

Figure 1:
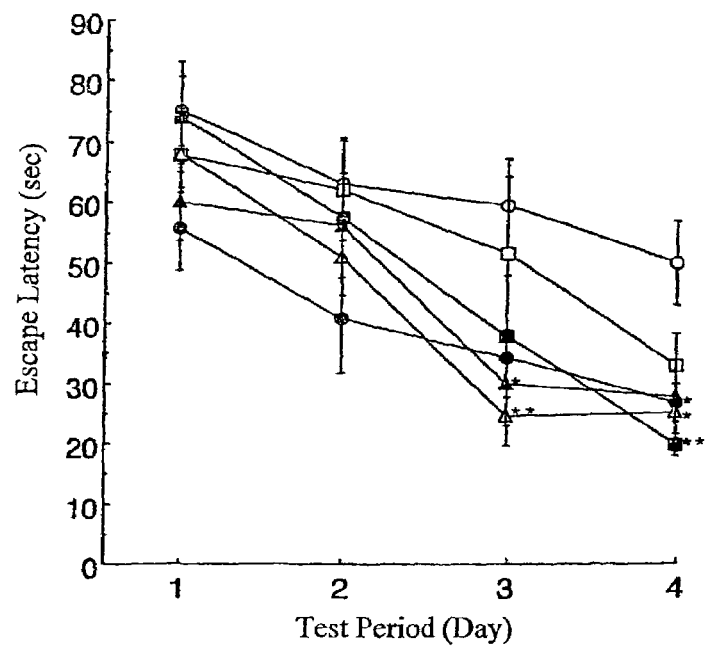
FIG. 1 shows results of water maze tests of rats administered orally with distilled water or red ginseng powder before and after MCA permanent occlusion.
Figure 1:
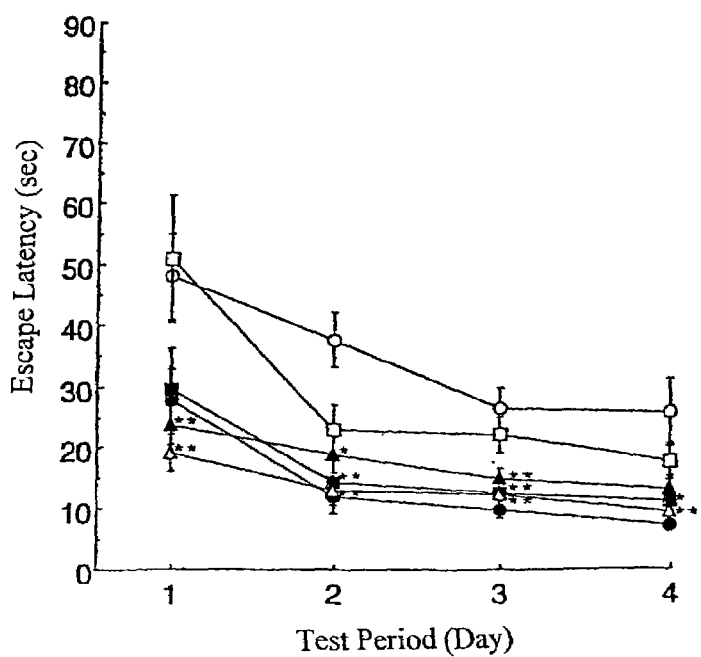

The present invention relates to a medicinal or pharmaceutical composition(s) for promoting the expression of a cell death-suppressing gene product $Bcl-x_L$ comprising ginseng, its extracts, ginseng components, metabolites thereof or salts thereof and/or a pharmaceutically acceptable carrier(s). Preferably, the present invention relates to the medicinal or pharmaceutical composition(s) for promoting the expression of a cell death-suppressing gene product $Bcl-x_L$ wherein the extracellular fluid levels of medicinal ginseng, its extracts, ginseng components, metabolites thereof or salts thereof in lesioned tissues are adjusted to 145 ng/ml or less, preferably 14.5 ng/ml or less or 1 ng/ml or less, more preferably 0.01-145000 fg/ml, further more preferably 1-145000 fg/ml.

Further, the present invention relates to a method for preventing, treating or curing diseases which can be prevented, treated or cured by promoting the expression of a cell death-suppressing gene product $Bcl-x_L$ comprising administering effective amounts of medicinal ginseng, its extracts, ginseng components, metabolites thereof or salts thereof, preferably amounts exhibiting the extracellular fluid concentrations of 145 ng/ml or less in lesioned tissues, more preferably 0.01-145000 fg/ml and more further preferably 1-145000 fg/ml, to patients with diseases which can be prevented, treated or cured by promoting the expression of a cell death-suppressing gene product $Bcl-x_L$.

Further, the present invention relates to the use of medicinal ginseng, its extracts, ginseng components, metabolites thereof or salts thereof for production of the medicinal or pharmaceutical compositions for promoting the expression of a cell death-inhibitory gene product $Bcl-x_L$.

Examples of tissues for promoting expression of the cell death-suppressing gene product $Bcl-x_L$ by the above medicinal or pharmaceutical compositions are brain tissue, nervous tissues, spinal cord tissue, liver and spleen. These compositions are useful for the prevention, therapy or treatment of brain and nervous diseases such as cerebrovascular dementia, cerebral infarction and cerebral apoplexy etc.

The medicinal or pharmaceutical compositions for promoting expression of the cell death-suppressing gene product $Bcl-x_L$ of the present invention can be used as the preparations for oral administrations or the preparations for intravenous administration.

The present invention relates to a medicinal or pharmaceutical composition(s) for suppressing the apoptosis of cells or apoptosis-like cell death comprising ginseng, its extracts, ginseng components, metabolites thereof or salts thereof and/or a pharmaceutically acceptable carrier(s). Preferably, the present invention relates to the medicinal or pharmaceutical composition(s) for suppressing the apoptosis of cells or apoptosis-like cell death wherein the extracellular fluid concentrations of medicinal ginseng, its extracts, ginseng components, metabolites thereof or salts thereof in lesioned tissues are adjusted to 145 ng/ml or less, preferably 14.5 ng/ml or less or 1 ng/ml or less, more preferably 0.01-145000 fg/ml, further more preferably 1-145000 fg/ml.

Further, the present invention relates to a method for preventing, treating or curing diseases which can be prevented, treated or cured by suppressing the apoptosis of cells or apoptosis-like cell death comprising administering effective amounts of medicinal ginseng, its extracts, ginseng components, metabolites thereof or salts thereof, preferably amounts exhibiting the extracellular fluid concentrations of 145 ng/ml or less in lesioned tissues, preferably 14.5 ng/ml or less or 1 ng/ml or less, more preferably 0.01-145000 fg/ml and more further preferably 1-145000 fg/ml, to patients with diseases which can be prevented, treated or cured by suppressing the apoptosis of cells or apoptosis-like cell death.

Further, the present invention relates to the use of medicinal ginseng, its extracts, ginseng components, metabolites thereof or salts thereof for production of the medicinal or pharmaceutical compositions for suppressing the apoptosis of cells or apoptosis-like cell death.

Examples of concerned cells of the present invention are brain cells, nerve cells (neurons), neuronal stem cells, glial cells, vascular endothelial cells, vascular smooth muscle cells, liver cells (hepatocytes), Kupffer's cells, sinusoid endothelial cells, fibroblasts, biliary epithelial cells, lipocytes, fat-storing cells, lymphocytes, leukocytes, reticulum cells, macrophages or plasma cells, and the medicinal or pharmaceutical compositions of the present invention are useful for therapy, prevention or treatment of diseases causing apoptosis of cells or apoptosis-like cell death.

The medicinal or pharmaceutical compositions for suppressing the apoptosis of cells or apoptosis-like cell death of the present invention can be used as the preparations for oral administration or the preparations for intravenous administration.

The present invention relates to a medicinal or pharmaceutical composition(s) for treating, preventing or curing brain and/or nervous diseases comprising ginseng, its extracts, ginseng components, metabolites thereof or salts thereof and/or a pharmaceutically acceptable carrier (s). Preferably, the present invention relates to the medicinal compositions for treating, preventing or curing brain and/or nervous diseases wherein the extracellular fluid concentrations of medicinal ginseng, its extracts, ginseng components, metabolites thereof or salts thereof in lesioned tissues are adjusted to 145 ng/ml or less, preferably 14.5 ng/ml or less or 1 ng/ml or less, more preferably 0.01-145000 fg/ml, further more preferably 1-145000 fg/ml.

Further, the present invention relates to a method for preventing, treating or curing brain and/or nervous diseases comprising administering effective amounts of medicinal ginseng, its extracts, ginseng components, metabolites thereof or salts thereof, preferably amounts exhibiting the extracellular fluid concentrations of 145 ng/ml or less in lesioned tissues, preferably 14.5 ng/ml or less or 1 ng/ml or less, more preferably 0.01-145000 fg/ml and more further preferably 1-145000 fg/ml, to patients with brain and/or nervous diseases.

Further, the present invention relates to the use of ginseng, its extracts, ginseng components, metabolites thereof or salts thereof for production of the medicinal or pharmaceutical compositions for preventing, treating or curing brain and/or nervous diseases.

Examples of brain and/or nervous diseases of the present invention hereinbefore are injuries to the nervous tissues or spinal cord tissue such as spinal cord injury; injuries to the nervous tissues or spinal cord tissue such as head injury or neurotrauma; diseases caused by apoptosis or apoptosis-like cell death of oligodendrocytes; cerebral edema, edema of the brain and nervous tissues or edema of the spinal cord tissue caused by cerebral apoplexy, cerebral infarction, cerebral hemorrhage, subarachnoidal hemorrhage, head injury, intracranial hemorrhage, spinal cord injury or neurotrama; cerebrovascular dementia; cerebral infarction, cerebral apoplexy, transient cerebral ischemic attack; paralysis of the upper extremities or lower extremities, urination disorders, dysautonomia, hypogonadism, dyschezia or neurogenic bladder caused by injuries or trauma to the nervous tissues or spinal cord tissue.

The medicinal or pharmaceutical compositions for treatment, prevention or therapy of brain and/or nervous diseases of the present invention can be used as the preparations for oral administration or the preparations for intravenous administration.

The present invention relates to agents for treating, preventing or curing brain and/or nervous diseases or cerebral edema comprising medicinal ginseng, its extracts, ginseng components, metabolites thereof or salts thereof.

The present invention relates to a medicinal or pharmaceutical composition(s) for treating, preventing or curing cardiopathy or cardiac diseases comprising ginseng, its extracts, ginseng components, metabolites thereof or salts thereof and/or a pharmaceutically acceptable carrier(s). Preferably, the present invention relates to the medicinal or pharmaceutical composition(s) for treating, preventing or curing cardiopathy or cardiac diseases wherein the extracellular fluid concentrations of medicinal ginseng, its extracts, ginseng components, metabolites thereof or salts thereof in lesioned tissues are adjusted to 145 ng/ml or less, preferably 14.5 ng/ml or less or 1 ng/ml or less, more preferably 0.01-145000 fg/ml, further more preferably 1-145000 fg/ml.

Further, the present invention relates to a method for preventing, treating or curing cardiopathy or cardiac diseases comprising administering effective amounts of medicinal ginseng, its extracts thereof, ginseng components, metabolites thereof or salts thereof, preferably amounts exhibiting the extracellular fluid concentrations of 145 ng/ml or less in lesioned tissues, preferably 14.5 ng/ml or less or 1 ng/ml or less, more preferably 0.01-145000 fg/ml and more further preferably 1-145000 fg/ml, to patients with cardiopathy or cardiac diseases.

Further, the present invention relates to the use of ginseng, its extracts, ginseng components, metabolites thereof or salts thereof for production of the medicinal or pharmaceutical composition(s) for preventing, treating or curing cardiopathy or cardiac diseases.

Cardiac diseases of the present invention are preferably those accompanied by apoptosis of cardiac cells or apoptosis-like cardiac cell death.

The medicinal or pharmaceutical compositions of the present invention for treatment, prevention or therapy of cardiac diseases can be used as the preparations for oral administration or the preparations for intravenous administration.

The present invention relates to a preparation(s) for intravenous administration comprising medicinal ginseng, its extracts, ginseng components, metabolites thereof or salts thereof and a pharmaceutically acceptable carrier(s). More particularly, the present invention relates to the preparation(s) for intravenous administration for treating, preventing or curing brain and/or nervous diseases, such as, spinal cord injuries, head injuries, neurotrauma, cerebrovascular dementia, cerebral infarction, cerebral apoplexy or transient cerebral ischemic attack, or cardiac (heart) diseases accompanied by apoptosis of cardiac cells or apoptosis-like cardiac cell death. Preferably, the present invention relates to preparations at the low concentrations for intravenous administration wherein the extracellular fluid concentrations of medicinal ginseng, its extracts, ginseng components, metabolites thereof or salts thereof in lesioned tissues are adjusted to 145 ng/ml or less, preferably 14.5 ng/ml or less or 1 ng/ml or less, more preferably 0.01-145000 fg/ml, further more preferably 1-145000 fg/ml. The preparations for intravenous administration of the present invention can be any of the preparations for single intravenous infusion and the preparations for repetitive or continuous intravenous infusion.

Further, the present invention relates to a method for preventing, treating or curing brain and nervous diseases and/or cardiac diseases comprising administering the preparations for intravenous administration containing effective amounts of medicinal ginseng, its extracts, ginseng components, metabolites thereof or salts thereof, amounts exhibiting the extracellular fluid concentrations of 145 ng/ml or less in lesioned tissues, preferably 14.5 ng/ml or less, or 1 ng/ml or less more preferably 0.01-145000 fg/ml and more further preferably 1-145000 fg/ml, to patients with brain and nervous diseases and/or cardiac diseases.

Further, the present invention relates to the use of medicinal ginseng, its extracts, ginseng components, metabolites thereof or salts thereof for production of the preparations for intravenous administration for preventing, treating or curing brain and nervous diseases and/or cardiac diseases.

The present invention relates to a medicinal or pharmaceutical composition(s) for treating, preventing, curing or ameliorating edema(ta) of the biological tissues or living tissues comprising ginsenoside $Rb_1$, metabolites thereof or salts thereof and/or a pharmaceutically acceptable carrier(s). Preferably, the present invention relates to the medicinal or pharmaceutical composition(s) for treating, preventing, curing or reducing edema(ta) of the biological tissues or living tissues wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1$-$10^4$ fg/ml (approximately 0.9-9000 fM).

Further, the present invention relates to a method for preventing, treating or curing edema(ta) of the biological tissues or living tissues comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1\text{-}10^4$ fg/ml (approximately 0.9-9000 fM) in lesioned tissues, to patients with edema(ta).

Further, the present invention relates to the use of ginsenoside $Rb_1$, metabolites thereof or salts thereof for production of the medicinal or pharmaceutical compositions for preventing, treating or curing edema(ta) of the biological tissues or living tissues.

Examples of edema of the biological tissues or living tissues are cerebral edema, edema of the brain and nervous tissues or edema of the spinal cord tissue caused by cerebral apoplexy, cerebral infarction, cerebral hemorrhage, subarachnoidal hemorrhage, head injuries, intracranial hemorrhage, spinal cord injuries or neurotrauma.

The medicinal or pharmaceutical compositions for preventing, treating, curing or reducing edema(ta) of the biological tissues or living tissues of the present invention are preferably used as the preparations for intravenous administration such as the preparation for single intravenous infusion or the preparation for repetitive or continuous intravenous infusion.

The present invention relates to a medicinal or pharmaceutical composition(s) for prevention, therapy or treatment of bedsore (decubitus) comprising ginsenoside $Rb_1$, metabolites thereof or salts thereof and/or a pharmaceutically acceptable carrier(s). Preferably, the present invention relates to the medicinal or pharmaceutical composition(s) for preventing, curing or treating bedsores wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1\text{-}10^4$ fg/ml (approximately 0.9-9000 fM).

Further, the present invention relates to a method for prevention, treatment or therapy of bedsores comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1\text{-}10^4$ fg/ml (approximately 0.9-9000 fM) in lesioned tissues, to patients with bedsores or decubitus.

Further, the present invention relates to the use of ginsenoside $Rb_1$, metabolites thereof or salts thereof for production of the medicinal or pharmaceutical compositions for preventing, treating or curing bedsores (decubitus).

Example of bedsore is bedsore caused by spinal cord injury.

The medicinal or pharmaceutical compositions for preventing, treating or curing bedsore of the present invention are used preferably as the preparations for intravenous administration such as the preparation for single intravenous infusion or the preparation for repetitive or continuous intravenous infusion.

The present invention relates to a medicinal or pharmaceutical composition(s) for prevention, treatment or therapy of neuroparalysis comprising ginsenoside $Rb_1$, metabolites thereof or salts thereof and/or a pharmaceutically acceptable carrier(s). Preferably, the present invention relates to the medicinal or pharmaceutical composition(s) for preventing, treating or curing neuroparalysis wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1\text{-}10^4$ fg/ml (approximately 0.9-9000 fM).

Further, the present invention relates to a method for prevention, treatment or therapy of neuroparalysis comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1\text{-}10^4$ fg/ml (approximately 0.9-9000 fM) in lesioned tissues, to patients with neuroparalysis.

Further, the present invention relates to the use of ginsenoside $Rb_1$, metabolites thereof or salts thereof for production of the medicinal or pharmaceutical composition(s) for preventing, treating or curing neuroparalysis.

Example of neuroparalysis is paralysis or paresis of the upper extremities and/or the lower extremities caused by spinal cord injury.

The medicinal or pharmaceutical composition(s) for preventing, treating or curing neuroparalysis of the present invention is preferably used as the preparations for intravenous administration such as the preparation for single intravenous infusion or the preparation for repetitive or continuous intravenous infusion.

The present invention relates to the medicinal or pharmaceutical compositions for prevention, treatment or therapy of urination disturbance or disorder, hypogonadism or dyschezia, comprising ginsenoside $Rb_1$, metabolites thereof or salts thereof and/or a pharmaceutically acceptable carrier(s). Preferably, the present invention relates to the medicinal or pharmaceutical compositions for preventing, treating or curing urination disturbance or disorder, hypogonadism or dyschezia wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1\text{-}10^4$ fg/ml (approximately 0.9-9000 fM).

Further, the present invention relates to a method for prevention, treatment or therapy of urination disturbance or disorder, hypogonadism or dyschezia comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1\text{-}10^4$ fg/ml (approximately 0.9-9000 fM) in lesioned tissues, to patients with urination disorder or disturbance, hypogonadism or dyschezia.

Further, the present invention relates to the use of ginsenoside $Rb_1$, metabolites thereof or salts thereof for production of the medicinal or pharmaceutical compositions for preventing, treating or curing urination disorder or disturbance, hypogonadism or dyschezia.

The medicinal or pharmaceutical compositions for prevention, treatment or therapy of urination disorder or disturbance, hypogonadism or dyschezia of the present invention are preferably used as the preparations for intravenous administration such as the preparation for single intravenous infusion or the preparation for repetitive or continuous intravenous infusion.

The present invention relates to a medicinal or pharmaceutical composition(s) for prevention, treatment or therapy of neurogenic bladder comprising ginsenoside $Rb_1$, metabolites thereof or salts thereof and/or a pharmaceutically acceptable carrier(s). Preferably, the present invention relates to the medicinal or pharmaceutical composition(s) for preventing, treating or curing neurogenic bladder wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1-10^4$ fg/ml (approximately 0.9-9000 fM).

Further, the present invention relates to a method for prevention, treatment or therapy of neurogenic bladder comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1-10^4$ fg/ml (approximately 0.9-9000 fM) in lesioned tissues, to patients with neurogenic bladder.

Further, the present invention relates to the use of ginsenoside $Rb_1$, metabolites thereof or salts thereof for production of the medicinal or pharmaceutical composition(s) for preventing, treating or curing neurogenic bladder.

The medicinal or pharmaceutical composition(s) for preventing, treating or curing neurogenic bladder of the present invention can be preferably used as the preparations for intravenous administration such as the preparation for single intravenous infusion or the preparation for repetitive or continuous intravenous infusion.

The present invention relates to a medicinal or pharmaceutical composition(s) for promoting the expression of a cell death-suppressing gene product $Bcl-x_L$ in oligodendrocytes comprising ginsenoside $Rb_1$, metabolites thereof or salts thereof and/or a pharmaceutically acceptable carrier(s). Preferably, the present invention relates to the medicinal or pharmaceutical composition(s) for promoting the expression of a cell death-suppressing gene product $Bcl-x_L$ in oligodendrocytes wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1-10^4$ fg/ml (approximately 0.9-9000 fM).

Further, the present invention relates to a method for preventing, treating or curing diseases which can be prevented, treated or cured by promoting the expression of a cell death-suppressing gene product $Bcl-x_L$ in oligodendrocytes comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1-10^4$ fg/ml (approximately 0.9-9000 fM) in lesioned tissues, to patients with diseases which can be prevented, treated or cured by promoting the expression of a cell death-suppressing gene product $Bcl-x_L$ in digodendrocytes.

Further, the present invention relates to the use of ginsenoside $Rb_1$, metabolites thereof or salts thereof for production of the medicinal or pharmaceutical composition(s) for promoting the expression of a cell death-suppressing gene product $Bcl-x_L$ in oligodendrocytes.

The present invention relates to a protective agent(s) for oligodendrocytes comprising ginsenoside $Rb_1$, metabolites thereof or salts thereof.

The medicinal or pharmaceutical composition(s) for promoting expression of the oligodendrocyte death-suppressing gene product $Bcl-x_L$ of the present invention can be preferably used as the preparations for intravenous administration such as the preparation for single intravenous infusion or the preparation for repetitive or continuous intravenous infusion.

The present invention relates to a medicinal or pharmaceutical composition(s) for suppressing apoptosis of myocardial cells or apoptosis-like cardiac cell death comprising ginsenoside $Rb_1$, metabolites thereof or salts thereof and/or a pharmaceutically acceptable carrier(s). Preferably, the present invention relates to the medicinal or pharmaceutical composition(s) for suppressing apoptosis of myocardial cells or apoptosis-like cardiac cell death wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably $1-10^4$ fg/ml (approximately 0.9-9000 fM).

Further, the present invention relates to a method for preventing, treating or curing diseases which can be prevented, treated or cured by suppressing apoptosis of myocardial cells or apoptosis-like cardiac cell death comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably $1-10^4$ fg/ml (approximately 0.9-9000 fM) in lesioned tissues, to patients with diseases which can be prevented, treated or cured by suppressing apoptosis of myocardial cells or apoptosis-like cardiac cell death.

Further, the present invention relates to the use of ginsenoside $Rb_1$, metabolites thereof or salts thereof for production of the medicinal or pharmaceutical composition(s) for suppressing apoptosis of myocardial cells or apoptosis-like cardiac cell death.

The present invention relates to a protective agent(s) for oligodendrocytes comprising ginsenoside $Rb_1$, metabolites thereof or salts thereof.

The medicinal or pharmaceutical composition(s) for suppressing apoptosis of myocardial cells or apoptosis-like cell death of the present invention can be preferably used as the preparations for intravenous administration such as the preparation for single intravenous infusion or the preparation for repetitive or continuous intravenous infusion.

The present invention relates to a medicinal or pharmaceutical composition(s) for promoting the expression of a cell death-suppressing gene product $Bcl-x_L$ in myocardial cells comprising ginsenoside $Rb_1$, metabolites thereof or salts thereof or a pharmaceutically acceptable carrier(s). Preferably, the present invention relates to the medicinal or pharmaceutical composition(s) for promoting the expression of a cell death-suppressing gene product $Bcl-x_L$ in myocardial cells wherein the extracellular fluid concentrations of ginsenoside $Rb_1$, metabolites thereof or salts thereof in lesioned tissues are adjusted to 10 ng/ml or less or approximately 9 nM or less, preferably 1 ng/ml or less or approximately 0.9 nM or less, more preferably 0.01-100 fg/ml (approximately 0.009-90 fM), further more preferably 1-10⁴ fg/ml (approximately 0.9-9000 fM).

Further, the present invention relates to a method for preventing, treating or curing diseases which can be prevented, treated or cured by promoting the expression of a cell death-suppressing gene product Bcl-$x_L$ in myocardial cells comprising administering effective amounts of ginsenoside $Rb_1$, metabolites thereof or salts thereof, preferably amounts exhibiting the extracellular fluid concentrations of 10 ng/ml or less or approximately 9 nM or less, more preferably 1 ng/ml or less or approximately 0.9 nM or less, further more preferably 0.01-100 fg/ml (approximately 0.009-90 fM), rather more preferably 1-10⁴ fg/ml (approximately 0.9-9000 fM) in lesioned tissues, to patients with diseases which can be prevented, treated or cured by promoting the expression of a cell death-suppressing gene product Bcl-$x_L$ in myocardial cells.

Further, the present invention relates to the use of ginsenoside $Rb_1$, metabolites thereof or salts thereof for production of the medicinal or pharmaceutical composition(s) for promoting the expression of a cell death-suppressing gene product Bcl-$x_L$ in myocardial cells.

The present invention relates to a protective agent(s) for myocardial cells comprising ginsenoside $Rb_1$, metabolites thereof or salts thereof.

The medicinal or pharmaceutical composition(s) for promoting expression of the myocardial cell death-suppressing gene product Bcl-$x_L$ of the present invention can be preferably used as the preparations for intravenous administration such as the preparation for single intravenous infusion or the preparation for repetitive or continuous intravenous infusion.

The present invention relates to dihydroginsenoside $Rb_1$ represented by the following formula (II):

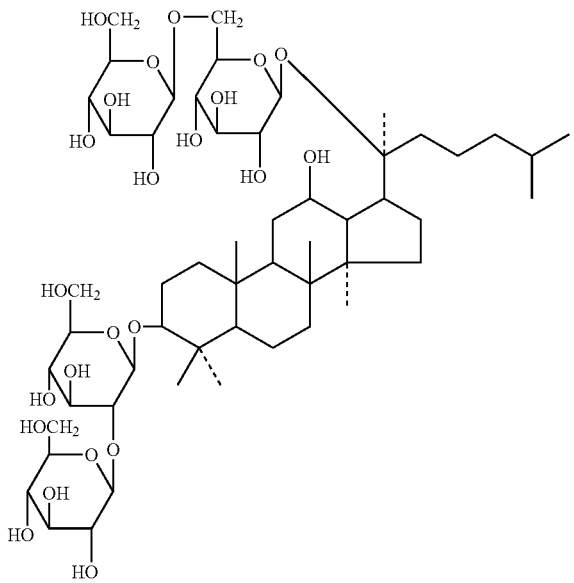

(II)

or metabolites thereof or salts thereof.

The present invention relates to a medicinal or pharmaceutical composition(s) for suppressing apoptosis of cells or apoptosis-like cell death comprising dihydroginsenoside $Rb_1$ represented by the above formula (II), metabolites thereof or salts thereof and/or a pharmaceutically acceptable carrier(s).

The present invention relates to a method for preventing, treating or curing diseases which can be prevented, treated or cured by suppressing apoptosis of cells or apoptosis-like cell death comprising administering effective amounts of dihydroginsenoside $Rb_1$ represented by the above formula (II), metabolites thereof or salts thereof to patients with diseases which can be prevented, treated or cured by suppressing apoptosis of cells or apoptosis-like cell death.

Further, the present invention relates to the use of dihydroginsenoside $Rb_1$, metabolites thereof or salts thereof for production of the medicinal or pharmaceutical composition(s) for suppressing apoptosis of cells or apoptosis-like cell death.

Examples of the concerned cells are brain cells or nerve cells in the ischemic penumbra.

The medicinal or pharmaceutical composition(s) for suppressing apoptosis of cells or apoptosis-like cell death of the present invention can be preferably used as the preparations for intravenous administration such as the preparation for single intravenous infusion or the preparation for repetitive or continuous intravenous infusion.

The present invention relates to a medicinal or pharmaceutical composition(s) for prevention, treatment or therapy of brain and nervous diseases comprising dihydroginsenoside $Rb_1$ represented by the above formula (II), metabolites thereof or salts thereof and/or a pharmaceutically acceptable carrier(s).

The present invention relates to a method for preventing, treating or curing brain and nervous diseases comprising administering effective amounts of dihydroginsenoside $Rb_1$ represented by the above formula (II), metabolites thereof or salts thereof to patients with brain and nervous diseases.

Further, the present invention relates to the use of dihydroginsenoside $Rb_1$, metabolites thereof or salts thereof for production of the medicinal or pharmaceutical composition(s) for preventing, treating or curing brain and nervous diseases.

Examples of brain and nervous diseases of the present invention hereinbefore are injuries to the nervous tissues or spinal cord tissue such as spinal cord injury; injuries to the nervous tissues or spinal cord tissue such as head injuries or neurotrauma; diseases caused by apoptosis or apoptosis-like cell death of oligodendrocytes; cerebral edema, edema of the brain and nervous tissues or edema of the spinal cord tissue caused by cerebral apoplexy, cerebral infarction, cerebral hemorrhage, subarachnoidal hemorrhage, head injuries, intracranial hemorrhage, spinal cord injury or neurotrauma; cerebrovascular dementia; cerebral infarction, cerebral apoplexy, transient cerebral ischemic attack; paralysis or paresis of the upper extremities or lower extremities, urination disorder, dysautonomia, hypogonadism, dyschezia or neurogenic bladder caused by injuries or trauma to the nervous tissues or spinal cord tissue.

The medicinal or pharmaceutical composition(s) for treatment, prevention or therapy of brain and nervous diseases of the present invention can be preferably used as the preparations for intravenous administration such as the preparation for single intravenous infusion or the preparation for repetitive or continuous intravenous infusion.

The present invention relates to a method for exploring novel active ingredients or compounds for prevention, therapy or treatment of diseases of the nervous tissues or spinal cord tissue comprising using ginseng, its extracts, components of ginseng, metabolites thereof or salts thereof as leading compounds.

Examples of medicinal ginseng, its extracts, components of ginseng, metabolites thereof or salts thereof of the present invention are red ginseng powder, its extracts, crude saponin fractions of ginseng, non-saponin fractions, purified saponins, saponin fraction constituents or salts thereof, and a component contained in the saponin fractions of ginseng is preferably ginsenoside $Rb_1$. Examples of diseases of the nervous tissues or spinal cord tissue hereinbefore are diseases caused by nervous tissue injuries or spinal cord injury or cerebral infarction.

The present invention also relates to agents for prevention, therapy or treatment of diseases of the nervous tissues or spinal cord tissue, as obtained by any methods described hereinabove.

Further, the present invention relates to the use of any of constituents of saponin fractions of ginseng or metabolites thereof as leading compounds for exploring novel active ingredients or compounds for prevention, therapy or treatment of diseases of the nervous tissues or spinal cord tissue, novel agents for the therapy of neurotrauma, novel agents for the therapy of spinal cord injury, novel agents for the therapy of head injury, novel agents for protecting brain cells or novel agents for protecting nerve cells, or novel medicinal or pharmaceutical compositions for preventing, curing or treating diseases caused by injuries to the nervous tissue or spinal cord tissue.

The present invention relates to a method for detecting novel compounds having protective action on brain cells or nerve cells (neurons) by using components contained in ginseng as leading compounds or use thereof.

Examples of "medicinal ginseng, its extracts, components of ginseng, metabolites thereof or salts thereof" of the present invention are ginseng itself hereinbelow explained; extracts of ginseng; extracts comprising the said extracts; preparations containing any of them; fractions comprising ginseng or extracts thereof such as crude saponin fractions, saponin fractions and purified soponins; ginseng components; saponin fraction constituents such as saponin fractions; metabolites thereof; and salts thereof. In the explanation hereinbelow, "(medicinal) ginseng, its extracts, components of ginseng, metabolites thereof or salts thereof" of the present invention or part thereof is sometimes expressed, for convenience, as "any one or any of constituents of the crude saponin fractions of (medicinal) ginseng, metabolites thereof or salt thereof" or "crude saponin fraction(s) of (medicinal) ginseng or salts thereof". The present invention can be expressed by using these terms as follows.

The present invention relates to a medicinal or pharmaceutical composition(s) for suppressing apoptosis or apoptosis-like cell death of oligodendrocytes comprising any or any one of constituents of the crude saponin fraction(s) of ginseng, metabolites thereof or salt thereof. The present invention also relates to the crude saponin fraction(s) of ginseng or any one of constituents thereof, metabolites thereof or salt thereof useful as an agent(s) for suppressing the secondary degeneration of the nervous tissues. These medicinal or pharmaceutical compositions of the present invention are preferably used as the preparations for intravenous administration at low doses. More particularly, the medicinal or pharmaceutical compositions are preferably used as the preparation for single intravenous administration or the preparation for repetitive or continuous intravenous administration.

The present invention also relates to the novel ginsenoside $Rb_1$ derivative, i.e. dihydroginsenoside $Rb_1$ useful as a cytoprotective agent, prepared by using ginsenoside $Rb_1$ as a leading compound, which is one of physiologically active substances or active components contained in ginseng or the crude saponin fraction(s) of ginseng. More particularly, the present invention relates to a medicinal or pharmaceutical composition(s) for prevention, treatment or therapy of cerebral infarction or cerebral apoplexy comprising dihydroginsenoside $Rb_1$, metabolites thereof or salts thereof, or a medicinal or pharmaceutical composition(s) for suppressing apoptosis of nerve cells (neurons) or apoptosis-like nerve cell death, or necrosis of nerve cells. Further, the present invention relates to a medicinal or pharmaceutical composition(s) useful as the preparations for intravenous administration comprising dihydroginsenoside $Rb_1$, metabolites thereof or salts thereof, i.e. the preparations at low concentrations or low dosages for continuous or repetitive administration or for single intravenous infusion.

The present invention provides for the first time that the components in medicinal ginseng are active as the compounds having the therapeutic effects on neurotrauma or spinal cord injury and the protective actions on brain cells or nerve cells. Based on the novel findings of the present invention, the present invention provides a method for exploring novel compounds having protective actions on brain cells or nerve cells by using the active components in ginseng as leading compounds. Further, the present invention provides the use of the active ginseng components as leading compounds for exploring novel compounds having the protective actions on brain cells or nerve cells.

Further, the present invention provides: a preparation(s) at low doses for intravenous administration for prevention, treatment or therapy of cerebral edema, brain and nervous tissue edema or spinal cord tissue edema comprising ginsenoside $Rb_1$, metabolites thereof or salts thereof; a preparation(s) at low doses for intravenous administration for prevention, treatment or therapy of bedsore (decubitus) accompanied by spinal cord injury comprising ginsenoside $Rb_1$, metabolites thereof or salts thereof; a preparation(s) for intravenous administration for promoting the expression of a cell death-suppressing gene Bcl-$x_L$ in the nervous tissues comprising ginsenoside $Rb_1$, metabolites thereof or salts thereof; a medicinal or pharmaceutical composition(s) for promoting expression of a cell death-suppressing gene Bcl-$x_L$ in oligodendrocytes comprising ginsenoside $Rb_1$, metabolites thereof or salts thereof; a protective agent(s) for oligodendrocytes comprising ginsenoside $Rb_1$, metabolites thereof or salts thereof; a medicinal or pharmaceutical composition(s) for promoting the expression of a cell death-suppressing gene Bcl-$x_L$ in myocardial cells comprising ginsenoside $Rb_1$, metabolites thereof or salts thereof; and a medicinal or pharmaceutical composition(s) for suppressing apoptosis or apoptosis-like cell death of myocardial cells comprising low concentrations of ginsenoside $Rb_1$, metabolites thereof or salts thereof.

The present invention further provides a medicinal or pharmaceutical composition(s) for prevention, therapy or treatment of diseases caused by injuries or trauma to the nervous tissues or spinal cord tissue comprising the crude saponin fraction(s) of ginseng, any or any one of constitutional components thereof, metabolites thereof or salts thereof. More particularly, the present invention provides a medicinal or pharmaceutical composition(s) for prevention, therapy or treatment of the secondary degeneration of the nervous tissues caused by injuries to the nervous tissues, a medicinal or pharmaceutical composition(s) for prevention, therapy or treatment of diseases caused by spinal cord injury, head injury or injuries (trauma) to the nervous tissues or spinal cord tissue, a medicinal or pharmaceutical composition(s) for prevention, therapy or treatment of diseases caused by nervous tissue or spinal cord tissue injuries accompanied by demyelination. The present invention also provides a medicinal or pharmaceutical composition(s) for suppressing apoptosis or apoptosis-like cell death of oligodendrocytes comprising the crude saponin fraction(s) of ginseng, any or any one of constitutional components thereof, metabolites thereof or salts thereof. The present invention further provides the crude saponin fraction(s) of medicinal ginseng, any or any one of constitutional components thereof, metabolites thereof or salts thereof useful as suppressive agents for the secondary degeneration of the nervous tissues.

The present invention provides an active ingredients for prevention, therapy or treatment of diseases or lesions hereinbefore, or a method for the use of the active ginseng components or metabolites thereof as leading compounds for exploring brain cell-protective agents or neuroprotective agents.

Further, the present invention provides a novel derivative of ginsenoside $Rb_1$, one of components or physiologically active substances of ginseng, i.e. dihydroginsenoside $Rb_1$ useful as a cytoprotective agent, which can be prepared by using ginsenoside $Rb_1$ as a leading compound. More particularly, the present invention provides a medicinal or pharmaceutical composition(s) for prevention, treatment or therapy of cerebral infarction or cerebral apoplexy comprising dihydroginsenoside $Rb_1$, metabolites thereof or salts thereof, or a medicinal or pharmaceutical composition(s) for suppressing apoptosis of neurons or apoptosis-like nerve cell death in the lesions of cerebral infarction and/or cerebral apoplexy. The present invention also provides a medicinal or pharmaceutical compositions that can be used as the preparations for intravenous administration comprising dihydroginsenoside $Rb_1$, metabolites thereof or salts thereof, namely the medicinal or pharmaceutical composition(s) in the form of the preparations at low concentrations or low dosages for repetitive or continuous intravenous administration or for single intravenous administration.

Examples of the medicinal ginseng, extracts thereof, components of ginseng, or metabolites thereof in the present invention are ginseng, dried product thereof, part thereof, powders or granules thereof, extracts thereof such as red ginseng extract, fractions thereof such as crude saponin fractions, purified saponin fractions or non-saponin fractions, components such as purified saponins or ginsenosides isolated therefrom, and active metabolites of these components. As for preferable examples of ginseng, extracts thereof, components of ginseng, or metabolites thereof, red ginseng powder can be mentioned, but this is not limitative.

Preferable red ginseng powder of the present invention is a known substance prepared by using six year roots of *Panax ginseng* C. A. Meyer in Korean Tobacco Ginseng Public Corp., and stability of its quality has been confirmed by us in the published paper (Wen, T.-C. et al., Acta Neuropathol., 91, 15-22, 1996). In Japan, that is named as Seikansho red ginseng powder connected with the distributor corporation.

In the explanation hereinbelow, the red ginseng powder or extract thereof will be used and exemplified as (medicinal) ginseng, extract thereof, components of ginseng, or metabolites thereof of the present invention.

The medicinal or pharmaceutical compositions of the present invention can be used as the single preparation containing ginseng, its extract(s), components of ginseng, or metabolites thereof as an active ingredient, however a combined preparation with drugs for reducing risk factors of cerebral infarction (e.g. vitamins, cerebral circulation and metabolism-improving agents, active oxygen or free radical-scavenging agents, drugs for therapy or treatment of hyperlipidemia, etc.) can also be used.

The medicinal or pharmaceutical compositions of the present invention can contain the pharmaceutically acceptable carrier(s). Examples of these carriers which can be used are substances conventionally used in drug preparations such as diluents, lubricants, binders, and disintegrators. Using these carriers, formulations of dosage form such as tablets, powders, powder, sustained release preparations, granules, capsules and suppositories, can be prepared, and if required, coating preparations can be prepared. Parenterally administered preparations can also be prepared.

Oral administration of the red ginseng or extract(s) thereof of the present invention can significantly reduce cerebral infarct lesion as a result of suppressing apoptosis-like nerve cell death in the ischemic penumbra, and has the unique action mechanism upregulating the expression of a cell death-suppressing gene product $Bcl-x_L$ protein to protect nerve cells or neurons in the brain. It can also be applied as the neuroprotective agent for not only acute and chronic phase cerebral infarction but also acute and chronic phase cerebral hemorrhage and subarachnoidal hemorrhage or transient cerebral ischemic attack.

Namely, the red ginseng powder of the present invention or extract(s) thereof is a drug which can be administered orally at home to patients who are suspected to suffer from cerebral apoplexy as far as their consciousness and swallowing function are maintained. Further, if the aged people, who are so called the cerebral apoplexy candidates with underlying diseases such as diabetes mellitus, hypertension, cerebral arteriosclerosis, atrial fibrillation and cerebral aneurysm or anamnesis of cerebral apoplexy, ingested red ginseng powder in advance, and even if they are suffer from cerebral apoplectic attack at the worst, their cerebral apoplectic lesions and higher nervous functional disorders will be significantly improved as compared with patients who did not ingest red ginseng powder.

The pathological state of cerebral ischemia is known to occur accompanied by cardiac insufficiency, severe anemia, shock, respiratory failure, cardiac arrest, ventricular fibrillation, administration of antihypertensive drugs and hypotension etc. In order to protect the brain from such diseases and to improve prognosis of patients, the medicinal or pharmaceutical composition(s) comprising red ginseng powder or extract(s) thereof is very effective. Further, red ginseng powder or extract(s) thereof is known historically to exhibit almost no ill effects. In the present experiments, no ill effects were detected as a result of our careful observation on animals to which red ginseng powder was orally administered.

Judging from the facts that oral administration of ginseng, its extract(s), components of ginseng, or metabolites thereof, preferably red ginseng powder of the present invention promotes the expression of a cell death-suppressing gene product $Bcl-x_L$ protein in the nervous tissues and that oral administration of red ginseng powder suppresses apoptosis-like cell death in the ischemic penumbra, the medicinal or pharmaceutical composition(s) of the present invention comprising ginseng, its extracts, components of ginseng, or metabolites thereof, preferably red ginseng powder or extract(s) thereof is thought to show efficacy on primary and secondary neurodegenerative diseases accompanied with apoptosis-like nerve cell death (Alzheimer's disease, Pick' disease, spinocerebellar degeneration, Parkinson's disease, demyelinating diseases, chorea, amyotrophic lateral sclerosis, glaucoma, senile macular degeneration, diabetic retinopathy, central retinal arterial occlusion, central retinal venous occlusion, retinal detachment, pigmentary degeneration of the retina, AIDS encephalopathy, hepatic encephalopathy, encephalitis, cerebral palsy, head injuries, spinal cord injuries, carbon monoxide poisoning, asphyxia of the newborn, peripheral neuropathy, spastic paraplegia, progressive supranuclear palsy, circulatory disorders of the spinal cord, mitochondrial encephalomyopathy, meningitis, etc.).

If a dose of drug administered in the adult weighing 60 kg, is set as 1, the dose of the same drug administered in the newborn weighing 3 kg, is generally about ⅓ thereof. Namely, the dose of drug per body weight 1 kg in the newborn is about 3 times larger than that in the adult. Estimating from this fact, in rat (body weight 250-300 g) or in gerbil (body weight 70-80 g), which is lighter in body weight than the newborn, the dose amount of drug per body weight 1 kg will be increased at least about 4 times as compared with the human.

Generally, blood concentration of drug is thought to depend on the glomerular filtration rate (GFR). Since GFR is known to correlate with the area of body surface, Crawford's equation, i.e. dose amount for adult X area of body surface ($m^2$)/1.73, can be used as for the calculation of dose amount of drug determined by the area of body surface. Since the area of body surface of human, body weight 60 kg, stature 170 cm, is about 1.7 $m^2$ and the area of body surface of newborn, body weight 2 kg, stature 45 cm, is about 0.16 $m^2$, according to this equation, if the dose of drug in the human, body weight 60 kg, stature 170 cm, is set as 1, the dose of drug in the newborn, body weight 2 kg, stature 45 cm, will be about ⅒. Namely, since the amount of drug administered per kg of body weight is 1/60 in the adult, body weight 60 kg, stature 170 cm, and about 1/20 in the newborn, body weight 2 kg, stature 45 cm (i.e. 3-fold of the adult), even though the dose of drug is calculated from the area of body surface, the dose of drug per kg of body weight is increased according to the decrease in body weight as described hereinbefore. Consequently, in SH-SP rats and gerbils, which are lighter in body weight than the newborn of body weight 2 kg, the amount of drug administered per kg of body weight will be at least about 4-fold larger as compared with the amount of administration of drug per kg of human adult (body weight 60 kg).

Based on the present experimental results that oral administration of red ginseng powder to SH-SP rats (body weight 250-300 g) with permanent occlusion of the middle cerebral artery (MCA), at doses of 0.75-1.2 g/kg/day, for 5 weeks before and after MCA permanent occlusion, regresses cerebral infarct lesions and improves place navigation disability (cerebrovascular dementia), the amount of administration in human patients with cerebral apoplexy of body weight 60 kg or vertebrates (pets and livestock) is calculated totally as 11.25 g-18 g in a day, if the amount of administration is calculated as a quarter per kg of body weight. Consequently, the amount of oral administration of the medicinal or pharmaceutical composition (red ginseng powder) of the present invention in human patients with cerebral apoplexy is, although depending on individual variations or disease states, 2.0 g-90 g in a day, preferably 5.625 g-36 g, more preferably 11.25 g-18 g. In case where red ginseng powder is used for prevention, treatment or therapy of the previously described primary or secondary neurodegenerative diseases as the agent for enhancing Bcl-$x_L$ protein expression in the nervous tissues, preferably the similar dosage is orally administered to patients. In cases of oral administration of red ginseng powder extracts (red ginseng extracts, crude saponin fractions, non-saponin fractions and various purified saponins), the extract from the same amount of red ginseng powder hereinabove is preferably administered. Most preferable administration of ginseng (red ginseng powder) or extract(s) thereof may be 10 g-30 g/day by dividing 3-4 times a day in 60 kg of mammalian.

As explained hereinabove, for treatment, prevention or therapy of brain and nervous diseases, relatively highly doses of red ginseng powder should be administered orally, however the present inventors have found that in case of orally administering red ginseng powder as the agent for enhancing the expression of Bcl-$x_L$ in the peripheral organs, relatively low dosages are sufficient. Namely, based on the present experimental results that oral administration of red ginseng powder in a dose of 200 mg/kg/day in gerbils enhances Bcl-$x_L$ protein expression in the liver and spleen, the amount necessary for promoting Bcl-$x_L$ protein expression in the peripheral organs of human, body weight 60 kg, if calculated as ¼ per body weight, can be 50 mg/kg/day. Consequently, in case where the medicinal or pharmaceutical composition of the present invention (red ginseng powder) is used as an agent for enhancing Bcl-$x_L$ protein expression in the peripheral organs of human, the amount of oral administration in a day is, depending on individual difference and disease states of patients, 0.6 g-15 g, preferably 1.5 g-6 g, more preferably 2 g-4 g. When red ginseng extract(s) or crude saponin fractions extracted from the same amount of red ginseng powder is administered orally, similarly the expression of Bcl-$x_L$ protein in the peripheral organs can be increased.

The cell death-inhibitory gene product Bcl-$x_L$ is the protein that can be said as the last fortress for cell survival, and is distributed not only in the brain and nervous tissues but also in all peripheral organs and tissues, for example the liver, spleen, tissues of the immune system, tissues of the circulatory system and skin, and supports the survival of cells. Consequently, results of the present experiments showing increases in the expression of Bcl-$x_L$ protein in the peripheral organs such as the liver and spleen by low doses of orally administered red ginseng powder, indicate that low doses of red ginseng powder are effective for treatment, prevention and/or therapy of diseases of the peripheral organs and tissues accompanied by cell death, and various symptoms accompanied by aging. Among the diseases of the peripheral organs and tissues accompanied by cell death, the following diseases are included: ischemia—reperfusion injuries of cardiac muscle, liver and kidneys, cardiomyopathy, cardiac failure, myocardial infarction, peripheral circulatory failure, bedsore, wound, burn, cutaneous ulcer, oral aphtha, stomatitis, pollinosis, vernal conjunctivitis, atopic dermatitis, AIDS, autoimmune diseases, immunodeficiency diseases, graft rejection, muscular dystrophy, corneal injury, pulmonary infarction, bone fracture, myositis, peritendonitis, polio, necrotic faciitis, ischemic contracture, spina bifida, radiation injury, disturbance by ultraviolet rays, infectious diseases, collagen diseases, aortitis syndrome, acute arterial embolism, myotenositis, compartmental syndrome, meningocele, constriction ring syndrome, pseudoarthrosis, thromboangiitis obliterans, arteriosclerosis obliterans, Raynaud's disease, Raynaud's syndrome, thrombophlebitis, epiphysiolysis, osteochondrosis, food poisoning, enterohemorrhagic *E. coli* infectious disease, pancreatitis, hepatitis, nephritis, diabetic nephropathy, diabetic cardiomyopathy and glossalgia. In the broad sense, wound includes bedsore, burns and skin ulcer. Other organic diseases and/or pathological conditions accompanied by cell death are described in the book (Today's guide for therapy: Ed. Hinohara, Shigeaki and Abe, Masakazu, Igaku-Shoin Publ., 1995). Red ginseng powder or components thereof are thought to be effective for prevention, treatment or therapy of all diseases and pathological conditions above described.

Red ginseng powder, its extract(s), crude saponin fractions or constitutional components thereof can be used, through their cytoprotective action, for farming of fishes and crustaceans, cultivation and rearing of farm products, cosmetic composition, bath gel, health foods, health drugs, eyewash, facial wash, cultivation of tobacco and hydroponics. Of course, they can protect cells from endocrine disruptors, trauma, toxins, microorganisms, biohazards and environmental pollution.

The medicinal or pharmaceutical composition of the present invention are less toxic and the upper limit of dosage can be set considerably high, and is 180 g per day or less, preferably 100 g or less.

The medicinal or pharmaceutical composition of the present invention comprising ginsenoside $Rb_1$ is preferably comprised of ginsenoside $Rb_1$, metabolites thereof or salts thereof at low concentrations. Further, the present invention is preferably the preparations for parenteral administration comprising ginsenoside $Rb_1$, metabolites thereof or salts thereof at low concentrations.

These medicinal or pharmaceutical compositions of the present invention are preferably used as the preparations for intravenous administration. However if the extracellular fluid concentrations of the medicinal or pharmaceutical compositions in lesion can be kept low, the preparations of any optional routes of administration can be selected. These include, for example, agents for local external use in lesion, injections for local external use, preparations for oral administration, nasal drops, ophthalmic agents, ear drops, suppositories, subcutaneous injections, intracutaneous injections, intramuscular injections, inhalations, sublingual tablets and transdermal drugs.

In addition, the present invention in relation to ginsenoside $Rb_1$ relates to agents for long term treatment, prevention or therapy of brain and nervous tissue diseases accompanied by edema, agents for treatment, prevention or therapy of decubitus, agents for protecting oligodendrocytes, agents for enhancement of $Bcl-x_L$ expression or agents for protection of myocardial cells comprising the above described preparations for intravenous administration or preparations for local external use in lesion.

Further, the present invention provides the use of ginsenoside $Rb_1$ or metabolites thereof as a leading compound(s) for exploring novel other effective components or compounds for prevention, therapy or treatment of diseases caused by nervous tissue or spinal cord tissue injuries or for prevention, therapy or treatment of cerebral infarction and cerebral apoplexy. It is also possible to select any other administration routes after preparing prodrugs by modifying part of the chemical structure of ginsenoside $Rb_1$. Further, a target molecule(s) of ginsenoside $Rb_1$ or metabolites thereof is identified and novel compounds for modifying function of the target molecule(s) are synthesized to direct development of drugs for the therapy or treatment of cerebral infarction, cerebral apoplexy, spinal cord injury, neurotrauma and trauma.

Consequently, the present invention provides ginsenoside $Rb_1$ or metabolites thereof as a leading compound(s) for exploring novel active components or compounds for prevention, therapy or treatment of these diseases.

Ginsenoside $Rb_1$ of the present invention is represented by the chemical structure (I) hereinbefore, and can be isolated and purified according to the method of Shibata et al. (Shibata, S. et al., Economic and Medicinal Plant Research, World Scientific, Philadelphia, pp. 217-284, 1985). The compound purified by such methods has its purity 98% or more, which was confirmed by thin layered chromatography and NMR spectrum (Kawashima, Y. and Samukawa, K., J. Med. Pharmacol. Soc. Wakan-Yaku, 3, 235-236, 1986).

Ginsenoside $Rb_1$ of the present invention can be used in its free form and is also used as suitable salts thereof. The solvate such as hydrate can also be used.

Concentrations of ginsenoside $Rb_1$ of the present invention are preferably low, more concretely, extracellular fluid concentration is 1 ng/ml or less, preferably 10 pg/ml or less, more preferably 100 fg/ml or less. In case of use in the preparation(s) for intravenous administration of ginsenoside $Rb_1$ of the present invention, the preparation(s) is preferably adjusted so that the extracellular fluid concentrations in lesions of patients are kept at the concentrations as described hereinabove. Sufficient effects of the medicinal or pharmaceutical composition(s) and preparations of the present invention can be obtained even when the extracellular fluid concentrations in lesioned tissues are in the range of approximately 0.01-100 fg/ml or 1-10000 fg/ml.

It has already been found that the intravenously administered small amount of ginsenoside $Rb_1$ is transferred quickly into the brain and nervous systems, unlike peripherally (intraperitoneally) administered ginsenoside $Rb_1$ (Japanese Patent Application No. Hei 10-365560, PCT/JP99/02550, Brain cell or nerve cell-protective agents comprising ginsenoside $Rb_1$). The preparation(s) for intravenous administration of the present invention is sufficient if it can be directly administered intravascularly, preferably intravenously, and it can be used as the preparation for single intravenous administration or as the preparation for repetitive or continuous intravenous administration after dissolving the medicinal or pharmaceutical compositions of the present invention in physiological saline, distilled water, phosphate buffer, glucose solution, liposome or lipid emulsion etc. Further, the formulations which can be used by adding to the preparations for intravenous administration such as compositions for drip-infusion may be preferable. Further, prodrugs are prepared by modifying a part(s) of the chemical structure of ginsenoside $Rb_1$, as a result, optional routs of administration and optional methods of administration can also be selected. For example, the hydroxyl group(s) or hydroxyl base(s) of ginsenoside $Rb_1$ is esterified to prepare the prodrug(s), passing through the blood-brain barrier, hydrolyzing with endogenous esterase(s) to increase intracerebral transfer of ginsenoside $Rb_1$.

As described in Japanese Patent Application No. Hei 10-365560, PCT/JP99/02550 (Brain cell or nerve cell-protective agents comprising ginsenoside $Rb_1$), repetitive or continuous intravenous administration of low doses of ginsenoside $Rb_1$ reduces cerebral infarct lesion to about ¼ size of the non-administered group; has a unique mechanism of action indicating the upregulation of cell death-suppressing gene product $Bcl-x_L$ expression; protects nerve cells in the brain; and can be used as neuroprotective agent for not only acute phase or chronic phase of cerebral infarction (cerebral thrombosis and cerebral embolism) but also acute or chronic phase of cerebral hemorrhage and subarachnoidal hemorrhage, or transient cerebral ischemic attack. Namely, ginsenoside $Rb_1$ at low dosages and/or at low concentrations, which does not induce hemorrhagic tendency, is the medicinal or pharmaceutical composition, which is possible to be infused intravenously, to patients, who are suspected to have cerebral apoplexy, in ambulances. Further, administration of ginsenoside $Rb_1$ to patients with cerebral infarction who undergo thrombolytic therapy improves prognosis of the patients.

In addition, as described in Japanese Patent Application No. Hei 11-340850, PCT/JP99/06804 (Cerebrovascular regeneration/reconstruction promoters and nerve tissue secondary degeneration inhibitors comprising ginsenoside $Rb_1$), repetitive or continuous intravenous infusion of ginsenoside $Rb_1$ for maximum 28 days not only reduces a volume of cerebral infarct (cerebral embolism) lesion to about ¼, but also makes to recover the destroyed and decreased vascular networks to the normal condition in the ischemic penumbra. Consequently, the intravenous administration of ginsenoside $Rb_1$ promotes regeneration and reconstruction of the destroyed or decreased cerebrovascular networks after cerebral apoplexy, and even if the intravenous administration of ginsenoside $Rb_1$ is terminated thereafter, once rescued cerebral tissues can function normally after passing time. Namely, in addition to the direct protective effects of ginsenoside $Rb_1$ on nerve cells (neurons), such as enhancement of $Bcl-x_L$ protein expression and suppression of apoptosis-like nerve cell death, ginsenoside $Rb_1$ of the present invention is expected to protect damaged brain through the indirect and long-term protective mechanism mediated by the regeneration and reconstruction of cerebrovascular networks. As described above, ginsenoside $Rb_1$ is thought to be the first substance in the history of human being as the compound which can reduce to ¼ in size of cerebral infarct lesion in the acute phase as well as in one month after the onset by intravenous administration after onset of cerebral infarction, i.e. permanent cerebrovascular occlusion. Consequently, in future, ginsenoside $Rb_1$ or metabolites thereof can be used as a leading compound(s) and thereby various agents for protection of brain cells or nerve cells can be explored, created and produced.

In the general clinical field, there are many cases appearing repeatedly, in which the higher nervous functions are continuously deteriorated even though no new attack occurred after cerebral apoplexy. Especially there are cases with continuously deteriorating sequelae after cerebral apoplexy. A reason for this may be that the regeneration or reconstruction of the damaged or reduced cerebrovascular networks caused by cerebral apoplectic attack is sometimes insufficient. Low doses of intravenous administration, sublingual administration, rectal administration or nasal administration of ginsenoside $Rb_1$ are expected to exhibit significant effects in ameliorating such sequelae after cerebral apoplexy.

As described in the invention of Japanese Patent Application No. Hei 11-340850, PCT/JP99/06804 (Cerebrovascular regeneration/reconstruction promoters and nerve tissue secondary degeneration inhibitors comprising ginsenoside $Rb_1$), since the intravenous administration of ginsenoside $Rb_1$ of the present invention exhibits a novel effect and efficacy in promoting vascular regeneration or reconstruction, it may also be effective for treatment or therapy of other diseases with symptoms of blood flow disorders (e.g. aortitis syndrome, acute peripheral arterial occlusion, thromboangiitis obliterans, arteriosclerosis obliterans, Raynaud's disease, hemorrhoids or Raynaud's syndrome). Of course, in diseases with major symptoms of these blood flow disorders, to inhibit cell death in tissues suffering from blood flow disorders is also unforgotten efficacy of ginsenoside $Rb_1$. Consequently, ginsenoside $Rb_1$ is expected to reduce tissue injuries or damage resulting from blood flow disorders of the peripheral tissues through at least two action mechanisms.

As described in the invention of Japanese Patent Application No. Hei 11-340850, PCT/JP99/06804 (Cerebrovascular regeneration/reconstruction promoters and nerve tissue secondary degeneration inhibitors comprising ginsenoside $Rb_1$), since the pharmaceutical composition comprising ginsenoside $Rb_1$ inhibits the occurrence of secondary lesions in the brain regions having synaptic contacts with the primary brain lesion, it also exhibits favorable efficacy and/or effects on the secondary lesions of many neurodegenerative diseases and demyelinating diseases (e.g. Alzheimer's disease, Pick's disease, spinocerebellar degeneration, Parkinson's disease, chorea, polyglutamine diseases, amyotrophic lateral sclerosis, multiple sclerosis, etc.), and is expected to improve QOL (Quality of Life) for patients as a result of reducing progression of higher nervous function disorders caused by these diseases. As described in Japanese Patent Application No. Hei 10-365560 and PCT/JP99/02550 ("Brain cell or nerve cell-protective agents comprising ginsenoside $Rb_1$"), ginsenoside $Rb_1$ is thought to exhibit efficacy against the primary lesions of these neurodegenerative diseases through its inhibitory effect against apoptosis-like nerve cell death and its enhancing effect on $Bcl-x_L$ expression.

Further, as described in the invention of Japanese Patent Application No. Hei 11-340850, PCT/JP99/06804 (Cerebrovascular regeneration/reconstruction promoters and nerve tissue secondary degeneration inhibitors comprising ginsenoside $Rb_1$), the intravenous administration of ginsenoside $Rb_1$ significantly ameliorates paralysis or paresis of animals with spinal cord injuries. It is well known that the nervous tissues are the most vulnerable to traumatic injuries as compared with other peripheral tissues. The fact that the pharmaceutical composition comprising ginsenoside $Rb_1$ exhibits significant effects for treatment, prevention and/or therapy of spinal cord injuries indicates that ginsenoside $Rb_1$ is effective for treatment or therapy of traumatic injuries to the peripheral tissues as well as the central nervous tissues. As shown in the following example, in rats with spinal cord injuries in which compression was loaded to the lower thoracic spinal cord, paralysis of both lower limbs (paraplegia) was ameliorated and the rats could stand up as a result of administering ginsenoside $Rb_1$ after their injuries. The rats with spinal cord injuries, to which only physiological saline (i.e. vehicle) was administered, remained paralyzed in both lower limbs and could not stand up. In addition, intravenous administration of Solu-Medol (methylprednisolone), which is used for treatment or therapy of spinal cord injuries at present, could not ameliorate paralysis of both lower limbs (paraplegia) in rats with spinal cord injuries. Judging from these facts, the curative or therapeutic effects of ginsenoside $Rb_1$ on spinal cord injuries are thought to be the most powerful known. Consequently, it is expected that, in the future, ginsenoside $Rb_1$ or its metabolites will be used as a leading compound(s) in development of various remedies for spinal cord injuries, neurotrauma and trauma.

Low doses of ginsenoside $Rb_1$ of the present invention exhibit novel effects and efficacy to improve brain edema, edema of the nervous tissues or edema of the spinal cord tissue by repetitive or continuous intravenous administration. Consequently, in the occasion of cerebral hemorrhage, cerebral infarction, cerebral embolism, subarachnoidal hemorrhage, head injuries, intracranial hemorrhage, spinal cord injuries, at the time of convulsive attack, after convulsive attack, during neurosurgical operations, before and after neurosurgical operations, during surgical operations of vertebral columns, before and after surgical operations of vertebral columns, during surgical operations of the spinal cord, or before and after surgical operations of the spinal cord, if ginsenoside $Rb_1$ is administered intravenously, edema(ta) of brain and nervous tissues and spinal cord tissue accompanied by the above diseases, lesions, symptoms and syndromes, can be prevented, treated or cured.

Further, it was newly found that low doses of intravenous administration of ginsenoside $Rb_1$ of the present invention are useful for prevention, treatment or therapy of bedsore (decubitus). Consequently, ginsenoside $Rb_1$ exhibits excellent effects and efficacy on bedsore of the bedridden patients, especially bedsore of the bedridden patients with neurotrauma, head injury, cerebral apoplexy, spinal cord injury, peripheral nerve disorders, neuralgia, neurodegenerative diseases and demyelinating diseases.

In addition, ginsenoside $Rb_1$ of the present invention exhibits novel actions of suppressing apoptosis of oligodendrocytes or apoptosis-like cell death in the concentration range of $10^4$ fg/ml or less and increasing the expression of a cell death-suppressing gene product $Bcl-x_L$ in oligodendrocytes. Consequently, low concentrations and low dosages of ginsenoside $Rb_1$ will be effective for diseases accompanied by cell death of oligodendrocytes (for example, multiple sclerosis, Binswanger's disease, chronic hypopurfusion failure of brain, leuko-encephalitis and adrenoleukodystrophy etc.).

It was also found that intravenous administration of ginsenoside $Rb_1$ of the present invention increased expression of a cell death-suppressing gene product $Bcl-x_L$ in the brain and nervous tissues. Since the brain and nervous tissues include neurons, glial cells (astrocytes, microglia and oligodendrocytes), neuronal stem cells, vascular endothelial cells and vascular smooth muscle cells, the fact that intravenous administration of ginsenoside $Rb_1$ increases the expression of the cell death-suppressing gene product $Bcl-x_L$ in the brain and nervous tissues indicates that any one or plural cell species of the brain and nervous tissue constituent cells hereinbefore increase the expression of $Bcl-x_L$ by intravenous administration of ginsenoside $Rb_1$. Namely, ginsenoside $Rb_1$ is effective for diseases and symptoms accompanied by apoptosis of cells or apoptosis-like cell death hereinbefore (e.g. collagen diseases, arteriosclerosis, nephritis, hepatitis and vascular injury). Recently, the neuronal stem cell transplantation is paid attention as one of therapeutic methods for intractable nervous diseases, and ginsenoside $Rb_1$ can be used as the protective agent for neuronal stem cells.

In addition to the preferable effects and efficacy of ginsenoside $Rb_1$ on the central nervous tissue or brain and nerve cells hereinbefore, ginsenoside $Rb_1$ of the present invention suppresses apoptosis of myocardial cells or apoptosis-like myocardial cell death at the low concentration range of 1 ng/ml or less, more particularly at the low concentration range of 10 pg/ml or less, and increases the expression of a cell death-suppressing gene product $Bcl-x_L$ in the myocardial cells. Consequently, low doses and low concentrations of ginsenoside $Rb_1$ of the present invention exhibit effects and efficacy on all diseases accompanied by cell death of myocardial cells (e.g. myocardial infarction, Heart failure, cardiac insufficiency, cardiomyopathy, angina pectoris, arrhythmia, etc.).

Further, a specific feature of the medicinal preparations comprising ginsenoside $Rb_1$ of the present invention, which should not be overlooked, is the fact that they do not show any adverse effects. For example, as described in Japanese Patent Application No. Hei 10-365560 and PCT/JP99/02550 ("Brain cell or nerve cell-protective agents comprising ginsenoside $Rb_1$"), even though ginsenoside $Rb_1$ is added to control cultured nerve cells or neurons, which are not treated with sodium nitroprusside (SNP), a nitric oxide (NO) donor, it shows no effect on the metabolic activity. Moreover, ginsenoside $Rb_1$ at low extracellular concentrations (1-100 fg/ml) protects only nerve cells injured by treating with SNP. Consequently, ginsenoside $Rb_1$ does not affect normal neuronal functions but can give favorable effects only on the lesion tissues. This point can be emphasized as a more superior property of ginsenoside $Rb_1$ than glutamate receptor antagonists under developing as neuroprotective agents at present.

It has also been reported that intracerebroventricular administration of ginsenoside $Rb_1$ exerts no effects on brain temperature, cerebral blood flow or blood pressure (Lim J.-H. et al. Neurosci. Res., 28, 191-200, 1997; Zhang B. et al., J. Stroke Cerebrovasc. Dis., 7, 1-9, 1998). We have confirmed that intravenous infusion of ginsenoside $Rb_1$, at the dose of 60 µg/day, does not affect the cerebral blood flow. It is also known that ginsenoside $Rb_1$ at low concentrations or low doses does not promote bleeding tendency. No adverse effect was detected within a range of careful observation on animals, to which ginsenoside $Rb_1$ of the present invention was administered.

As described in Japanese Patent Application No. Hei 10-365560 and PCT/JP99/02550 ("Brain cell or nerve cell-protective agents comprising ginsenoside $Rb_1$") and in the present invention, ginsenoside $Rb_1$ of the present invention, when intravenously administered in a repetitive or continuous way to rats with permanent MCA occlusion (body weight about 300 g), in a dose of 6 µg or 60 µg/day, causes reduction of cerebral infarct area to about ¼ of the non-administered group and significantly ameliorates ischemia-induced place navigation disability (cerebrovascular dementia) as well as brain edema. Furthermore, ginsenoside $Rb_1$ of the present invention, in its equivalent doses, promotes cerebrovascular regeneration or reconstruction in the ischemic penumbra of the rats with permanent MCA occlusion, and significantly inhibits the secondary lesion of the thalamus (degeneration) in addition to reducing the cerebrocortical infarct lesion (the primary lesion). Repetitive or continuous intravenous administration of ginsenoside $Rb_1$, in the doses of 60 µg/day or 12 µg/day, to rats with spinal cord injuries (lower thoracic cord-injured rats) significantly ameliorates paraplegia and nerve paralysis (neuroparalysis).

Based on these experimental results, dose range to human patients with cerebral apoplexy (body weight 60 kg) is calculated as 1.2 mg-12 mg/day. Consequently, daily doses of the pharmaceutical composition of the present invention to human patients with cerebral apoplexy or spinal cord injuries is, though depending on individual difference and disease states of patients, 0.1 mg or more, preferably 1 mg or more, more preferably 10 mg or more. However, since required dose amount per body weight is, generally, decreased as body weight of animals increases, a dose of 1/10 or less of this amount is thought to exhibit sufficient effects in human. When ginsenoside $Rb_1$ is used for prevention, treatment or therapy of diseases other than brain and nervous diseases, it is preferable to select the equivalent dose of the above, or in doses of its 1/10 to 1/100,000. Since the medicinal or pharmaceutical composition of the present invention has less adverse effect, it can be administered considerably in large amount as an upper limit of dosage, and the upper limit of dosage is 1 g or less/day, preferably 0.1 g or less/day.

The method for administration of the medicinal or pharmaceutical composition of the present invention is preferably intravenous administration and the amount of administration hereinabove described can be administered consecutively or repetitively. Ginsenoside $Rb_1$, an active compound or ginseng ingredient of the present invention is a sort of saponin, and can be formulated by conventional methods. For example, the aqueous medicinal or pharmaceutical composition (ginsenoside $Rb_1$) of the present invention can be prepared as preparations for intravenous administration by dissolving lyophilized crystals of ginsenoside $Rb_1$ in physiological saline, distilled water, phosphate buffer or glucose solution etc. Lipid microsphere or liposome preparation can also be used. The concentrations of ginsenoside $Rb_1$ in the preparations for intravenous administration can optionally be adjusted unless so high, for example 0.01-10 mg/ml, preferably 0.1-1 mg/ml.

In the animal experiments of the present invention, ginsenoside $Rb_1$ was intravenously administered continuously or repetitively for 28 days after permanent occlusion of the cortical branch(es) of the left middle cerebral artery (MCA). Since in the actual case of cerebral apoplexy at an acute phase, if no therapy is performed after the onset, the cerebral infarct lesion is expanded as the results of rapid progresses of cerebrovascular destruction, degeneration and atrophy in the ischemic penumbra as well as the occurrence of brain edema within 2 weeks after onset, and the secondary lesion subsequent to the primary ischemic lesion becomes irreversible. If an intravenous administration of ginsenoside $Rb_1$ is performed during at least this period, it is profitable for reduction of cerebral infarct lesion, regeneration and reconstruction of the disrupted or destroyed vascular networks in the ischemic penumbra, suppression of the secondary lesion and for an improvement of brain edema.

The medicinal or pharmaceutical composition(s) of the present invention comprising crude saponin fraction of ginseng is preferably comprised of the crude saponin fraction(s) of ginseng, metabolites thereof or salts thereof at low concentrations. Further, the medicinal or pharmaceutical composition(s) of the present invention is preferably the preparations for parenteral administration such as those for intravenous administration and mucosal administration. More particularly, the medicinal or pharmaceutical composition(s) of the present invention is preferably the preparations for parenteral administration comprising the crude saponin fraction(s) of ginseng, components thereof, metabolites thereof or salts thereof at low concentrations.

Further, the present invention relates to the preparations for parenteral administration, preferably the preparations for intravenous administration, comprising the crude saponin fraction(s) of medicinal ginseng, components thereof, metabolites thereof or salts thereof at low concentrations.

These medicinal or pharmaceutical compositions of the present invention are preferably the preparations for intravenous administration, however if the extracellular fluid concentrations of the medicinal or pharmaceutical composition(s) in lesions are kept low, the preparations of any optional route of administration can be selected. These include, for example, agents for local external use in lesions, injections for local external use, preparations for oral administration, sustained release preparations, nasal drops, ophthalmic agents, ear drops, suppositories, subcutaneous injections, intracutaneous injections, intramuscular injections, inhalations, sublingual tablets and transdermal drugs.

In addition, the present invention relates to the agents for long term treatment, prevention or therapy of spinal cord injury, head injury or neurorauma comprising the above described preparations for intravenous administration or preparations for local external use in lesions.

Further, the present inventors have found for the first time that the crude saponin fraction(s) of medicinal ginseng, components thereof, metabolites thereof or salts thereof exhibited excellent effects for the therapy or treatment of spinal cord injury by intravenous administration at low dose. Consequently, the present invention provides the use of crude saponin fractions of medicinal ginseng, components thereof, metabolites thereof or salts thereof as a leading compound(s) for exploring novel other effective components or compounds for prevention, therapy or treatment of diseases caused by nervous tissue or spinal cord tissue injuries or cerebral apoplexy. It is also possible to select any other administration routes after preparing prodrugs by modifying a part(s) of the chemical structure(s) of components contained in the crude saponin fractions of ginseng. Further, target molecules of components of crude saponin fraction of ginseng or metabolites thereof are identified and novel compounds for modifying function of the target molecules are synthesized to direct development of drugs for treatment or therapy of spinal cord injury, neurotrauma and trauma.

Consequently, the present invention provides components of the crude saponin fractions of ginseng or metabolites thereof as leading compounds for exploring novel active components or compounds for prevention, therapy or treatment of these diseases.

The crude saponin fraction of the present invention is obtained by the conventional method that: red ginseng is extracted with methanol; the extract is suspended in water and washed with ether; and separated by water saturated 1-butanol. Yield: about 8%. The crude saponin fraction used in example hereinbelow is the same as is used in the previous report by one of the present inventors (Sakanaka) (Wen, T.-C. et al., Acta Neuropathol., 91, 15-22, 1996).

The crude saponin fraction(s) and components thereof of the present invention can be used in its free form and is also used as suitable salts thereof. The solvate such as hydrate can also be used.

The concentrations of the crude saponin fraction(s) of ginseng of the present invention are preferably low, and more concretely, the extracellular concentrations are 145 ng/ml or less, preferably 14.5 ng/ml or less, more preferably 145 pg/ml or less, further more preferably 1450 fg/ml or less. When the crude saponin fractions(s) of the present invention is used as a preparation for intravenous administration, the preparation should be adjusted so that the extracellular fluid concentrations of the crude saponin fraction(s) in lesioned tissues of patients are preferably kept at the levels hereinabove. The medicinal or pharmaceutical composition(s) and the preparation(s) of the present invention comprising the crude saponin fraction(s) can achieve the sufficient effect when the extracellular concentrations of the crude saponin fraction(s) in lesioned tissues are in the range of about 14.5-1450 fg/ml. Further, the components contained in the crude saponin fraction(s) of ginseng are preferably low in concentration, and more concretely, their extracellular concentrations are maintained to the levels of 10 ng/ml or less, preferably 1 ng/ml or less, more preferably 10 pg/ml or less, further preferably 100 fg/ml or less. In case where the constitutional components of the crude saponin fraction(s) are used an the preparations for intravenous administration, the extracellular concentrations in lesioned tissues of patients are preferably adjusted to the levels hereinabove described. The medicinal or pharmaceutical composition(s) or preparation(s) of the present invention comprising of any one of constitutional components of the crude saponin fraction(s) of the present invention can exhibit sufficient effects even in the extracellular concentration range of about 0.01-100 fg/ml in lesioned tissues.

The preparations for intravenous administration of the present invention are sufficient if they can be directly administered intravascularly, preferably intravenously, and they can be used as the preparation for single intravenous infusion or as the preparation for repetitive or continuous intravenous administration after dissolving the crude saponin fraction(s) or its constitutional components in physiological saline, distilled water, phosphate buffer, glucose solution, liposome and lipid emulsion etc. Further, formulations which can be used by adding to the preparations for intravenous administration such as a composition(s) for drip-infusion may be preferable. Prodrugs are prepared by modifying a part(s) of the chemical structure of ginsenoside $Rb_1$, as a result, optional routs of administration and optional methods of administration can also be selected.

Further, the intravenous administration of the crude saponin fraction(s) of ginseng of the present invention significantly ameliorates paralysis or paraplegia of animals with spinal cord injuries. It is well known that the nervous tissues are the most vulnerable to traumatic injury as compared with other peripheral tissues. The fact that the medicinal or pharmaceutical composition comprising the crude saponin fraction(s) of ginseng exhibits significant effects for treatment and therapy of spinal cord injuries indicates that the crude saponin fraction(s) of ginseng is effective for traumatic injuries, wound and burn of the peripheral tissues other than the central nervous tissue. As shown in the following example 10, in rats with spinal cord injuries in which compression was loaded to the lower thoracic cord, paralysis of both lower limbs (paraplegia) was ameliorated and the rats could stand up as a result of administering a crude saponin fraction of medicinal ginseng after their injuries. This effect is comparable to the effect of intravenously administered ginsenoside $Rb_1$. The rats with spinal cord injuries, to which only physiological saline (i.e. vehicle) was administered, remained paralyzed in both lower limbs and could not stand up. In addition, intravenous administration of Solu-Medol (methylprednisolone), which is used for treatment or therapy of spinal cord injuries at present, could not ameliorate paralysis of both lower limbs (paraplegia) in rats with spinal cord injuries. Judging from these facts, the therapeutic effects of the crude saponin fraction(s) of medicinal ginseng or components thereof as well as ginsenoside $Rb_1$ for spinal cord injuries are thought to be the most powerful known. Consequently, it is expected that, in the future, constitutional components of the crude saponin fraction(s) of medicinal ginseng or metabolites thereof will be used as leading compounds in development of various remedies for spinal cord injuries, neurotrauma and trauma.

As described above, in the present invention, low doses of the crude saponin fraction(s) of medicinal ginseng exhibit, like the repetitive or continuous intravenous administration of ginsenoside $Rb_1$ at low doses, excellent therapeutic effects on spinal cord injury by repetitive or continuous intravenous administration. Judging from this fact, the repetitive or continuous intravenous administration of the crude saponin fraction(s) of medicinal ginseng or components thereof is thought to exhibit effects and efficacy similar to those of ginsenoside $Rb_1$ at low concentrations and low doses on the other brain and nervous tissue diseases (e.g. cerebral apoplexy and cerebral infarction). Further, the effects, efficacy, usages and actions of ginsenoside $Rb_1$ found by us in Japanese Patent Application No. Hei 10-365560, PCT/JP99/02550 (Brain cell or nerve cell-protective agents comprising ginsenoside $Rb_1$) and Japanese Patent Application No. Hei 11-340850, PCT/JP99/06804 (Cerebrovascular regeneration/reconstruction promoters and nerve tissue secondary degeneration inhibitors comprising ginsenoside $Rb_1$) are likely to be owned by the crude saponin fraction(s) of medicinal ginseng or components thereof. Of course, the crude saponin fraction(s) of medicinal ginseng or any one of components thereof exhibits excellent protective actions on brain and nerve cells, upregulated expression of a cell death-suppressing gene $Bcl-x_L$, therapeutic effects on cerebral infarction and cerebral apoplexy, therapeutic effects on spinal cord injury and neurotrauma, protective actions on myocardial cells, therapeutic effects on bedsore (decubitus) and improving effects on brain edema.

Further, a specific feature of the crude saponin fraction(s) of medicinal ginseng of the present invention, which should not be overlooked, is the fact that it does not show any adverse effects as a drug(s).

As described in Japanese Patent Application No. Hei 10-365560 and PCT/JP99/02550 ("Brain cell or nerve cell-protective agents comprising ginsenoside $Rb_1$") and example 8 hereinafter, repetitive or continuous intravenous administration of ginsenoside $Rb_1$ to rats with permanent MCA occlusion (body weight about 300 g), in the doses of 6 μg and 60 μg/day, resulted in reduction of the cerebral infarct area to about ¼ of the non-administered group and significantly ameliorated ischemia-induced place navigation disability (cerebrovascular dementia). Furthermore, ginsenoside $Rb_1$ of the present invention, in its equivalent doses of intravenous administration, promotes cerebrovascular regeneration or reconstruction in the ischemic penumbra of the rats with permanent MCA occlusion as well as significant improvement of brain edema, and significantly inhibits the secondary lesion (degeneration) of the thalamus in addition to the reduction of cerebrocortical infarct lesion (the primary lesion). Repetitive or continuous intravenous administration of ginsenoside $Rb_1$, in a dose of 60 μg/day or 12 μg/day, to rats with spinal cord-injuries (lower thoracic spinal cord-injured rats) significantly ameliorates paraplegia and nerve paralysis (neuroparalysis). Further, in example 10 of the present invention, repetitive or continuous intravenous administration of a crude saponin fraction of medicinal ginseng (870 μg/day) exhibited almost equivalent therapeutic effects on spinal cord injury as compared with the repetitive or continuous intravenous administration of ginsenoside $Rb_1$ (60 μg/day).

Based on these experimental results, dose range of the crude saponin fraction(s) to human patients with cerebral apoplexy is calculated as 0.29 mg/kg/day-2.9 mg/kg/day. However, since required dose amount per body weight is, generally, decreased as the body weight of animals increases, dosage may be set to about ½ to 1/20 of this amount in human. Namely, daily doses of the crude saponin fraction(s) by intravenous administration for prevention, therapy or treatment of brain and nervous diseases are, although depending on individual difference and disease states of patients, set to preferably 14.5 μg/kg-1450 μg/kg. When the crude saponin fraction(s) is used for prevention, treatment or therapy of diseases other than brain and nervous diseases, it is preferable to select the equivalent doses of the above, or doses of its 1/10 to 1/100,000. When any of the constitutional components of the crude saponin fraction(s) is administered intravenously, the dose is approximately 1/10 of the above. Since the medicinal or pharmaceutical compositions of the present invention have less adverse effects, they can be administered considerably in large amount as an upper limit of dosage, and the upper limit of dosage is 1 g or less/day, preferably 0.1 g or less/day in human, body weight 60 kg.

The method for administration of the medicinal or pharmaceutical composition(s) comprising the crude saponin fraction(s) of the present invention is intravascular administration, preferably intravenous administration and the amount of administration hereinabove described can be administered consecutively or repetitively. The crude saponin fraction(s) of medicinal ginseng of the present invention can be formulated by conventional methods. For example, the aqueous medicinal composition(s) of the present invention can be prepared as preparations for intravenous administration by dissolving lyophilized crystals of the crude saponin fraction(s) in physiological saline, distilled water, phosphate buffer or glucose solution etc. Lipid microsphere or liposome preparation can also be used. Concentrations of the crude saponin fractions in the preparations for intravenous administration can optionally be adjusted unless so high, for example 0.1-100 mg/ml, preferably 1-10 mg/ml. Further, any or any one of the constitutional components of the crude saponin fraction(s) can be formulated according to the method hereinabove, and its concentrations in the preparations are preferably to set to about ¹⁄₁₀ of the crude saponin fraction(s).

The medicinal or pharmaceutical composition comprising dihydroginsenoside $Rb_1$ of the present invention is, as far as we know, a novel compound. The medicinal or pharmaceutical composition comprising dihydroginsenoside $Rb_1$ of the present invention is preferably comprised of dihydroginsenoside $Rb_1$, metabolites thereof or salts thereof at low concentrations. Further, the medicinal or pharmaceutical composition of the present invention is preferably in the form of parenteral administration such as intravenous administration and mucosal administration. More particularly, the medicinal or pharmaceutical composition of the present invention is preferably used as the preparations for parenteral administration comprising dihydroginsenoside $Rb_1$, metabolites thereof or salts thereof at low concentrations.

Further, the present invention relates to the preparations for parenteral administration, preferably the preparations for intravenous administration, comprising dihydroginsenoside $Rb_1$, metabolites thereof or salts thereof at low concentrations for prevention, therapy or treatment of brain and nervous diseases or any diseases accompanied with cell death.

These medicinal or pharmaceutical compositions of the present invention are preferably in the form of the preparations for intravenous administration, however the preparations of any optional routes of administration can be selected. These include, for example, agents for local external use in lesion, injections for local external use, preparations for oral administration, nasal drops, ophthalmic agents, ophthalmic ointments, ear drops, suppositories, subcutaneous injections, intracutaneous injections, intramuscular injections, inhalations, sublingual tablets and transdermal drugs.

Further, the present invention relates to the agents for long term treatment, prevention or therapy of brain and nervous diseases or the agents for protecting brain cells or nerve cells comprising the above described preparations for intravenous administration or preparations for local external use in lesions.

Further, the present inventors have found for the first time that novel dihydroginsenoside $Rb_1$ newly obtained by reduction of ginsenoside $Rb_1$, metabolites thereof or salts thereof exhibited an excellent decreasing action on cerebral infarct lesion. Consequently, the present invention proves that ginsenoside $Rb_1$ or metabolites thereof can be used as a leading compound(s) for exploring novel other effective components or compounds for prevention, therapy or treatment of diseases caused by nervous tissue or spinal cord tissue injuries or cerebral apoplexy. It is also possible to select any other administration routes after preparing prodrugs by modifying a part(s) of the chemical structure of dihydroginsenoside $Rb_1$. Further, target molecules of dihydroginsenoside $Rb_1$ or metabolites thereof are identified and novel compounds for modifying function of the target molecules are synthesized to direct development of drugs for treatment or therapy of cerebral apoplexy, head injury, spinal cord injury, neurotrauma and trauma.

Consequently, the present invention provides components of ginseng or metabolites thereof as leading compounds for exploring novel active components or compounds for prevention, therapy or treatment of these diseases.

Dihydroginsenoside $Rb_1$ of the present invention is represented by the chemical structure (II) hereinbefore, and can be produced by hydrogenation of our own highly purified ginsenoside $Rb_1$. The compound prepared by such methods has its purity 98% or more, which was confirmed by NMR spectrum.

Dihydroginsenoside $Rb_1$ of the present invention can be used in its free form and is also used as suitable salts thereof. The solvates such as hydrate can also be used.

The concentrations of dihydroginsenoside $Rb_1$ of the present invention are preferably low, more concretely, the extracellular fluid concentrations are 100 ng/ml or less, preferably 10 pg/ml or less, more preferably 100 fg/ml or less. In case of use of dihydroginsenoside $Rb_1$ of the present invention in the form of preparations for intravenous administration, the preparations are preferably adjusted so that the extracellular fluid concentrations of dihydroginsenoside $Rb_1$, metabolites thereof or salts thereof in lesions of patients are kept at the levels as described hereinabove. The medicinal or pharmaceutical composition(s) and preparations of the present invention can exhibit sufficient effects even when the extracellular fluid concentrations of dihydroginsenoside $Rb_1$, metabolites thereof or salts thereof in lesioned tissues are approximately 0.01-100 fg/ml or 1-10000 fg/ml.

The preparations comprising dihydroginsenoside $Rb_1$ or salts thereof for intravenous administration of the present invention are sufficient if they can be directly administered intravascularly, preferably intravenously, and they can be used as the preparation for single intravenous infusion (administration) or as the preparation for repetitive or continuous intravenous administration after dissolving dihydroginsenoside $Rb_1$, metabolites thereof or salts thereof in physiological saline, distilled water, phosphate buffer, glucose solution, liposome and/or lipid emulsion etc. Further, the formulations which can be used by adding to the preparations for intravenous administration such as a composition(s) for drip-infusion may be preferable. Prodrugs are also prepared by modifying a part(s) of the chemical structure of dihydroginsenoside $Rb_1$, as a result, optional routes of administration and optional methods of administration can also be selected. For example, a hydroxyl base(s) of dihydroginsenoside $Rb_1$ is esterified to prepare the prodrug, passing through the blood-brain barrier, hydrolyzing with endogenous esterase to increase intracerebral transfer of dihydroginsenoside $Rb_1$.

Intravenous administration of dihydroginsenoside $Rb_1$ of the present invention, like that of ginsenoside $Rb_1$, reduces volume of cerebral infarction lesion to about ¼ of the non-administered group, indicating that it can be used as a neuroprotective agent for not only acute phase or chronic cerebral infarction (cerebral thrombosis and cerebral embolism) but also acute or chronic phase of cerebral hemorrhage and subarachnoidal hemorrhage, or transient cerebral ischemic attack. Namely, dihydroginsenoside $Rb_1$ is the drug, which is possible to be infused intravenously, to patients, who are suspected to have cerebral apoplexy, in ambulances. Further, administration of dihydroginsenoside $Rb_1$ to patients with cerebral infarction who will undergo thrombolytic therapy improves prognosis of the patients.

In addition, it was found that repetitive or continuous intravenous administration of low doses of dihydroginsenoside $Rb_1$ of the present invention not only reduced cerebral infarct lesion to about ¼, but also suppressed apoptosis-like cell death in the ischemic penumbra, further it has possibility to suppress necrosis of nerve cells, glial cells and vascular endothelial cells in the ischemic core. Namely, dihydroginsenoside $Rb_1$ of the present invention can exhibit almost the same therapeutic effect on cerebral infarction as ginsenoside $Rb_1$. Furthermore, judging from the fact that the dosage of intravenous administration of dihydroginsenoside $Rb_1$ is similar to that of intravenous administration of ginsenoside $Rb_1$, dihydroginsenoside $Rb_1$ is likely to have the almost same pharmacological actions as those of ginsenoside $Rb_1$. Namely, the effects, efficacy, usages and actions of ginsenoside $Rb_1$ or metabolites thereof found by the present inventors (Sakanaka and Tanaka) in Japanese Patent Application No. Hei 10-365560, PCT/JP99/02550 (Brain cell or nerve cell-protective agents comprising ginsenoside $Rb_1$), Japanese Patent Application No. Hei 11-243378, PCT/JP99/06804 (Cerebrovascular regeneration/reconstruction promoters and nerve tissue secondary degeneration inhibitors comprising ginsenoside $Rb_1$) and Japanese Patent Application No. 2000-163026 (Agents for promoting dermal tissue regeneration comprising ginsenoside $Rb_1$) appear to be in common with those of dihydroginsenoside $Rb_1$ or metabolites thereof. Of course, newly found effects, efficacy, usages and actions of ginsenoside $Rb_1$ in the present invention are also elicited by dihydroginsenoside $Rb_1$ or metabolites thereof. More concretely, the medicinal or pharmaceutical composition(s) comprising dihydroginsenoside $Rb_1$, metabolites thereof or salts thereof exhibits excellent protective actions on brain and nerve cells, upregulated expression of a cell death-suppressing gene $Bcl-x_L$, therapeutic effects on cerebral infarction and cerebral apoplexy, therapeutic effects on spinal cord injury and neurotrauma, suppressive actions on secondary degeneration of the nervous tissues, promotion of cerebrovascular regeneration and/or reconstruction, protection of myocardial cells, therapeutic effects on bedsore and improvement of brain edema.

Since the medicinal or pharmaceutical composition(s) comprising dihydroginsenoside $Rb_1$, metabolites thereof or salts thereof suppresses apoptosis-like neuron death, apoptosis of neurons or apoptosis of glial cells, and exhibits efficacy for many neurodegenerative diseases (Alzheimer's disease, Pick's disease, spinocerebellar degeneration, Parkinson's disease, chorea, polyglutamine diseases, amyotrophic lateral sclerosis, etc.) and demyelinating diseases (leukoencephalitis, Binswanger's disease, chronic cerebral hypoperfusion disorder, multiple sclerosis, etc.), it ameliorates the disorder of higher nervous functions caused by these diseases and improves QOL (quality of life) of patients.

Further, a specific feature of the pharmaceutical composition comprising dihydroginsenoside $Rb_1$ of the present invention, which should not be overlooked, is that it, like ginsenoside $Rb_1$, does not show any adverse effects.

As described in Japanese Patent Application No. Hei 10-365560 and PCT/JP99/02550 ("Brain cell or nerve cell-protective agents comprising ginsenoside $Rb_1$"), repetitive or continuous intravenous administration of ginsenoside $Rb_1$ to rats with permanent MCA occlusion (body weight about 300 g), in a dose of 6 μg/day or 60 μg/day, resulted in reduction of the cerebral infarct lesion and ameliorated ischemia-induced place navigation disability (cerebrovascular dementia). On the other hand, dihydroginsenoside $Rb_1$ of the present invention, in the dose of 6 μg/day, reduced the cerebrocortical infarcted lesion (the primary lesion) of rats with permanent MCA occlusion and its effect was equal to that of ginsenoside $Rb_1$ (6 μg/day). Consequently, it is thought that intravenous administration of dihydroginsenoside $Rb_1$, in the dose of 60 μg/day, to rats with MCA permanent occlusion exhibits an effect similar to that of intravenous administration of ginsenoside $Rb_1$ in the dose of 60 μg/day.

Based on these experimental results, the optimal dose range of dihydroginsenoside $Rb_1$ for human patients (body weight 60 kg) with cerebral apoplexy is calculated as 1.2 mg/day-12 mg/day. Consequently, daily doses of the medicinal composition of the present invention in the human patients with cerebral apoplexy are, although depending on individual difference and the disease states of patients, set to 0.1 mg/day or more, preferably 1 mg/day or more, more preferably 10 mg/day or more. However, since required dose amount per body weight is, generally, decreased as body weight of animals increases, dosages of 1/10 or less of this amount in human are presumably effective. When dihydroginsenoside $Rb_1$ is administered to patients with brain and nervous diseases, in which the blood-brain barrier is slightly damaged, (e.g. neuro degenerative diseases such as Alzheimer's disease, Parkinson's diseases, amyotrophic lateral sclerosis and polyglutamine diseases, demyelinating diseases, neurotrauma, transient ischemic attack, spinal cord injury and head injury), the optimal doses are presumably equal to the above or 5-10 times higher than the above. When dihydroginsenoside $Rb_1$ is administered for prevention, treatment or therapy of diseases other than brain and nervous diseases, it is preferable to select the equivalent doses of the above, or doses of its 1/10 to 1/100,000. Since the medicinal or pharmaceutical composition(s) of the present invention has less adverse effects, it can be administered considerably in large amount as an upper limit of dosage, and the upper limit of dosage is 1 g or less/day, preferably 0.1 g or less/day.

The method for administration of the medicinal or pharmaceutical composition(s) comprising dihydroginsenoside $Rb_1$, metabolites thereof or salts thereof of the present invention is intravascular administration, preferably intravenous administration and the amount of administration hereinabove described can be administered consecutively or repetitively. One of active ingredients or compounds of the present invention, dihydroginsenoside $Rb_1$ can be formulated by conventional methods. For example, the aqueous medicinal or pharmaceutical composition(s) of the present invention can be prepared as preparations for intravenous administration by dissolving lyophilized crystals of dihydroginsenoside $Rb_1$, metabolites thereof or salts thereof in physiological saline, distilled water, phosphate buffer or glucose solution etc. Lipid microsphere or liposome preparation can also be used. The concentrations of dihydroginsenoside $Rb_1$, metabolites thereof or salts thereof in the preparations for intravenous administration can optionally be adjusted unless so high, for example 0.01-10 mg/ml, preferably 0.1-1 mg/ml.

Next, the actions of medicinal ginseng, its extracts, components of ginseng, metabolites thereof or salts thereof, ginsenoside $Rb_1$, crude saponin fraction(s) of ginseng and dihydroginsenoside $Rb_1$ are explained in detail. We have examined the actions of oral administration of red ginseng powder as an example of medicinal ginseng (red ginseng powder prepared from six years roots of Panax ginseng C. A. Meyer in Korean Tobacco Ginseng Public Corp.). For that purpose, for example, male SH-SP rats at the age of 12-13 weeks, weighing 250-300 g, were used. Animals were bred in a room furnished with 12 hours light and dark cycles, and water and feeds were supplied ad libitum. The cortical branch of the left middle cerebral artery (MCA) of SH-SP rats were coagulated under inhalation anesthesia according to the method described by the inventors (Sakanaka and Tanaka) (Igase, K., et al., J. Cereb. Blood Flow Metab., 19, 298-306, 1999; Sadamoto, Y., et al., Biochem. Biophys. Res. Commun., 253, 26-32, 1998). Red ginseng powder was mixed with distilled water and administered orally once a day for one week before MCA permanent occlusion and for 32 days after MCA permanent occlusion (0.6 g/kg/day, 0.75 g/kg/day, 0.9 g/kg/day or 1.2 g/kg/day, n=5-8)

Control animals with MCA permanent occlusion (ischemic control animals) and sham-operated animals were administered orally with the same amount of distilled water.

After MCA permanent occlusion, according to the method of the inventors (Zhang B. et al., J. Stroke Cerebrovasc. Dis., 7, 1-9, 1998; Igase, K., et al., J. Cereb. Blood Flow Metab., 19, 298-306, 1999; Sadamoto, Y., et al., Biochem. Biophys. Res. Commun., 253, 26-32, 1998), water maze tests were performed for 4 days consecutively at the 2nd week and at the 4th week, respectively, and the place navigation abilities of SH-SP rats were determined.

Results are shown in FIG. 1. In FIG. 1, the upper drawing is the results of the 2nd week and the lower drawing is the results of 4th week after permanent MCA occlusion. Statistical analyses were conducted by ANOVA+Fisher's PLSD. Data are represented as mean±SE. *: $P<0.05$, **: $P<0.01$. In FIG. 1, open circles indicate the results of ischemic rats administered with distilled water; closed circles indicate the results of rats with sham operation; open squares indicate the results of ischemic rats administered with red ginseng powder in a dose of 0.6 g/kg/day; closed squares indicate the results of ischemic rats administered with red ginseng powder in a dose of 0.75 g/kg/day; open triangles indicate the results of ischemic rats administered with red ginseng powder in a dose of 0.9 g/kg/day; and closed triangles indicate the results of ischemic rats administered with red ginseng powder in a dose of 1.2 g/kg/day.

As shown in FIG. 1, the place navigation abilities of animals after MCA-permanent occlusion (after cerebral infarction) were significantly improved in the groups administered with red ginseng powder in doses of 0.75-1.2 g/kg/day. The most preferable effect was observed in the group administered with red ginseng powder in a dose of 0.9 g/kg/day. No significant differences in swimming speed were observed among the six experimental groups.

Figure 2:
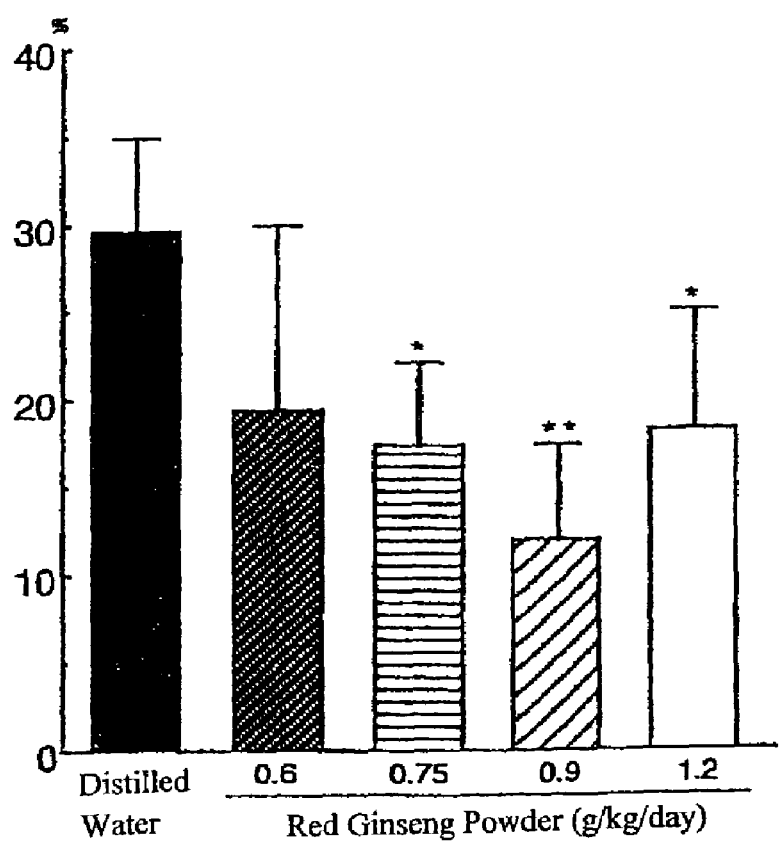
FIG. 2 shows results of ratio of cerebrocortical infarction of animals administered orally with distilled water or red ginseng powder before and after MCA permanent occlusion.

After termination of water maze tests at the 4th week, the SH-SP rats were anesthetized with chloral hydrate, and they were perfused and fixed transcardially with 0.1 mole phosphate buffer containing 4% paraformaldehyde. The brains were dissected out and cerebrocortical infarct lesions were photographed (refer to FIG. 3). The left cerebrocortical infarct areas were divided by the left cerebral hemispheric areas to calculate ratios of the cerebrocortical infarction (%). Results are shown in FIG. 2. Statistical analyses were conducted by Mann-Whitney U-test. Data are represented as mean±SE. *: $P<0.05$, **: $P<0.01$. On the left side is a control using distilled water, and on its right side are data with 4 doses of red ginseng powder. Data indicate from the left to the right: 0.6 kg/day administered group (black slant lines); 0.75 g/kg/day administered group (horizontal lines); 0.9 g/kg/day administered group (slant lines); and 1.2 g/kg/day administered group (open).

As shown in FIG. 2, the ratios of the cerebrocortical infarction were also significantly decreased in the groups of ischemic animals administered with red ginseng powder, 0.75-1.2 g/kg/day, as compared with the group of ischemic animals administered with distilled water. Especially, the most effective results were obtained in the red ginseng powder-administered group in a dose of 0.9 g/kg/day and the average ratio of cerebrocortical infarction was decreased to less than ½ of the group administered with distilled water. Accordingly, the actual infarct volume is reduced to about ¼ by the oral administration of red ginseng powder in a dose of 0.9 g/kg/day.

Figure 3:
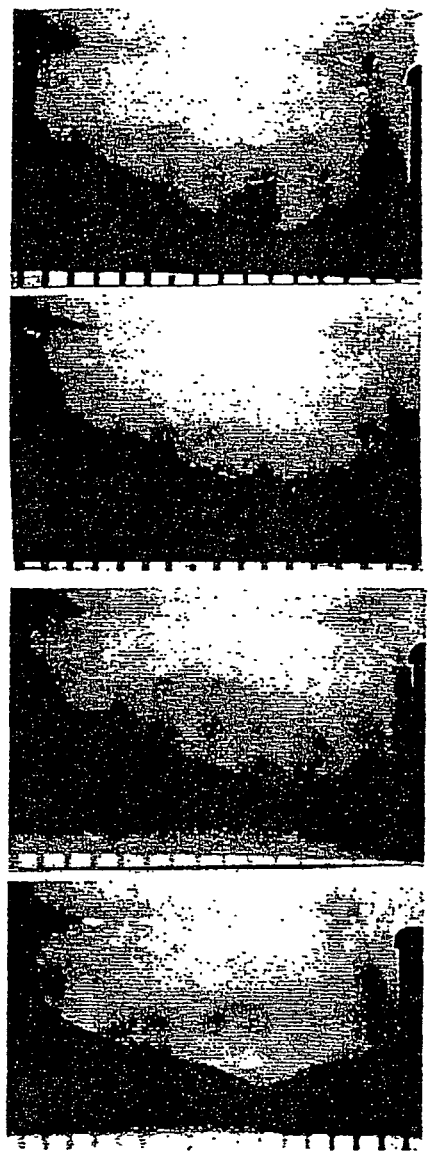
FIG. 3 shows photographs of cerebrocortical infarct lesions. The upper photographs are 4 cases of distilled water-administered ischemia group and the lower photographs are 4 cases of red ginseng powder (0.9 g/kg/day)-administered ischemia group.
Figure 3:
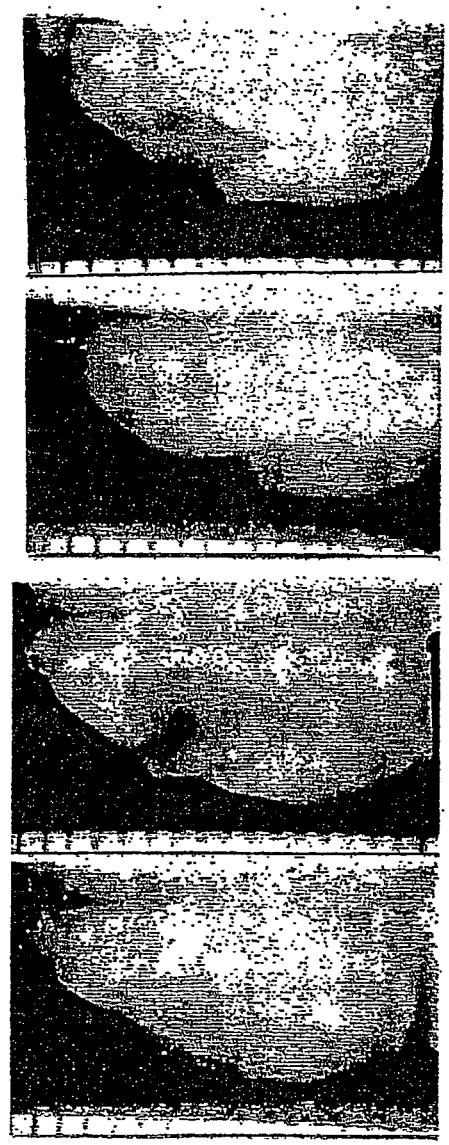

In FIG. 3, the upper photographs show cerebral infarct lesions in the group of ischemic animals administered with distilled water (4 cases), and the lower photographs show cerebral infarcted lesions in the group of ischemic animals administered with red ginseng powder, 0.9 g/kg/day (4 cases).

Figure 4:
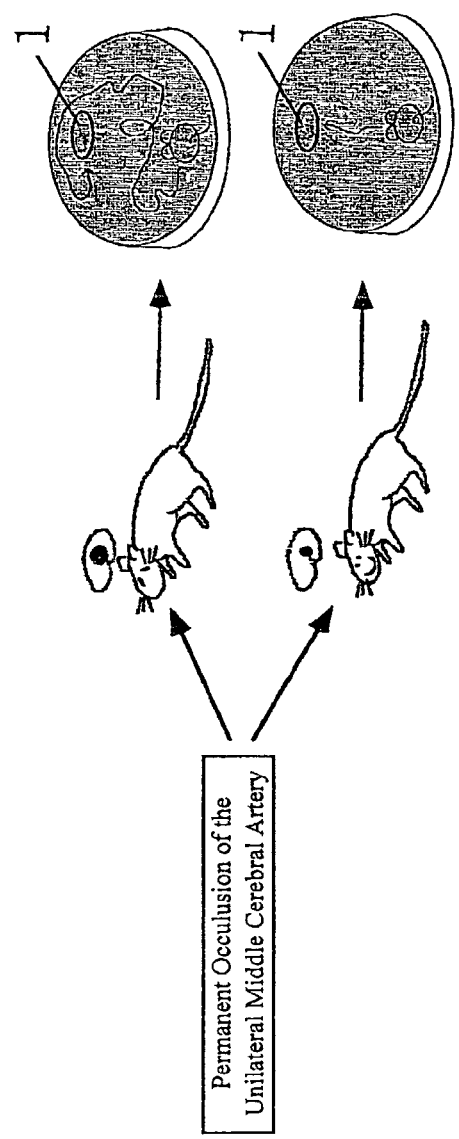
FIG. 4 shows a schematic illustration summarizing the results of example 1.

FIG. 4 illustrates a schematic representation of the summarized methods and results of the experiments. The middle cerebral arteries of test rats were permanently occluded and divided into 2 groups. For one group, red ginseng powder was administered orally (lower illustration in FIG. 4), and another group was given orally distilled water (upper illustration in FIG. 4). Subsequently, in the water maze tests, time until the rats arrived at the goal platform (escape latency) was measured.

In the group of ischemic animals administered with distilled water, the large cerebral infarct area as well as cerebral edema was observed, and animals needed long time to arrive at the goal platform in the water maze test. Contrary to that, in the group of ischemic animals administered with red ginseng powder, the cerebral infarct area was decreased and cerebral edema was also reduced. As a result, animals arrived at the goal platform within short time in the water maze test.

Animals with MCA permanent occlusion (cerebral infarction rats) used in the present experiments are obviously severer than the transient forebrain ischemia model of gerbils (animal model for human transient cerebral ischemic attack) and they are an animal model similar to human patients with cerebral infarction. Consequently, the fact that oral administration of red ginseng powder exhibits significant favorable effects on these permanent MCA-occluded animals, indicated that red ginseng powder is useful for prevention, treatment or therapy of cerebral infarction and cerebral edema. Red ginseng powder is the first product which has never known in the world as a drug showing such the epoch-making effect by oral administration.

In Japanese Patent Application No. Hei 10-365560 (Brain cell or nerve cell-protective agents comprising ginsenoside $Rb_1$), the inventors (Sakanaka and Tanaka) invented that repetitive or continuous intravenous administration of ginsenoside $Rb_1$ at low doses, a main component of red ginseng powder, significantly reduced cerebral infarct area of rats with MCA permanent occlusion. However, recently, the inventors have confirmed that oral administration of ginsenoside $Rb_1$ per se did not show protective effects on nerve cells. Consequently, at present, red ginseng powder is the extremely useful medicinal or pharmaceutical composition for oral administration applied for prevention, treatment or therapy of acute phase cerebral infarction and accompanied learning disability. Actually, it is reported that ginsenoside $Rb_1$ could not be detected in the blood stream even after oral administration of ginsenoside $Rb_1$ and/or red ginseng powder, furthermore, oral administration of ginsenoside $Rb_1$ itself alone did not exhibit any physiological actions (Akao, Mitsuaki, et al. The Ginseng Review, 22, 97-102, 1996).

The components of red ginseng powder are roughly divided into crude saponin fraction and non-saponin fraction. The crude saponin fraction is mainly composed of protopanaxadiol saponins, protopanaxatriol saponins and oleanolic acid saponins. A representative of protopanaxadiol saponins is ginsenoside $Rb_1$; a representative of protopanaxatriol saponins is ginsenoside $Rg_1$; and a representative of oleanolic acid saponins is ginsenoside Ro (Shibata, S., et al., Economic and medicinal plant research, World Scientific, Philadelphia, pp. 217-284, 1985). At present, besides these three representative purified saponins, chemical structures of about 30 purified saponins have been determined. Judging from the facts that oral administration of red ginseng powder obviously showed a neuroprotective effect (neuron death-suppressing effect) and oral administration of ginsenoside $Rb_1$ per se did not show such an effect, it can be presumed that large numbers of substances showing neuroprotective effects other than ginsenoside $Rb_1$ are contained in the red ginseng powder. However, since the possibility that decomposition of ginsenoside $Rb_1$ is suppressed by oral administration of red ginseng powder and ginsenoside $Rb_1$ below the detection limit is absorbed into blood from the digestive tract can not be denied, it is not impossible to speculate that trace amounts of ginsenoside $Rb_1$ transferred into the blood and the other neuroprotective substance(s) in red ginseng powder exhibit synergistic effects to produce significant reduction of cerebral infarct lesion and to improve ischemia-induced place navigation disability. Candidate substances with neuroprotective actions other than ginsenoside $Rb_1$ in red ginseng powder are purified saponins or ginsenosides, the chemical structures of which have been determined, and unknown components in the crude saponin and non-saponin fractions.

If the MCA is permanently occluded, nerve cells, which are supported by nutrition or blood supply from the MCA alone, i.e. nerve cells in the ischemic core, are rapidly necrotized to form cerebral infarct lesion unless reopening the MCA; consequently any drugs can not rescue brain tissues in the ischemic core. Cell death is classified roughly into necrosis and apoptosis according to the morphological features. In relation to nerve cell death, the concept of necrosis has been established, regarding to neuronal apoptosis, although a similar phenomenon can be observed in the pathologic matured brain, there are few examples of the neuronal apoptosis showing typical characteristics as observed in lymphocytes. Consequently, in this specification, slowly progressing nerve cell death which is different from necrosis is defined as "apoptosis of nerve cells" or "apoptosis-like nerve cell (neuron) death". However, it is well known that nerve cell death cannot be always classified into necrosis and apoptosis-like cell death. For example, ischemic nerve cells initially exhibit apoptosis-like morphological features when entering cell death, and beyond a certain stage of cell death, they suddenly show features of necrosis. This is called post-apoptotic necrosis. Consequently, in the present specification, if such classification is difficult, the term nerve cell death or neuron death is simply used.

In the ischemic penumbra, which is different from the ischemic core where necrosis of nerve cells occurs, even if the supply of blood from the MCA is terminated, insufficient blood supply is continued at least in part, from the cortical branches of the anterior cerebral artery and the posterior cerebral artery. Therefore, the nerve cells in the ischemic penumbra may survive in the critical condition for some time after permanent MCA occlusion. It is well known that, if no countermeasures are taken, apoptosis-like nerve cell death is gradually developed in the ischemic penumbra, and the ischemic penumbra eventually enters infarct lesion. From the clinical standpoint, to rescue the nerve cells in the original ischemic penumbra is the most important thing to do, however as far as we know, medicinal or pharmaceutical compositions for oral administration exhibiting potent neuroprotective effect to make possible such action have not been developed.

The inventors have proved that when red ginseng powder was administered orally in SH-SP rats from one week before permanent MCA occlusion to four weeks after the MCA occlusion, the volume of cerebrocortical infarct of the rats was reduced to about ¼ of the non-administered rats as well as significantly improving the ischemia-induced place navigation disorder. This means that if patients with underlying diseases such as diabetes mellitus, cerebral arteriosclerosis, hypertension and atrial fibrillation, i.e. candidates having cerebral infarction in near future, and aged people or patients with past history of cerebral apoplexy, ingest red ginseng powder in advance, and if they suffer from cerebral apoplectic attack at the worst, their cerebral apoplectic lesions will be significantly improved and cerebrovascular dementia will be suppressed by subsequent oral administration of red ginseng powder. Further, reducing the volume of cerebral infarct lesion to about ¼ of the non-administered animals by oral administration of red ginseng powder demonstrates that oral administration of the same drug significantly suppressed apoptosis of nerve cells or apoptosis-like nerve cell death in the ischemic penumbra.

Generally, a neuroprotective factor or agent exhibits the maximum effect when directly administered into the cerebral ventricles or into the brain parenchyma, and in case of intravenous or intraperitoneal administration, its favorable effects and efficacy seem to drastically decrease or disappear due to the blood-brain barrier that prevents the neuroprotective factor or agent from entering the brain parenchyma. Even in the oral administration of the neuroprotective agent or factor, there are many hurdles to be overcome, for example decomposition and absorption in the digestive tract, amount and rate of transfer into blood, decomposition in blood, hindrance at the blood-brain barrier, etc. Recently, as described in Japanese Patent Application No. Hei 10-365560 (Brain cell or nerve cell-protective agents comprising ginsenoside $Rb_1$), the present inventors (Sakanaka and Tanaka) have found the excellent neuroprotective agents for intravenous administration, but even in these neuroprotective agents for intravenous administration (i.e. ginsenoside $Rb_1$), we have confirmed recently that its oral administration did not exhibit neuroprotective action. Of course, although the possibility is left open that ginsenoside $Rb_1$ can be used as agents for oral administration by mixing, encapsulating or combining it with a carrier(s) inhibiting decomposition in the digestive tract (e.g. gelatin, oil layer, shellac, etc.) or promoting absorption in the digestive tract, at present, considering the effect and efficacy of red ginseng powder as a neuroprotective agent for oral administration, it is the most excellent neuroprotective agent for oral administration in the world.

Next, we have initiated experiments on oral administration of red ginseng powder after MCA permanent occlusion and investigated its effect. Since the most preferable results were obtained, when red ginseng powder in the dose of 0.9 g/kg/day was administered, in the previous experiments wherein red ginseng powder was administered orally before and after MCA permanent occlusion, the present experiments were conducted in this dosage. The cortical branch of the left middle cerebral artery (MCA) of male SH-SP rats at the age of 12-13 weeks, weighing 250-300 g, were coagulated under inhalation anesthesia, and anesthesia was terminated. After the animals were awakened from the anesthesia, red ginseng powder in dose of 0.9 g/kg/day was administered orally once a day for 32 days. The control animals with MCA permanent occlusion (infarcted control animals) were administered with distilled water alone.

After MCA permanent occlusion, according to the method of the inventors (Sakanaka and Tanaka) (Zhang B. et al., J. Stroke Cerebrovasc. Dis., 7, 1-9, 1998; Igase, K., et al., J. Cereb. Blood Flow Metab., 19, 298-306, 1999; Sadamoto, Y., et al., Biochem. Biophys. Res. Commun., 253, 26-32, 1998), water maze tests were performed for 4 days at the 2nd week and at the 4th week, respectively, and the place navigation abilities of SH-SP rats were determined.

Figure 5:
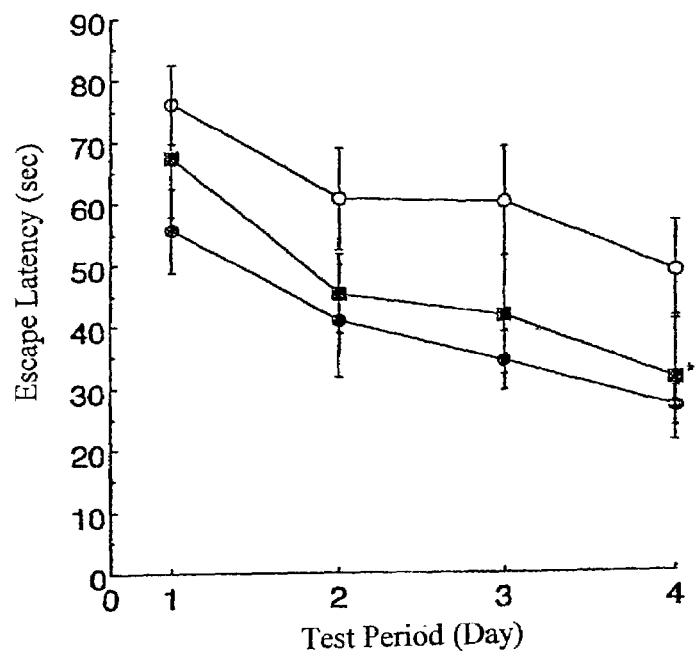
FIG. 5 shows results of water maze tests of rats administered orally with distilled water or red ginseng powder after MCA permanent occlusion.
Figure 5:
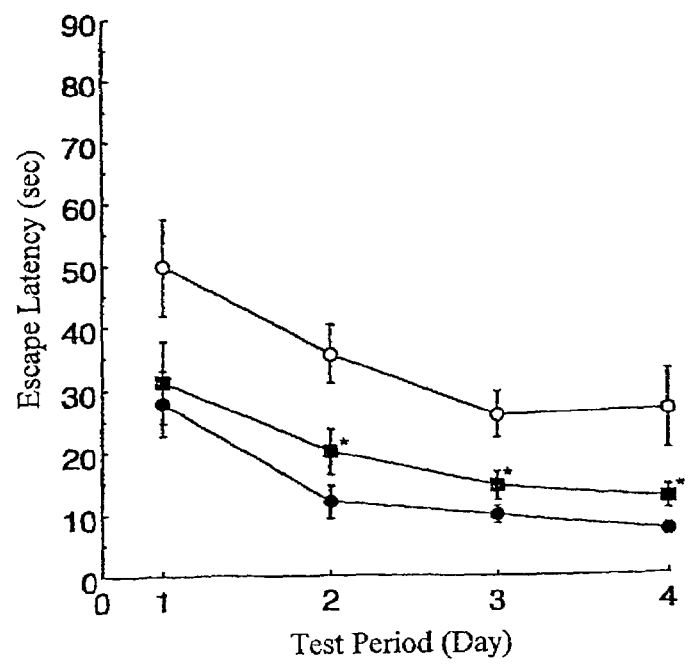

Results are shown in FIG. 5. In FIG. 5, the upper drawing indicates the results of the 2nd week and the lower drawing indicates the results of 4th week after permanent MCA occlusion. Statistical analyses were conducted by ANOVA+ Fisher's PLSD. Data are represented as mean±SE. *: $P<0.05$. In FIG. 5, open circles indicate the results of ischemic rats administered with only distilled water; closed squares indicate the results of ischemic rats administered with red ginseng powder in a dose of 0.9 g/kg/day. For reference, the experimental values of the group of the sham-operated animals used in FIG. 1 are shown with closed circles.

As shown in FIG. 5, the place navigation abilities of animals after MCA-permanent occlusion (after cerebral infarction) were significantly improved in the group administered with red ginseng powder in a dose of 0.9 g/kg/day. Preferable effects were observed at the 4th week after permanent MCA occlusion. No significant differences in the swimming speed of SH-SP rats were noted between the two groups.

Figure 6:
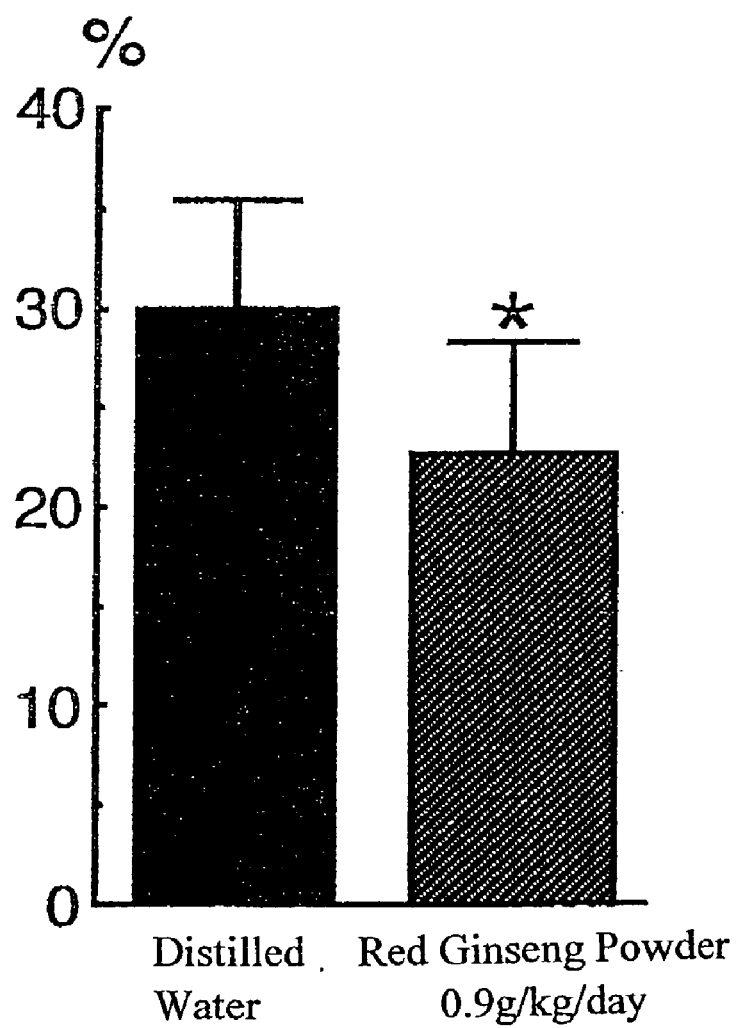
FIG. 6 shows results of ratio of cerebrocortical infarction of animals administered orally with distilled water or red ginseng powder, 0.9 g/kg/day, after MCA permanent occlusion.

After termination of water maze tests at the 4th week, the SH-SP rats were anesthetized with chloral hydrate, and they were perfused and fixed transcardially with 0.1 mole phosphate buffer containing 4% paraformaldehyde. The brains were dissected out and cerebrocortical infarct lesions were photographed. Areas of the left cerebral hemisphere and the left cerebrocortical infarct lesions were measured on the photographs by using an image analyzer. The left cerebrocortical infarct areas were divided by the left cerebral hemispheric areas to calculate ratios of the cerebrocortical infarction (%). Results are shown in FIG. 6. Statistical analyses were conducted by Mann-Whitney U-test. Data are represented as mean±SE. *: $P<0.05$. On the left side is data of the ischemic control group administered with distilled water alone, and on its right side is data of the ischemic group administered with red ginseng powder in a dose of 0.9 g/kg/day (black slant lines).

As shown in FIG. 6, the ratio of cerebrocortical infarction was also significantly decreased in the group of ischemic animals administered with red ginseng powder in a dose of 0.9 g/kg/day, as compared with the group of ischemic animals administered with distilled water. However, this effect was less potent than that of orally administered red ginseng powder before and after permanent MCA occlusion. Consequently, it is important to ingest red ginseng powder before suffering from cerebral infarction, and if unfortunately patients are suffered from cerebral infarction, oral administration of red ginseng powder should be continued. Of course, when red ginseng powder is administered orally after MCA permanent occlusion, the effect is insufficient as compared with the effect of low doses of ginsenoside $Rb_1$ administered intravenously after MCA permanent occlusion (Japanese Patent Application No. Hei 10-365560, Brain cell or nerve cell-protective agents comprising ginsenoside $Rb_1$). Nevertheless, considering that promptly acting agents for intravenous administration such as ginsenoside $Rb_1$ are not used commonly, initiating the oral administration of red ginseng powder after the onset of cerebral infarction is thought to be possible as the next best.

As compared with the intravenous administration or intravenous drip infusion of drugs which can be conducted in medical institutions, the oral administration of red ginseng powder has at least advantages possible to perform at any time and any places, if consciousness and swallowing function of patients with cerebral infarction are maintained. If consciousness and swallowing function of patients are not sufficient, through the incubation of a feeding tube or nasogastric tube, red ginseng powder can be administered for long term not only in the medical institutions but also at home, and thus the advantages for use of red ginseng powder are very high. In addition, since red ginseng powder has been used for several thousand years by human being and its safety has been established, the present invention demonstrates that orally administering red ginseng powder to patients with acute phase cerebral infarction at the earliest opportunity is an important and essential selective countermeasure in the therapy of the disease, until intravenous administration of ginsenoside $Rb_1$ is applied in the general clinical field in future.

Next, the present inventors investigated the mechanism(s) by which the oral administration of red ginseng powder protected nerve cells. If the mechanism of action of red ginseng powder is elucidated, it is expected that new favorable effects and efficacy of red ginseng powder will be invented. For that purpose, we have paid attention to the cell death-suppressing gene product Bcl-$x_L$ protein. Bcl-$x_L$ protein is expressed in all tissues including nervous tissues, tissues of the immune system, dermal tissues and tissues of the circulatory system, and plays an important role in the survival of cells. (Adams J. M. and Cory S., Science, 281, 1322-1326, 1998; Boise, L. H., et al., Cell, 74, 597-608, 1993; Gottschalk A. R., et al., Proc. Natl. Acad. Sci. USA, 91, 7350-7354, 1994; Gonzalez-Garcia M., et al., Proc. Natl. Acad. Sci. USA, 92, 4304-4308, 1995).

Whether oral administration of red ginseng powder increases the expression of Bcl-$x_L$ protein or not was investigated by using the transient forebrain ischemia model of gerbils. In our prior report (Wen, T.-C., et al., J. Exp. Med., 188, 635-649, 1998), the experimental system for investigation of Bcl-$x_L$ expression in the hippocampal CA1 field after transient forebrain ischemia has been established, and the effects of oral administration of red ginseng powder on Bcl-$x_L$ protein expression were examined with this system.

Figure 7:
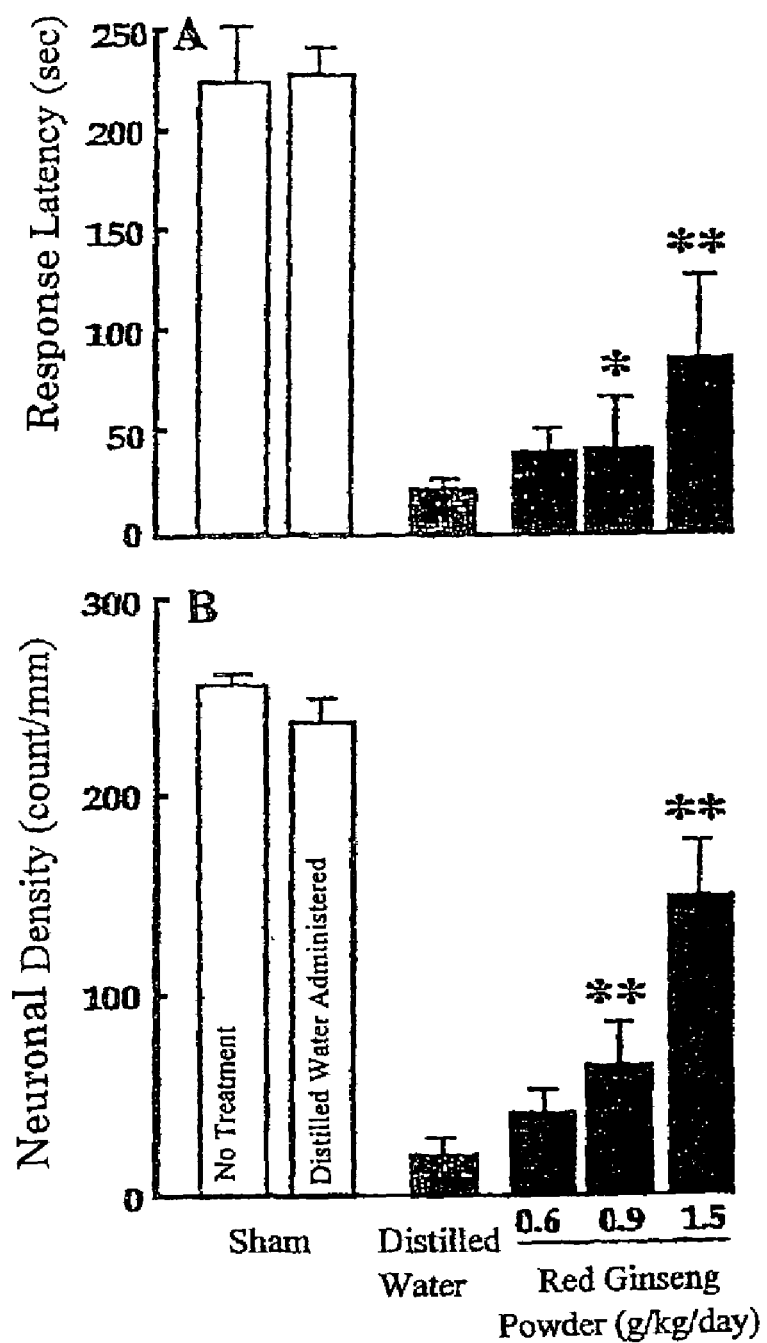
FIG. 7 shows the response latency time and the hippocampal CA1 neuronal density of gerbils administered orally with red ginseng powder or distilled water, once a day for one week before 5-minute transient forebrain ischemia. The upper figure (A) shows the response latency time of passive avoidance learning experiments, and the lower figure (B) shows the neuronal densities. Open columns indicate sham-operated groups; gray columns indicate distilled water-administered ischemia group; and closed columns indicate red ginseng powder-administered ischemia group.

As shown in FIG. 7, the one of the inventors of the present invention (Sakanaka) had reported that when red ginseng powder was administered orally in a dose of 0.9 g/kg/day or 1.5 g/kg/day, once a day for 7 days before 5-minute forebrain ischemia in gerbils, nerve cell death in the hippocampal CA1 field was significantly prevented and the response latency time in the passive avoidance tests was significantly prolonged as compared with the group of animals administered with distilled water (Wen, T.-C., et al., Acta Neuropathol., 91, 15-22, 1996).

The upper graph in FIG. 7 shows the response latency time (second) of the passive avoidance learning experiments and the lower graph in FIG. 7 shows the neuronal densities (number/mm). Two open columns on the left side show sham-operated groups; the left column shows sham operation without treatment, and the right column shows sham operation administered with distilled water. Four closed columns on the right side show, from the left to right: distilled water-administered ischemic group; red ginseng powder (0.6 g/kg/day)-administered ischemic group; red ginseng powder (0.9 g/kg/day)-administered ischemic group; and red ginseng powder (1.5 g/kg/day)-administered ischemic group.

Figure 8:
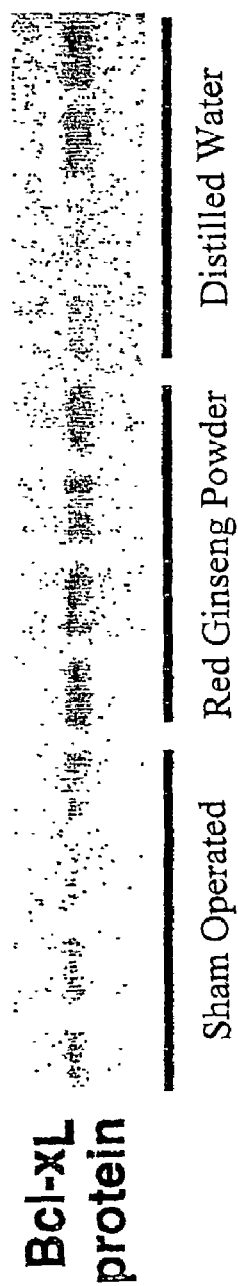
FIG. 8 is photographs instead of drawings, showing results of Western blot analyses of Bcl-$x_L$ protein expression in the hippocampal CA1 field of sham-operated animals, ischemic animals administered orally with distilled water and ischemic animals administered orally with red ginseng powder (1.5 g/kg/day).

Especially, since in the group with ischemic animals administered with red ginseng powder in the dose of 1.5 g/kg/day, favorable effects were observed as compared with the group of animals administered with 0.9 g/kg/day, in the present experiments, red ginseng powder was administered orally in the dose of 1.5 g/kg/day, once a day for 7 days before 5-minute forebrain ischemia, and red ginseng powder was further administered orally after 5-minute forebrain ischemia. Tissues of the hippocampal CA1 field were collected at the 24th hour after the final administration of red ginseng power. Subsequently, cells in the tissues were lysed with sample buffer for electrophoresis and the lysates were electrophoresed. Proteins separated by electrophoresis were transferred to nitrocellulose membrane to perform Western blotting by using anti-Bcl-$x_L$ protein antibody. The sham-operated animals and the control animals with 5-minute forebrain ischemia (ischemic control animals) were orally administered with the equal amount of distilled water alone. In order to investigate whether oral administration of red ginseng powder at the high dose of 1.5 g/kg/day affects the expression of Bcl-$x_L$ protein in the peripheral organs or not, liver and spleen were dissected out and Western blotting was performed by the same procedures. Details of the above experimental procedures are described in our previous report (Wen, T.-C., et al., J. Exp. Med., 188, 635-649, 1998). Results are shown in FIG. 8. FIG. 8 is a photograph showing results of Bcl-$x_L$ protein expression in the hippocampal CA1 field of animals administered with red ginseng powder 1.5 g/kg/day. Four of the left are bands of sham-operated animals; four of the center are bands of ischemic animals administered orally with red ginseng powder; and four of the right are bands of ischemic animals administered orally with distilled water alone.

Figure 9:
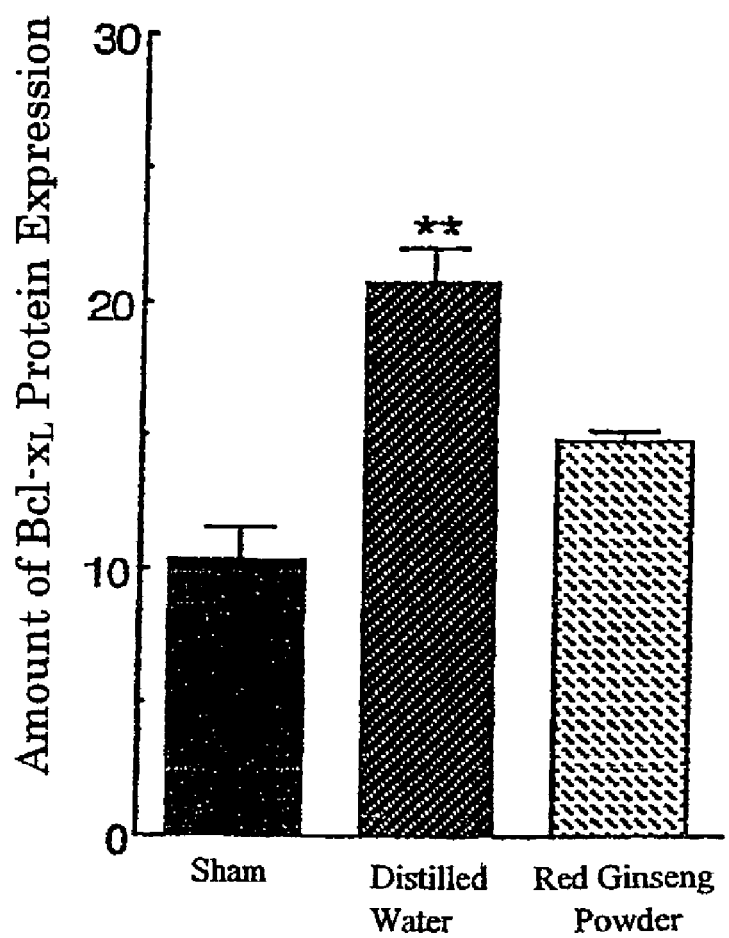
FIG. 9 shows graphs quantifying the results of Western blotting in FIG. 8 by densitometry.

Further, bands reacted with the anti-Bcl-$x_L$ protein antibody in the respective four specimens were quantified by using an image analyzer. Results are shown in FIG. 9. In FIG. 9, vertical axis indicates relative amount of Bcl-$x_L$ protein expression. In the graph from the left, sham-operated group (black), red ginseng powder-administered group (black slant lines), and distilled water-administered group (broken slant lines) are shown. Statistical analyses were conducted by ANOVA+Scheffe's post hoc test. **: P<0.01.

As shown in FIG. 8, when red ginseng powder was administered orally in the dose of 1.5 g/kg/day, once a day for 7 days before 5-minute forebrain ischemia, and the equal amount of red ginseng powder was further administered once orally after 5-minute forebrain ischemia, Bcl-$x_L$ protein expression in the hippocampal CA1 field at 24 hours after ischemia was increased in all cases as compared with the sham-operated group and the ischemic group administered with distilled water. As a result of quantifying the bands reacted with the anti-Bcl-$x_L$ protein antibody by using an image analyzer, it was found that oral administration of red ginseng powder significantly increased the expression of Bcl-$x_L$ protein in the hippocampal CA1 field (FIG. 9). However, even though such the high dose of red ginseng powder was administered orally, the expression of Bcl-$x_L$ protein in the liver and spleen was not increased.

We (the present inventors) have further investigated whether or not oral administration of a low dose of red ginseng powder for a longer term than one week increases the expression of Bcl-$x_L$ protein. For example, red ginseng powder was administered orally in the dose of 200 mg/kg/day, once a day for 4 weeks before 5-minute forebrain ischemia, and immediately after 5-minute ischemia, red ginseng powder was further orally administered once. The hippocampal CA1 field was dissected out at 24 hours after ischemia, and Western blotting with the use of the anti-Bcl-$x_L$ protein antibody was performed in the same manner as shown in FIG. 8. The sham-operated animals and the control animals with 5-minute forebrain ischemia (ischemic control animals) were orally administered with the equal amount of distilled water alone. In order to investigate whether oral administration of red ginseng powder at the dose of 200 mg/kg/day affects the expression of Bcl-$x_L$ protein in the peripheral organs or not, the liver and spleen were dissected out and Western blotting was performed by the same procedures.

Figure 10:
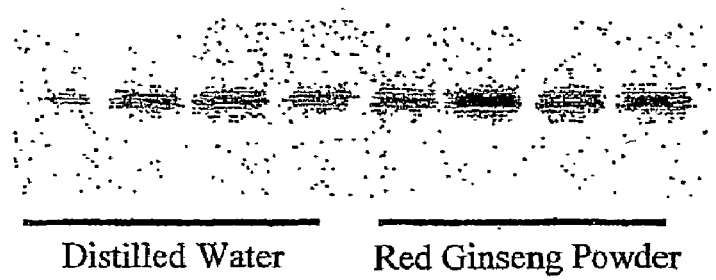
FIG. 10 (A) is photographs instead of drawings, showing results of Western blot analyses of Bcl-$x_L$ protein expression in the liver of animals administered with distilled water or red ginseng powder (200 mg/kg/day).
Figure 10:
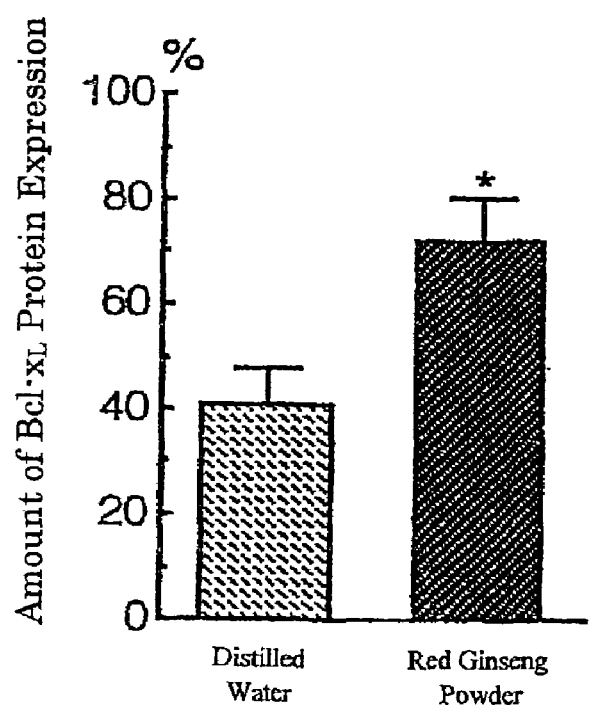

FIG. 10 shows results of Bcl-$x_L$ protein expression in the liver of animals administered with red ginseng powder in a dose of 200 mg/kg/day. FIG. 10 A (upper photograph) is a photograph showing results of Western blotting, and four of the left are distilled water-administered cases, and four of the right are red ginseng powder-administered cases. FIG. 10 B (lower) shows results of quantifying the bands reacted with the anti-Bcl-$x_L$ protein antibody by using an image analyzer. Vertical axis of FIG. 10 B shows relative amount of Bcl-$x_L$ protein expression: the left of the graph shows the results of the distilled water-administered group (broken slant lines); and the right shows the results of the red ginseng powder-administered group (black slant lines). Statistical analyses were conducted by ANOVA+Scheffe's post hoc test. *: P<0.05.

Figure 11:
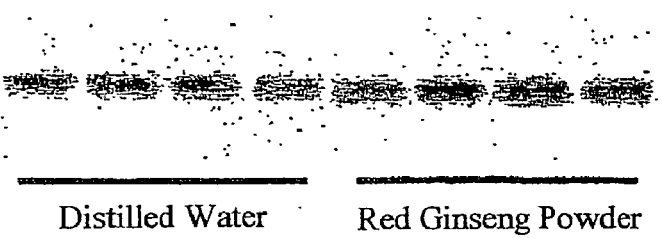
FIG. 11 (A) is photographs instead of drawings, showing results of Western blot analyses of Bcl-$x_L$ protein expression in the spleen of animals administered with distilled water or red ginseng powder (200 mg/kg/day).
Figure 11:
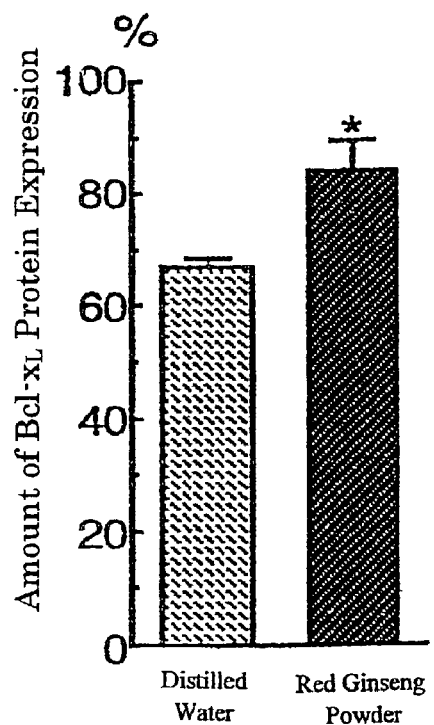

FIG. 11 shows results of Bcl-$x_L$ protein expression in the spleen of animals administered with red ginseng powder in a dose of 200 mg/kg/day. FIG. 11 A (upper photograph) is a photograph showing results of Western blotting, and four of the left are distilled water-administered cases, and four of the right are red ginseng powder-administered cases. FIG. 11 B (lower) shows results of quantifying the bands reacted with the anti-Bcl-$X_L$ protein antibody by using an image analyzer. Vertical axis of FIG. 11 B shows relative amount of Bcl-$x_L$ protein expression: the left of the graph shows the results of the distilled water-administered group (broken slant lines); and the right shows the results of the red ginseng powder-administered group (black slant lines). Statistical analyses were conducted by ANOVA+Scheffe's post hoc test. *: P<0.05.

No significant increase in the expression of Bcl-$x_L$ protein in the hippocampal CA1 field was noted even after red ginseng powder in the dose of 200 mg/kg/day was administered for 4 weeks. Further, red ginseng powder was administered orally in the dose of 200 mg/kg/day, once a day for 4 weeks before 5-minute forebrain ischemia, and red ginseng powder was further administered orally for one week after 5-minute ischemia. The passive avoidance learning disability and nerve cell death in the hippocampal CA1 in gerbils could not be ameliorated. This fact means that if the expression of Bcl-$x_L$ protein is not increased by the oral administration of red ginseng powder at the low dose, no protective effect on nerve cells is exhibited. In other words, it is thought that as the results of administering orally the high dose of red ginseng powder, 1.5 g/kg/day, for one week to gerbils, as shown in FIG. 8, Bcl-$x_L$ protein expression in the hippocampal CA1 region is increased, and thereby as shown in FIG. 7, ischemic nerve cell death in the same region is reduced. Among bioactive substances protecting nerve cells in the hippocampal CA1 region by increasing Bcl-$x_L$ protein in the hippocampal CA1 through intracerebroventricular administration, we (Sakanaka, Tanaka and Maeda) have identified interleukin 3 (Wen T.-C., et al., J. Exp. Med., 188, 635-649, 1998), but red ginseng powder is only one drug having the same action as interleukin 3 by oral administration at present in the world as far as we know. Perhaps, in the ischemic penumbra of the rats with permanent MCA occlusion, oral administration of the high dose of red ginseng powder in advance caused an increase in the expression of Bcl-$x_L$ protein to reduce cerebral infarct area. The amount of red ginseng powder necessary for increasing the expression of Bcl-$x_L$ protein in the ischemic penumbra of the rats with permanent MCA occlusion is smaller than that of gerbils, and based on the results in FIG. 2, it appears to be 0.75-1.2 g/kg/day.

As described hereinbefore, it should be noted that the amount of administration of red ginseng powder necessary for suppressing nerve cell death is different between gerbils and SH-SP rats. It is thought that oral administration of red ginseng powder, in a dose of 1.5 g/kg/day, obviously protects nerve cells of gerbils, weighing about 75 g, from ischemic damage, but it can be understood from the results of FIG. 2 that oral administration of red ginseng powder in a dose of 0.9 g/kg/day to SH-SP rats, weighing about 300 g, exhibits a better neuroprotective effect than the administration of red ginseng powder in a dose of 1.2 g/kg/day. Consequently, inversely proportional to the increase in body weight of animals, the optimal dose of red ginseng powder necessary for exhibiting neuroprotective actions appears to be decreased. This may apply to human cases. For example, if a dose of drug administered in the adult, body weight 60 kg, is set as 1, the dose of the same drug administered in the newborn, body weight 3 kg, is generally about ½ thereof. Namely, the dose of drug per body weight 1 kg in the newborn is about 3 times larger than that in the adult. Estimating from this fact, in rats or gerbils, which are lighter in body weight than the newborn, the dose amount of drug per body weight 1 kg will be about 1.5 times of the dose amount in the newborn. Namely, the dose amount of red ginseng powder per kg of body weight in rats or gerbils is increased at least about 4 times as compared with that in the human.

According to the results in FIG. 2, the cerebrocortical infarct lesions of SH-SP rats with MCA-permanent occlusion were significantly improved by administering red ginseng powder in a dose of 0.75-1.2 g/kg/day before and after MCA-permanent occlusion. Consequently, the similar favorable effects can be expected when red ginseng powder is administered in the doses of 0.185-0.3 g/kg/day in human weighing 60 kg. Dosage of red ginseng powder necessary for protecting brain cells (including glial cells) or nerve cells in human weighing 60 kg appears to be, though depending on individual differences and pathological conditions of patients, 2.0 g-90 g, preferably 5.625 g-36 g, more preferably 11.25 g-18 g. Further, similar protective effects on brain cells or nerve cells can be expected if red ginseng extract(s) or crude saponin fraction(s) extracted from the equal amount of red ginseng powder is administered orally. The crude saponin fraction(s) can be used in the form of agents for oral administration, agents for intravenous administration, sustained release preparations, nasal drops, inhalations, sublingual tablets, suppositories, local infusion, transdermal drugs for external use, local ointments, intramuscular injections and subcutaneous injections. Especially, when the crude saponin fraction(s) is used for intravenous injection, as shown in example 10 hereinbelow, its dosage must be lower than the oral administration. Example of red ginseng powder used is preferably the red ginseng powder prepared from six years roots of *Panax ginseng* C. A. Meyer in Korean Tobacco Ginseng Public Corp. However, if the components are similar to that and if it contains more than a definite amount of neuroprotective components, neuroprotective effects can be obtained by oral administration of red ginseng powder or white ginseng from any countries or any provisions.

As described above, even though red ginseng powder was administered for 4 weeks at the dose of 200 mg/kg/day in gerbils before cerebral ischemia, the expression of Bcl-$x_L$ protein in the hippocampal CA1 field did not increase. However as the results of orally administering the same dose of red ginseng powder in the same experimental schedule, the expressions of Bcl-$x_L$ protein in the liver and the spleen were significantly increased as shown in FIG. 10 and FIG. 11. Based on the present experimental findings that oral administration of red ginseng powder in a dose of 200 mg/kg/day in gerbils increases Bcl-$x_L$ protein expressions in liver and spleen, the amount of red ginseng powder necessary for promoting Bcl-$x_L$ protein expression in the liver and spleen of human, body weight 60 kg, appears to be, depending on individual difference and disease states of patients, 0.6 g-15 g/day, preferably 1.5 g-6 g/day, more preferably 2 g-4 g/day, if the above theory for calculating administering dose/kg is applied. If either red ginseng extract(s), crude saponin fraction(s) or non-saponin fraction(s) extracted from the same amount of red ginseng powder is administered orally, the expression of Bcl-$x_L$ protein in the peripheral organs appears to be similarly increased. The crude saponin fraction(s) and non-saponin fraction(s) can be used in the form of agents for oral administration, agents for intravenous administration, nasal drops, inhalations, sublingual tablets, suppositories, local infusion, sustained release preparations, transdermal drugs for external use, local ointments, intramuscular injections, intracutaneous injections and subcutaneous injections. Especially, when the crude saponin fraction(s) is used as an agent(s) for intravenous administration, the dosage must be lower than that in case of the oral administration.

The features of the present invention are that the expression of Bcl-$x_L$ protein in the brain and nervous tissues is increased by oral administration of the high dose(s) of red ginseng powder to exhibit neuroprotective effects, and the expression of Bcl-$x_L$ protein in the peripheral organs such as the liver and spleen is increased by oral administration of the low dose(s) of red ginseng powder. Since the nervous tissues include nerve cells, neural stem cells, glial cells, vascular endothelial cells, vascular smooth muscle cells, and the liver and the spleen include liver cells, hepatocytes, immunocompetent cells, leukocytes, lymphocytes, erythrocytes, Kupffer's cells, fibroblasts, Ito cells, biliary epithelial cells and sinusoid endothelial cells, upregulated expression of Bcl-$x_L$ protein is likely to occur in any one of these cells by oral administration of red ginseng powder. We have identified interleukin 3 and ginsenoside $Rb_1$ as substances for increasing the expression of Bcl-$x_L$ protein (Wen T.-C., et al., J. Exp. Med., 188, 635-649, 1998; Japanese Patent Application No. Hei 10-365560, Brain cell or nerve cell-protective agents comprising ginsenoside $Rb_1$), but the high dose(s) of red ginseng powder is only one drug to increase the expression of Bcl-$x_L$ protein by oral administration at present in the world. Since oral administration of a red ginseng component, ginsenoside $Rb_1$ itself does not exhibit neuroprotective action, it is thought to be improbable that oral administration of ginsenoside $Rb_1$ per se can increase the expression of Bcl-$x_L$ protein. Of course, since interleukin 3, which can increase the expression of Bcl-$x_L$ protein in the brain only by intracerebroventricular administration to exhibit neuroprotective action, is a peptide, it is immediately digested in the digestive tract when orally administered, moreover it can not pass through the blood-brain barrier. Thus, neuroprotective effect may not be exhibited by oral administration of interleukin 3. Intracerebroventricular administration of ginsenoside $Rb_1$ or prosaposin-related peptides (Japanese Patent Application No. Hei 11-185155) can reduce significantly cerebral infarction of rats with MCA permanent occlusion, furthermore, it exhibits cytoprotective action through upregulating Bcl-$x_L$ expression at extremely low concentrations. Judging from these facts, among the other growth factors, cytokines, chemokines and non-peptide compounds (e.g. prostaglandins, isocarbacyclines), if there is a compound reducing cerebral infarct lesion by intracerebroventricular administration, it may exhibit cytoprotective action through regulation of Bcl-2 protein family expression in the similar low molar concentration range. Further, effects, efficacy and use of ginsenoside $Rb_1$ and prosaposin-related peptides are in common.

The fact that oral administration of the high dose(s) of red ginseng powder did not affect the expression of Bcl-$x_L$ protein in the liver or the spleen, is thought to be important for maintaining biological homeostasis. Namely, oral administration of the high dose(s) of red ginseng powder results in absorbing excessively Bcl-$x_L$ protein expression-promoting components in the red ginseng powder from the digestive tract, and the components arrive at the peripheral organs such as the liver and spleen through the blood circulation. In such peripheral organs, even if the expression of Bcl-$x_L$ protein is temporarily increased, subsequently receives down-regulation to return to the control value. Another possibility is that the upregulation of Bcl-$x_L$ protein expression in the peripheral organs does not occur even though the high dose(s) of red ginseng powder is administered orally. Consequently, the fact that the organism (living body) reacts with only a certain dose range of orally administered red ginseng powder, supports that even though red ginseng powder is administered massively or for long term almost no ill effects are noted. Further, when red ginseng powder is orally administered either at high doses or at low doses, the epithelial tissues of the digestive tract must be exposed to high concentrations of Bcl-$x_L$ protein expression-promoting components. Nevertheless, there are no reports indicating that digestive tract cancer is generated in high frequency in humans administered orally with red ginseng powder, and almost no reports indicating occurrence of side effects or ill effects in the digestive tract are known. By the way, even if the excess Bcl-$x_L$ protein expression-promoting components flow in the blood as a result of oral administration of the high dose(s) of red ginseng powder, only small amounts of the Bcl-$x_L$ protein expression-promoting components appear to pass through the blood-brain barrier. Consequently, as far as the brain is concerned, when the high doses of red ginseng powder is administered orally, optimal amounts of the Bcl-$x_L$ protein expression-promoting components reach the nerve cells or brain cells to increase the expression of Bcl-$x_L$ protein in situ.

Contrary to that, when the low dose(s) of red ginseng powder is administered orally, small amounts of the Bcl-$x_L$ protein expression-promoting components are transferred into blood as compared with oral administration of the high dose(s) of red ginseng powder. As a result, such small but optimal amounts of the Bcl-$x_L$ protein expression-promoting components are likely to increase Bcl-$x_L$ protein expression in the peripheral organs such as the liver and spleen. However, even if the low dose(s) of red ginseng powder is administered orally, blood concentrations of Bcl-$x_L$ protein expression-promoting components do not become so high and the components arriving at the brain after passing through the blood-brain barrier is insufficient. Consequently, Bcl-$x_L$ protein expression in the brain does not increase and the neuroprotective effect may not been seen.

The present inventors speculate that physiologically active substances or drugs can act on cells only when their extracellular fluid concentrations are within a certain range. This concept is going to be accepted in the field of life science. This will be explained in detail by mentioning erythropoietin. One of the inventors (Sakanaka) has already demonstrated that the protective action of erythropoietin on the hippocampal CA1 pyramidal neurons can be noted when erythropoietin is administered intracerebroventricularly only within the daily dose range between 2.5 units and 25 units, and that no neuroprotective action can be seen when the daily doses of erythropoietin are larger or smaller than that (Sakanaka, M. et al., Proc. Natl. Acad. Sci. USA, 95, 4635-4640, 1998).

Candidates for Bcl-$x_L$ protein expression-promoting components in red ginseng powder are various purified saponins or ginsenosides in the crude saponin fraction(s) and non-saponin fraction(s). Purified saponins in the crude saponin fraction(s)(protopanaxadiol saponins, protopanaxatriol saponins or oleanoic acid saponins) are described in Shojis' review (Shoji, Junzo, Chemistry of saponins in ginseng, pp. 251-261, "Ginseng" '95, Kumagaya, Akira, Ed. 1994, Kyoritsu Publ.). About 4 mg of the representative of protopanaxadiol saponins, ginsenoside $Rb_1$ is contained in red ginseng powder 1 g. When red ginseng powder is administered orally, as a result, if decomposition of ginsenoside $Rb_1$ in the digestive tract is suppressed or absorption of ginsenoside $Rb_1$ in the digestive tract is promoted, and if ginsenoside $Rb_1$ transferred into blood can be detected at least in a trace amount, ginsenoside $Rb_1$ is also nominated as one of the components for promoting the expression of Bcl-$x_L$ protein. However, it is reported that oral administration of ginsenoside $Rb_1$ per se does not exhibit ginsenoside $Rb_1$ in serum or organs (Akao, Mitsuaki, et al., The Ginseng Review, 22, 97-102, 1996). There may be almost no possibility that oral administration of ginsenoside $Rb_1$ per se promotes the expression of Bcl-$x_L$ protein in the nervous tissues or the peripheral tissues. Actually, according to previous reports, oral administration of ginsenoside $Rb_1$ itself did not exhibit any physiological actions, and the present inventors have confirmed that oral administration of ginsenoside $Rb_1$ dissolved in distilled water as a vehicle did not exhibit neuroprotective action. Consequently, as described in Japanese Patent Application No. Hei 10-365560 (Brain cell or nerve cell-protective agents comprising ginsenoside $Rb_1$), in order for ginsenoside $Rb_1$ to exhibit neuroprotective action, it is necessary to maintain the concentrations of ginsenoside $Rb_1$ in blood above a certain level.

It is said that the mitochondrion-associated protein $Bcl-x_L$ inhibits binding of Apaf1 to procaspase 9 as a result of its binding with Apaf (Adams J. M. and Cory S., Science, 281, 1322-1326, 1998). If a decrease or a functional decline in $Bcl-x_L$ protein occurs, Apaf1 is released from $Bcl-x_L$ protein to activate procaspase 9 together with a leakage of cytochrome C from mitochondria (Adams J. M. and Cory S., Science, 281, 1322-1326, 1998). Once cytoplasmic procaspase 9 is activated, subsequently caspase 9 and caspase 3 are activated, and a process, in which cells are autolyzed by the actions of these proteases to enter apoptosis, is accelerated. At the stage activating procaspase 9, the cell appears to be committed to death. Consequently, prevention or inhibition of the activation of the procaspase 9 by an enhancer(s) of $Bcl-x_L$ protein expression (ginsenoside $Rb_1$) is a wise method to preclude cell death.

One of the inventors (Sakanaka) reported that when red ginseng powder was administered orally for one week after 5-minute forebrain ischemia, nerve cell death in the hippocampal CA1 area of gerbils was not protected (Wen, T.-C., et al., Acta Neuropathol., 91, 15-22, 1996). Consequently, it was thought in the age of 1996 that application to red ginseng powder on patients with severer brain infarction than transient brain ischemia, e.g. permanent cerebrovascular occlusion, was thought to be unreasonable. However, in SH-SP rats with MCA permanent occlusion which is severer than transient forebrain ischemic attack of gerbils and reflects the pathological state of human cerebral infarction, postischemic oral administration of red ginseng powder for 4 weeks ameliorated the place navigation disorder and reduced cerebral infarct lesion as shown in FIG. 5 and FIG. 6 in the present invention. Consequently, according to the present invention, it was demonstrated that oral administration of red ginseng powder for about 4 weeks after cerebral infarction exhibited therapeutic effects on cerebral infarction.

We have speculated that in the forebrain ischemia model in gerbils, if red ginseng powder was administered orally for about 4 weeks after ischemia, protective effect on neurons in the hippocampal CA1 field may be confirmed. However, in the 5-minute forebrain ischemia model of gerbils, almost all nerve cells in the hippocampal CA1 field fall into death within one week after ischemia. Consequently, in order to determine the effect of oral administration of red ginseng powder for 4 weeks, this model is thought to be improper. Then we used a 3-minute forebrain ischemia model of gerbils and determined the effect of oral administration of red ginseng powder for 4 weeks.

One of the inventors of the present invention (Sakanaka) reported that when the brain temperature of gerbils was maintained at 37° C.±0.2° C. and blood flow of the bilateral common carotid arteries was clamped for 3 minutes and reperfused, about one half of nerve cells in the hippocampal CA1 field degenerated after one week (Sakanaka, M., et al., Proc. Natl. Acad. Sci. USA, 95, 4635-4640, 1998). Further, the present inventors (Sakanaka, Tanaka and Maeda) demonstrated that fragmentation of nerve cell nuclei, an index of apoptosis-like cell death, in the remaining nerve cells was further in progress at this moment, using TUNEL staining (Wen, T.-C., et al., J. Exp. Med., 188, 635-649, 1998; Peng, H., et al., J. Cereb. Blood Flow Metab., 18, 349-360, 1998). Consequently, it was demonstrated that in the hippocampal CA1 field of gerbils with 3-minute but not 5-minute forebrain ischemia, the degeneration of nerve cells progressed after one week of ischemia. We have investigated the effect of oral administration of red ginseng powder for 4 weeks after ischemia using the 3-minute forebrain ischemia model, in which nerve cell death continued relatively for a long term.

According to the method of the inventors (Sakanaka, M., et al., Proc. Natl. Acad. Sci. USA, 95, 4635-4640, 1998; Wen, T.-C., et al., J. Exp. Med., 188, 635-649, 1998; Peng, H., et al., J. Cereb. Blood Flow Metab., 18, 349-360, 1998), blood flow of the bilateral common carotid arteries was clamped for 3 minutes while maintaining the brain temperature of gerbils at 37° C.±0.2° C. under inhalation anesthesia. After the animals awoke, red ginseng powder dissolved in distilled water was administered orally at the dose of 1.5 g/kg/day once a day for 28 days. Sham-operated animals and control animals with 3-minute forebrain ischemia (ischemic control animals) were orally administered with the equal amount of distilled water alone. Thereafter, the step-down passive avoidance task experiments were performed, and the animals were anesthetized with pentobarbital, and were perfused and fixed transcardially with phosphate buffer containing 4% paraformaldehyde and 2.5% glutaraldehyde. The brains were dissected out, embedded in paraffin to prepare paraffin sections 5 µm thick. The neuronal density in 1 mm of the hippocampal CA1 field in each animal was measured according to the method of the inventors (Sakanaka, M., et al., Proc. Natl. Acad. Sci. USA, 95, 4635-4640, 1998; Wen, T.-C., et al., J. Exp. Med., 188, 635-649, 1998; Peng, H., et al., J. Cereb. Blood Flow Metab., 18, 349-360, 1998). Hereinafter, outlines of the step-down passive avoidance task experiment described in the above reference will be described.

On 28 days after 3-minute forebrain ischemia, the gerbil was placed on the safe platform of a conventional step-down passive avoidance apparatus, but at first, the gerbil stepped down onto the grid floor several times, and it received a foot shock by electricity, then returned to the safe platform. During 5-minutes training, most of the gerbils eventually stayed on the safe platform. 24 hours later, the gerbil was again placed on the safe platform while the shock generator was turned off, and the time until it stepped down onto the grid floor (the response latency) was measured as an index of the learning ability of animal.

Figure 12:
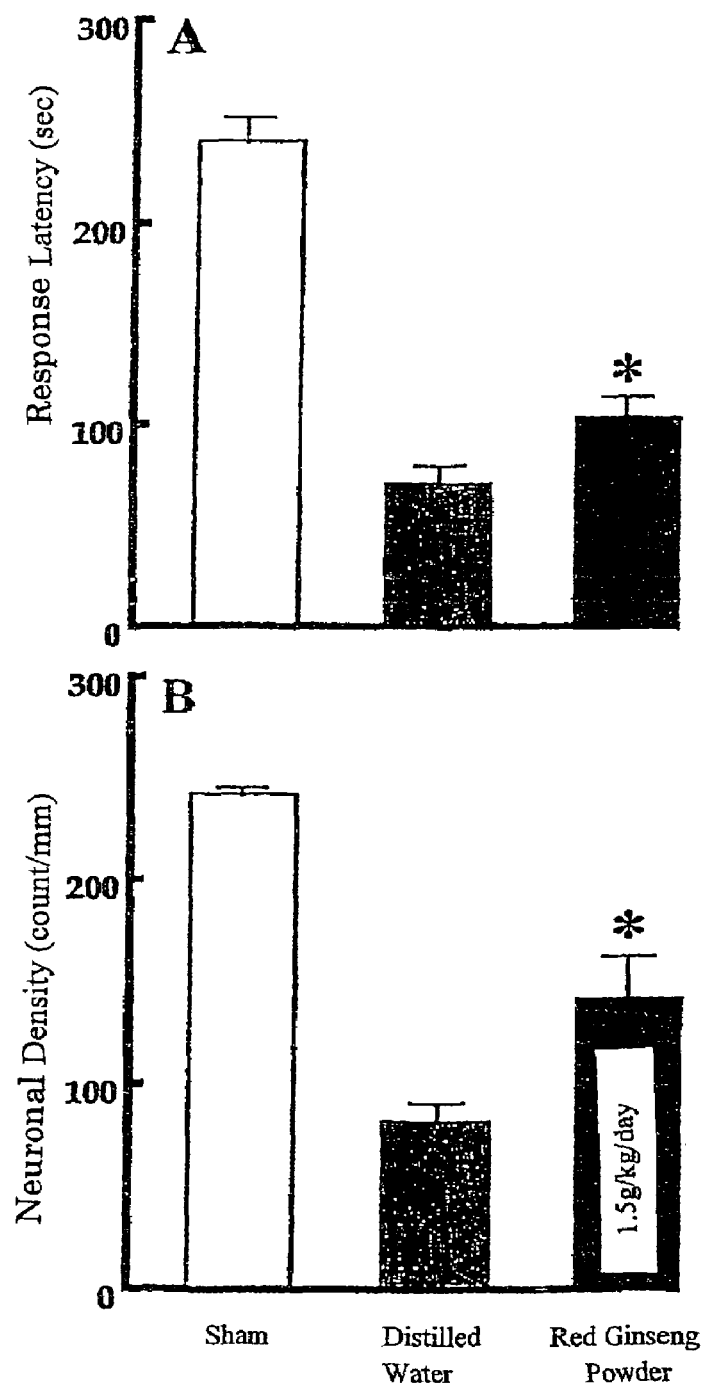
FIG. 12 shows the response latency time and the hippocampal CA1 neuronal density of gerbils administered with red ginseng powder or distilled water, once a day for 28 days after 3-minute forebrain ischemia. The upper figure (A) shows the response latency time of the passive avoidance learning experiments, and the lower figure (B) shows the neuronal densities. Open columns indicate sham-operated group; gray columns indicate distilled water-administered ischemia group; and closed columns indicate red ginseng powder-administered ischemia group.
Figure 13:
FIG. 13 shows light microscopic photographs of the hippocampal CA1 field of (A) a sham-operated animal, (B) a distilled water-administered 3-minute ischemia animal, and (C) a red ginseng powder-administered 3-minute ischemia animal, respectively. Bar indicates 100 μm.

Results are shown in FIG. 12 and FIG. 13. FIG. 12 (A) (upper graph) shows the response latency in the passive avoidance task experiments and FIG. 12 (B) (lower graph) shows neuronal density per 1 mm of the hippocampal CA1 field (numbers/mm). The left of each graph (open column) shows data of sham-operated animals; the center (black) shows data of animals administered with distilled water; and the right (black) shows data of animals administered with red ginseng powder in a dose of 1.5 g/kg/day. As shown in FIG. 12 (A), when red ginseng powder was administered orally for 4 weeks after 3-minute forebrain ischemia, the response latency of the passive avoidance task experiment was significantly extended as compared with that of the passive avoidance task experiment in the group of ischemic animals administered with distilled water. Further, as shown in FIG. 12 (B), when red ginseng powder was administered orally, the neuronal density in the hippocampal CA1 was significantly increased as compared with the group of ischemic animals administered with distilled water.

FIG. 13 shows the light microscopic photographs of the hippocampal CA1 field of (A) (upper photograph) a sham-operated animal; (B) (center photograph) an ischemic animal administered with distilled water; and (C) (lower photograph) an ischemic animal administered with red ginseng powder. As shown in FIG. 13, in the 3-minute ischemic animals administered with distilled water (B), nerve cells (neurons) further degenerated (to die) on the later days after 1 week and the surving neurons in the hippocampal CA1 field at one week after ischemia, which were about ½ of the normal neurons in number, were decreased up to about ¼ of the normal neurons at the 28th day after ischemia as compared with the sham-operated animals (A). However, when red ginseng powder was administered orally for 28 days after 3-minute ischemia, the neuron death that occurred from the 1st week to 28th day after ischemia was significantly suppressed.

Consequently, this animal model indicates that even in case of the relatively mild 3-minute ischemia, nerve cells or neurons in the brain are gradually going to death and the higher neuronal functions are damaged. The phenomenon of long term neuronal degeneration similar to this animal model can be found sometimes in patients experienced with mild transient cerebral ischemic attack (TIA), cerebral infarction, cerebral hemorrhage or subarachnoidal hemorrhagic attack, patients with carbon monoxide poisoning and in patients with nerve neurodegenerative diseases. Common features observed in these patients are that the higher neuronal function disorder become severe since the nerve cell death in the brain slowly progresses as time passes even if the initial higher neuronal function disorder is relatively mild. The experimental fact that oral administration of red ginseng powder upregulating the expression of $Bcl-x_L$ protein after 3-minute ischemia suppresses gradually progressing neuronal degeneration in the hippocampal CA1 field indicates that oral administration of the high dose(s) of red ginseng powder is effective for treatment or therapy of the above described patients. As explained above, oral administration of red ginseng powder exhibits favorable effects and efficacy for any diseases or symptoms accompanying cell death through upregulation of $Bcl-x_L$ protein expression. Consequently, in case where any diseases accompanying cell death are newly identified, red ginseng powder, red ginseng extracts, crude saponin fractions or ginsenosides can be used as the first choice drug.

After the experiments with oral administration of red ginseng powder, the present inventors investigated whether brain edema after cerebral infarction (cerebral embolism) is improved by repetitive or continuous intravenous administration of small dose(s) of ginsenoside $Rb_1$ or not.

Male SH-SP rats, at the age of 12-13 weeks, were used. Animals were bred in a room furnished with 12 hours light and dark cycles and water and feeds were supplied ad libitum. The cortical branch of the left middle cerebral artery (MCA) of SH-SP rats were coagulated and cut under inhalation anesthesia. Immediately after MCA permanent occlusion, ginsenoside $Rb_1$ dissolved in physiological saline was infused once intravenously (6 μg or 60 μg), subsequently intravenously infused continuously for 28 days by using an Alza osmotic minipump (6 μg/day or 60 μg/day).

Control animals with MCA permanent occlusion (ischemic control animals) and sham-operated animals were administered with the same amount of physiological saline alone.

At 32 days after MCA permanent occlusion, the SH-SP rats were anesthetized with chloral hydrate, and they were perfused and fixed transcardially with 0.1 mole phosphate buffer containing 4% paraformaldehyde. The brains were dissected out and cerebrocortical infarct lesions were photographed.

Figure 14:
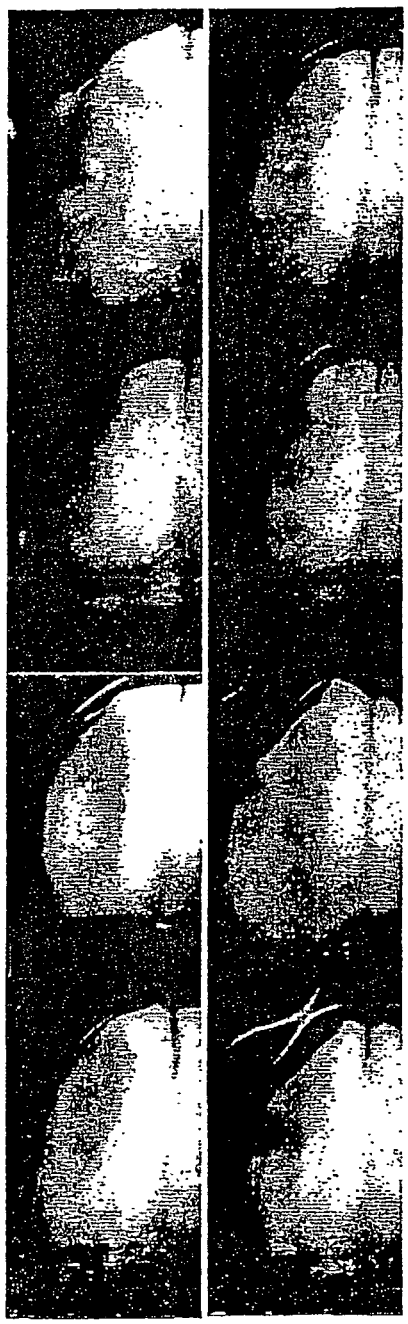
FIG. 14 shows photographs of cerebrocortical infarct lesion. The upper photographs are 8 cases of the ischemia group administered intravenously with physiological saline and the lower photographs are 8 cases of the ischemia group administered intravenously with ginsenoside $Rb_1$ (6 μg/day).
Figure 14:
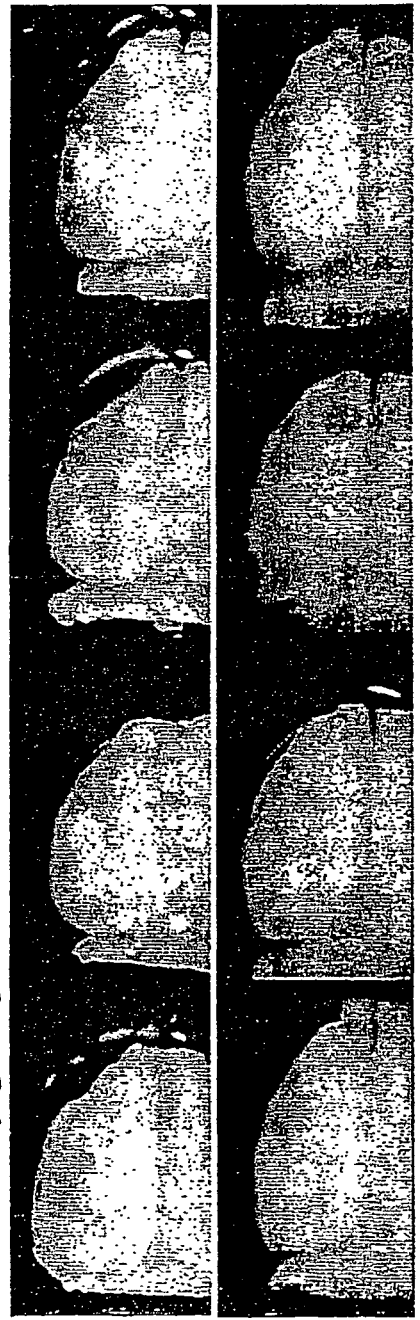

Results are shown in FIG. 14.

In FIG. 14, the upper photographs are stereomicroscopic photographs of brains of 8 animals with cerebral infarction (cerebral embolism) administered with physiological saline, taken from the dorsal side. In FIG. 14, the lower photographs are stereomicroscopic photographs of brains of 8 animals with cerebral infarction (cerebral embolism) administered with ginsenoside $Rb_1$ (6 μg/day), taken from the dorsal side. Since the top edge of the brain is arranged toward the direction of right side, the left cerebral hemisphere with darkened cerebral infarct lesion is observed on the upper side of the cerebral longitudinal fissure. The normal right cerebral hemisphere observed on the lower side of the cerebral longitudinal fissure was included partially in the stereomicroscopic photographs. As shown in the upper photographs of FIG. 14, in cases of cerebral infarction administered with physiological saline, the darkened cerebral infarct lesions in the left cerebral hemisphere expanded largely. Moreover, the left cerebral hemisphere is larger than the right cerebral hemisphere in all cases, although some differences among the cases are observed. Especially, among the cases of cerebral infarction administered with physiological saline, in the brain of the right end on the first row and in the second brain from the left on the second row, the left cerebral hemisphere is obviously larger than the right cerebral hemisphere. This indicates that brain edema appears in the left cerebral hemisphere with permanent MCA occlusion and the brain pressure or the intracranial pressure is presumably increased.

As shown in lower photographs of FIG. 14, in the cases of cerebral infarction (cerebral embolism) administered intravenously with ginsenoside $Rb_1$ (6 μg/day), cerebral infarct lesions are obviously reduced in all cases and no differences in size between the left cerebral hemisphere and the right cerebral hemisphere is observed. Namely, cerebral edema disappears by repetitive or continuous intravenous administration of ginsenoside $Rb_1$ as does oral administration of red ginseng powder.

In Japanese Patent Application No. Hei 10-365560, PCT/JP99/02550 (Brain cell or nerve cell-protective agents comprising ginsenoside $Rb_1$), Japanese Patent Application No. Hei 11-340850, PCT/JP99/06804 (Cerebrovascular regeneration/reconstruction promoters and nerve tissue secondary degeneration inhibitors comprising ginsenoside $Rb_1$), the present inventors (Sakanaka and Tanaka) measured areas of the left cerebral hemispheres and the left cerebrocortical infarct lesions on the photographs by using an image analyzer. The left cerebrocortical infarct areas were divided by the left cerebral hemispheric areas to calculate ratios of the cerebrocortical infarction (%). As the results, the ratio of cerebrocortical infarction was significantly reduced in the groups of cerebral infarction with intravenous administration of ginsenoside $Rb_1$ as compared with the group of cerebral infarction with administration of physiological saline. Since the ratio of cerebrocortical infarction is calculated based on the area of infarction, and the mean value of the ratio in the groups intravenously administered with ginsenoside $Rb_1$ is reduced to about 50% or less compared with that of the group administered with physiological saline, the actual volume of infarction appears to be reduced to about ¼ by intravenous administration of ginsenoside $Rb_1$. Needless to day, ginsenoside $Rb_1$, which can decrease the volume of cerebral infarct lesion to about ¼ of the volume of cerebral infarct lesion in animals administered with physiological saline after 32 days of permanent occlusion of MCA by low doses of repetitive or continuous intravenous administration after permanent occlusion of a part of cerebral blood vessels (e.g. MCA), is the first compound in the history. The low doses of ginsenoside $Rb_1$ may protect brain cells (including glial cells) or nerve cells in the ischemic penumbra for long term from ischemic invasion through multiple excellent action mechanisms such as suppressive action on apoptosis-like nerve cell death, promoting action on Bcl-$x_L$ expression and promoting action on regeneration and/or reconstruction of cerebral blood vessels (Japanese Patent Application No. Hei 10-365560, PCT/JP99/02550: Brain cell or nerve cell-protective agents comprising ginsenoside $Rb_1$; Japanese Patent Application No. Hei 11-340850, PCT/JP99/06804: Cerebrovascular regeneration/reconstruction promoters and nerve tissue secondary degeneration inhibitors comprising ginsenoside $Rb_1$). Further, as far as low doses of ginsenoside $Rb_1$ are intravenously administered, ginsenoside $Rb_1$ does not promote hemorrhagic tendency. Therefore, ginsenoside $Rb_1$ at low doses can be administered to patients, who developed cerebral infarction, cerebral hemorrhage or subarachnoidal hemorrhage, before diagnosing the pathological type of cerebral apoplexy by CT inspection. Consequently, ginsenoside $Rb_1$ has broader usages, effects and efficacy than the conventional thrombolytic agents.

In addition to the above favorable action mechanisms of the low concentrations of ginsenoside $Rb_1$, the present invention found that ginsenoside $Rb_1$ can be used as excellent agents for preventing, treating or curing cerebral edema. Generally, the pathological conditions of cerebral edema or brain and nervous tissue edema frequently appear in cases of cerebral hemorrhage, cerebral infarction, cerebral embolism, subarachnoidal hemorrhage, intracranial hemorrhage, head injuries, neurotrauma, poisoning, encephalitis, brain tumor, meningitis, spinal cord injuries, during convulsive attack, after convulsive attack, under neurosurgical operations, after neurosurgical operations, under surgical operations of the vertabrae, after surgical operations of the spinal cord, in cases of the resuscitation after cardiac arrest or apnea, and cerebral edema or brain and nervous tissue edema makes worse the vital prognosis and neurological symptoms of patients. Consequently, the present experimental findings wherein repetitive or continuous intravenous administration of ginsenoside $Rb_1$ at low doses could treat or cure cerebral edema after onset of cerebral infarction (cerebral embolism) indicate the usefulness of ginsenoside $Rb_1$ on prevention, treatment or therapy of edema(ta) of brain and nervous tissues accompanied by the above diseases, sicknesses, symptoms or syndromes.

Further, the pathological state of edema in the living or viable tissues is known to occur not only in the cerebral tissues in which a cerebral vessel(s) is permanently occluded but also in the peripheral organs or tissues with peripheral vascular occlusion and blood flow disturbance. Consequently, based on the present experimental results that cerebral edema was improved or cured by intravenous administration of the low doses of ginsenoside $Rb_1$ after permanent occlusion of a cerebral vessel(s) (MCA), indicate that ginsenoside $Rb_1$ is effective for circulatory disorders in the peripheral tissues or peripheral organs (e.g. aortitis syndrome, collagen diseases, acute peripheral arterial embolism, thromboangiitis obliterans, arteriosclerosis obliterans, Raynaud's disease, Raynaud's syndrome, trauma, hemorrhoids, myocardial infarction, bedsores, diabetic skin ulcer, peripheral circulation disorder or failure, angina pectoris and ischemia—reperfusion injuries of cardiac muscle, liver and kidneys). Of course, among the above diseases, edema(ta) of the lesioned tissues accompanied by hemorrhoids or bedsores is treated by externally or intrarectally applying an appropriate base(s) admixed with ginsenoside $Rb_1$.

In Japanese Patent Application No. Hei 10-365560, PCT/JP99/02550 (Brain cell or nerve cell-protective agents comprising ginsenoside $Rb_1$), we (Sakanaka and Tanaka) have already invented that repetitive or continuous intravenous administration of ginsenoside $Rb_1$ at low doses reduced cerebral infarct lesion to the extent that could not be imagined from the previously reported protective actions on the ischemic brain by peripheral (intraperitoneal) administration of the higher doses of ginsenoside $Rb_1$, single intravenous administration of the higher doses of ginsenoside $Rb_1$ or intracerebroventricular administration of ginsenoside $Rb_1$. Namely, the above invention found that cerebral infarct lesion (cerebral embolism lesion) was reduced to about ¼ of the control group (cerebral infarction rats administered with physiological saline) even at one month after the onset of cerebral embolism by continuous intravenous administration of ginsenoside $Rb_1$ (6-60 μg/day) at low doses for 28 days after permanent occlusion of the MCA (i.e. after the onset of cerebral embolism) in SH-SP rats. Consequently, ginsenoside $Rb_1$ is the first medicinal or pharmaceutical composition which can be administered intravenously after the onset of cerebral embolism or infarction to reduce cerebral infarct lesion (cerebral embolism lesion), at one month after the onset, to about ¼ of the control animals. Ginsenoside $Rb_1$ is a component in the crude saponin fraction(s) of ginseng and is not detected in blood by oral administration. Further, according to our experience, oral administration of ginsenoside $Rb_1$ per se did not exhibit any protective action on the ischemic brain, as a result, until we have made the patent application (Japanese Patent Application No. Hei 10-365560, PCT/JP99/02550: Brain cell or nerve cell-protective agents comprising ginsenoside $Rb_1$), the pharmacological action of ginsenoside $Rb_1$, especially by its oral administration, has been denied (Kobashi, et al., Ginseng '95, pp. 6-18, Kumagaya, Akira Ed., Kyoritsu Publishing Co.). Consequently, in Japanese Patent Application No. Hei 10-365560, PCT/JP99/02550 (Brain cell or nerve cell-protective agents comprising ginsenoside $Rb_1$), it was demonstrated for the first time that repetitive or continuous intravenous administration of ginsenoside $Rb_1$ had excellent effects, efficacy and usages independent of medicinal ginseng.

Figure 15:
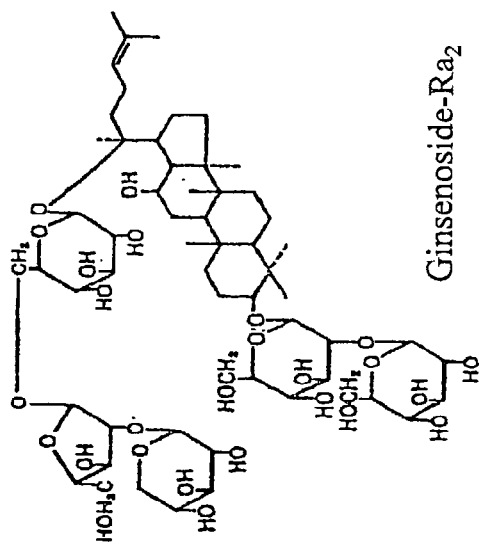
FIG. 15 shows chemical structures of representative saponins contained in medicinal ginseng.
Figure 15:
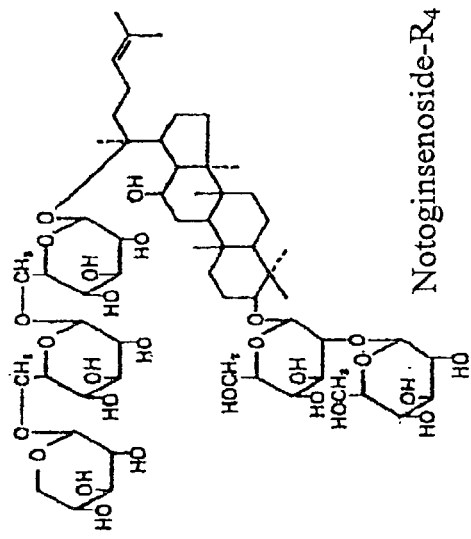
Figure 15:
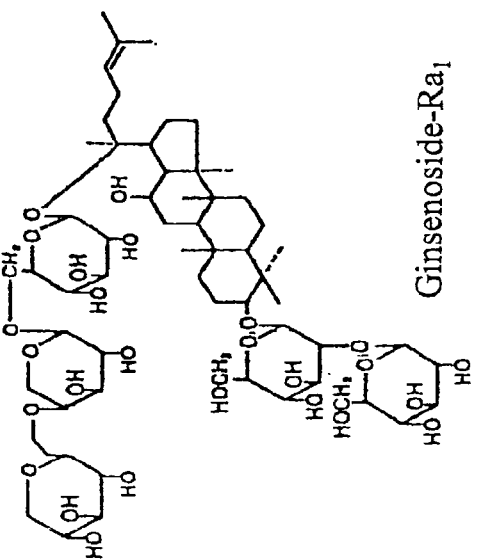
Figure 15:
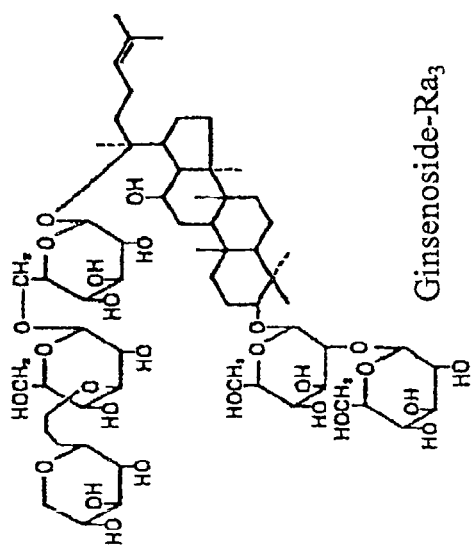
Figure 15:
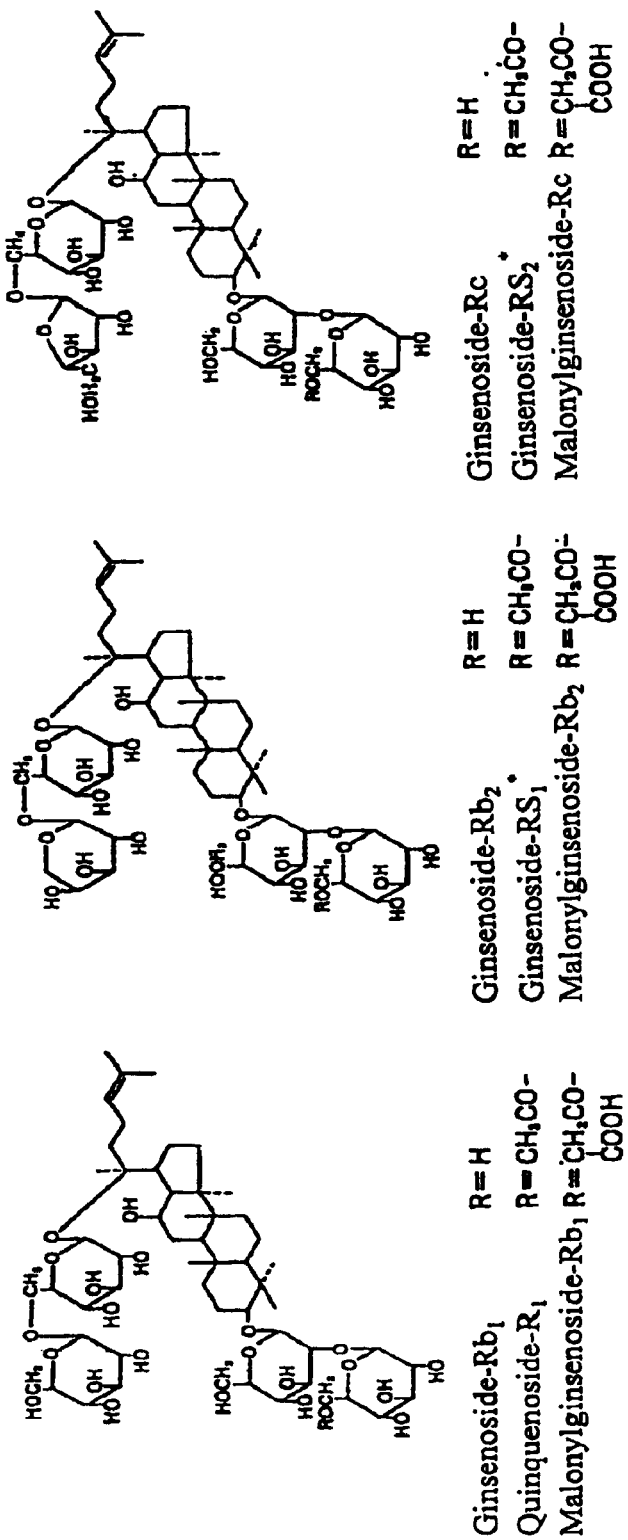
Figure 15:
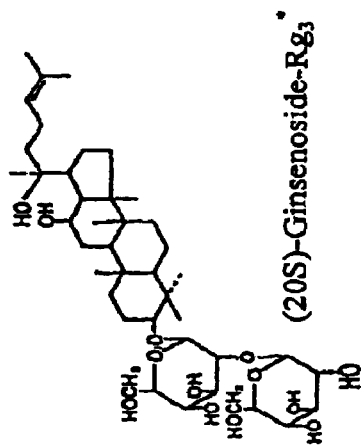
Figure 15:
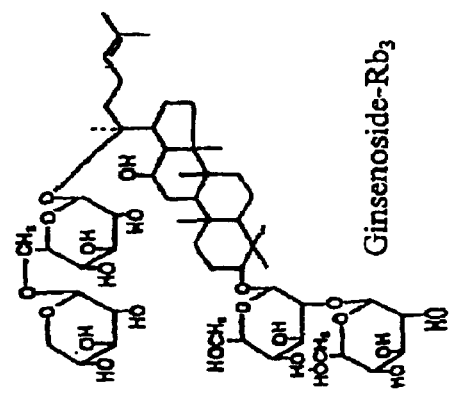
Figure 15:
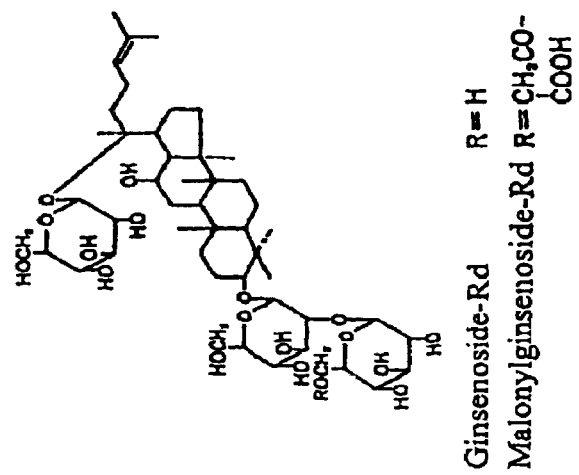
Figure 15:
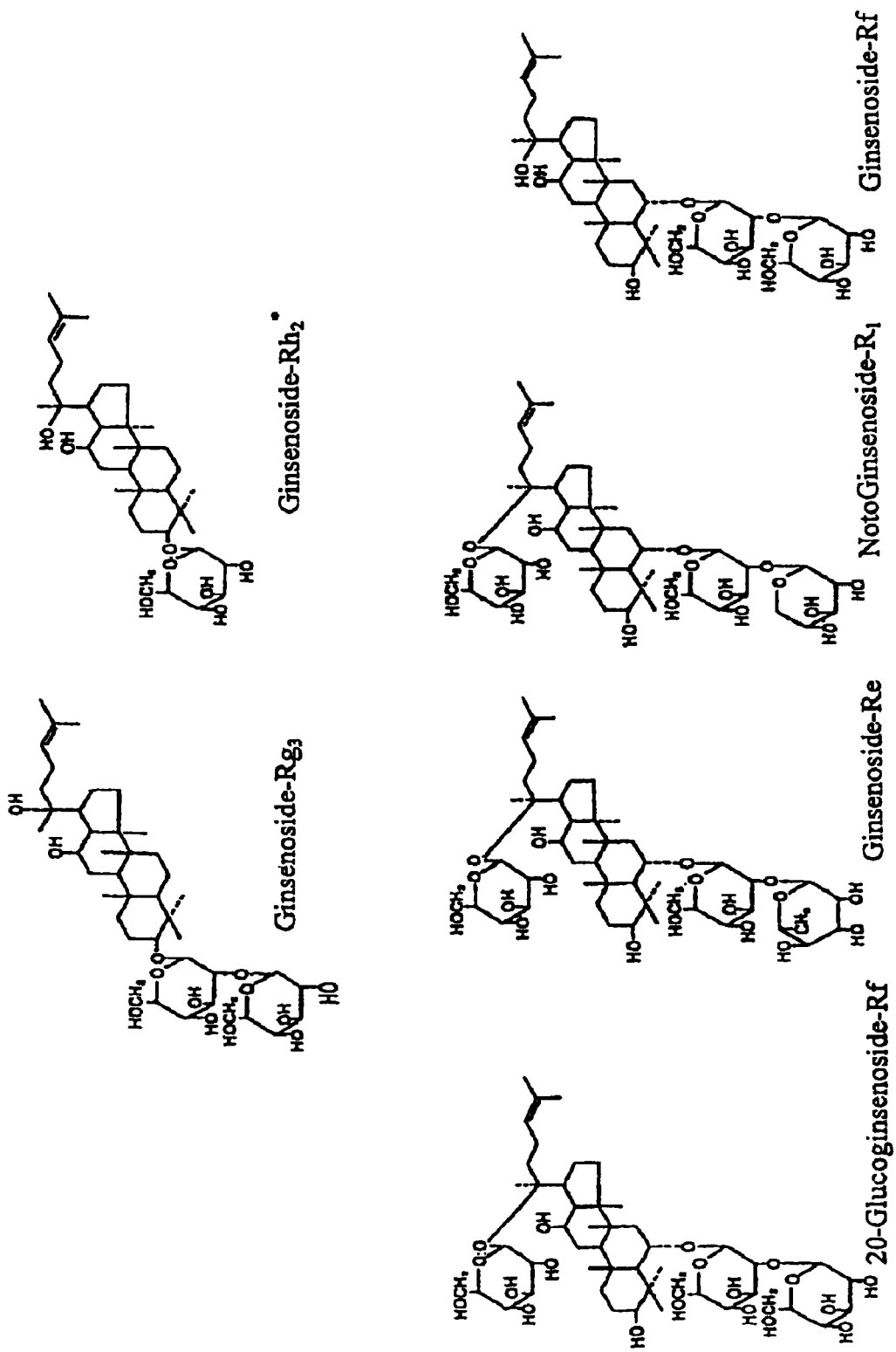
Figure 15:
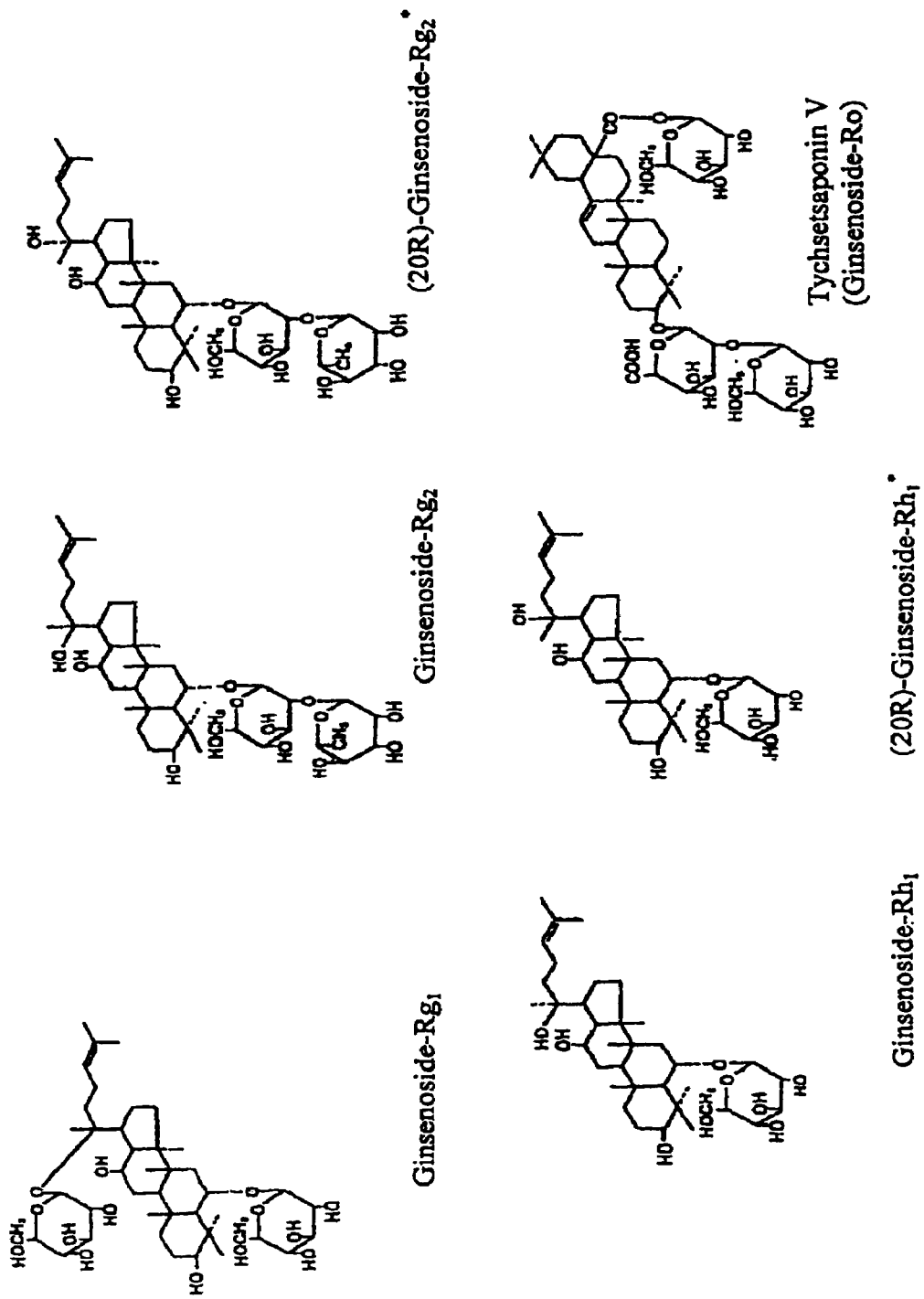

Oral administration of ginsenoside $Rb_1$ itself does not exhibit any protective actions on the ischemic brain, but oral administration of red ginseng powder exhibits an excellent protective action on the ischemic brain, even though inferior to the intravenous administration of ginsenoside $Rb_1$ as shown in the present invention. These findings indicate that red ginseng powder contains cytoprotective components other than ginsenoside $Rb_1$. Further, in Japanese Patent Application No. Hei 10-365560, PCT/JP99/02550 (Brain cell or nerve cell-protective agents comprising ginsenoside $Rb_1$) and in Japanese Patent Application No. Hei 11-243378, PCT/JP99/06804 (Cerebrovascular regeneration/reconstruction promoters and nerve tissue secondary degeneration inhibitors comprising ginsenoside $Rb_1$), we (Sakanaka and Tanaka) have invented that repetitive or continuous intravenous administration of ginsenoside $Rb_1$ at low doses exhibited excellent therapeutic effects on spinal cord injury and neurotrauma. Consequently, the possibility is left open that other purified saponins having similar chemical structures to ginsenoside $Rb_1$ have the same favorable effects. In order to prove this speculation, the present inventors have investigated the effects of repetitive or continuous intravenous administration of a crude saponin fraction of medicinal ginseng (red ginseng powder) using model rats with spinal cord injury. As shown in FIG. 15, since besides ginsenoside Rb$_1$ there are at least about 30 types of purified saponins or ginsenosides in the crude saponin fraction(s) of medicinal ginseng having similar chemical structures (Shoji, Ginseng '95, pp. 251-261, Kumagaya, Akira Ed., Kyoritsu Publishing Co.), if repetitive or continuous intravenous administration of a low dose(s) of the crude saponin fraction(s) (crude ginseng saponins, CGS) exhibits therapeutic effects on spinal cord injury similar to ginsenoside Rb$_1$, it can be said that any one of purified saponins in the crude saponin fraction(s) can be used for prevention, treatment or therapy of neurotrauma or spinal cord injury.

In FIG. 15, ginseng saponins or ginsenosides in the crude saponin fractions are shown: FIG. 15: ginsenoside Ra$_1$; ginsenoside Ra$_2$; ginsenoside Ra$_3$; notoginsenoside Ra$_4$; ginsenoside Rb$_1$(R=H); quinquenoside R$_1$ (R=CH$_3$O—); malonylginsenoside Rb$_1$ (R=HOOC—CH$_2$CO—); ginsenoside Rb$_2$ (R=H); ginsenoside RS$_1$ (R=CH$_3$CO—); malonylginsenoside Rb$_2$ (R=HOOC—CH$_2$CO—); ginsenoside Rc (R=H); ginsenoside RS$_2$ (R=CH$_3$CO—); malonylginsenoside Rc (R=HOOC—CH$_2$CO—); ginsenoside Rd (R=H); malonylginsenoside Rd (R=HOOC—CH$_2$CO—); ginsenoside Rb$_3$; (20S) ginsenoside Rg$_3$; ginsenoside Rg$_3$; ginsenoside Rh$_2$; 20-glucoginsenoside Rf; ginsenoside Re; notoginsenoside R$_1$; ginsenoside Rf; ginsenoside Rg$_1$; ginsenoside Rg$_2$; (20R)-ginsenoside Rg$_2$; ginsenoside Rh$_1$; (20R)-ginsenoside Rh$_1$; and tychsetsaponin V (ginsenoside Ro).

The present inventors have investigated the effects of repetitive or continuous intravenous administration of ginsenoside Rb$_1$ using rats with spinal cord injury and the effects were compared with those of repetitive or continuous intravenous administration of a crude saponin fraction of medicinal ginseng. If pressure is loaded on certain spinal segments such as the lower thoracic cord, not only nerve cells (neurons) in the gray matter of the same region but also fiber tracts or pathways in the white matter of the same region are damaged. The damages to the fiber tracts or pathways of the white matter are further developed to the distal portions (caudal portions) as well as causing the secondary degeneration of the origins of the fiber tract or pathways, namely the upper nerve cell bodies (i.e. origins) which project fibers (nerve processes) to the fiber tracts or pathways. As a result, the damages to the fiber tracts or pathways of the white matter in the lower thoracic cord, which received compression loading, induce the secondary degeneration of the origins (nerve cell bodies) sending fibers (also termed nerve processes or axons) to the fiber tracts or pathways as well as the secondary degeneration of fiber tracts located distal to the lower thoracic cord (i.e. lumbar cord and sacral cord) to cause paraplegia of both limbs. Further, since the innervation from the brain regions proximal to the lumbar cord and sacral cord is cut off due to damage to the lower thoracic cord, the secondary degeneration of nerve cells in the gray matters of the lumbar cord and sacral cord is further induced, as a result, paraplegia of the limbs can not be recovered. For that model of the spinal cord injury, the present inventors have used male Wistar rats (body weight about 300 g) loaded with 20 g of compression on the lower thoracic cord for 20 minutes.

Under inhalation anesthesia by a mixture of nitrous oxide and halothane, the rats were loaded with 20 g of compression on the lower thoracic cord for 20 minutes. After more than 30 minutes passed, ginsenoside Rb$_1$ dissolved in physiological saline was injected once into the left femoral vein (12 μg or 60 μg), thereafter continuous or repetitive intravenous administration of ginsenoside Rb$_1$ was performed for 7 days by using an Alza osmotic minipump (12 μg/day or 60 μ/day). Control animals and sham-operated animals were administered with the same amount of physiological saline (vehicle) alone. The open field locomotor scores [Basso, Bettie and Bresnakan (BBB) scores] were measured in each animal before loading spinal cord injury, on the day of spinal cord injury and from 1st day to 7th day after the spinal cord injury for use as an index of motor functions (Basso D. M. et al., J. Neurotrauma, 13, 343-359, 1996). BBB scores of the sham-operated rats (normal rats) were 20-21.

Figure 16:
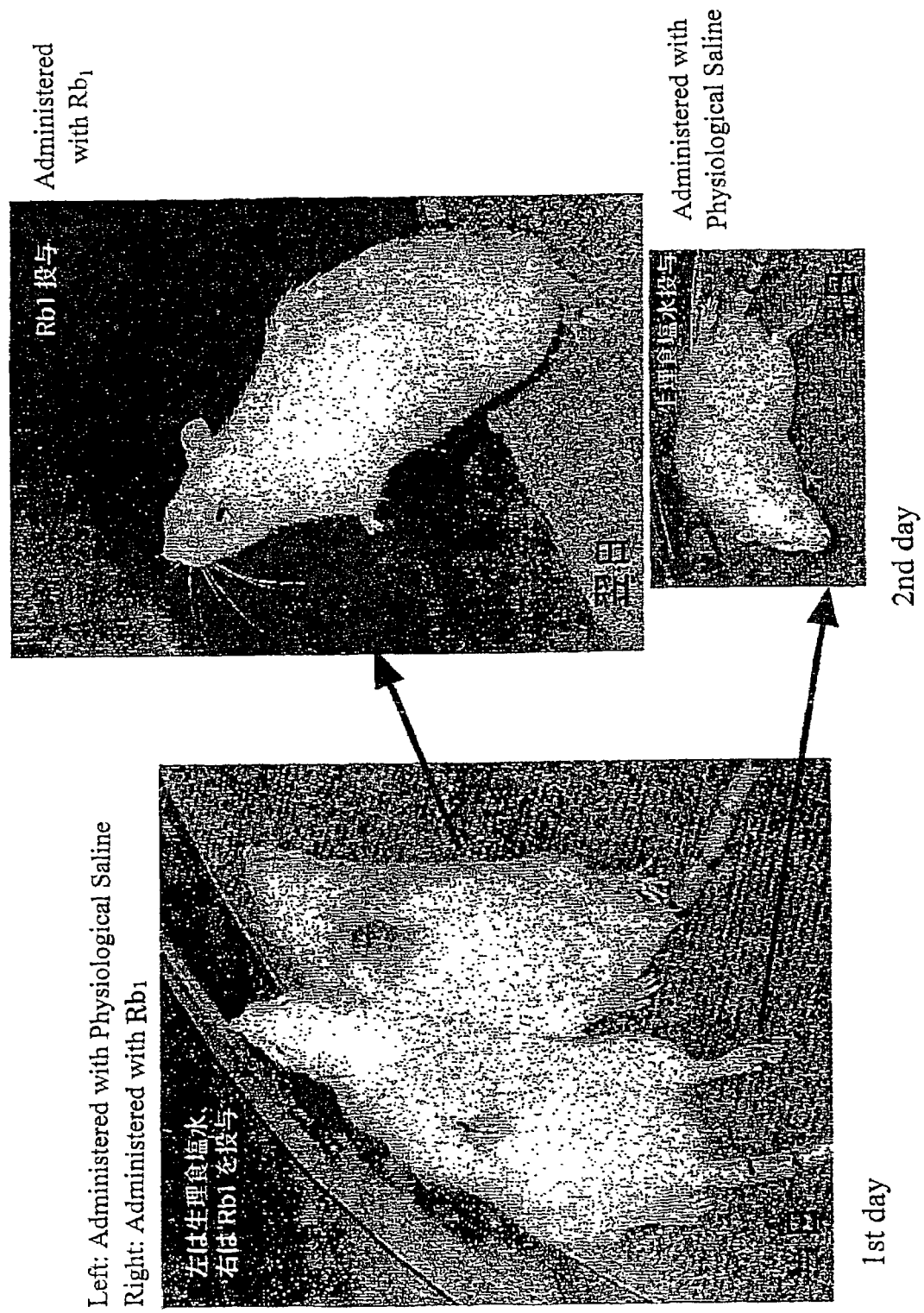
FIG. 16 is photographs instead of drawings, showing rats administered intravenously with physiological saline or ginsenoside $Rb_1$ (60 μg/day) in the day of spinal cord injury and in the next day of spinal cord injury.

FIG. 16 is composed of photographs in replace from drawings, showing the results of a control rat administered with physiological saline on the 1st and the 2nd day after spinal cord injury, and the results of another rat administered with ginsenoside Rb$_1$ (60 μg/day) on the 1st and the 2nd day after spinal cord injury. In FIG. 16, the lower photograph shows 2 rats on the day of spinal cord injury, and the rat on the left side is administered with physiological saline, and the rat on the right side is administered intravenously with ginsenoside Rb$_1$ (60 μg/day). The upper left photograph in FIG. 16 is the rat administered with ginsenoside Rb$_1$ on the next day of spinal cord injury, and on the right side is the rat administered with physiological saline.

As shown in FIG. 16, the rats administered with physiological saline or ginsenoside Rb$_1$ obviously exhibited paraplegia in both hindlimbs on the day when the compression of 20 g was loaded on the lower thoracic cord for 20 minutes. However, when intravenous administration of ginsenoside Rb$_1$ (60 μg/day) was started at more than 30 minutes after loading the compression of 20 g on the lower thoracic cord for 20 minutes, the paraplegia of both hindlimbs was significantly ameliorated 1-2 days later, and the rat could stand up with the aid of a holding bar as shown in FIG. 16. However, paraplegia of the hindlimbs of the rat administered with physiological saline alone was not ameliorated.

Figure 17:
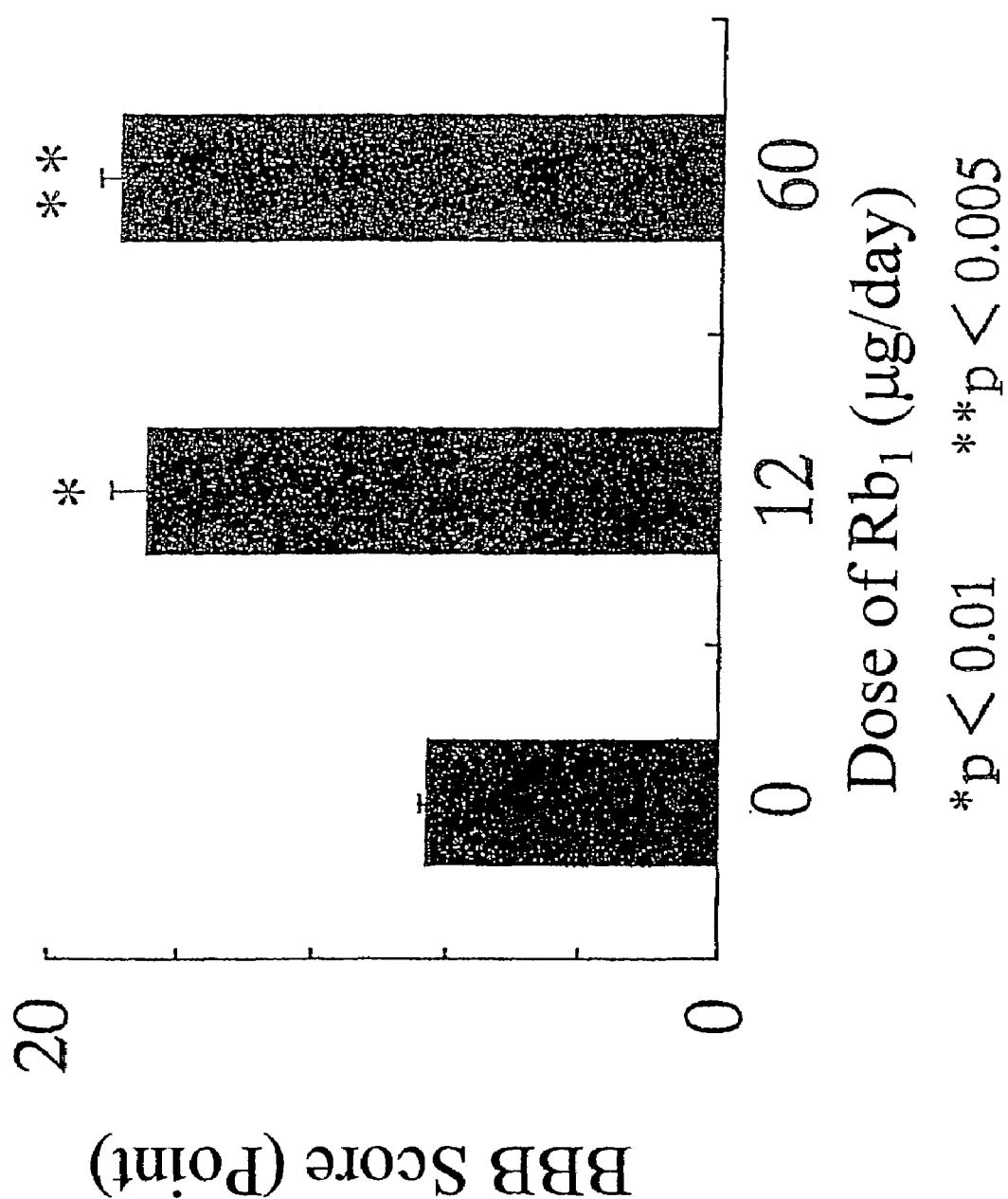
FIG. 17 shows BBB scores of rats administered intravenously with physiological saline or ginsenoside $Rb_1$ (12 μg/day and 60 μg/day) on the 7th day after spinal cord injury.

FIG. 17 shows a graph which quantifies the motor abilities of rats by using BBB scores at the 7th day after spinal cord injuries. In FIG. 17, the vertical axis indicates points of BBB score, and the horizontal axis indicates dosage of ginsenoside Rb$_1$ (μg/day). Statistical analyses were performed by Mann-Whitney U-test. Data are represented as mean±SE. *: $p<0.01$, **: $p<0.005$.

As shown in FIG. 17, the motor abilities of rats with spinal cord injuries were significantly ameliorated in a dose-dependent manner by intravenously administered ginsenoside Rb$_1$.

Solu-Medrol (methylprednisolone), which is used as a remedy for spinal cord injuries in the clinical field at a dose of 30 mg/kg, was intravenously infused into the femoral veins of rats with spinal cord injuries on the same schedule prepared by the inventors for administering ginsenoside Rb$_1$. However no significant ameliorating effects on paralysis or paraplegia were noted, and about 40% of the experimental animals (4 out of 10 rats) died within 7 days after spinal cord injuries. In the Solu-Medrol-administered rats, healing of the operative dorsal wounds was obviously delayed as compared with that of the rats administered with physiological saline. However, in the cases of the ginsenoside Rb$_1$-administered rats, no such ill effects were noted. This fact indicates that ginsenoside Rb$_1$ is superior to Solu-Medrol as a remedy for spinal cord injuries and neurotrauma. Furthermore, the required dose of ginsenoside Rb$_1$ is lower than that of Solu-Medrol. In addition, ginsenoside Rb$_1$ has neither an immunosuppressive action nor a peptic ulcer-inducing action like Solu-Medrol has. Consequently, ginsenoside Rb$_1$ is expected to be a quite safe remedy for spinal cord injuries and neurotrauma.

Based on the present experimental results using rats with spinal cord injuries, the therapeutic effects of the preparations for intravenous administration comprising ginsenoside $Rb_1$ on spinal cord injuries are thought to be historically the strongest in the world. Presumably, ginsenoside $Rb_1$ or its metabolites can exhibit extremely strong therapeutic actions for improving spinal cord injuries. This supports the notion that ginsenoside $Rb_1$ or its metabolites can be a leading compound(s) for the treatment or therapy of spinal cord injuries or neurotrauma.

The present experimental results furthermore support that low doses of ginsenoside $Rb_1$ inhibit secondary degeneration of neural (nervous) tissues after spinal cord injuries. It is well known that nervous tissues are the most vulnerable to traumatic injuries when compared with other peripheral tissues. The fact that a medicinal or pharmaceutical composition comprising ginsenoside $Rb_1$ exhibits markedly favorable effects for therapy, prevention and/or treatment of spinal cord injuries suggests that ginsenoside $Rb_1$ is also effective for therapy or treatment of trauma, wound and/or burn to peripheral tissues other than the central nervous tissue.

Since the therapeutic effects of ginsenoside $Rb_1$ on spinal cord injuries and neurotrauma are epoch-making, this suggests that novel pharmaceutical compounds for therapy or treatment of spinal cord injuries can be synthesized by using ginsenoside $Rb_1$ or its metabolites as a leading compound(s). Further, as a result of identifying the target molecule(s) of ginsenoside $Rb_1$ or its metabolites, novel compounds which can modify the functions of the target molecule(s), are synthesized. Then the development of remedies for spinal cord injuries, neurotrauma or traumatic injuries can be directed.

Further, in cases of spinal cord injuries, apoptosis of glial cells, especially oligodendrocytes, occurs. This injury-induced apoptosis results in demyelination and then in deterioration and progression of neuronal symptoms (Crowe, M. J. et al., Nature Med. 3, 73-76, 1997; Emery, E. et al., J. Neurosurg. 89, 911-920, 1998). The experimental results in which intravenously administered ginsenoside $Rb_1$ significantly ameliorates paralysis or paraplegia of both hindlimbs of rats with spinal cord injuries, indicate that ginsenoside $Rb_1$ inhibits apoptosis of the oligodendrocytes or apoptosis-like nerve cell death and thereby ameliorates symptoms of spinal cord injuries. Consequently, ginsenoside $Rb_1$ of the present invention at low doses and at low concentrations is thought to be useful for prevention, therapy or treatment of brain and nervous diseases accompanied by demyelination (multiple sclerosis, Binswanger's disease, demyelinating encephalitis, chronic hypoperfusion disorder of brain, etc.) through protection of oligodendrocytes. Further, the experimental results, in which intravenously administered ginsenoside $Rb_1$ ameliorates paralysis of both hindlimbs of rats with spinal cord injuries (paraplegia), suggest that injured nerve fibers or neural tissues can be regenerated as a result of administering ginsenoside $Rb_1$.

Next, in order to investigate whether or not the crude saponin fraction(s) of medicinal ginseng exhibits the same effects as those of ginsenoside $Rb_1$ administered continuously or repetitively into the vein, we have administered intravenously in a repetitive or continuous manner a crude saponin fraction at a low dose to the animal models with spinal cord injuries as described above. The crude saponin fraction administered in the present invention was the same as that described in the report by one of the inventors (Sakanaka) (Wen, T.-C., et al., Acta Neuropathol. 91, 15-22, 1996).

Figure 18:
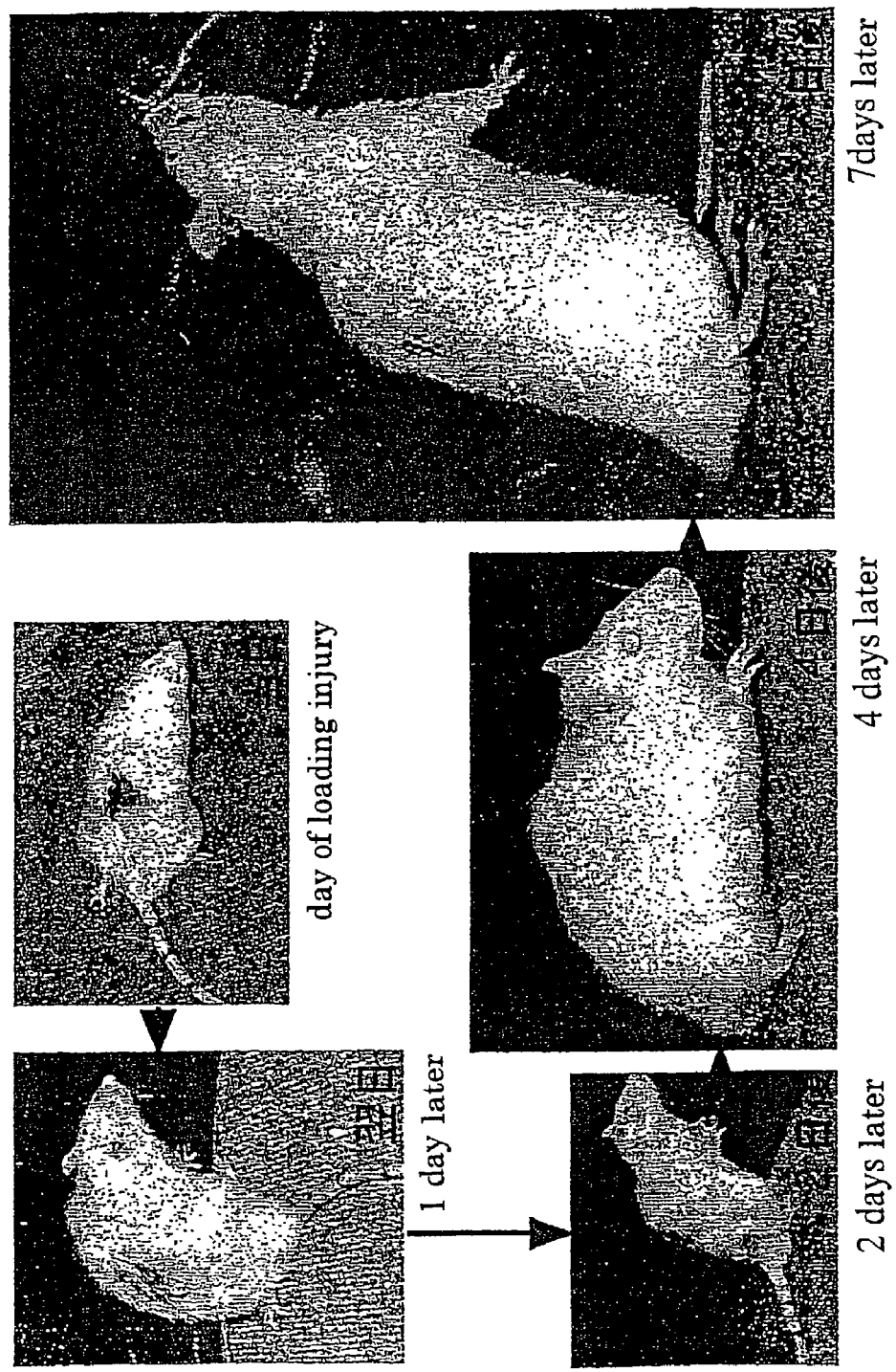
FIG. 18 is photographs instead of drawings showing a rat administered intravenously with a crude saponin fraction of medicinal ginseng (870 μg/day) during 0-7 days after spinal cord injury.
Figure 19:
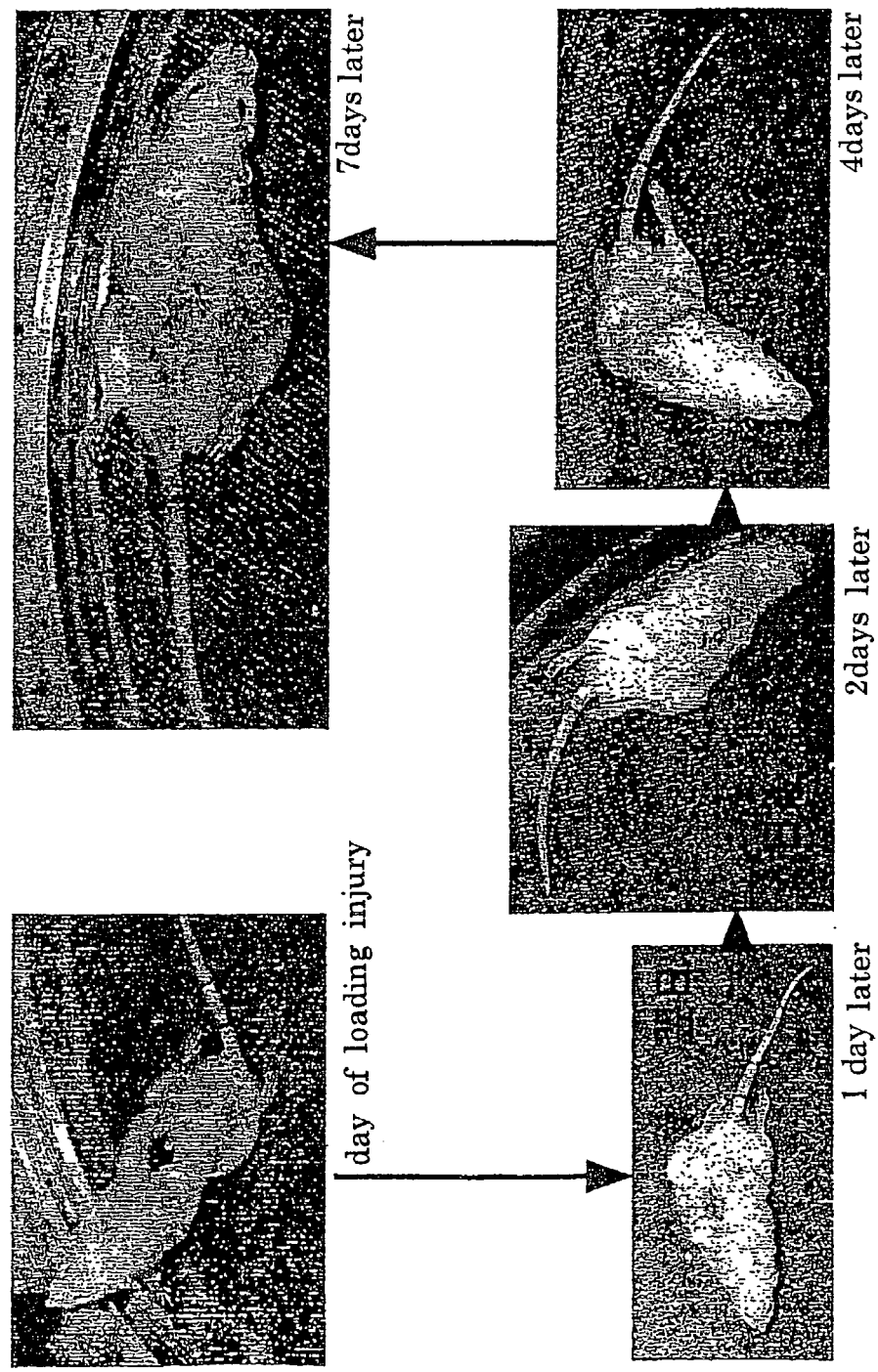
FIG. 19 is photographs instead of drawings showing a rat administered intravenously with physiological saline during 0-7 days after spinal cord injury.

Under inhalation anesthesia by a mixture of nitrous oxide and halothane, the rats were loaded with 20 g of compression on the lower thoracic cord for 20 minutes. More than 30 minutes later, the crude saponin fraction dissolved in physiological saline was infused once into the left femoral vein (870 μg), thereafter continuous intravenous administration of the crude saponin fraction was performed for 7 days by using an Alza osmotic minipump (870 μg/day). Control animals with spinal cord injuries were administered with the same amount of physiological saline (vehicle) alone. Results are shown in FIG. 18 and FIG. 19. FIG. 18 shows the results of a rat administered with the crude saponin fraction and FIG. 19 shows the results of a control rat administered with physiological saline (vehicle). These figures are photographs in place of drawings. In FIG. 18, the left central photograph shows the rat on the day of loading spinal cord injury; the lower left photograph shows the rat on the next day; the lower right photograph shows the rat 2 days after spinal cord injury; the right central photograph shows the rat 4 days after spinal cord injury; and the upper large photograph shows the rat 7 days after spinal cord injury. In FIG. 19: the lower left photograph shows the rat on the day of loading spinal cord injury; the lower right photograph shows the rat on the next day; the right central photograph shows the rat 2 days after spinal cord injury; the upper right photograph shows the rat 4 days after spinal cord injury; and the upper left large photograph shows the rat 7 days after spinal cord injury.

As shown in FIG. 18, on the day of loading spinal cord injuries, the rats exhibited paraplegia in both hindlimbs and could not stand up in spite of intravenous administration of the crude saponin fraction. However, the paraplegia of both hindlimbs of rats was significantly ameliorated thereafter, and the rats could stand up by holding the outer wall of the open field (height 8 cm). On the other hand, as shown in FIG. 19, in the rats administered with physiological saline alone after loading spinal cord injury, paraplegia of the hindlimbs was not ameliorated even at 1 week after spinal cord injuries.

Solu-Medrol (methylprednisolone), which is used as a remedy for spinal cord injuries in the clinical field at a dose of 30 mg/kg, was intravenously infused into the femoral veins of rats with spinal cord injuries on the same schedule prepared by the inventors for administering the crude saponin fraction. However, no significant ameliorating effects on paralysis or paraplegia were noted. In the Solu-Medrol-administered rats, healing of the operative dorsal wounds was obviously delayed as compared with that of the rats administered with physiological saline. However, in the cases of the crude saponin fraction-administered rats, no such ill effects were noted. This fact indicates that the crude saponin fraction(s) is superior to Solu-Medrol as a remedy for spinal cord injuries and/or neurotrauma. Furthermore, the required dose(s) of the crude saponin fraction(s) is smaller or lower than that of Solu-Medrol. In addition, the crude saponin fraction(s), unlike Solu-Medrol, has neither an immunosuppressive action nor a peptic ulcer-inducing action. Consequently, the crude saponin fraction(s) is expected to be a quite safe remedy for spinal cord injuries and neurotrauma.

Based on the present experimental results using rats with spinal cord injuries, the therapeutic effects of the preparations for intravenous administration comprising the crude saponin fraction(s) at low doses on spinal cord injuries are thought to be as excellent as those of ginsenoside $Rb_1$. Consequently, any one or any of purified saponins in the crude saponin fraction(s) or its metabolites may exhibit extremely potent therapeutic actions on spinal cord injuries.

This supports the fact that any one or any of purified saponins in the crude saponin fraction(s) or its metabolites can be a leading compound(s) for exploring novel compounds for the treatment of spinal cord injuries or neurotrauma. Results of the present experiments support that any one or any of purified saponins (FIG. 15) in the crude saponin fraction(s) suppresses the secondary degeneration of nervous tissues (neural tissues) after spinal cord injuries. In the present experiments, a crude saponin fraction of *Panax ginseng* C. A. Meyer is used, but any crude saponin fractions from other ginseng (e.g. Sanchi (Sanshichi) ginseng, Denhichi ginseng, Himalayan ginseng, American ginseng and Tikusetu ginseng and so forth) are likely to exhibit the same results. Consequently, any components in the crude saponin fractions of ginseng appear to be useful for prevention, treatment or therapy of spinal cord injuries, neurotrauma or head injuries.

It is well known that neural or nervous tissues are the most vulnerable to traumatic injuries when compared with other peripheral tissues. The fact that a medicinal or pharmaceutical composition comprising the crude saponin fraction(s) exhibits favorable effects for therapy and/or treatment of spinal cord injuries suggests that low doses or low concentrations of the crude saponin fraction(s) also appear to be effective for treatment or therapy of traumatic injuries to peripheral tissues other than the central nervous tissue.

Further, it is reported that in cases of spinal cord injuries, among glial cells, especially oligodendrocytes are damaged to enter apoptosis, then demyelination occurs and neurological symptoms are deteriorated and made worse (Crowe, M. J. et al., Nature Med. 3, 73-76, 1997; Emery, E. et al., J. Neurosurg. 89, 911-920, 1998). The experimental results in which the intravenously administered crude saponin fraction at a low dose significantly ameliorates paralysis or paraplegia of both hindlimbs of rats with spinal cord injuries, indicate that any one or any of purified saponins in the crude saponin fraction(s) inhibits apoptosis of oligodendrocytes or apoptosis-like nerve cell death and thereby ameliorates symptoms of spinal cord injuries. Consequently, any one or any of purified saponins in the crude saponin fraction(s) of the present invention is thought to be useful for prevention, treatment or therapy of brain and nervous diseases accompanied by demyelination (multiple sclerosis, Binswanger's disease, demyelinating encephalitis, chronic hypoperfusion disorder of brain, etc.) through protection of oligodendrocytes. Further, the experimental results, in which the intravenously administered crude saponin fraction ameliorates paralysis of both hindlimbs of rats with spinal cord injuries (paraplegia), suggest that injured nerve fibers or neural (nervous) tissues can be regenerated as a result of administering the crude saponin fraction(s).

In neural or nervous tissues with spinal cord injuries, edema occurs frequently in the said spinal cord tissues, and neurological symptoms (paraplegia of upper or lower extremities, sexual function disorders, hypogonadism, urination or defecation difficulties, etc.) are deteriorated. The present experimental results that repetitive or continuous intravenous administration of the low doses of the crude saponin fraction(s) exhibits excellent therapeutic effects on spinal cord injuries, indicate usefulness of the crude saponin fraction(s) or any one of components in the crude saponin fraction(s) for prevention, treatment or therapy of edema in the spinal cord tissue.

Based on the above results, the preparations for intravenous administration comprising low doses of the crude saponin fractions or salts thereof suppress the secondary degeneration of neural (nervous) tissues caused by spinal cord injuries. Further, the medicinal or pharmaceutical composition(s) comprising the crude saponin fraction(s) can be a remedy for spinal cord injuries, neurotrauma or head injuries as well as exhibiting effectiveness and efficacy for peripheral tissue injuries or trauma.

Since the therapeutic effects of the crude saponin fractions on spinal cord injuries and neurotrauma are epoch-making, this suggests that novel pharmaceutical compounds for treatment or therapy of spinal cord injuries can be synthesized by using components in the crude saponin fraction(s) or its metabolites as leading compounds. Further, as a result of identifying the target molecules of components in the crude saponin fraction(s) or its metabolites, novel compounds which can modify the functions of the target molecules, are synthesized. Then the development of remedies for spinal cord injuries, neurotrauma or other traumatic injuries can be directed.

In the above-described experimental results using rats with spinal cord injuries, repetitive or continuous intravenous administration of a crude saponin fraction of ginseng (870 μg/day) exhibited the same favorable effects as those of repetitive or continuous intravenous administration of ginsenoside $Rb_1$ (60 μg/day). This indicates that if the crude saponin fraction(s) is repetitively or continuously administered at about 14.5 times larger amount than ginsenoside $Rb_1$, effective concentrations of the crude saponin fraction(s) in the extracellular fluid of lesion tissues can be maintained. In Japanese Patent Application No. Hei 10-365560, PCT/JP99/02550 (Brain cell or nerve cell-protective agents comprising ginsenoside $Rb_1$) and examples 15 and 16 hereinbelow, we (Sakanaka and Tanaka) have demonstrated that ginsenoside $Rb_1$ can exhibit effectiveness and efficacy when its extracellular fluid concentrations in lesioned tissues are kept at 1 ng/ml or less, preferably 10 pg/ml or less, more preferably 100 fg/ml or less. Consequently, with regard to low doses of the crude saponin fraction(s) of the present invention, it is preferable that the preparations comprising the crude saponin fraction(s) are adjusted so that its extracellular fluid concentrations in lesioned tissues are kept at 14.5 ng/ml or less, preferably 145 pg/ml or less, more preferably 1450 fg/ml or less. Since sufficient favorable effects can be obtained when the extracellular fluid concentrations of ginsenoside $Rb_1$ in lesion tissues are kept at 1-100 fg/ml (Japanese Patent Application No. Hei 10-365560, PCT/JP99/02550: Brain cell or nerve cell-protective agents comprising ginsenoside $Rb_1$), the medicinal or pharmaceutical composition(s) or the preparations comprising the crude saponin fraction(s) of the present invention exhibits, sufficient favorable effects at the extracellular fluid concentrations of about 14.5-1450 fg/ml in lesioned tissues.

Repetitive or continuous intravenous administration of ginsenoside $Rb_1$ (60 μg/day) exhibits excellent therapeutic effects on cerebral apoplexy and cerebral infarction as demonstrated by the present inventors (Sakanaka and Tanaka) in Japanese Patent Application No. Hei 10-365560, PCT/JP99/02550 (Brain cell or nerve cell-protective agents comprising ginsenoside $Rb_1$). As shown in the experiments described above, repetitive or continuous intravenous administration of the crude saponin fraction (870 μg/day) exhibits excellent therapeutic effects on spinal cord injuries like the repetitive or continuous intravenous administration of ginsenoside $Rb_1$ (60 μg/day). On the basis of these facts, the repetitive or continuous intravenous administration of the crude saponin fraction (870 μg/day) can be expected to exhibit excellent therapeutic effects on cerebral apoplexy and cerebral infarction as the repetitive or continuous intravenous administration of ginsenoside $Rb_1$ (60 µg/day) dose. Further, the repetitive or continuous intravenous administration of ginsenoside $Rb_1$ in a dose of 6 µg/day also exhibits excellent therapeutic effects on cerebral apoplexy and cerebral infarction. Consequently, the repetitive or continuous intravenous administration of the crude saponin fraction(s) in a dose of 87 µg/day is also likely to exhibit excellent therapeutic effects on cerebral apoplexy and cerebral infarction. Namely, the crude saponin fraction(s) of ginseng exhibits excellent protective effects on brain cells or nerve cells at the doses of 87 µg/day-870 µg/day in rats weighing about 300 g. Consequently, excellent protective effects on brain cells or nerve cells can be obtained by the repetitive or continuous intravenous administration of the crude saponin fraction(s) at the daily doses of 2.9 mg/kg-0.29 mg/kg. However, this is an estimated value of dosing the crude saponin fraction(s) in rats weighing about 300 g, and when the crude saponin fraction(s) is intravenously administered to human, dose/kg may be ½-1/20 of the above. Namely, intravenous administration of the crude saponin fraction(s) in human is, although depending on individual difference and pathological conditions of patients, preferably to set at 1450 µg/kg/day or less and 14.5 µg/kg/day or more.

As shown in example 14 hereinbelow, repetitive or continuous intravenous administration of ginsenoside $Rb_1$ (60 µg/day) increases the expression of $Bcl-x_L$ gene in the brain and nervous tissues. Consequently repetitive or continuous intravenous administration of the crude saponin fraction(s) (870 µg/day) is likely to increase the expression of $Bcl-x_L$ gene. Namely, the crude saponin fraction(s) promotes the expression of $Bcl-x_L$ gene in the neural (nervous) tissues when its extracellular fluid concentrations in lesioned tissues are 14.5 ng/ml or less, preferably 145 pg/ml or less, more preferably 1450 fg/ml or less.

Further, the fact that repetitive or continuous intravenous administration of the crude saponin fraction(s) is useful for prevention, treatment or therapy of spinal cord injuries, cerebral infarction or cerebral apoplexy demonstrates that any one or any of components in the crude saponin fraction(s) exhibits the excellent effectiveness and efficacy against brain and/or nervous diseases hereinbefore. Of course, plural components in the crude saponin fraction(s) may exhibit excellent effects and efficacy against brain and/or nervous diseases hereinbefore. Examples of purified saponins, the representative components in the crude saponin fraction(s), are ginsenoside Ro, ginsenoside $Rb_1$, ginsenoside $Rb_2$, ginsenoside Rc, ginsenoside Rd, ginsenoside Re, ginsenoside Rf, ginsenoside $Rg_1$, ginsenoside $Rg_2$, ginsenoside $Rg_3$, ginsenoside $Rh_1$, ginsenoside $Rh_2$, etc. Among them, the content of ginsenoside $Rb_1$ is known to be 2 times more than that of the other purified saponins. Considering that ginsenoside $Rb_1$ exhibits a nerve cell- or brain cell-protective action at the extracellular concentrations in lesion of 1 ng/ml or less, preferably 10 pg/ml or less, more preferably 100 fg/ml or less, the other purified saponins are also likely to exhibit protective actions on brain cells or nerve cells at the same extracellular concentrations or 1/10 thereof or less. However, components in the crude saponin fraction(s) are not limited within the purified saponins mentioned hereinabove.

Based on the present experimental results mentioned above, it was demonstrated that the crude saponin fraction(s) of medicinal ginseng or any one of constitutional components of the crude saponin fraction(s) exhibits excellent protective actions on brain cells or nerve cells and therapeutic effects on spinal cord injuries, head injuries or neurotrauma as ginsenoside $Rb_1$ dose. Consequently, low concentrations and low doses of the crude saponin fraction(s) or any one of constitutional components in the crude saponin fraction(s) of the present invention have all effects, efficacy and usages of ginsenoside $Rb_1$ described by the inventors in Japanese Patent Application No. Hei 10-365560, PCT/JP99/02550 (Brain cell or nerve cell-protective agents comprising ginsenoside $Rb_1$) and Japanese Patent Application No. Hei 11-243378, PCT/JP99/06804 (Cerebrovascular regeneration/reconstruction promoters and nerve tissue secondary degeneration inhibitors comprising ginsenoside $Rb_1$). Namely, the low concentrations or the low doses of the crude saponin fraction(s) or any one of constitutional components in the crude saponin fraction(s) can increase the expression of a cell death-suppressing gene product $Bcl-x_L$ or regulate the expressions of the other $Bcl-x_L$ family proteins, thereby, suppressing apoptosis of nerve cells or apoptosis-like nerve cell death, as ginsenoside $Rb_1$ dose. Further, the low concentrations and low doses of the crude saponin fraction(s) or any one of constitutional components in the crude saponin fraction(s) can exhibit effectiveness and efficacy for all brain and nervous diseases accompanied by nerve cell death as ginsenoside $Rb_1$ does. Examples of these brain and nervous diseases are Alzheimer's disease, cerebral apoplexy, cerebral infarction, cerebral thrombosis, cerebral embolism, subarachnoidal hemorrhage, transient cerebral ischemic attack, Pick's disease, spinocerebellar degeneration, Parkinson's disease, demyelinating diseases, polyglutamine diseases such as chorea, amyotrophic lateral sclerosis, glaucoma, senile macular degeneration, diabetic retinopathy, central retinal arteriovenous occlusion, retinal detachment, pigmentary degeneration of the retina, AIDS encephalopathy, hepatic encephalopathy, encephalitis, cerebral palsy, head injuries, spinal cord injuries, carbon monoxide poisoning, asphyxia of the newborn, peripheral neuropathy, spastic paraplegia, progressive supranuclear palsy, circulatory disorder of the spinal cord, Shy-Drager disease, sphingolipidosis, mitochondrial encephalomyopathy, meningitis, etc.

The cell death-suppressing gene product $Bcl-x_L$ is the protein that can be said as the last fortress for cell survival, and it is distributed not only in the brain and neural (nervous) tissues but also in all peripheral organs and tissues, for example liver, spleen, tissues of the immune system, tissues of the circulatory system and skin, and supports the survival of cells. Consequently, based on the above presumption that low concentrations and low doses of the crude saponin fraction(s) or any one of constitutional components of the crude saponin fractions increases the expression of $Bcl-x_L$ protein in the same way as ginsenoside $Rb_1$, the low concentrations and low doses of the crude saponin fraction(s) or any one of constitutional components of the crude saponin fraction(s) are effective for treatment, prevention and/or therapy of all diseases of the peripheral organs and tissues accompanied by cell death. Among the diseases of the peripheral organs and tissues accompanied by cell death, following diseases are included: ischemia-reperfusion injuries of cardiac muscles, liver and kidneys, cardiomyopathy, cardiac failure, myocardial infarction, angina pectoris, peripheral circulatory failure, bedsores, wound, cutaneous ulcer, cutaneous wound, trauma, burn, radiation injury, atopic dermatitis, aging, injuries by ultraviolet rays, electric injuries, depilation, alopecia, xeroderma, pollinosis, dry skin, autoimmune diseases, immunodeficiency diseases, graft rejection, muscular dystrophy, corneal injuries, infectious diseases, collagen diseases, aortitis syndrome, acute arterial embolism, thromboangiitis obliterans, peptic ulcer, arteriosclerosis obliterans, Raynaud's disease, Raynaud's syndrome, hemorrhoids, thrombophlebitis, pancreatitis, hepatitis, nephritis, diabetic nephropathy, diabetic cardiomyopathy, glossalgia, etc. Other organic diseases or pathological conditions accompanied by cell death are described in the book ("Today's guide for therapy": Ed. Shigeaki, Hinohara and Masakazu, Abe, Igaku-Shoin Publ., 1995). The crude saponin fractions of medicinal ginseng or components thereof are thought to be effective for prevention, treatment or therapy of all diseases and pathological conditions described above. The low concentrations or the low doses of the crude saponin fraction(s) or any one of constitutional components of the crude saponin fraction(s) of the present invention can be used as health drugs for improving immune dysfunction, cutaneous dysfunction, circulation dysfunction, digestive dysfunction and hypogonadism accompanied with aging. Further, the low concentrations or the low doses of the crude saponin fraction(s) or any one of the constitutional components of the crude saponin fractions can be utilized as a cosmetic composition(s) for preventing, treating or managing the symptoms of aging of skin (shrink or atrophy of skin, white hair, gray hair, scurf, dandruff, exfoliation of the stratum corneum, exfoliation of cells in the stratum corneum, dry skin, depilation, alopecia, crack, slackening or loosening of skin, itching, dryness, crack, freckle, ephelis, pigmentation, sunburn, wrinkles, lines, furrows, blotch, spots etc.). Further, they can be used for cultivation and rearing of the farm products, farming of fishes and crustaceans, treatment or therapy of diseases of pets, chemical peeling, storage of flowers, hydroponics and extension or prolongation of flowering.

In Japanese Patent Application No. Hei 11-243378, PCT/JP99/06804 (Cerebrovascular regeneration/reconstruction promoters and nerve tissue secondary degeneration inhibitors comprising ginsenoside $Rb_1$), we (Sakanaka and Tanaka) found that repetitive or continuous intravenous administration of ginsenoside $Rb_1$ at small doses could stand up bedridden rats with spinal cord injuries through a cerebrovascular regeneration and reconstruction-promoting action, a suppressive action on the secondary degeneration of nerve cells and through a suppressive action on apoptosis of oligodendrocytes or apoptosis-like cell death. Results of the present experiments, in which the low concentrations or the low doses of the crude saponin fraction(s) or any one of the constitutional components of the crude saponin fractions of the present invention can exhibit the excellent therapeutic effects on spinal cord injuries as ginsenoside $Rb_1$ dose, indicate that the low concentrations or the low doses of the crude saponin fraction(s) or any one of the constitutional components of the crude saponin fractions can be a remedy for spinal cord injuries, head injuries or neurotrauma. Namely, effectiveness, efficacy and usage of ginsenoside $Rb_1$ described by us (Sakanaka and Tanaka) in Japanese Patent Application No. Hei 11-243378, PCT/JP99/06804 (Cerebrovascular regeneration/reconstruction promoters and nerve tissue secondary degeneration inhibitors comprising ginsenoside $Rb_1$) and Japanese Patent Application No. 2000-163026 (Agents for promoting dermal tissue regeneration comprising ginsenoside $Rb_1$) are in common with those of the low concentrations or the low doses of the crude saponin fraction(s) or those of any one of the constitutional components of the crude saponin fractions. Of course, as methods for administration of the crude saponin fraction(s) or any one of constitutional components of the crude saponin fractions, any route of administration can be selected if the extracellular fluid concentrations of the crude saponin fraction(s) or constitutional components thereof in lesioned tissues can be kept low as described above. Concretely, low concentrations and/or low doses of the crude saponin fraction(s) or any one of the constitutional components of the crude saponin fractions can be used not only as agents for intravenous administration but also as agents for external use or injection to local lesions. Further, as methods for administration of the crude saponin fraction(s) or constitutional components of the crude saponin fraction(s), any route of administration including subcutaneous injections, intramuscular injections, eye drops, nasal drops, ear drops, inhalations, suppositories, oral administrations, sublingual administrations and transdermal administrations can be selected. When the crude saponin fraction(s) or any one of constitutional components of the crude saponin fraction(s) is used as an agent for oral administration, if the crude saponin fraction(s) or any one of constitutional components of the crude saponin fraction(s) is administered alone, favorable effects may not always be expected. Consequently, it may be necessary that the crude saponin fraction(s) or any one of constitutional components of the crude saponin fraction(s) is mixed or encapsulated with a carrier(s) which inhibits its decomposition in the digestive tract or with a carrier(s) which promotes its absorption in the digestive tract, and then it is administered orally. Further, if metabolites of the crude saponin fraction(s) or metabolites of constitutional components of the crude saponin fraction(s) are identified to have equal effectiveness and efficacy to the crude saponin fraction(s) or constitutional components of the crude saponin fraction(s) or to have more effectiveness and efficacy than the crude saponin fraction(s) or constitutional components thereof, the active metabolites can be administered against diseases for which the low concentrations and/or the low dose of the crude saponin fraction(s) or constitutional components of the crude saponin fraction(s) can be applied by the administration methods described above. Further, a dispersant comprising the low concentrations and/or the low doses of the crude saponin fraction(s) or any one of constitutional components of the crude saponin fraction(s) of the present invention and macromolecular compounds, is prepared and spray-dried to select any one of the administration routes mentioned above. Furthermore, the crude saponin fraction(s) or any one of constitutional components thereof is coated with micro-particles of macromolecular compounds to select any one of the administration routes. Of course, a prodrug is prepared with the use of any one of constitutional components of the crude saponin fraction(s), and then any route of administration can be selected.

In addition, the low concentrations and/or the low doses of the crude saponin fraction(s) or any one of constitutional components of the crude saponin fraction(s) appear to be effective for protection or maintenance of cultured keratinocyte sheets for skin graft. Other organs or tissues for transplantation (liver, kidney, heart, pancreas, lung, digestive tract, cornea, blood vessel, etc.) are immersed or perfused with the crude saponin fraction(s) or any one of the constitutional components of the crude saponin fractions(s) during a term before the transplantation operation is performed. As a result, cell injury or destruction of vascular network of these organs can be suppressed, and results of the transplantation operation can be improved. The crude saponin fraction(s) or any one of the constitutional components of the crude saponin fraction(s) at low concentrations and/or at low doses appears to be effective for protection or maintenance of blood cell components and platelets for transfusion, frozen ova, frozen sperms or stem cells.

Based on the present experimental results using rats with spinal cord injuries, the therapeutic effects of the preparations for intravenous administration comprising ginsenoside Rb₁ or the crude saponin fraction(s) on spinal cord injuries are thought to be historically the most potent in the world. Presumably, ginsenoside Rb$_1$, its metabolites or any one of the constitutional components of the crude saponin fraction(s) can exhibit extremely potent therapeutic actions for improving spinal cord injuries. This supports the notion that ginsenoside Rb$_1$, its metabolites or any one of the constitutional components of the crude saponin fraction(s) can be a leading compound(s) for the treatment or therapy of spinal cord injuries, neurotrauma or head injuries. Further, if a novel remedy or compound for spinal cord injuries is developed by applying ginsenoside Rb$_1$, its metabolites or any one of constitutional components of the crude saponin fraction(s) as a leading compound(s), it is likely that such a novel remedy or compound will show effectiveness and efficacy for cerebral infarction or cerebral apoplexy. Of course, it is possible to prepare a novel medicinal or pharmaceutical composition(s) for the treatment or therapy of cerebral infarction or cerebral apoplexy by applying ginsenoside Rb$_1$, its metabolites or any one of the constitutional components of the crude saponin fraction(s) as a leading compound(s). In that case, the said novel composition or compound for treatment or therapy of cerebral infarction or cerebral apoplexy can be a medicinal or pharmaceutical composition for treatment or therapy of spinal cord injuries, neurotrauma or head injuries. Among newly synthesized ginsenoside Rb$_1$ derivatives, the compound which has a high possibility for practical use as a medicinal or pharmaceutical composition for treatment or therapy of spinal cord injuries, neurotrauma or head injuries, and as a protective agent for brain cells or nerve cells is dihydroginsenoside Rb$_1$ represented by the following formula (II):

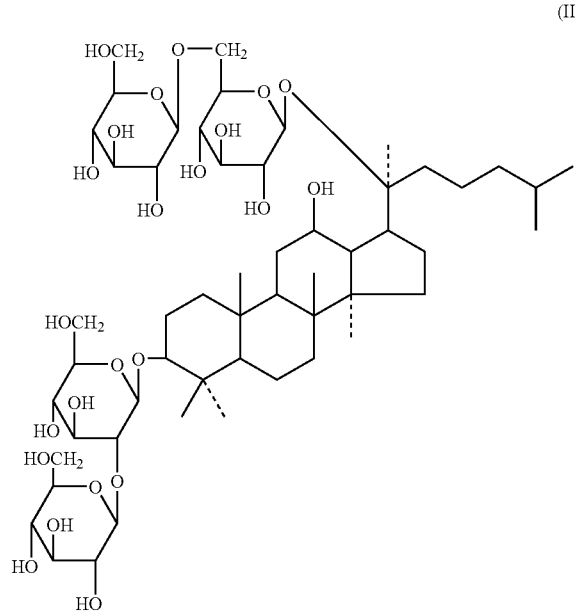

This compound can be prepared by reducing the double bond (i.e. hydrogenation) in the side chain bound to the dammarane skeleton or structure of ginsenoside Rb$_1$, if high purity of ginsenoside Rb$_1$ which the present inventors have is available.

Figure 20:
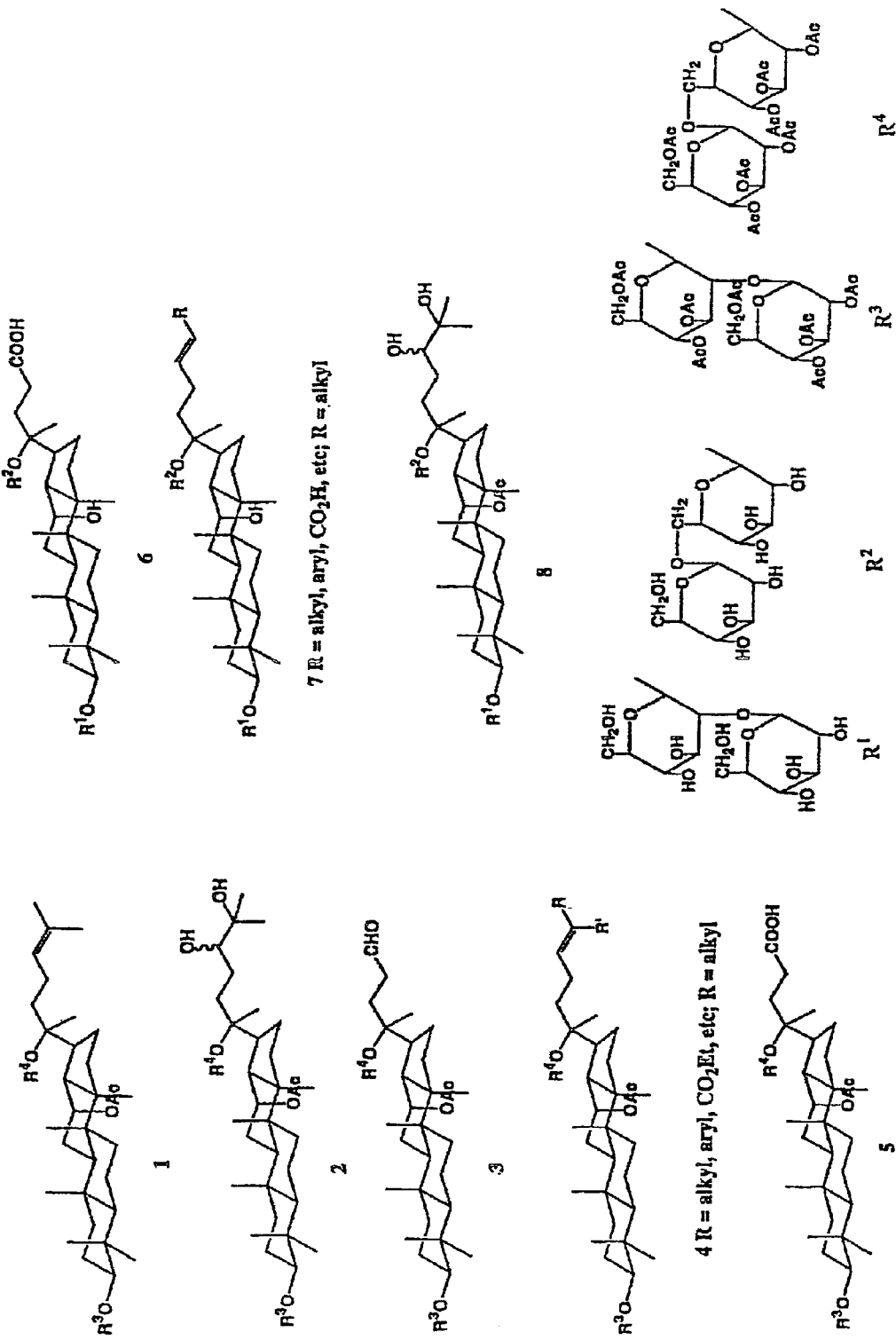
FIG. 20 shows chemical derivatives of ginsenoside $Rb_1$.

In addition, chemical derivatives of ginsenoside Rb$_1$ as shown in FIG. 20 are expected to exhibit protective actions on brain cells or protective actions on nerve cells. FIG. 20 illustrates examples of modification of the dammarane skeleton or structure (steroid-like skeleton or structure) of ginsenoside Rb$_1$. These are examples of: (1) an acetylated derivative(s); (2) an acetylated derivative in which the double bond in the side chain is dihydrated or dehydroxylated; (3) an acetylated derivative wherein the double bond in the side chain is splitted and terminal moiety is aldehyde; (4) acetylated derivatives with or without carboxyl wherein the double bond in the side chain is extended; (5) an acetylated carboxyl derivative wherein the double bond in the side chain is splitted; (6) a carboxyl derivative wherein the double bond in the side chain is splitted; (7) derivatives wherein a terminal methyl in the side chain is replaced with hydrogen and the other terminal methyl is replaced with alkyl, aryl or carboxyl, etc; (8) a derivative in which the double bond in the side chain is dehydroxylated.

Chemical derivatives of ginsenoside Rb$_1$ in FIG. 20 are, in principle, those wherein the side chain (carbon chain) bound to the dammarane skeleton or structure (steroid-like skeleton or structure) is modified. Since this carbon chain exists commonly in most of about 30 types of purified saponins in the crude saponin fraction(s) (FIG. 15), if a component for treatment or therapy of spinal cord injuries, neurotrauma or head injuries or a component for protecting nerve cells other than ginsenoside Rb$_1$ in the crude saponin fraction(s) is identified, it can be used for exploring novel compounds for protecting nerve cells by reducing (hydrogenating) the carbon chain of the said component or the purified saponin, or by modifying the same with idea shown in FIG. 20. The components of the crude saponin fraction(s) used as leading compounds are not limited within the above purified saponins. Further, novel compounds, which can be prepared by using constitutional components of the crude saponin fraction(s) as leading compounds, are not limited within the compounds, in which the carbon chain bound to the above dammarane skeleton or structure (steroid-like skeleton or structure) is chemically modified.

Based on the results described above, it is found that the preparations for intravenous administration comprising the crude saponin fraction(s) or salts thereof suppresses the secondary degeneration of neural (nervous) tissues caused by spinal cord injuries. Further, the medicinal or pharmaceutical composition(s) comprising the crude saponin fraction(s) can be an epoch-making remedy for spinal cord injuries, neurotrauma or head injuries as well as exhibiting effectiveness and efficacy for peripheral tissue injuries.

Since the therapeutic effects of the crude saponin fraction(s) on spinal cord injuries and neurotrauma are epoch-making, this suggests that novel pharmaceutical compounds for treatment or therapy of spinal cord injuries or neurotrauma can be synthesized by using components in the crude saponin fraction(s), purified saponins (ginsenosides) or metabolites thereof as leading compounds. Further, as a result of identifying the target molecules of components in the crude saponin fraction(s), purified saponins or metabolites thereof, novel compounds, which can modify the functions of the target molecules, are synthesized. Then the development of remedies for spinal cord injuries, neurotrauma or traumatic injuries can be directed.

In Japanese Patent Application No. Hei 11-340850, PCT/JP99/06804 (Cerebrovascular regeneration/reconstruction promoters and nerve tissue secondary degeneration inhibitors comprising ginsenoside Rb$_1$), similar to the intravenous administration of the crude saponin fraction(s) described above, we (Sakanaka and Tanaka) loaded 20 g of compression on the lower thoracic cord of rats for 20 minutes, and more than 30 minutes later, we started administration of ginsenoside $Rb_1$ into the left femoral vein. Namely, at about 1 hour after starting compression loading on the lower thoracic cord, ginsenoside $Rb_1$ was intravenously infused to see its therapeutic effects on spinal cord injury. However, in case of human spinal cord injuries, the period of 2 hours after the onset of spinal cord injury is critical, and it is said that the prognosis of patients is improved by performing some treatment within this time. Before the therapeutic effects of ginsenoside $Rb_1$ on spinal cord injuries are invented, any compounds, which can be administered intravenously within 1 hour after the onset of spinal cord injury, to make animals with spinal cord injury-induced paraplegia of the lower limbs stand up, have not been found. Concretely, it is unknown and not demonstrated that the above described "some treatment" means what treatment or therapy is. Then, next, the present inventors initiated intravenous administration of ginsenoside $Rb_1$ at 2 hours after the onset of spinal cord injury, and its effectiveness was investigated.

Under inhalation anesthesia by a mixture of nitrous oxide and halothane, wistar rats (body weight about 300 g) were loaded with 20 g of compression on the lower thoracic cord for 20 minutes. After they were awakened from anesthesia, the rats with paraplegia in both hindlimbs were allowed to stay for 1 hour and 40 minutes in the cage. Namely, the rats with paraplegia in both hindlimbs were allowed to stay for about 2 hours without any managements or treatments since 20 g of compression on the lower thoracic cord was loaded. Immediately thereafter, ginsenoside $Rb_1$ (60 µg) dissolved in physiological saline was infused once into the left femoral vein, and further, continuous intravenous administration of ginsenoside $Rb_1$ (60 µg/day) was performed for 7 days by using an Alza osmotic minipump. Control animals with spinal cord injuries were administered with the same amount of physiological saline (vehicle) alone.

Figure 21:
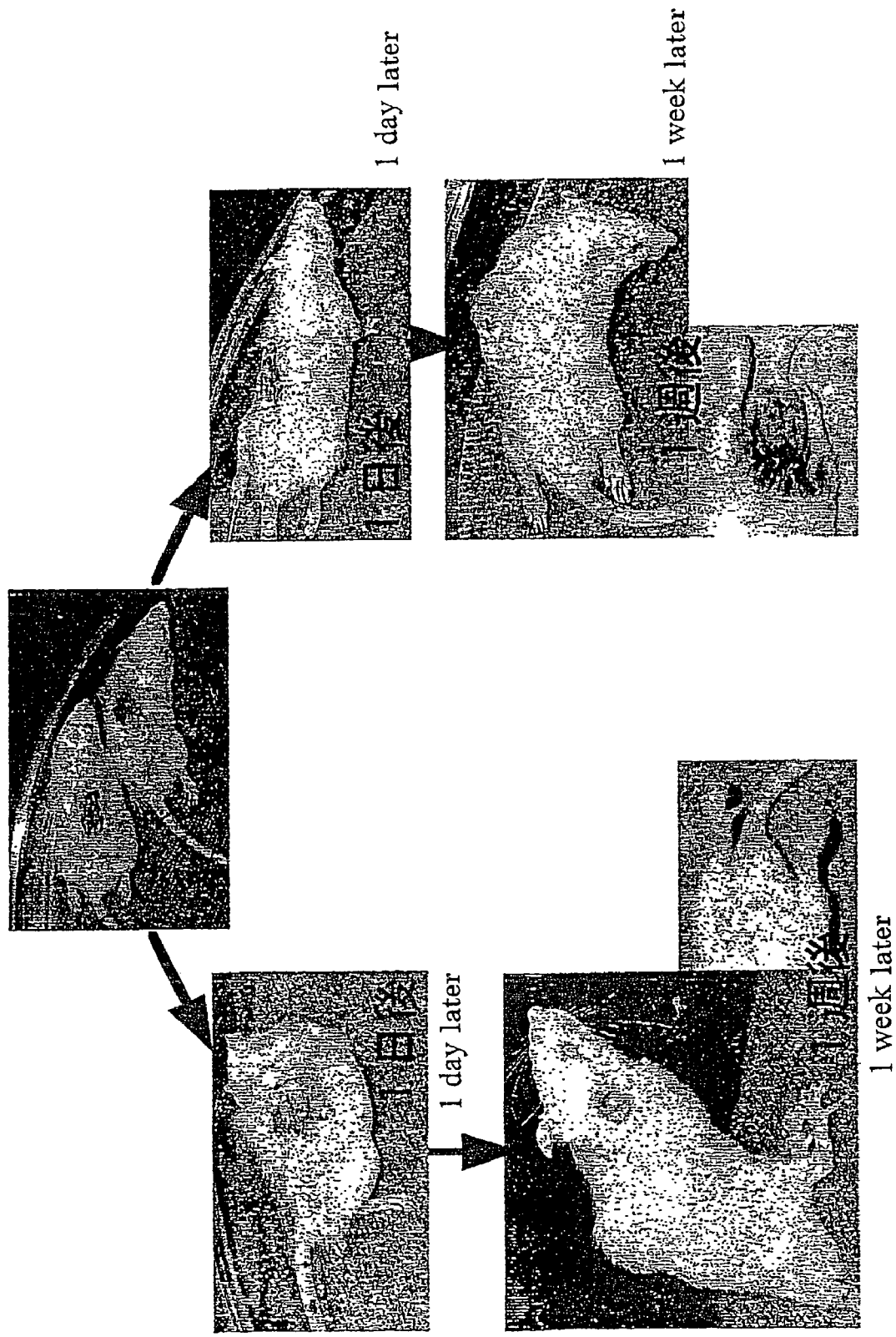
FIG. 21 is photographs instead of drawings, showing rats administered intravenously with physiological saline or ginsenoside $Rb_1$ (60 μg/day) from 2 hours after spinal cord injury.

Results are shown in FIG. 21. FIG. 21 includes photographs in stead of drawing, showing progress of rats with paraplegia of lower extremities. On the middle left is a photograph showing rats immediately after the onset of paraplegia of lower extremities. Lower photographs show the rat administered with ginsenoside $Rb_1$ (60 µg) from 2 hours after the onset of spinal cord injury. Upper photographs show the control rat administered with physiological saline alone. Left: 1 day later. Right: 1 week later.

As shown in FIG. 21, the rat with intravenous administration of ginsenoside $Rb_1$ starting at 2 hours after initiation of the compression loading on the lower thoracic cord exhibited paraplegia in both hindlimbs and could not stand up on the day of spinal cord injury. On the next day, the rat could not still stand up, although it showed slight improvement of paraplegia in both hindlimbs. Thereafter, the paraplegia of both hindlimbs of the rat was gradually ameliorated from 3-4 days after the onset of spinal cord injury, and as shown in FIG. 21, the rat could stand up by holding the outer wall of the open field (height 8 cm) at 1 week after spinal cord injury. On the other hand, as shown in FIG. 21, in the rat with intravenous administration of physiological saline (vehicle) alone starting at 2 hours after loading compression on the lower thoracic cord, paraplegia of the hindlimbs was not ameliorated even at 1 week after spinal cord injury. In addition, in the rats administered only physiological saline, even individual differences were noted, as shown in FIG. 21, bedsore was frequently observed in the lower abdomen. However, bedsore was hardly observed in animals administered with ginsenoside $Rb_1$.

Based on the results described above, intravenous administration of ginsenoside $Rb_1$, starting either at 1 hour after spinal cord injury or at 2 hours or more after spinal cord injury, shows excellent therapeutic effects. Also ginsenoside $Rb_1$ shows the effectiveness and the efficacy for bedsores accompanied by spinal cord injuries. This indicates that ginsenoside $Rb_1$ is effective for prevention, treatment or therapy of bedsores accompanied by not only spinal cord injuries but also other neurotrauma (head injuries and peripheral nerve injuries or disorders), cerebral apoplexy, demyelinating diseases or neurodegenerative diseases. Consequently, in cases of neurotrauma other than spinal cord injuries such as head injuries and peripheral nerve injuries or trauma, ginsenoside $Rb_1$ is likely to exhibit excellent effects even when its intravenous administration is started at 2 hours or more after onset of the injuries.

Further, it is known that in the nervous tissues with spinal cord injuries, edema frequently occurs in the said tissues and deteriorates neurological symptoms (paraplegia of upper and lower extremities, urination and defecation disorders). The present experimental finding that repetitive or continuous intravenous administration of ginsenoside $Rb_1$ at low doses exhibits excellent therapeutic effects on spinal cord injuries, indicates that ginsenoside $Rb_1$ is useful for prevention, treatment or therapy of edema in spinal cord tissues. Of course, ginsenoside $Rb_1$ can be an excellent agent for treatment or therapy of hypogonadism, dysuria, dyschezia, dysautonomia and neurogenic bladder accompanied by spinal cord injuries.

As shown in the experimental results of the present invention, since the therapeutic effects of ginsenoside $Rb_1$ on spinal cord injuries and neurotrauma are epoch-making, this suggests that novel pharmaceutical compounds for treatment or therapy of spinal cord injuries can be synthesized by using ginsenoside $Rb_1$ or its metabolites as a leading compound(s). Further, as a result of identifying the target molecule(s) of ginsenoside $Rb_1$ or its metabolites, novel compounds, which can modify the functions of the target molecule(s), are synthesized. Then the development of remedies for spinal cord injuries, neurotrauma or traumatic injuries can be directed.

Further, in cases of spinal cord injuries, apoptosis of glial cells, especially oligodendrocytes, occurs. This injury-induced apoptosis results in demyelination, and then in deterioration and progression of neurological symptoms (Crowe, M. J. et al., Nature Med. 3, 73-76, 1997; Emery, E. et al., J. Neurosurg. 89, 911-920, 1998). The experimental results in which intravenously administered ginsenoside $Rb_1$ significantly ameliorates paralysis of both hindlimbs of rats with spinal cord injuries, indicate that ginsenoside $Rb_1$ inhibits apoptosis of oligodendrocytes or apoptosis-like nerve cell death and thereby ameliorates symptoms of spinal cord injuries. Consequently, the low doses and/or the low concentrations of ginsenoside $Rb_1$ of the present invention are thought to be useful for prevention, treatment or therapy of brain and nervous diseases accompanied by demyelination (multiple sclerosis, Binswanger's disease, acute disseminated encephalomyelitis, demyelinating encephalitis, chronic hypoperfusion of brain etc.) through protection of oligodendrocytes. Further, the experimental results, in which intravenously administered ginsenoside $Rb_1$ at low doses and/or at low concentrations ameliorates paralysis of both hindlimbs of rats with spinal cord injuries (paraplegia), suggest that injured nerve fibers or nervous tissues can be regenerated as a result of administering low doses and low concentrations of the crude saponin fraction(s) or ginsenoside $Rb_1$.

As generally known, in myelinated nerve fibers within brain and nervous tissues, oligodendrocytes form myelin by ensheathing axons of neurons repeatedly. Further, in unmyelinated nerve fibers, processes of oligodendrocytes surround axons of neurons only once. In the brain and nervous tissues, nerve cells (neurons) and oligodendrocytes are at any time holding close positional relationship. The present inventors performed co-cultures of nerve cells and oligodendrocytes to investigate whether or not ginsenoside $Rb_1$ promotes survival of both cells. For that purpose, nerve cells (neurons) were isolated from cerebral cortices of fetal rats at gestational day 17. The mixed brain cell culture was initiated to isolate oligodendrocytes by using the forebrain of newborn rats. Fifty thousands of oligodendrocytes and 500,000 nerve cells were cocultured. To this culture system was added 1 fg/ml to 10 pg/ml ginsenoside $Rb_1$ in DMEM containing 1% fetal calf serum, and the mixed cells were cultured for 5 days. Subsequently, samples for electrophoresis were prepared and contents of the neuron-specific protein MAP2 (microtubule-associated protein 2) and the oligodendrocyte-specific protein CNPase (cyclic nucleotide phosphatase) in the culture well were assayed by means of Western blotting.

Figure 22:
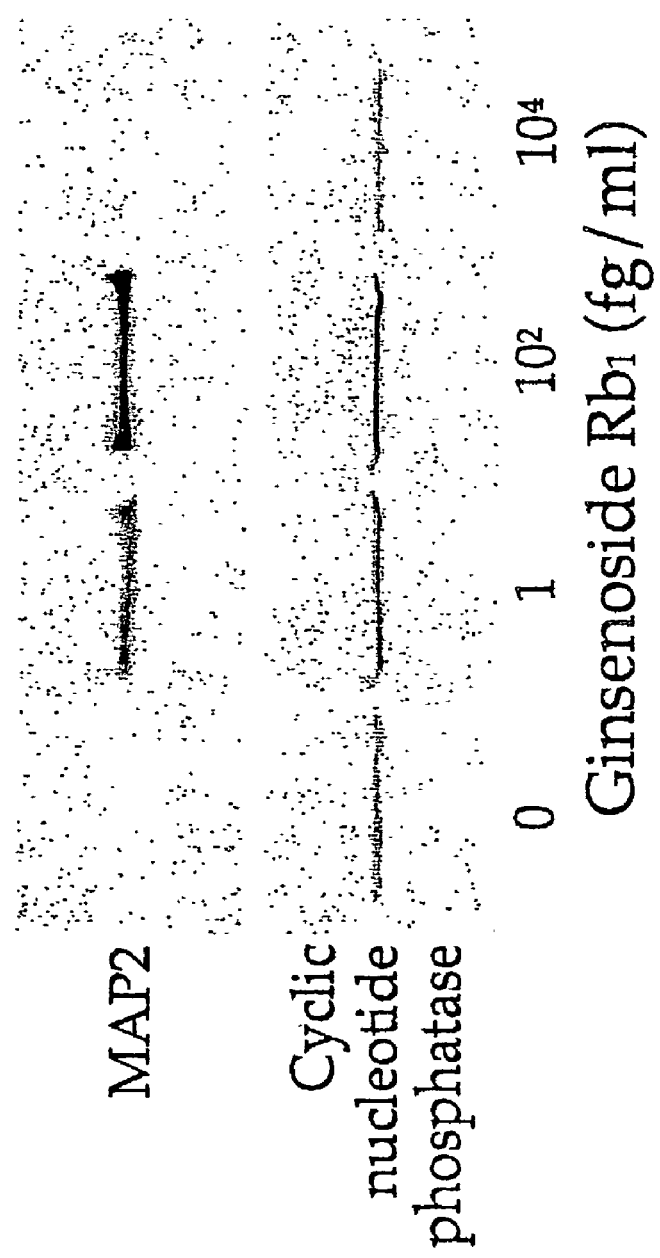
FIG. 22 is photographs instead of drawings, showing results of Western blot analyses which demonstrate the cell survival-promoting effect of ginsenoside $Rb_1$ on co-cultures of nerve cells (neurons) and oligodendrocytes. Treatment with ginsenoside $Rb_1$ at concentrations of 1-100 fg/ml apparently made intense the MAP2 and CNPase bands which are markers for neurons and oligodendrocytes, respectively. Namely, it can be said that survival of nerve cells and oligodendrocytes was promoted by the low extracellular concentrations of ginsenoside $Rb_1$.

Results are shown in FIG. 22. FIG. 22 is composed of photographs showing results of Western blotting, which indicate promoting effects of ginsenoside $Rb_1$ on the survival of the co-cultured nerve cells and oligodendrocytes.

In FIG. 22, the upper photograph shows Western blotting of MAP2 and the lower photograph shows that of CNPase. A horizontal direction indicates the concentrations of ginsenoside $Rb_1$ (fg/ml). When ginsenoside $Rb_1$ at the concentrations from 1 fg/ml to 100 fg/ml was added to the coculture of nerve cells and oligodendrocytes, the band of MAP 2 and the band of CNPase were obviously intense as compared with non-ginsenoside $Rb_1$-added and $10^4$ fg/ml ginsenoside $Rb_1$-added groups. This indicates that when low concentrations of ginsenoside $Rb_1$ were added to the co-culture system at the concentrations of 1 fg/ml to 100 fg/ml, amounts of MAP2 and CNPase were obviously increased. Namely, the survival of nerve cells and oligodendrocytes were promoted by ginsenoside $Rb_1$. This fact strongly supports the effectiveness of low concentrations of ginsenoside $Rb_1$ for preventing, treating or curing diseases accompanied by oligodendrocyte death (multiple sclerosis, brain and nervous diseases accompanied by demyelination such as Binswanger's disease, etc.). Molecular weight of ginsenoside $Rb_1$ is about 1109.46, and 1 fg/ml of ginsenoside $Rb_1$ corresponds to about 0.9 fM ginsenoside $Rb_1$.

In order to investigate whether ginsenoside $Rb_1$ enhances the expression of $Bcl-x_L$ in oligodendrocytes or not, for example, ginsenoside $Rb_1$ at the concentrations from 1 fg/ml to 10 pg/ml was added to the primary cultured rat oligodendrocytes. After culture for 6 hours, total RNA was extracted and $Bcl-x_L$ mRNA was assayed by RT-PCR. β-actin mRNA was used as an internal standard of RT-PCR. Further, a part of oligodendrocytes was used as a sample for SDS electrophoresis after treatment with ginsenoside $Rb_1$, and anti-apoptotic factor $Bcl-x_L$ in the culture well was examined by immunoblotting (Western blotting). Oligodendrocytes were isolated from the mixed brain cell culture by using the forebrain of newborn rats.

Figure 23:
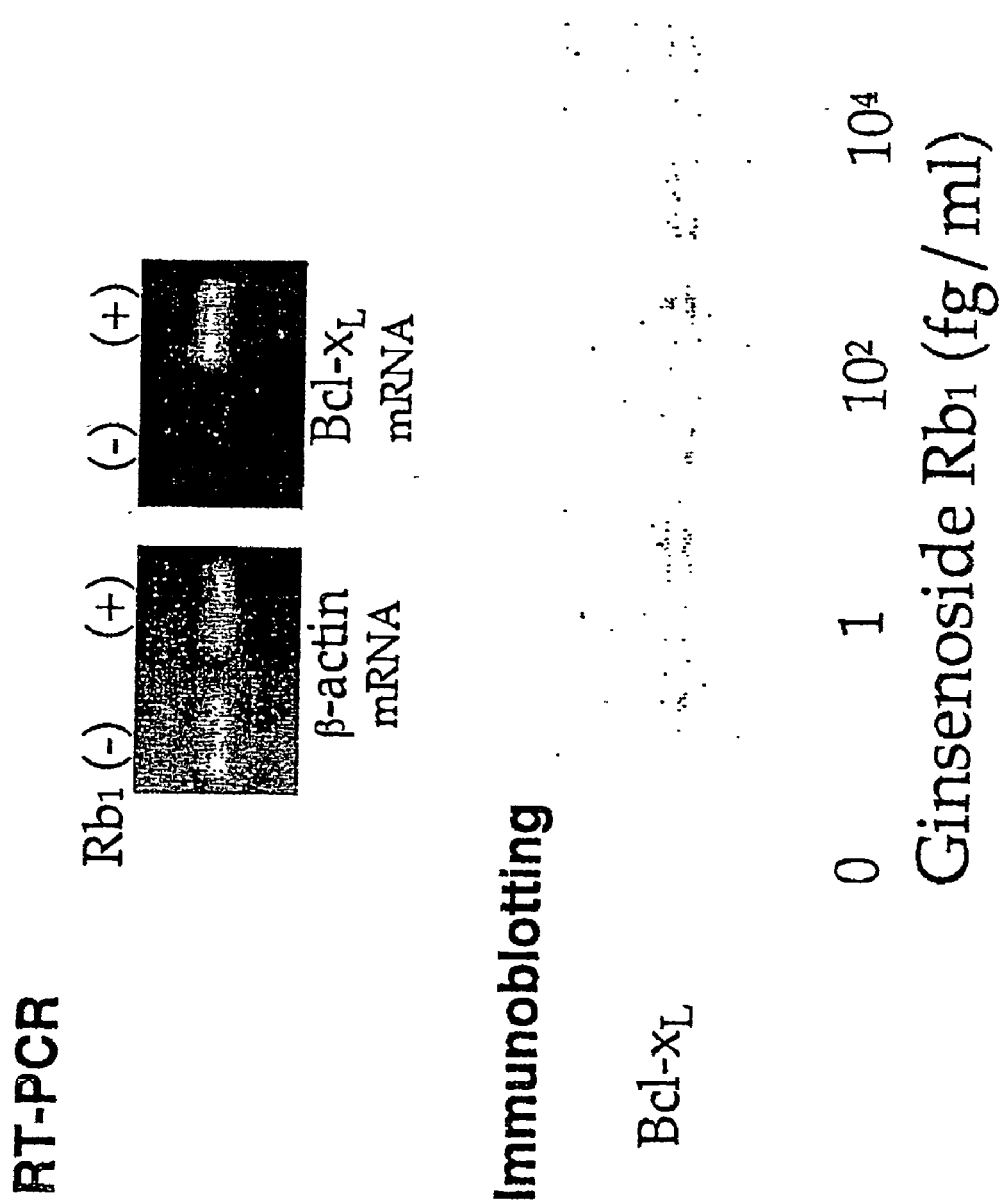
FIG. 23, the upper photographs are results of RT-PCR showing an increase in Bcl-$x_L$ mRNA expression in oligodendrocytes treated with ginsenoside $Rb_1$ at a concentration of 100 fg/ml; and the lower photographs are results of Western blot analyses (immunoblotting) showing an increase in Bcl-$x_L$ protein expression in oligodendrocytes treated with ginsenoside $Rb_1$ at concentrations of 1-100 fg/ml.

Results are shown in FIG. 23. FIG. 23 is composed of photographs instead of drawings showing results of immunoblotting (Western blotting) which indicate the promoting effect of ginsenoside $Rb_1$ on the expression of $Bcl-x_L$ in oligodendrocytes. In FIG. 23, the upper photographs show results of RT-PCR and the lower photographs show results of immunoblotting (Western blotting). On the left in the upper are cases of β-actin mRNA expression, and on the right are cases of $Bcl-x_L$ mRNA expression. In the figure, $Rb_1$ (−) indicates no addition of ginsenoside $Rb_1$ and $Rb_1$(+) indicates ginsenoside $Rb_1$ added at a concentration of 100 fg/ml. Horizontal direction in the lower indicates concentration of ginsenoside $Rb_1$ (fg/ml).

The RT-PCR indicates that when ginsenoside $Rb_1$ was added to culture medium at the concentration of 100 fg/ml, expression of $Bcl-x_L$ mRNA in oligodendrocytes was obviously enhanced. Further, results of immunoblotting (Western blotting) indicate that $Bcl-x_L$ protein was increased by adding ginsenoside $Rb_1$ to the oligodendrocyte culture. The results of these experiments strongly support that in brain and nervous diseases causing demyelination and spinal cord injuries, intravenous administration of low doses of ginsenoside $Rb_1$ exhibits protective actions on oligodendrocytes.

In Japanese Patent Application No. Hei 10-365560, PCT/JP99/02550 (Brain cell or nerve cell-protective agents comprising ginsenoside $Rb_1$), the present inventors (Sakanaka and Tanaka) demonstrated that when ginsenoside $Rb_1$ was added to cultured neurons at the concentrations of about 1~100 fg/ml, expression of $Bcl-x_L$ in the neurons was enhanced. The present inventors investigated whether or not intravenous administration of low doses of ginsenoside $Rb_1$ increases expression of $Bcl-x_L$ mRNA in brain tissues. For this purpose, for example, SH-SP rats (body weight 250-300 g), at the age of 12 weeks, were used. Immediately after permanent occlusion of the MCA in SH-SP rats under inhalation anesthesia, ginsenoside $Rb_1$ dissolved in physiological saline was infused once intravenously (60 µg), and subsequently ginsenoside $Rb_1$ was intravenously infused continuously at the dose of 60 µg/day. Control animals with MCA permanent occlusion and sham-operated animals received the same amount of physiological saline after MCA permanent occlusion.

Figure 24:
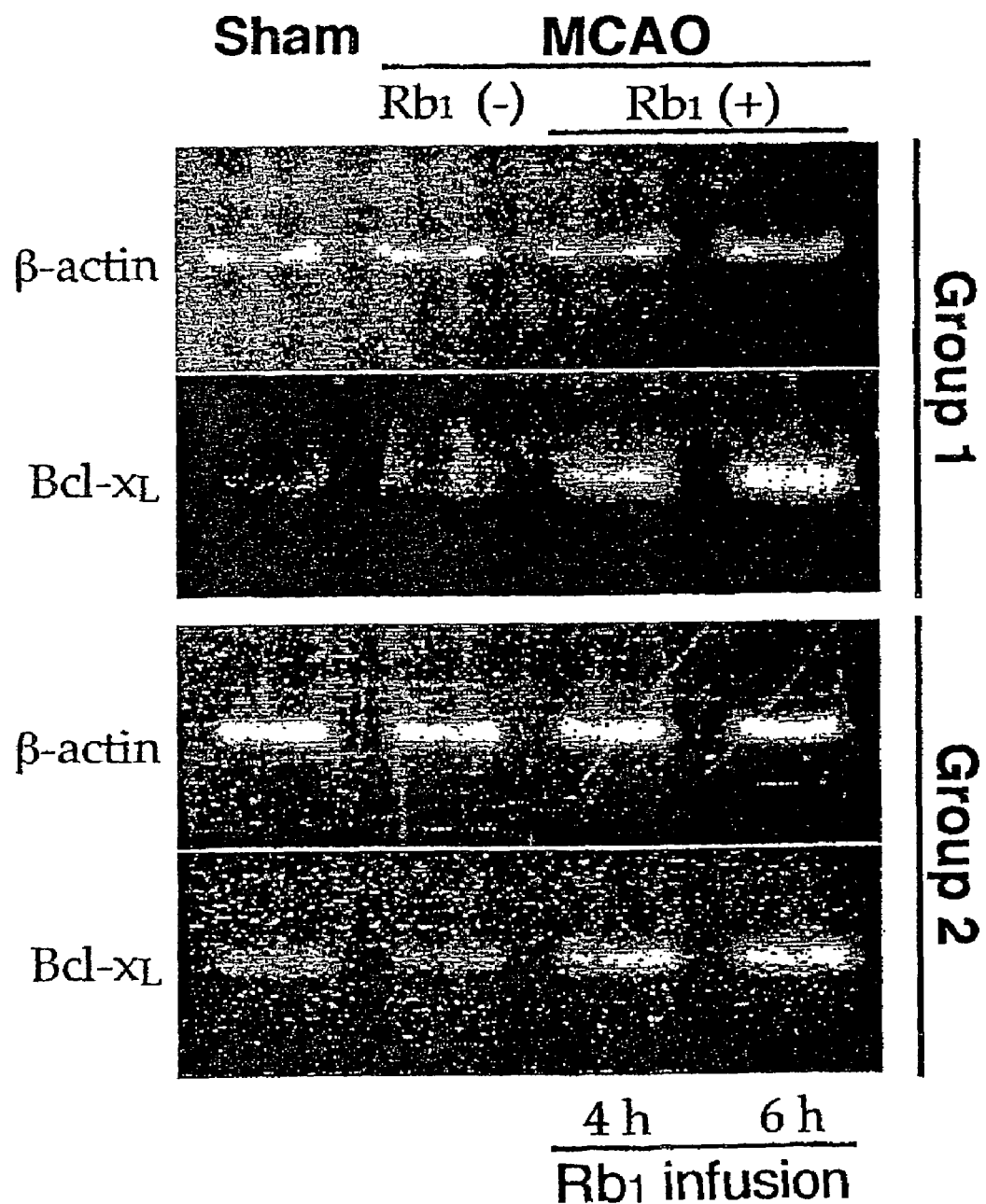
FIG. 24 is photographs instead of drawings, showing experimental results of RT-PCR wherein the expression of Bcl-$x_L$ mRNA in the brain tissue is increased by intravenous administration of ginsenoside $Rb_1$ (60 μg/day).

Results are shown in FIG. 24. FIG. 24 indicates results of RT-PCR showing the promoting effect of ginsenoside $Rb_1$ on the expression of $Bcl-x_L$ in vivo. In FIG. 24, the upper 2 photographs: group 1 animals and the lower 2 photographs: group 2 animals. The upper photographs in individual groups: β-actin mRNA and the lower photographs: $Bcl-x_L$ mRNA. Sham indicates sham-operated animals; $Rb_1$(−) indicates animals with cerebral infarction administered with physiological saline; and $Rb_1$(+) indicates animals with cerebral infarction administered intravenously with ginsenoside $Rb_1$ at the 4th hour after MCA permanent occlusion (left in $Rb_1$(+)), and at the 6th hour after MCA permanent occlusion (right in $Rb_1$(+)).

Group 1 shows a sham-operated animal; an animal with MCA permanent occlusion administered with physiological saline (after MCA permanent occlusion, i.e. at the 4th hour after cerebral infarction); an animal with cerebral infarction administered with ginsenoside $Rb_1$ (at the 4th hour after MCA permanent occlusion); and an animal with cerebral infarction administered with ginsenoside $Rb_1$ (at the 6th hour after MCA permanent occlusion). Group 2 consists of animals with the same experimental conditions. Sham indicates sham-operated animals; $Rb_1$(−) indicates animals with cerebral infarction administered with physiological saline; and $Rb_1$(+) indicates animals with cerebral infarction administered intravenously with ginsenoside $Rb_1$. At the 4th hour or the 6th hour after the sham operation and MCA permanent occlusion, animals were anesthetized with chloral hydrate, and the left cerebral cortex (i.e. the cerebral cortex on the side of MCA permanent occlusion) was dissected out and total RNA was prepared for RT-PCR. The mRNA of β-actin was used as the internal standard.

As shown in FIG. 24, both in Group 1 and Group 2, the expressions of Bcl-$x_L$ mRNA in the cerebral cortex were obviously increased both at the 4th hour and the 6th hour after MCA permanent occlusion in the animals intravenously administered with ginsenoside $Rb_1$ as compared with the sham-operated animals and the cerebral infarction animals administered with physiological saline.

The nervous tissues in the cerebral cortex include neurons, neural stem cells, glial cells (astrocytes, microglia and oligodendrocytes), vascular endothelial cells, vascular smooth muscle cells, etc. Consequently, the present experimental results showing upregulation of cerebrocortical Bcl-$x_L$ mRNA expression by intravenous administration of ginsenoside $Rb_1$ indicate that any one of cells constituting the cerebral cortex potentiates the expression of Bcl-$x_L$ mRNA in response to intravenous administration of ginsenoside $Rb_1$. Therefore, ginsenoside $Rb_1$ exhibits Bcl-$x_L$ expression-enhancing actions on all cell species. In rats not only with cerebral infarction but also with spinal cord injuries, intravenous administration of ginsenoside $Rb_1$ (60 µg/day) is likely to increase the expression of Bcl-$x_L$ mRNA in the spinal cord tissues. Based on the experimental results hereinbefore that intravenous administration of the low doses and low concentrations of ginsenoside $Rb_1$ makes bedridden rats with spinal cord injuries stand up, intravenous administration of the low doses and low concentrations of the crude saponin fraction(s) also increases the expression of Bcl-$x_L$ mRNA in the brain and nervous tissues.

The present inventors have studied effectiveness and efficacy of medicinal ginseng (red ginseng powder), crude saponin fractions and ginsenoside $Rb_1$ using nervous tissues or neural tissue-constituent cells (nerve cells and oligodendrocytes). Next, we have studied effect of ginsenoside $Rb_1$ on the heart. For that purpose, for example, changes in the expression of Bcl-$x_L$ mRNA and Bcl-$x_L$ protein were examined with RT-PCR and immunoblotting, when primary cultured myocardial cells were cultured for 18 hours in the presence of ginsenoside $Rb_1$. Myocardial cells were prepared as follows. The hearts of fetal rats at gestational day 17 were treated with trypsin EDTA to prepare dispersed cells, which were cultured for several days in DMEM containing 10% FCS (fetal calf serum). In RT-PCR, β-actin mRNA was used as the internal standard. In the immunoblotting, troponin T, a striated muscle-specific protein, was used as the internal standard, and expression of Bcl-$x_L$ protein was examined. In the immunoblotting, the same experiments were repeated 10 times by using different lots of myocardial cells, and Bcl-$x_L$ immunoreaction-positive bands were analyzed by densitometry and statistical analysis was performed.

Figure 25:
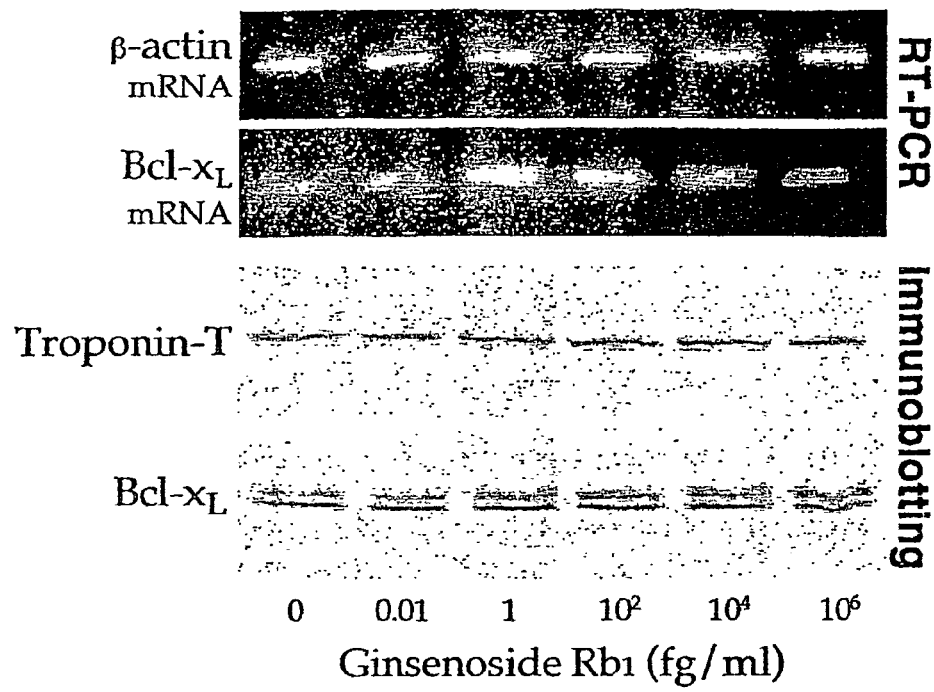
FIG. 25, the upper photographs: photographs of RT-PCR showing that the expression of Bcl-$x_L$ mRNA in myocardial cells is increased by ginsenoside $Rb_1$ at concentrations of 1-100 fg/ml. The middle photographs: photographs of immunoblot showing that the expression of Bcl-$x_L$ protein in myocardial cells is increased by ginsenoside $Rb_1$ at concentrations of 1-$10^4$ fg/ml. The lower photograph: graph quantifying the results of immunoblotting by densitometry.
Figure 25:
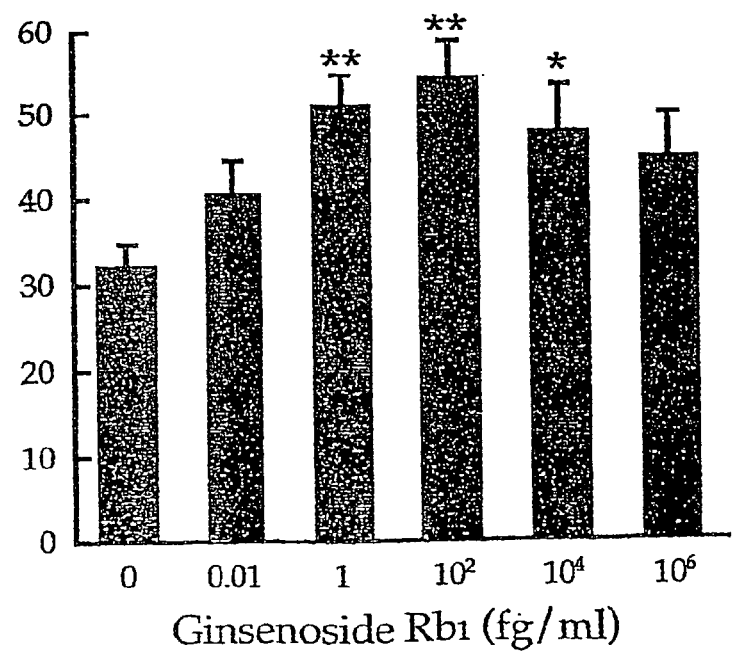

Results are shown in FIG. 25. In FIG. 25, the upper photographs show results of RT-PCR, and the middle photographs show results of immunoblotting (Western blotting). The horizontal direction indicates concentration of ginsenoside $Rb_1$ (fg/ml). In FIG. 25, the lower graph shows results of densitometric analysis of the bands of Western blotting. Statistical analyses were conducted by ANOVA+Fisher's PLSD. n=10. *: $p<0.05$, **: $p<0.01$ As shown in FIG. 25, the expression of Bcl-$x_L$ mRNA was obviously increased in the presence of ginsenoside $Rb_1$ at concentrations of 1 fg/ml-100 fg/ml. With regard to the Bcl-$x_L$ protein level, ginsenoside $Rb_1$ in the concentration range between 1 fg/ml and $10^4$ fg/ml significantly enhanced the expression of Bcl-$x_L$ protein. In the present experiments, although a mismatch between the expression of Bcl-$x_L$ mRNA and that of Bcl-$x_L$ protein was noted at $10^4$ fg/ml of ginsenoside $Rb_1$, it is speculated that the expression of Bcl-$x_L$ mRNA was already down-regulated at 18 hours after administration of such a high concentration of ginsenoside $Rb_1$ ($10^4$ fg/ml).

We have investigated whether or not ginsenoside $Rb_1$ could actually suppress myocardial cell death in the concentration range for increasing the expression of Bcl-$x_L$ protein. For that purpose, for example, the protective effect of ginsenoside $Rb_1$ on myocardial cells was examined when the primary cultured myocardial cells were cultured without addition of glucose. Ginsenoside $Rb_1$ in the concentration range from 0 to 1 ng/ml was added to myocardial cells in serum-free DMEM without containing glucose, and the myocardial cells were cultured for 4 or 5 days. Subsequently, the samples for electrophoresis were prepared, and immunoblotting (Western blotting) was performed by using anti-striated muscle specific α-actinin antibody.

Figure 26:
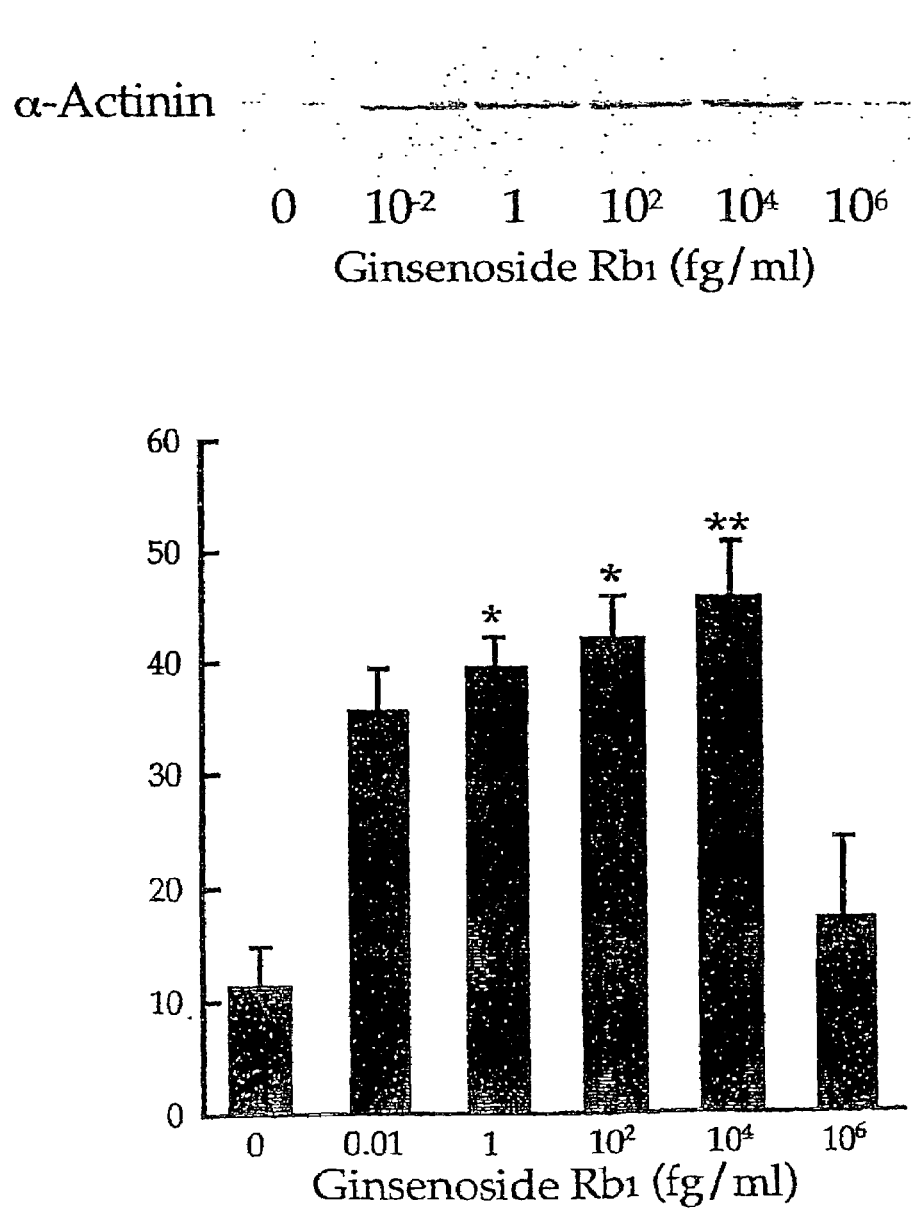
FIG. 26, the upper photograph: photograph of Western blotting of α-actinin showing that the survival of myocardial cells is promoted by treatment with ginsenoside $Rb_1$ at concentrations of 1-$10^4$ fg/ml. The lower graph: graph quantifying the results of Western blotting (immunoblotting) by densitometry. Since numbers of cases are slightly small, i.e. n=3, significant effects are not noted in the cases treated with ginsenoside $Rb_1$ at concentration of 0.01 fg/ml. However, if numbers of cases are increased, even such a low concentration of ginsenoside $Rb_1$ (0.01 fg/ml) will exhibit a significant protective effect on the myocardial cells.

Results are shown in FIG. 26. In FIG. 26, the upper photograph shows results of Western blotting of α-actinin. The horizontal direction indicates concentration of ginsenoside $Rb_1$ (fg/ml). The lower graph in FIG. 26 shows densitometric analysis of the results of the Western blotting. Statistical analyses were conducted by ANOVA+Scheffe's post hoc test. n=3. *: $p<0.05$, **: $p<0.01$ As shown in FIG. 26, when the culture was conducted only with the glucose-free and serum-free medium, the myocardial cells disappeared already at 4-5 days after culture, and band of α-actinin could not be detected. When ginsenoside $Rb_1$ was added to the culture medium in the concentration range from 1 fg/ml to $10^4$ fg/ml, large numbers of pulsating myocardial cells were observed, and the striated muscle-specific α-actinin was significantly detected by immunoblotting.

According to the above results, it was found that ginsenoside $Rb_1$ could increase the expression of myocardial cell Bcl-$x_L$ in the slightly broader concentration range (0.01-$10^4$ fg/ml or 1-$10^4$ fg/ml) than in the effective concentration range for nerve cells and had the protective action on myocardial cells.

In Japanese Patent Application No. Hei 10-365560, PCT/JP99/02550 (Brain cell or nerve cell-protective agents comprising ginsenoside $Rb_1$), whether ginsenoside $Rb_1$ at the concentrations of 1 fg/ml, 100 fg/ml and $10^5$ fg/ml suppresses apoptosis-like nerve cell death or not, and whether it promotes the expression of Bcl-$x_L$ protein in the nerve cells or not, were investigated, and as a result significant effects were obtained at the concentrations of 1 fg/ml and 100 fg/ml. However, actually, ginsenoside $Rb_1$ at the concentration of $10^4$ fg/ml increases the expression of Bcl-$x_L$ protein in myocardial cells and suppresses cell death of myocardial cells. Consequently, in nerve cells or neurons, the possibility is left open that ginsenoside $Rb_1$ in the similar concentration range (from 1 fg/ml to $10^4$ fg/ml) promotes the expression of Bcl-$x_L$ protein and suppresses apoptosis-like nerve cell death.

According to the experimental results that ginsenoside $Rb_1$ at the low concentrations of 1 to $10^4$ fg/ml increases the expression of a cell death-suppressing gene product Bcl-$x_L$ in the myocardial cells and suppresses myocardial cell death in the glucose-free condition, low concentrations of ginsenoside $Rb_1$ appear to exhibit effectiveness and efficacy for all diseases accompanied by myocardial cell death (e.g. myocardial infarction, myocarditis, Kawasaki's disease, cardiomyopathy, cardiac insufficiency, heart failure, cardiac arrest, angina pectoris, etc.). In cases of heart surgery, addition of low concentrations of ginsenoside $Rb_1$ to the artificial cardiopulmonary perfusate can effectively protect myocardial cells and heart. Of course, in the occasion of cardiopulmonary resuscitation, intravenous administration of low doses and low concentrations of ginsenoside $Rb_1$ makes damage to myocardial cells after resuscitation as small as possible. Further, if the low concentrations of ginsenoside $Rb_1$ are administered intravenously, rectally, sublingually or nasally to patients with hypoglycemic attack or patients who are suffered from hypoglycemic attack or suffering from hypoglycemic attack frequently, the myocardial cell damage caused by hypoglycemia will be ameliorated more efficiently. Of course, preferable effects on myocardial cells mentioned above appear to be brought about by using low doses and low concentrations of the crude saponin fraction(s) as well.

In the present invention, the enhanced expression of $Bcl-x_L$ by ginseng (red ginseng powder) or ginsenoside $Rb_1$ has been described. As is well known, Bcl-2 family proteins consist of cell death-suppressing (anti-apoptotic) factors such as Bcl-2, $Bcl-x_L$, Bcl-w, etc. and cell death-promoting (proapoptotic) factors such as Bax, Bad, Bid, Bik, etc. It is well known that these Bcl-2 family proteins have organ-specific and cell-specific expression patterns. Consequently, although in the present invention and in Japanese Patent Application No. Hei 10-365560, PCT/JP99/02550 (Brain cell or nerve cell-protective agents comprising ginsenoside $Rb_1$) in the name of us (Sakanaka and Tanaka), it was found that ginsenoside $Rb_1$ increases the expression of $Bcl-x_L$ in nerve cells (neurons) or myocardial cells, in the other organs or cells, ginsenoside $Rb_1$ is likely to promote the expression of cell death-suppressing factors other than $Bcl-x_L$ or to suppress the expression of cell death-promoting factors as described above. Of course, ginsenoside $Rb_1$ is likely to promote the expression of cell death-suppressing factors (e.g. Bcl-2 and Bcl-w) or to suppress the expression of cell death-promoting factors in neural tissues or nerve cells, too.

In the signal transduction of cell death, the cell death-suppressing gene product $Bcl-x_L$ locates upstream of procaspase 9, caspase 9, procaspase 3 or caspase 3, and the fact that ginsenoside $Rb_1$ increases the expression of $Bcl-x_L$ and strongly suppresses nerve cell death, demonstrates that ginsenoside $Rb_1$ also suppresses activation of caspases.

In the prior patent application (Japanese Patent Application No. Hei 11-243378, Brain cell or nerve cell-protective agents comprising medicinal ginseng), we have described that novel compounds having brain cell- or nerve cell-protective actions can be explored by using candidate substances of the active components contained in ginseng as a leading compound(s). We have attempted to demonstrate this fact in the present invention. For that purpose, for example, dihydroginsenoside $Rb_1$ represented by the above chemical formula (II) was used. As far as we know, dihydroginsenoside $Rb_1$ is a novel compound and can be produced by reducing (i.e., hydrogenating) ginsenoside $Rb_1$, which is owned by us, in the presence of a catalyst, palladium charcoal.

In order to analyze pharmacological actions of dihydroginsenoside $Rb_1$, male SH-SP rats, at the age of 16 weeks, weighing 300-320 g, were used. Animals were bred in a room furnished with 12 hours light and dark cycles, and water and feeds were supplied ad libitum. The cortical branch of the left middle cerebral artery (MCA) of each animal was coagulated and cut under inhalation anesthesia. Immediately after MCA permanent occlusion, dihydroginsenoside $Rb_1$ dissolved in physiological saline was infused once intravenously (6 μg), and subsequently it was intravenously infused continuously for 24 hours by using an Alza osmotic minipump (6 μg/day).

Control animals with MCA permanent occlusion (ischemic control animals) received the same amount of physiological saline (vehicle). At 24 hours after MCA permanent occlusion, a lethal dose of pentobarbital was injected intraperitoneally into individual rats. Immediately after death of the animals, the brains were dissected out and frontal sections with 2 mm thickness were prepared. The sections were immersed in 1% 2,3,5-triphenyl-tetrazolium chloride (TTC) solution for 30 minutes at 37° C. and fixed with 10% formalin for more than 12 hours.

Figure 27:
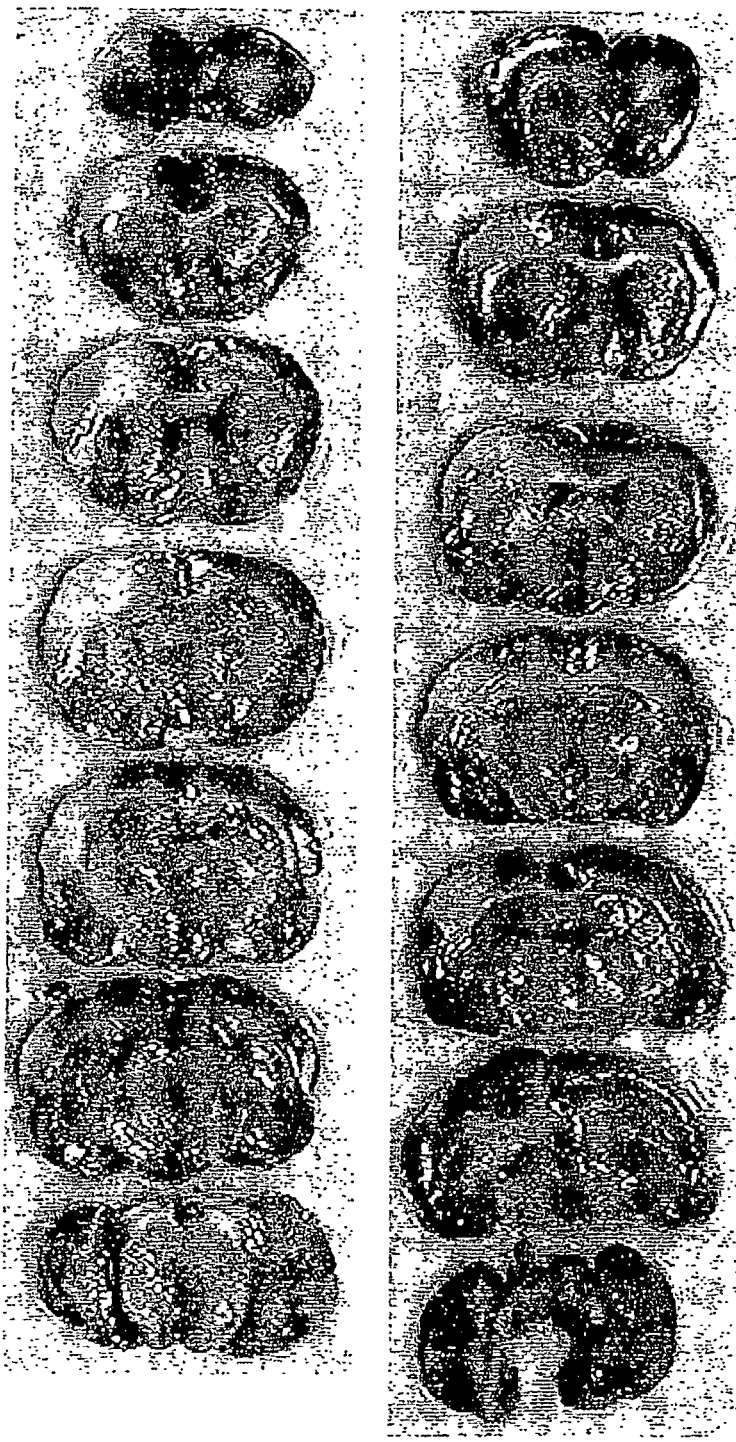
FIG. 27 is photographs instead of drawings, showing results of TTC staining of rat brains (2 cases) administered intravenously with physiological saline after permanent occlusion of the MCA (i.e. after the onset of cerebral infarction).
Figure 28:
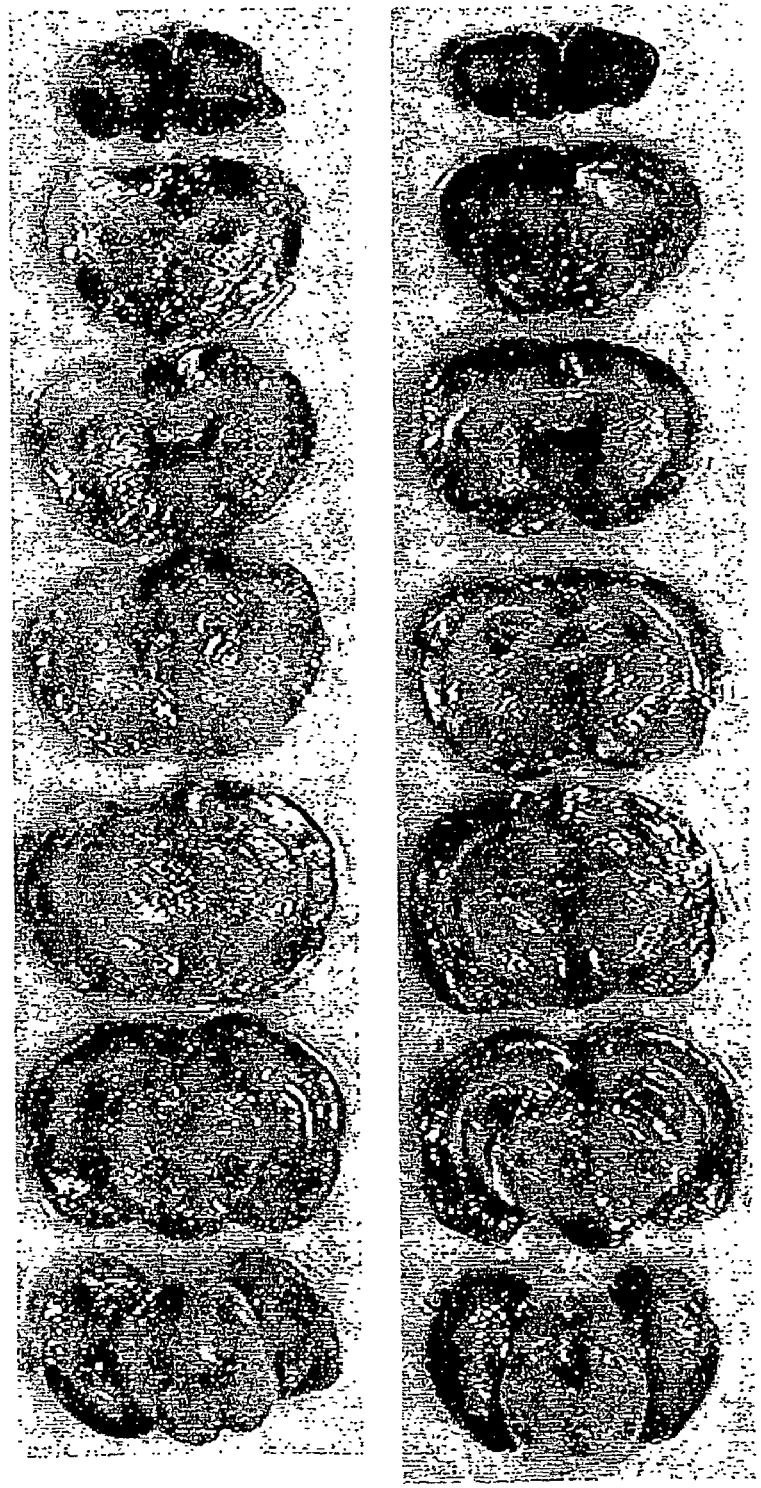
FIG. 28 is photographs instead of drawings, showing results of TTC staining of rat brains (2 cases) administered intravenously with dihydroginsenoside $Rb_1$ (approximately 6 µg/day) after permanent occlusion of the MCA (i.e. after the onset of cerebral infarction).

Results are shown in FIG. 27 and FIG. 28. In FIG. 27, 2 cases administered with physiological saline, and in FIG. 28, 2 cases administered intravenously with dihydroginsenoside $Rb_1$ are shown.

As shown in FIG. 27, in the rats administered with physiological saline after MCA permanent occlusion, the cerebral infarct lesion, which was not stained with TTC, was observed with white color in the cerebral cortex on the left side. On the other hand, as shown in FIG. 28, in the rats administered intravenously with dihydroginsenoside $Rb_1$ after MCA permanent occlusion, the cerebral infarct lesion was markedly reduced. Especially, the brain in the right column in FIG. 28 showed a tremendously reduced cerebral infarct lesion, which is limited only in the surface layer of the cerebral cortex. This indicates that dihydroginsenoside $Rb_1$ not only suppresses apoptosis-like nerve cell death in the ischemic penumbra, but also suppresses necrosis of nerve cells and brain cells in the ischemic core.

The experimental results wherein dihydroginsenoside $Rb_1$ or metabolites thereof can show an action of reducing cerebral infarct lesion as like ginsenoside $Rb_1$ in SH-SP rats with MCA permanent occlusion, prove that novel neuroprotective agents or novel brain cell-protective agents, which act especially at low doses and low concentrations, can be prepared by using ginsenoside $Rb_1$ as a leading compound. Furthermore, since the effective dose of dihydroginsenoside $Rb_1$ for intravenous administration is almost identical with the effective dose of ginsenoside $Rb_1$ for intravenous administration, it is thought that dihydroginsenoside $Rb_1$ exhibits excellent neuroprotective actions and brain cell-protective actions at the low concentrations and at low doses as does ginsenoside $Rb_1$. Of course, the effectiveness, efficacy and usages of ginsenoside $Rb_1$ described by us in Japanese Patent Application No. Hei 10-365560, PCT/JP99/02550 (Brain cell or nerve cell-protective agents comprising ginsenoside $Rb_1$), are in common with those of dihydroginsenoside $Rb_1$. Namely, dihydroginsenoside $Rb_1$ increases the expression of a cell death-suppressing gene product $Bcl-x_L$ as does ginsenoside $Rb_1$, and suppresses apoptosis of nerve cells or apoptosis-like nerve cell death. Further, dihydroginsenoside $Rb_1$ exhibits effectiveness and efficacy for all brain and nervous diseases accompanied by nerve cell death as does ginsenoside $Rb_1$, (Alzheimer's disease, cerebral apoplexy, cerebral infarction, cerebral thrombosis, cerebral embolism, subarachnoidal hemorrhage, transient cerebral ischemic attack, Pick disease, spinocerebellar degeneration, Parkinson's disease, demyelinating diseases, polyglutamine diseases such as chorea, amyotrophic lateral sclerosis, glaucoma, senile macular degeneration, diabetic retinopathy, central retinal arteriovenous occlusion, retinal detachment, pigmentary degeneration of the retina, AIDS encephalopathy, hepatic encephalopathy, encephalitis, cerebral palsy, head injuries, spinal cord injuries, Shy-Drager disease, brain tumors, toxic neuropathies, carbon monoxide poisoning, asphyxia of the newborn, peripheral neuropathies, spastic paraplegia, progressive supranuclear palsy, circulatory disorders of the spinal cord, mitochondrial encephalomyopathy, meningitis, etc.).

The cell death-suppressing gene product Bcl-$x_L$ is the protein that can be said as the last fortress for cell survival, and is distributed not only in the brain and neural tissues but also in all peripheral organs and tissues, for example liver, spleen, tissues of the immune system, tissues of the circulatory system and skin, and supports the survival of cells. Consequently, based on the above speculation that dihydroginsenoside $Rb_1$ increases the expression of Bcl-$x_L$ in the same way as ginsenoside $Rb_1$, dihydroginsenoside $Rb_1$ is effective for treatment, prevention and/or therapy of all diseases of the peripheral organs and tissues accompanied by cell death. Among the diseases of the peripheral organs and tissues accompanied by cell death, following diseases are included: ischemia-reperfusion failure of cardiac muscle, liver and kidneys, cardiomyopathy, cardiac failure, myocardial infarction, angina pectoris, peripheral circulatory failures, bedsores, cutaneous ulcer, cutaneous wound, trauma, burn, radiation injuries, electric injuries, aging, damage by ultraviolet rays, depilation, alopecia, xeroderma, dry skin, autoimmune diseases, immunodeficiency diseases, graft rejection, muscular dystrophy, corneal injuries, infectious diseases, collagen diseases, aortitis syndrome, acute arterial embolism, thromboangiitis obliterans, peptic ulcer, arteriosclerosis obliterans, Raynaud's disease, Raynaud's syndrome, hemorrhoids, thrombophlebitis, pancreatitis, hepatitis, nephritis, diabetic nephropathy, diabetic cardiomyopathy, glossalgia, diabetes mellitus, arteriosclerosis, etc. Dihydroginsenoside $Rb_1$ of the present invention can be used as health drugs for improving a variety of symptoms of immune dysfunction, circulation dysfunction, digestive dysfunction, cutaneous dysfunction and hypogonadism accompanied with aging. Further, Dihydroginsenoside $Rb_1$ can be utilized as a cosmetic composition for preventing, treating or managing skin symptoms accompanied by aging (shrink or atrophy of skin, flabby skin, slackening or loosening of skin, scurf, dandruff, itching, white-hair, gray hair, exfoliation of the stratum corneum, exfoliation of cells in the stratum corneum, dry skin, crack, freckle, pigmentation, sunburn, dryness, lines, furrows, wrinkles, blotch, spots, etc.). In addition, dihydroginsenoside $Rb_1$ can be used as hair-restorers, hair-grooming agents, hair-raising agents, hair tonic and agents for prevention of depilation or alopecia. Of course, the effectiveness, efficacy or usages of ginsenoside $Rb_1$ described in Japanese Patent Application No. 2000-163026 (Agents for promoting dermal tissue regeneration comprising ginsenoside $Rb_1$) are in common with those of dihydroginsenoside $Rb_1$.

In Japanese Patent Application No. Hei 11-243378, PCT/JP99/06804 (Cerebrovascular regeneration/reconstruction promoters and nerve tissue secondary degeneration inhibitors comprising ginsenoside $Rb_1$), we (Sakanaka and Tanaka) have found that repetitive or continuous intravenous administration of low doses of ginsenoside $Rb_1$ could stand up bedridden rats with spinal cord injuries through cerebrovascular regeneration and reconstruction-promoting actions, suppressive actions on the secondary degeneration of nerve cells and through suppressive actions on apoptosis of oligodendrocytes or apoptosis-like cell death. Results of the present experiments, in which dihydroginsenoside $Rb_1$ shows the excellent therapeutic effects on cerebral infarction as does ginsenoside $Rb_1$, indicate that dihydroginsenoside $Rb_1$ can be a remedy for spinal cord injuries, head injuries or neurotrauma. Namely, the effectiveness efficacy or usages of ginsenoside $Rb_1$ described by the present inventors (Sakanaka and Tanaka) in Japanese Patent Application No. Hei 11-243378, PCT/JP99/06804 (Cerebrovascular regeneration/reconstruction promoters and nerve tissue secondary degeneration inhibitors comprising ginsenoside $Rb_1$) are in common with those of dihydroginsenoside $Rb_1$. Of course, as methods for administration of dihydroginsenoside $Rb_1$ of the present invention, any route of administration can be selected like ginsenoside $Rb_1$. Concretely, dihydroginsenoside $Rb_1$ can be used not only as agents for intravenous administration but also as agents for external use or for injection to local lesions. Further, as methods for administration of dihydroginsenoside $Rb_1$, any one of subcutaneous injection, intramuscular injection, eye ointment, eye drops, nasal drops, ear drops, inhalations, suppositories, oral administrations, sublingual administrations, transdermal administrations, etc. can be selected. When dihydroginsenoside $Rb_1$ is used as agents for oral administration, if dihydroginsenoside $Rb_1$ is administered alone, favorable effects may not always be expected. Consequently, it may be necessary that dihydroginsenoside $Rb_1$ is mixed, encapsulated or bound with a carrier(s) which inhibits decomposition of dihydroginsenoside $Rb_1$ in the digestive tract (shellac, gelatin, oil layer, etc.) or with a carrier(s) which promotes absorption of dihydroginsenoside $Rb_1$ in the digestive tract, and it is administered orally. Further, if metabolites of dihydroginsenoside $Rb_1$ are identified to have effectiveness and efficacy equal to dihydroginsenoside $Rb_1$ or to have more effectiveness and efficacy than dihydroginsenoside $Rb_1$, the active metabolites can be administered against diseases for which dihydroginsenoside $Rb_1$ can be applied by the administration methods described above. Further, a dispersant comprising dihydroginsenoside $Rb_1$ of the present invention and macromolecular compounds is prepared and spray-dried to select any route of administration. Furthermore, dihydroginsenoside $Rb_1$ is coated with microparticles of macromolecular compounds to select any route of administration. Further, a prodrug of dihydroginsenoside $Rb_1$ is prepared and any route of administration can be selected. For example, a hydroxyl base(s) of dihydroginsenoside $Rb_1$ is esterified to prepare a prodrug(s), and it is hydrolyzed with endogenous esterases after passing the blood-brain barrier to increase amount of transfer of dihydroginsenoside $Rb_1$ to the brain.

In addition, dihydroginsenoside $Rb_1$ appears to be effective for protection or maintenance of cultured keratinocyte sheets for skin graft. The other organs or tissues for transplantation (liver, kidney, heart, pancreas, lung, digestive tract, cornea and blood vessel, etc.) are immersed or perfused with the low concentrations of dihydroginsenoside $Rb_1$ during a term before transplantation operation is performed. As a result, cell injury or destruction of the vascular networks of these organs can be suppressed, and results of transplantation operation can be improved. Dihydroginsenoside $Rb_1$ is likely to be effective for protection or maintenance of blood cell components and platelets for transfusion, frozen ova, frozen sperms or stem cells.

Of course, the fact that dihydroginsenoside $Rb_1$ has the same effectiveness, efficacy or usages as those of ginsenoside $Rb_1$, which have been described in the present invention, is also easily accepted.

On the basis of the above experimental results on red ginseng powder, the agents for oral administration comprising red ginseng powder to potentiate the expression of Bcl-$x_L$ was demonstrated to be effective at high doses for treatment, prevention or therapy of brain or nervous diseases, for example, cerebrovascular dementia, cerebral infarction, cerebral hemorrhage, subarachnoidal hemorrhage, transient cerebral ischemic attack, neurodegenerative diseases, demyelinating diseases, cerebral palsy, spinal cord injuries, etc.

Further, oral administration of low doses of red ginseng powder was found to enhance expression of the cell death-suppressing gene product Bcl-$x_L$ protein in the peripheral organs such as liver and spleen. Consequently, oral administration of low doses of red ginseng powder is useful for peripheral organ diseases accompanied by cell death (myocardiopathy, cardiac insufficiency, heart failure, myocardial infarction, myocarditis, ischemia-reperfusion injuries of liver, kidney and heart, hepatitis, nephritis, diabetes mellitus, immunodeficiency diseases, bedsores, skin ulcer, wound, trauma, radiation injuries, ultraviolet injuries, etc.). Effects of oral administration of red ginseng powder for diseases of peripheral organs or tissues accompanied by cell death may be, at least in part, possibly described in Oriental medicine-related references or Chinese medicine-related references which are not known by the present inventors.

Further, according to the results of experiments using ginsenoside $Rb_1$ described above, repetitive or continuous intravenous administration of low doses of ginsenoside $Rb_1$ is useful for prevention, treatment or therapy of brain edema, shows excellent effects on bedsores accompanied by spinal cord injuries, and enhances the expression of Bcl-$x_L$ in brain and nervous tissues. Further, low concentrations of ginsenoside $Rb_1$ facilitate the survival of oligodendrocytes, increase the expression of Bcl-$x_L$ in the same cells, and promote the survival of myocardial cells as well as increasing the expression of Bcl-$x_L$ in the cells. In addition, we (the present inventors) have proven that intravenous administration of low concentrations and low doses of the crude saponin fraction(s) exhibits excellent therapeutic effects on cerebral infarction and spinal cord injuries, and showed that any one of components in the said fraction(s) can be a medicinal or pharmaceutical composition for treatment or therapy of spinal cord injuries, head injuries or neurotrauma.

Finally, it is found that a novel reduced compound of ginsenoside $Rb_1$, i.e. dihydroginsenoside $Rb_1$, exhibits excellent therapeutic effects on cerebral infarction by intravenous administration at low doses as does ginsenoside $Rb_1$. Namely, dihydroginsenoside $Rb_1$ has similar effectiveness, efficacy or usages to ginsenoside $Rb_1$ as described by us in Japanese Patent Application No. Hei 10-365560, PCT/JP99/02550 and Japanese Patent Application No. Hei 11-340850, PCT/JP99/06804. Of course, dihydroginsenoside $Rb_1$ has all of the effectiveness, efficacy or usages of ginsenoside $Rb_1$ reported by the other inventors and researchers. Based on the results of the present experiments using dihydroginsenoside $Rb_1$, it was proven that by applying ginsenoside $Rb_1$ as a leading compound various protective agents for nerve cells, protective agents for brain cells, agents for treatment or therapy of cerebral apoplexy, agents for treatment or therapy of neurodegenerative diseases, agents for treatment or therapy of spinal cord injuries, head injuries or neurotrauma, protective agents for cells, and so forth are developed.

On the other hand, red ginseng powder, low concentrations and low doses of ginsenoside $Rb_1$ and low concentrations and low doses of the crude saponin fraction(s) are known as substances having quite less ill effects.

The present invention provides agents for treatment therapy, and/or prevention of brain and nervous diseases, and protective agents for nerve cells and nervous tissues, comprising preparations for oral administration of relatively high doses of red ginseng powder, useful not only for acute phase or chronic phase cerebral infarction (cerebral thrombosis or cerebral embolism), but also for acute phase or chronic phase cerebral hemorrhage or subarachnoidal hemorrhage, or transient cerebral ischemic attack. Namely, red ginseng powder of the present invention is a drug which can be administered orally at home to patients who are suspected to suffer from cerebral apoplexy as far as their consciousness and swallowing function are maintained. Further, if the aged people, who are the so-called cerebral apoplexy candidates with underlying diseases such as diabetes mellitus, hypertension, cerebral arteriosclerosis, atrial fibrillation and cerebral aneurysm or with anamnesis of cerebral apoplexy, ingested red ginseng powder in advance, and thereafter even if they suffer from cerebral apoplectic attack at the worst, their cerebral apoplectic lesion and functional disorders of the higher nervous system will be markedly improved as compared with the patients who did not take red ginseng powder.

Judging from the facts that oral administration of red ginseng powder of the present invention at relatively high doses promotes the expression of the cell death-suppressing gene product, i.e. Bcl-$x_L$ protein, in neural or nervous tissues, and that oral administration of red ginseng powder of the present invention at relatively high doses suppresses apoptosis-like nerve cell death in the ischemic penumbra, the medicinal or pharmaceutical composition of the present invention comprising relatively high doses of red ginseng powder is useful for primary or secondary neurodegenerative diseases accompanied by apoptosis-like nerve cell death or apoptosis (Alzheimer's disease, Pick disease, spinocerebellar degeneration, Parkinson's disease, demyelinating diseases, polyglutamine diseases such as chorea, amyotrophic lateral sclerosis, glaucoma, senile macular degeneration, diabetic retinopathy, central retinal arteriovenous occlusion, retinal detachment, pigmentary degeneration of the retina, AIDS encephalopathy, hepatic encephalopathy, encephalitis, cerebral palsy, head injuries, spinal cord injuries, carbon monoxide poisoning, asphyxia of the newborn, peripheral neuropathy, spastic paraplegia, brain tumor, encephalitis, alcohol poisoning, toxic nervous diseases, sphingolipidosis, progressive supranuclear palsy, spinal vascular disorders, mitochondrial encephalomyopathy, meningitis, etc.). Red ginseng powder of the present invention is useful for improvement of various symptoms caused by aging-induced death of brain cell or neurons (decrement of memory, tremor, decreased muscle force, decreased working ability, decreased ability of thinking, decreased ability of orientation, decreased ability of calculation, decreased ability of learning, hypovolition, suppressed motivaton, decreased recognition ability, swallowing difficulty, speech difficulty, impaired judgement, and other higher nervous functional insufficiencies) and it can be used as health food and health drug (OTC preparations). Further, the medicinal or pharmaceutical composition of the present invention has almost no ill effects, and safe drugs are provided in the present invention.

The cell death-suppressing gene product Bcl-$x_L$ is the protein that can be said as the last fortress for cell survival, and is distributed not only in the brain and nervous tissues but also in many peripheral organs and tissues, for example, liver, spleen, tissues of the immune system, tissues of the circulatory system and skin, and supports the survival of cells. Consequently, based on the present experimental results that oral administration of low doses of red ginseng powder increases the expression of Bcl-$x_L$ protein in the peripheral organs such as liver and spleen, the low doses of red ginseng powder are effective for treatment, prevention and/or therapy of all diseases of the peripheral organs and tissues accompanied by cell death. Among the diseases of the peripheral organs and tissues accompanied by cell death, following diseases are included: ischemia-reperfusion injuries of cardiac muscle, liver and kidneys, cardiomyopathy, cardiac failure, heart failure, myocardial infarction, angina pectoris, peripheral circulatory insufficiency, bedsores, wound, cutaneous ulcer, cutaneous wound, trauma, autoimmune diseases, immunodeficiency diseases, graft rejection after organ transplantation, muscular dystrophy, corneal injuries, radiation injuries, ultraviolet rays injuries, infectious diseases, collagen diseases, aortitis syndrome, acute arterial embolism, thromboangiitis obliterans, arteriosclerosis obliterans, Raynaud's disease, diabetes mellitus, Raynaud's syndrome, thrombophlebitis, pancreatitis, hepatitis, nephritis, diabetic nephropathy, diabetic cardiomyopathy, glossalgia, etc. Other diseases and/or pathologic conditions accompanied by cell death are described in the book ("Today's guide for therapy": Ed. Shigeaki Hinohara and Masakazu Abe, Igaku-Shoin Publ., 1995). Red ginseng powder is effective for prevention, treatment or therapy of all diseases and pathological conditions above described. In a broad sense, bedsores, skin ulcer, burn, frostbite, etc. are included in cutaneous wound. Red ginseng powder of the present invention can be used as health drugs for improving immune dysfunction, circulation dysfunction, digestive dysfunction, cutaneous dysfunction, and hypogonadism accompanied with aging. Further, red ginseng powder can be utilized for prevention, treatment or therapy of not only human diseases but also diseases of pet and livestock. Further, it is applied for cultivation of marine products (fishes, crustaceans, eel, conger, etc.) or cultivation of farm products. In this case, red ginseng powder protects ocean resources and farm products against endocrine disruptors, toxins, injuries, trauma, microorganisms, biohazards, etc.

Further, compositions or components extracted from red ginseng powder (red ginseng extract, crude saponin fractions, various purified saponins, ginsenosides and non-saponin fractions) and metabolites thereof or chemical derivatives thereof are expected to exhibit the same effectiveness and efficacy as those of red ginseng powder.

It is possible to develop novel cytoprotective agents by using a component(s) for protecting brain cells (nerve cells, glial cells, etc.) in red ginseng powder, and further as a result of identifying target molecules or receptors for the components for protecting brain cells, novel compounds that modify or regulate the functions of target molecules or receptors can be synthesized. With regard to candidates for the components for protecting brain cells in red ginseng powder, the crude saponin fraction(s) of ginseng, purified saponins such as ginsenoside $Rb_1$, non-saponin fractions of ginseng or metabolites thereof can be taken into consideration, as described in the "detailed description of the invention". References which described the purified saponins and their metabolites in part are: Shoji's review (Junzo Shoji, "Chemistry of Ginseng", Ginseng '95, Akira Kumagaya, Ed., pp 251-161) and Obashi's review (Kyoichi Obashi, et al. "What is an actual active substance(s) in ginseng?—Oriental drugs are already changing in the digestive tube—", Ginseng '95, Akira Kumagaya, Ed., pp 213-221). Consequently, the present invention is essential for development of agents or pharmaceutical compositions for prevention, treatment or therapy of all diseases accompanied by cell death as described above.

Further, among the intracellular signal transduction molecules, certain molecule groups that are involved in fate of cells are elucidated by analyzing the cytoprotective mechanism of ginseng components, metabolites thereof or red ginseng powder (ginseng) itself. Subsequently, novel compounds for promoting or inhibiting the functions of these molecules are synthesized. As a result, drugs useful for preventing, treating or curing diseases accompanied by cell death and malignant tumors can be developed.

On the other hand, in the present invention, ginsenoside $Rb_1$ was found as an excellent agent for preventing, treating or curing brain edema. Generally, the pathological condition of brain edema or nervous tissue edema appears frequently in cases of cerebral hemorrhage, cerebral infarction, cerebral embolism, subarachnoidal hemorrhage, head injuries, brain tumors, encephalitis, heavy metal poisoning, neurotrauma and spinal cord injuries, at convulsive attack, after convulsive attack, during neurosurgical operations, before and after neurosurgical operations, during surgical operations of spine, before and after surgical operation of spine, at resuscitation after cardiac arrest or apnea, etc., and is known to deteriorate prognosis of life or neurological symptoms of patients. Consequently, the present experimental finding that repetitive or continuous intravenous administration of ginsenoside $Rb_1$ at low doses treats or cures brain edema after the onset of cerebral infarction (cerebral embolism) indicates that ginsenoside $Rb_1$ is useful for prevention, treatment or therapy of edema of brain and nervous tissues accompanied by the above mentioned diseases, disorders, symptoms and syndromes.

Further, the pathological condition of biological (living body) tissue edema is known to occur not only in brain tissues with permanently occluded cerebral blood vessels but also in cases of occlusion of peripheral blood vessels and in cases of disturbance of blood flow in the peripheral organs or tissues. Consequently, based on the present experimental finding that intravenous administration of small amounts of ginsenoside $Rb_1$ after permanent occlusion of a cerebral blood vessel (MCA) improved and cured brain edema, ginsenoside $Rb_1$ exhibits efficacy for circulatory disorders of peripheral tissues and peripheral organs (e.g. aortitis syndrome, collagen diseases, acute occlusion of peripheral arteries, acute arteriosclerosis obliterans, thromboangiitis obliterans, arteriosclerosis obliterans, thrombophlebitis, diabetic retinopathy, diabetic nephropathy, central retinal arteriovenous occlusion, acute peripheral circulatory insufficiency, shock, Raynaud's disease, Raynaud's syndrome, hemorrhoids, myocardial infarction, bedsores, peripheral circulatory insufficiency, angina pectoris, ischemia-reperfusion injuries of liver, kidney and heart, etc.). Of course, among diseases hereinabove, for edema of lesioned tissues accompanied by hemorrhoids and bedsores, ginsenoside $Rb_1$ is admixed with preferable base and applied as external spread, external spray or rectal use. If the extracellular fluid concentrations of ginsenoside $Rb_1$ in lesioned tissues are maintained at 1 ng/ml or less, preferably 10 pg/ml or less, more preferably 100 fg/ml or less, routes of its administration are not limited with the intravenous administration and any route of administration can be selected as described hereinbefore.

Further, the present invention showed that repetitive or continuous intravenous administration of low doses of ginsenoside $Rb_1$ exhibits effectiveness and efficacy against bedsores accompanied by spinal cord injuries. This indicates that ginsenoside $Rb_1$ is useful not only for bedsores in patients with spinal cord injuries but also for bedsores in patients with neurotrauma, peripheral nerve disorders, peripheral neuralgia, peripheral neuroparalysis, cerebral apoplexy, neurodegenerative diseases and demyelinating diseases. Of course, we have already demonstrated that low doses of ginsenoside $Rb_1$ exhibit excellent effectiveness and efficacy for the primary lesions of brain and nervous diseases.

It is known that in the nervous tissues having spinal cord injuries, edema occurs frequently in the said spinal cord tissues, and as a result, neurological symptoms are deteriorated severely (e.g. paraplegia of upper or lower extremities, dysuria, dyschezia and neurogenic bladder). Results of the present experiments showing excellent therapeutic effects on spinal cord injuries by repetitive or continuous intravenous administration of low doses of ginsenoside $Rb_1$, indicate that ginsenoside $Rb_1$ is not only useful for prevention, treatment or therapy of edema of spinal cord tissues but also useful for preventing, treating or curing autonomic neuropathy, dysuria, dyschezia and neurogenic bladder.

Further, low doses of ginsenoside $Rb_1$ potentiates the expressions of a cell death-suppressing gene product $Bcl-x_L$ in oligodendrocytes and myocardial cells and promotes survival of the same cells. Consequently, intravenous administration, intravenous repetitive or continuous administration, nasal administration, sublingual administration or intrarectal administration of low doses of ginsenoside $Rb_1$ appears to be effective for treatment or therapy of demyelinating diseases such as multiple sclerosis, Binswanger's disease, leukoencephalopathy, etc., chronic hypoperfusion disorders of brain, myocardial infarction, cardiac failure, cardiomyopathy, cardiac arrest, angina pectoris, etc. The above administration of ginsenoside $Rb_1$ at low doses during cardiopulmonary resuscitation, before and after cardiopulmonary resuscitation, during surgical operations of heart, before and after surgical operations of heart, etc. also appears to be effective.

Ginsenoside $Rb_1$ is, as described above, not only useful as medicinal or pharmaceutical compositions but also able to be used as compositions for health drugs or cosmetics to prevent aging in vivo, since it suppresses apoptosis-like cell death or apoptosis of all cells. Especially, ginsenoside $Rb_1$ is admixed or added into any cosmetics so that the extracellular fluid concentrations of ginsenoside $Rb_1$ in local regions or lesions of the skin are adjusted to 1 ng/ml or less, preferably 10 pg/ml or less, more preferably 100 fg/ml or less. Examples of cosmetics are any cosmetics, for example, skin lotion, milk lotion, foundation, cold cream, cleansing cream, face washing foam, night cream, beauty cream, face powder, gargle, eye wash, face wash, lip stick, lip cream, make-up base, UV liquid foundation, powder foundation, etc. Trace amounts of ginsenoside $Rb_1$ are admixed or added into these cosmetics and are useful for preventing senile symptoms of skin accompanied by aging (e.g. ultraviolet damage, spots on the skin, blotch, wrinkles, lines, furrows, freckle, roughness, crack, chaps, flabby, slackening or loosening of skin, itching, sunburn, etc.). Of course, low doses and low concentrations of ginsenoside $Rb_1$ can be used as hair-restorers, hair-raising agents, hair-grooming agents, hair tonic or as agents for preventing deterioration of depilation or alopecia.

Since the potentiating actions of ginsenoside $Rb_1$ on the expression of $Bcl-x_L$ are noted in all cells including nerve cells, glial cells, vascular endothelial cells, vascular smooth muscle cells, neural stem cells, etc., ginsenoside $Rb_1$ is, in this meaning, thought to be cytoprotective agents which exhibit excellent effects at low doses and low concentrations. Consequently, low doses and low concentrations of ginsenoside $Rb_1$ are thought to be extremely useful for all diseases, syndromes and symptoms accompanied by cell death not only in the central nervous tissue but also in peripheral tissues and peripheral organs. Further, low doses and low concentrations of ginsenoside $Rb_1$ are, in patients with cancer and sarcoma, useful for improving QOL (quality of life) and prolonging life of the patients by protecting normal cells in the healthy or intact tissues invaded by tumor cells.

We have found in the present invention that a novel and useful cytoprotective agent, dihydroginsenoside $Rb_1$, can be prepared by using ginsenoside $Rb_1$ as a leading compound. This indicates that by using other components in ginseng as a leading compound(s) novel and useful medicinal or pharmaceutical compositions as well as health drugs and health foods can be developed.

The results of the present experiments using rats with spinal cord injuries indicate that the therapeutic effects of the preparations for intravenous administration comprising low doses of the crude saponin fraction(s) on spinal cord injuries are almost equally excellent as compared with those of ginsenoside $Rb_1$. Consequently, any one of purified saponins in the crude saponin fraction(s) or metabolites thereof can exhibits extremely potent therapeutic actions on spinal cord injuries. This supports that any one of purified saponins in the crude saponin fraction(s) or metabolites thereof can be a leading compound(s) to find novel substances for treatment or therapy of spinal cord injuries or neurotrauma. The results of the present experiments support that any one of the purified saponins (FIG. 15) in the crude saponin fractions suppresses secondary degeneration of the nervous tissues after spinal cord injuries. In the present experiment, a crude saponin fraction of *Panax ginseng* C. A. Meyer was used, but by using crude saponin fractions of other types of ginseng (e.g. Sanchi (Sanshichi)-ginseng, Denhichi ginseng, Himalayan ginseng, American ginseng, Tikusetu ginseng, etc.) similar results can be obtained. Consequently, any one of components in the aforementioned crude saponin fractions in ginseng appear to be useful for prevention, treatment or therapy of spinal cord injuries, neurotrauma, neural traumatic injuries or head injuries.

It is well known that nervous tissues are the most vulnerable to traumatic injuries when compared with other peripheral tissues. The fact that the medicinal or pharmaceutical composition comprising low doses of the crude saponin fraction(s) exhibits marked effects for treatment and/or therapy of spinal cord injuries indicates that low doses of the crude saponin fraction(s) are also effective for treatment or therapy of traumatic injuries to the peripheral tissues other than the central nervous tissue.

Further, it is reported that in cases of spinal cord injuries, the damage to glial cells, especially oligodendrocytes, results in apoptosis, then demyelination occurs to make neurological symptoms worse (Crowe, M. J. et al., Nature Med. 3, 73-76, 1997; Emery, E. et al., J. Neurosurg. 89, 911-920, 1998). The experimental results, in which intravenous administration of the crude saponin fraction(s) markedly ameliorates paralysis or paraplegia of both hindlimbs of rats with spinal cord injuries, indicate that any one of purified saponins in the crude saponin fraction(s) inhibits apoptosis of oligodendrocytes or apoptosis-like nerve cell death and thereby ameliorates symptoms of spinal cord injuries. Consequently, any one of purified saponins in low concentrations and low doses of the crude saponin fraction(s) of the present invention is thought to be useful for prevention, treatment or therapy of brain and nervous diseases accompanied by demyelination (multiple sclerosis, Binswanger's disease, chronic hypoperfusion disorder of brain, leukoencephalitis, etc.) through protection of oligodendrocytes. Further, the experimental results, in which intravenous administration of the crude saponin fraction(s)

ameliorates paralysis of both hindlimbs of rats with spinal cord injuries (paraplegia), suggest that injured nerve fibers or nervous tissues can be regenerated as a result of administering the crude saponin fraction(s).

In nervous tissues with spinal cord injury, edema occurs frequently in the said spinal cord tissues, and neurological symptoms (paraplegia of lower extremities, urination disorder(s), dysuria, difficulty in urination, dyschezia, neurogenic bladder, etc.) are deteriorated. The present experimental finding that intravenous administration of the low doses of the crude saponin fraction(s) exhibits excellent therapeutic effects on spinal cord injuries, indicate usefulness of the crude saponin fraction(s) or any one of purified saponins in the crude saponin fraction(s) for prevention, treatment or therapy of spinal cord tissue edema, urination disorders, dysuria, dyschezia and/or neurogenic bladder accompanied by spinal cord injuries.

In the present experiments, further, it was found that the preparations for intravenous administration comprising the crude saponin fraction(s) or salts thereof suppress the secondary degeneration of nervous tissues caused by spinal cord injuries. Further, the medicinal or pharmaceutical composition(s) comprising low doses and low concentrations of the crude saponin fraction(s) can be expected to be an epock-making remedy for spinal cord injuries, neurotrauma, neural traumatic injuries or head injuries as well as exhibiting the effectiveness and efficacy for peripheral tissue injuries.

Since the therapeutic effects of low doses and low concentrations of the crude saponin fraction(s) on spinal cord injuries, neurotrauma and neural traumatic injuries are epoch-making, this suggests that novel pharmaceutical compounds for treatment or therapy of spinal cord injuries, neurotrauma and neural traumatic injuries can be synthesized by using components in the crude saponin fraction(s), purified saponins or metabolites thereof as leading compounds. Further, as a result of identifying the target molecules of components in the crude saponin fraction(s), purified saponins or metabolites thereof, novel compounds which can modify the functions of the target molecules, are synthesized. Then the development of remedies for spinal cord injuries, neural traumatic injuries, neurotrauma or traumatic injuries can be directed.

In the present invention, it was demonstrated that the crude saponin fraction(s) of ginseng or any one of constitutional components of the crude saponin fraction(s) exhibited an excellent protective action(s) on brain cells or nerve cells and therapeutic effects on spinal cord injuries, neurotrauma, head injuries or neural traumatic injuries as did ginsenoside $Rb_1$ at the low doses and low concentrations. Consequently, low doses and low concentrations of the crude saponin fraction(s) or any one of constitutional components of the crude saponin fraction(s) of the present invention have all effectiveness, efficacy and usages of ginsenoside $Rb_1$ described by the inventors (Sakanaka, Tanaka or Nakata) in Japanese Patent Application No. Hei 10-365560, PCT/JP99/02550 (Brain cell or nerve cell-protective agents comprising ginsenoside $Rb_1$) and Japanese Patent Application No. Hei 11-243378, PCT/JP99/06804 (Cerebrovascular regeneration/reconstruction promoters and nerve tissue secondary degeneration inhibitors comprising ginsenoside $Rb_1$) or Japanese Patent Application No. 2000-163026 (Agents for promoting dermal tissue regeneration comprising ginsenoside $Rb_1$). Namely, the low doses and low concentrations of the crude saponin fraction(s) or any one of the constitutional components of the crude saponin fractions can increase the expression of a cell death-suppressing gene product $Bcl-x_L$ and, as a result, can suppress apoptosis of nerve cells or apoptosis-like nerve cell death, similar to ginsenoside $Rb_1$. Further, the low doses and low concentrations of the crude saponin fraction(s) or any one of constitutional components of the crude saponin fraction(s), like ginsenoside $Rb_1$, can exhibit effectiveness and efficacy for all brain and nervous diseases accompanied by nerve cell death. Examples of these brain and nervous diseases are Alzheimer's disease, cerebral apoplexy, cerebral infarction, cerebral thrombosis, cerebral embolism, subarachnoidal hemorrhage, transient cerebral ischemic attack, Pick disease, spinocerebellar degeneration, Parkinson's disease, demyelinating diseases, polyglutamine diseases such as chorea, amyotrophic lateral sclerosis, glaucoma, senile macular degeneration, diabetic retinopathy, central retinal arteriovenous occlusion, retinal detachment, pigmentary degeneration of the retina, AIDS encephalopathy, hepatic encephalopathy, encephalitis, cerebral palsy, head injuries, spinal cord injuries, carbon monoxide poisoning, asphyxia of the newborn, peripheral neuropathy, spastic paraplegia, progressive supranuclear palsy, circulatory disorders of the spinal cord, mitochondrial encephalomyopathy, meningitis, etc.

The cell death-suppressing gene product $Bcl-x_L$ is the protein that can be said as the last fortress for cell survival, and it is distributed not only in the brain and nervous tissues but also in many peripheral organs and tissues, for example liver, spleen, tissues of the immune system, tissues of the circulatory system and skin, and supports the survival of cells. Consequently, based on the presumption that low doses and low concentrations of the crude saponin fraction(s) or any one of constitutional components of the crude saponin fractions can increase the expression of $Bcl-x_L$ protein in the same way as ginsenoside $Rb_1$, the low doses and low concentrations of the crude saponin fraction(s) or any one of constitutional components of the crude saponin fractions can be effectively used for treatment, prevention and/or therapy of all diseases of the peripheral organs and tissues accompanied by cell death. Among the diseases of the peripheral organs and tissues accompanied by cell death, following diseases are included: ischemia-reperfusion injuries of cardiac muscles, liver and kidneys, cardiomyopathy, cardiac failure, myocardial infarction, angina pectoris, peripheral circulatory failure, bedsores, wound, cutaneous ulcer, cutaneous wound, trauma, burn, radiation injuries, aging, ultraviolet rays disturbance, electric injuries, depilation, alopecia, xeroderma, autoimmune diseases, immunodeficiency diseases, graft rejection after organ transplantation, muscular dystrophy, corneal injuries, infectious diseases, collagen diseases, aortitis syndrome, acute arterial embolism, thromboangiitis obliterans, peptic ulcer, arteriosclerosis obliterans, Raynaud's disease, Raynaud's syndrome, hemorrhoids, thrombophlebitis, pancreatitis, hepatitis, nephritis, diabetic nephropathy, diabetic cardiomyopathy, glossalgia, etc. The low doses and low concentrations of the crude saponin fraction(s) or any one of the constitutional components of the crude saponin fractions of the present invention can be used as health drugs for improving immune dysfunction, circulation dysfunction, digestive dysfunction, cutaneous dysfunction and hypogonadism accompanied with aging. Further, the low doses and low concentrations of the crude saponin fraction(s) or any one of the constitutional components of the crude saponin fractions can be utilized as cosmetic compositions for preventing, treating or managing sanile symptoms accompanied by aging (ultraviolet rays disturbance, wrinkle, furrows, lines, spots, blotch, sunburn, etc.). Further, the low doses and low concentrations of the crude saponin fraction(s) or components thereof protect normal tissues in healthy cells invaded by tumor cells in patients with cancer or sarcoma, and are useful for improving QOL (quality of life) and prolonging survival of the patients.

In Japanese Patent Application No. Hei 11-243378, PCT/JP99/06804 (Cerebrovascular regeneration/reconstruction promoters and nerve tissue secondary degeneration inhibitors comprising ginsenoside $Rb_1$), the present inventors (Sakanaka and Tanaka) have found that repetitive or continuous intravenous administration of low doses of ginsenoside $Rb_1$ could stand up bedridden rats with spinal cord injuries through a cerebrovascular regeneration and reconstruction-promoting action(s), a suppressive action(s) on secondary degeneration of neural (nervous) tissues and a suppressive action(s) on apoptosis of oligodendrocytes or apoptosis-like cell death. Experimental results of the present invention, in which the low doses and low concentration of the crude saponin fraction(s) or any one of the constitutional components of the crude saponin fractions can exhibit the excellent therapeutic effects on spinal cord injuries as like ginsenoside $Rb_1$, indicate that the low doses and low concentrations of the crude saponin fraction(s) or any one of the constitutional components of the crude saponin fractions can be a remedy for spinal cord injuries, neurotrauma, head injuries or neural traumatic injuries. Namely, the effectiveness, efficacy or usages of ginsenoside $Rb_1$ described by us (Sakanaka and Tanaka) in Japanese Patent Application No. Hei 11-243378, PCT/JP99/06804 (Cerebrovascular regeneration/reconstruction promoters and nerve tissue secondary degeneration inhibitors comprising ginsenoside $Rb_1$) are in common with those of the low doses and low concentration of the crude saponin fraction(s) or any one of the constitutional components of the crude saponin fractions. Of course, as methods for administration of the crude saponin fraction(s) or constitutional components of the crude saponin fractions, any route of administration can be selected like ginsenoside $Rb_1$, if the extracellular fluid concentrations of the crude saponin fraction(s) or any one of the constitutional components of the crude saponin fraction(s) in lesioned tissues can be kept low as described above. Concretely, low doses and low concentrations of the crude saponin fraction(s) or any one of the constitutional components of the crude saponin fractions can be used not only as agents for intravenous administration but also as agents for external use or for injection to local lesions. Further, methods for administration of the crude saponin fraction(s) or any one of constitutional components of the crude saponin fraction(s) can be selected from any route of subcutaneous injection, intramuscular injection, eye drops, nasal drops, ear drops, inhalations, suppositories, oral administrations, sublingual administrations, transdermal administrations, etc. However, when the crude saponin fraction(s) or any one of constitutional components of the crude saponin fraction(s) is used as agents for oral administration, if the crude saponin fraction(s) or any one of constitutional components of the crude saponin fraction(s) is administered alone, the effectiveness may not always be expected. Consequently, it may be necessary that the crude saponin fraction(s) or any one of constitutional components of the crude saponin fraction(s) is mixed, encapsulated or bound with a carrier(s) which inhibits decomposition in the digestive tract or with a carrier(s) which promotes absorption in the digestive tract, and then administered orally. Further, if metabolites of the crude saponin fraction(s) or any one of constitutional components of the crude saponin fraction(s) are identified to have equal effectiveness and efficacy with the crude saponin fraction(s) or any one of constitutional components of the crude saponin fraction(s) or to have more effectiveness and efficacy than the crude saponin fraction(s) or any one of constitutional components of the crude saponin fraction(s), the active metabolites can be administered against diseases described above for which the low doses and low concentrations of the crude saponin fraction or any one of constitutional components of the crude saponin can be applied by the administration methods described above. Further, a dispersant of the crude saponin fraction(s) or any one of constitutional components of the crude saponin fraction(s) of the present invention and macromolecular compounds is prepared, and spray dried to select any route of administration. Furthermore, the crude saponin fraction(s) or any one of constitutional components of the crude saponin fraction(s) is coated with micro-particles of macromolecular compounds to select any route of administration. Of course, a prodrug is prepared with any one of constitutional components of the crude saponin fraction(s), and any route of administration can be selected.

In addition, the low doses and/or low concentrations of the crude saponin fraction(s) or any one of constitutional components of the crude saponin fraction(s) appear to be effective for protection or maintenance of cultured keratinocyte sheets for skin graft. Further, other organs or tissues for transplantation (liver, kidney, heart, pancreas, lung, digestive tract, digestive tube, cornea, blood vessel, etc.) are immersed in or perfused with the crude saponin fraction(s) or any one of the constitutional components of the crude saponin fraction(s) during a term before transplantation operation is conducted, and as a result, cell injury or damage to the vascular networks of these organs can be suppressed, and the results of transplantation operation can be improved. Further, the crude saponin fraction(s) or any one of the constitutional components of the crude saponin fraction(s) at low doses and low concentrations appears to be effective for protection or maintenance of blood cell components and platelets for transfusion, stem cells (ES cells), neural stem cells, etc. and for protection or maintenance of frozen ova or frozen sperms.

In the present invention, a novel reduced compound of ginsenoside $Rb_1$, i.e. dihydroginsenoside $Rb_1$, exhibited excellent therapeutic effects on cerebral infarction by its intravenous administration at low doses as did ginsenoside $Rb_1$. Namely, dihydroginsenoside $Rb_1$ is considered to have effectiveness, efficacy and usages similar to those of ginsenoside $Rb_1$ described in the prior patent application by the present inventors (Sakanaka and Tanaka) (Japanese Patent Application No. Hei 10-365560, PCT/JP99/02550 and Japanese Patent Application No. Hei 11-340850, PCT/JP99/06804). Based on the present experimental results using dihydroginsenoside $Rb_1$, it was proved that by applying ginsenoside $Rb_1$ as a leading compound large numbers of agents can be developed, i.e. agents for protecting nerve cells, agents for protecting brain cells, remedy for cerebral apoplexy, remedies for neurodegenerative diseases, remedies for spinal cord injuries, neurotrauma, head injuries and nerve injuries, agents for protecting cells, etc. Large numbers of purified saponins in ginseng have a common chemical structure similar to ginsenoside $Rb_1$, i.e. the side chain (carbon chain) is bound with the dammarane skeleton or structure (steroid-like skeleton or structure) (refer to FIG. 15). Consequently, with regard to purified saponins other than ginsenoside $Rb_1$ in ginseng, reduction of the double bond in the side chain (carbon chain) provides novel compounds having pharmacological actions, effectiveness, efficacy and usages similar to those of the original purified saponins.

The present experimental finding that dihydroginsenoside Rb$_1$ or metabolites thereof, like ginsenoside Rb$_1$, can reduce cerebral infarct lesion in SH-SP rats with permanent occlusion of the MCA, proves that novel agents for protecting nerve cells or novel agents for protecting brain cells can be prepared by applying ginsenoside Rb$_1$ as a leading compound. Furthermore, since the effective doses of intravenously administered dihydroginsenoside Rb$_1$ are almost identical with those of intravenously administered ginsenoside Rb$_1$, dihydroginsenoside Rb$_1$ is likely to exhibit at low concentrations and low doses excellent neuroprotective actions and brain cell-protective actions, similar to ginsenoside Rb$_1$. Consequently, dihydroginsenoside Rb$_1$ has all effectiveness, efficacy and usages of ginsenoside Rb$_1$ described by the inventors (Sakanaka and Tanaka) in Japanese Patent Application No. Hei 10-365560, PCT/JP99/02550 (Brain cell or nerve cell-protective agents comprising ginsenoside Rb$_1$). Namely, dihydroginsenoside Rb$_1$ is likely to increase the expression of a cell death-suppressive gene product Bcl-x$_L$, and as a result, it suppresses apoptosis of nerve cells or apoptosis-like nerve cell death, similar to ginsenoside Rb$_1$. Further, dihydroginsenoside Rb$_1$ exhibits effectiveness and efficacy for all brain and nervous diseases accompanied by nerve cell death as does ginsenoside Rb$_1$. Examples of these brain and nervous diseases are Alzheimer's disease, cerebral apoplexy, cerebral infarction, cerebral thrombosis, cerebral embolism, subarachnoidal hemorrhage, transient cerebral ischemic attack, Pick disease, spinocerebellar degeneration, Parkinson's disease, demyelinating diseases, polyglutamine diseases such as chorea, amyotrophic lateral sclerosis, glaucoma, senile macular degeneration, diabetic retinopathy, central retinal arteriovenous occlusion, retinal detachment, pigmentary degeneration of the retina, AIDS encephalopathy, hepatic encephalopathy, encephalitis, cerebral palsy, head injuries, spinal cord injuries, carbon monoxide poisoning, asphyxia of the newborn, peripheral neuropathy, spastic paraplegia, peripheral nerve paralysis, peripheral neuralgia, progressive supranuclear palsy, circulatory disorders of the spinal cord, mitochondrial encephalomyopathy, meningitis, etc.

The cell death-suppressing gene product Bcl-x$_L$ is the protein that can be said as the last fortress for cell survival, and it is distributed not only in the brain and nervous tissues but also in almost all peripheral organs and tissues, for example liver, spleen, tissues of the immune system, tissues of the circulatory system and skin, and supports the survival of cells. Consequently, based on the presumption described above that dihydroginsenoside Rb$_1$ increases the expression of Bcl-x$_L$ protein as ginsenoside Rb$_1$ does, dihydroginsenoside Rb$_1$ appears to be effective for treatment, prevention and/or therapy of all diseases of the peripheral organs and tissues accompanied by cell death. Among the diseases of the peripheral organs and tissues accompanied by cell death, following diseases are included: ischemia-reperfusion injuries of cardiac muscles, liver and kidneys, cardiomyopathy, cardiac failure, myocardial infarction, angina pectoris, peripheral circulatory failure, bedsores, cutaneous ulcer, cutaneous wound, trauma, burn, radiation injuries, aging, injuries or damage by ultraviolet rays, electric injuries, depilation, alopecia, xeroderma, autoimmune diseases, immunodeficiency diseases, graft rejection after organ transplantation, muscular dystrophy, corneal injuries, infectious diseases, collagen diseases, aortitis syndrome, acute arterial embolism, thromboangiitis obliterans, peptic ulcer, arteriosclerosis obliterans, Raynaud's disease, Raynaud's syndrome, hemorrhoids, thrombophlebitis, pancreatitis, hepatitis, nephritis, diabetic nephropathy, diabetic cardiomyopathy, glossalgia, etc. Other diseases and pathological conditions accompanied by cell death are described in the book ("Today's guide for therapy": Ed. Shigeaki Hinohara and Masakazu Abe, Igaku-Shoin Publ., 1995). Dihydroginsenoside Rb$_1$ protects normal cells in healthy tissues invaded by tumor cells in patients with cancer or sarcoma, and is useful for improving QOL (quality of life) and prolonging survival of the patients. Dihydroginsenoside Rb$_1$ of the present invention can be used as health drugs for improving immune dysfunction, circulation dysfunction, digestive dysfunction, cutaneous dysfunction and hypogonadism accompanied with aging. Further, dihydroginsenoside Rb$_1$ can be utilized as cosmetic compositions for preventing, treating or managing sanile symptoms accompanied by aging (shrink or atrophy of skin, white-hair, gray hair, scurf, dandruff, exfoliation of the stratum corneum exfoliation of cells in the stratum corneum, dry skin, senile xerosis, asteatotic dermatitis, slackening or loosening of skin, itching, roughness, dryness, crack, freckle, pigmentation, furrows, wrinkles, lines, spots, blotch, sunburn, etc.). Further, dihydroginsenoside Rb$_1$ can be used for chemical peeling. Dihydroginsenoside Rb$_1$ can also be used as hair-restorers, hair tonic, hair-raising agents, hair-grooming agents and/or agents for preventing deterioration of depilation or alopecia.

In Japanese Patent Application No. Hei 11-243378, PCT/JP99/06804 (Cerebrovascular regeneration/reconstruction promoters and nerve tissue secondary degeneration inhibitors comprising ginsenoside Rb$_1$), we (Sakanaka and Tanaka) have found that repetitive or continuous intravenous administration of low doses of ginsenoside Rb$_1$ could stand up bedridden rats with spinal cord injuries through a cerebrovascular regeneration and reconstruction promoting-action(s), a suppressive action(s) on the secondary degeneration of nervous tissues and a suppressive action(s) on apoptosis of oligodendrocytes or apoptosis-like cell death. The present experimental results, in which dihydroginsenoside Rb$_1$ exhibits the excellent therapeutic effects on cerebral infarction as does ginsenoside Rb$_1$, indicate that dihydroginsenoside Rb$_1$ can be a remedy for spinal cord injuries, head injuries, neurotrauma or neural traumatic injuries. Namely, the effectiveness, efficacy or usages of ginsenoside Rb$_1$ described by the present inventors (Sakanaka and Tanaka) in Japanese Patent Application No. Hei 11-243378, PCT/JP99/06804 (Cerebrovascular regeneration/reconstruction promoters and nerve tissue secondary degeneration inhibitors comprising ginsenoside Rb$_1$) are in common with those of dihydroginsenoside Rb$_1$. Of course, as methods for administration of dihydroginsenoside Rb$_1$, any route of administration can be selected, like ginsenoside Rb$_1$. Concretely, dihydroginsenoside Rb$_1$ can be used not only as agents for intravenous administration but also as agents for external use, for injection to local lesions or for spray on local lesions. Further, as methods for administration of dihydroginsenoside Rb$_1$, any one of subcutaneous injection, intramuscular injection, eye drops, eye ointments, nasal drops, ear drops, inhalations, suppositories, oral administrations, sublingual administrations, transdermal administrations, etc. can be selected. However, when dihydroginsenoside Rb$_1$ is used as agents for oral administration, if dihydroginsenoside Rb$_1$ is administered alone, the effectiveness may not always be expected. Consequently, it may be necessary that dihydroginsenoside Rb$_1$ is mixed, encapsulated or bound with a carrier(s) which inhibits decomposition in the digestive tract (shellac, gelatin, oil layer, etc.) or with a carrier(s) which promotes absorption in the digestive tract, and then administered orally. Further, if metabolites of dihydroginsenoside Rb$_1$ is identified to have equal effectiveness and efficacy with dihydroginsenoside Rb$_1$ or to have more effectiveness and efficacy than dihydroginsenoside Rb$_1$, the active metabolites can be administered against diseases described above for which dihydroginsenoside Rb$_1$ can be applied by the administration methods described earlier. Further, a dispersant of dihydroginsenoside Rb$_1$ of the present invention and macromolecular compound is prepared, and spray-dried to select any route of administration. Furthermore, dihydroginsenoside Rb$_1$ is coated with micro-particles of macromolecular compound to select any route of administration.

In addition, dihydroginsenoside Rb$_1$ appears to be effective for protection or maintenance of cultured keratinocyte sheets for skin graft. Other organs or tissues for transplantation (liver, kidney, heart, pancreas, lung, digestive tract, digestive tube, cornea, blood vessel, etc.), are immersed in or perfused with dihydroginsenoside Rb$_1$ during a term before transplantation operation is conducted, and as a result, cell injury or damage to the vascular networks of these organs can be suppressed, and the results of transplantation operation can be improved. Further, dihydroginsenoside Rb$_1$, like ginsenoside Rb$_1$, appears to be effective for protection or maintenance of blood cell components and platelets for transfusion, stem cells (ES cells), neural stem cells, etc. and for protection or maintenance of frozen ova, frozen sperms, frozen cells and frozen tissues.

EXAMPLES

The present invention will be explained in detail by concrete examples, but the present invention is not limited within these examples.

Example 1 (Experiment on Oral Administration of Red Ginseng Powder Before and After Cerebral Infarction)

Male SH-SP rats at the age of 12-13 weeks, weighing 250-300 g, were used. Animals were bred in a room furnished with 12 hours light and dark cycles and water and feeds were supplied ad libitum. The cortical branch of the left middle cerebral artery (MCA) of each animal was coagulated and cut under inhalation anesthesia according to the method described by the present inventors (Sakanaka and Tanaka) (Igase, K., et al., J. Cereb. Blood Flow Metab., 19, 298-306, 1999; Sadamoto, Y., et al., Biochem. Biophys. Res. Commun., 253, 26-32, 1998). Red ginseng powder was mixed with distilled water and administered orally once a day for one week before MCA permanent occlusion and for 32 days after MCA permanent occlusion (0.6 g/kg/day, 0.75 g/kg/day, 0.9 g/kg/day or 1.2 g/kg/day, n=5-8)

Control animals with MCA permanent occlusion (ischemic control animals) and sham-operated animals were orally administered with the same amount of distilled water.

After MCA permanent occlusion, according to the method of the inventors (Sakanaka and Tanaka) (Zhang B. et al., J. Stroke Cerebrovasc. Dis., 7, 1-9, 1998; Igase, K., et al., J. Cereb. Blood Flow Metab., 19, 298-306, 1999; Sadamoto, Y., et al., Biochem. Biophys. Res. Commun., 253, 26-32, 1998), water maze tests were performed for 4 days at the 2nd week and at the 4th week, respectively, and the place navigation abilities of SH-SP rats were determined.

Results are shown in FIG. 1. In FIG. 1, the upper drawing is the results of the 2nd week and the lower drawing is the results of 4th week. In FIG. 1, open circles indicate the results of ischemic rats administered with distilled water; closed circles indicate the results of rats with sham operation; open squares indicate the results of ischemic rats administered with red ginseng powder in a dose of 0.6 g/kg/day; closed squares indicate the results of ischemic rats administered with red ginseng powder in a dose of 0.75 g/kg/day; open triangles indicate the results of ischemic rats administered with red ginseng powder in a dose of 0.9 g/kg/day; and closed triangles indicate the results of ischemic rats administered with red ginseng powder in a dose of 1.2 g/kg/day.

As shown in FIG. 1, the place navigation abilities of animals after MCA-permanent occlusion (after cerebral infarction) were significantly improved in the groups administered with red ginseng powder in doses of 0.75-1.2 g/kg/day, as compared with the group of ischemic animals administered with distilled water. The most favorable effect was observed in the group administered with red ginseng powder in a dose of 0.9 g/kg/day. Data are represented as mean±SE. Statistical analyses were conducted by ANOVA+ Fisher's PLSD. No significant differences in swimming speed of SH-SP rats were observed among the six experimental groups.

After termination of water maze tests at the 4th week, the SH-SP rats were anesthetized with chloral hydrate, and they were perfused and fixed transcardially with 0.1 mole phosphate buffer containing 4% paraformaldehyde. The brains of the animals were dissected out and the cerebrocortical infarcted lesions were photographed. The left cerebrocortical infarcted areas were divided by the left cerebral hemispheric areas to calculate ratios of the cerebrocortical infarction (%). Results are shown in FIG. 2. Data are represented as mean±SE. Statistical analyses were conducted by Mann-Whitney U-test.

As shown in FIG. 2, ratios of the cerebrocortical infarction were also significantly decreased in the groups of ischemic animals administered with red ginseng powder in the doses of 0.75-1.2 g/kg/day, as compared with the group of ischemic animals administered with distilled water. The most favorable effect was observed in the group administered with red ginseng powder in a dose of 0.9 g/kg/day, and the mean value of the ratio of the cerebrocortical infarction was reduced to less than ½ of the group of ischemic animals administered with distilled water. Accordingly, the actual infarcted volume was reduced to about ¼ by the oral administration of red ginseng powder in a dose of 0.9 g/kg/day.

In FIG. 3, the upper photographs show cerebral infarct lesions in the group of ischemic animals administered with distilled water (4 cases), and the lower photographs in FIG. 3 show cerebral infarct lesions in the group of ischemic animals administered with red ginseng powder in a dose of 0.9 g/kg/day (4 cases).

FIG. 4 shows schematic illustration of the summarized results of the experiments. In the group of ischemic animals administered with distilled water, the large cerebral infarcted lesion as well as cerebral edema was observed, but in the group of ischemic animals administered with red ginseng powder, cerebral infarcted area was decreased and cerebral edema was also reduced. As a result, animals arrived at the objective platform within a short time in the water maze test.

Example 2 (Experiments on Oral Administration of Red Ginseng Powder After Cerebral Infarction)

The cortical branch of the left middle cerebral artery (MCA) of each male SH-SP rat at the age of 12-13 weeks, weighing 250-300 g, was coagulated and cut under inhalation anesthesia, and red ginseng powder in a dose of 0.9 g/kg/day was administered orally once a day for 32 days (n=7). Control animals with permanent MCA occlusion (infarcted control animals; n=8), were administered with only distilled water.

After MCA permanent occlusion, according to the method of the inventors (Sakanaka and Tanaka) (Zhang B. et al., J. Stroke Cerebrovasc. Dis., 7, 1-9, 1998; Igase, K., et al., J. Cereb. Blood Flow Metab., 19, 298-306, 1999; Sadamoto, Y., et al., Biochem. Biophys. Res. Commun., 253, 26-32, 1998), water maze tests were performed for 4 days at the 2nd week and at the 4th week, respectively, and the place navigation abilities of SH-SP rats were determined.

Results are shown in FIG. 5. In FIG. 5, the upper drawing is the results of the 2nd week and the lower drawing is the results of 4th week. In FIG. 5, open circles indicate the results of ischemic rats administered with only distilled water (n=8); closed squares indicate the results of ischemic rats administered with red ginseng powder in a dose of 0.9 g/kg/day (n=8). For reference, the experimental values of the group of the sham-operated animals used in FIG. 1 are shown with closed circles.

As shown in FIG. 5, the place navigation abilities of animals after MCA-permanent occlusion (after cerebral infarction) were significantly improved in the group orally administered with red ginseng powder in a dose of 0.9 g/kg/day, as compared with the group of ischemic animals administered with distilled water. Preferable effect was observed at the 4th week after MCA occlusion. Data are represented as mean±SE. Statistical analyses were conducted by ANOVA+Fisher's PLSD.

After termination of water maze tests at the 4th week, the SH-SP rats were anesthetized with chloral hydrate, and they were perfused and fixed transcardially with 0.1 mole phosphate buffer containing 4% paraformaldehyde. The brains of the animals were dissected out and cerebrocortical infarcted lesions were photographed. Areas of the left cerebral hemisphere and the left cerebrocortical infarct lesions were measured on the photographs by using an image analyzer. The left cerebrocortical infarcted areas were divided by the left cerebral hemispheric areas to calculate ratios of the cerebrocortical infarction (%). Results are shown in FIG. 6. Data are represented as mean±SE. Statistical analyses were conducted by Mann-Whitney U-test.

As shown in FIG. 6, the ratio of the cerebrocortical infarction was also significantly decreased in the group of ischemic animals administered with red ginseng powder in a dose of 0.9 g/kg/day, as compared with the group of ischemic animals administered with distilled water.

Example 3 (Experiments for Analyzing Upregulation by Red Ginseng Powder at High Dose of Bcl-$x_L$ Protein Expression in Neural Tissues)

Whether or not oral administration of red ginseng powder increases the expression of Bcl-$x_L$ protein was investigated by using the transient forebrain ischemic model of gerbils. In our previous report (Wen, T.-C., et al., J. Exp. Med., 188, 635-649, 1998), the experimental system for investigation of Bcl-$x_L$ expression in the hippocampal CA1 field after transient forebrain ischemia has been established, and effects of oral administration of red ginseng powder were examined with the use of this system.

As shown in FIG. 7, one of the present inventors (Sakanaka) had reported that when red ginseng powder was administered orally in a dose of 0.9 g/kg/day or 1.5 g/kg/day, once a day for 7 days before transient forebrain ischemia for 5 minute in gerbils, nerve cell death in the hippocampal CA1 field was significantly prevented and the response latency time in the passive avoidance test was extended, as compared with the group of animals administered with distilled water (Wen, T.-C., et al., Acta Neuropathol., 91, 15-22, 1996). Especially, a good effect was observed in the group of ischemic animals administered with red ginseng powder in the dose of 1.5 g/kg/day, as compared with the group of animals administered with 0.9 g/kg/day. Therefore, in the present experiments, red ginseng powder was administered orally in the dose of 1.5 g/kg/day, once a day for 7 days from 1 week before transient forebrain ischemia for 5 minute, and red ginseng powder was further administered orally after 5 minute ischemia (n=4). Tissues of the hippocampal CA1 field were collected at the 24th hour after the final administration of red ginseng power. Thereafter cells were lysed with sample buffer for electrophoresis and electrophoresed. Proteins separated by the electrophoresis were transferred to nitrocellulose membrane to perform Western blotting by using anti-Bcl-$x_L$ protein antibody. For the animals undergone sham operation (n=4) and the control animals with transient forebrain ischemia for 5 minute (ischemic control animals, n=4), the equal amount of distilled water was given orally. In order to investigate whether oral administration of red ginseng powder at the high dose of 1.5 g/kg/day affects the expression of Bcl-$x_L$ protein in peripheral organs or not, liver and spleen were collected and Western blotting was performed by the same procedures. Details of the above experimental procedures are described in our previous report (Wen, T.-C., et al., J. Exp. Med., 188, 635-649, 1998). Results are shown in FIG. 8.

Further, bands reacted with the anti-Bcl-$x_L$ protein antibody were quantified by using an image analyzer. Results are shown in FIG. 9.

As shown in FIG. 8, when red ginseng powder was administered orally in the dose of 1.5 g/kg/day, once a day for 7 days from 1 week before transient forebrain ischemia for 5 minute, and the equal amount of red ginseng powder was further administered orally after the ischemic insult, expression of Bcl-$x_L$ protein in the tissues of the hippocampal CA1 field after 24 hours was increased in all cases as compared with the sham-operated group and the ischemic group administered with distilled water. As a result of quantifying the bands reacted with the anti-Bcl-$x_L$ protein antibody with the use of an image analyzer, as shown in FIG. 9, it was found that oral administration of red ginseng powder significantly increased the expression of Bcl-$x_L$ protein in the hippocampal CA1 field. However, even though such the high dose of red ginseng powder was administered orally, the expression of Bcl-$x_L$ protein in the liver and spleen was not increased. Statistical analyses were conducted by ANOVA+Scheffe's post hoc test.

Example 4 (Experiments for Analyzing Upregulation by Red Ginseng Powder at Low Dose of Bcl-$x_L$ Protein Expression in Liver and Spleen)

We further investigated whether or not oral administration of low dose of red ginseng powder for a term longer than one week increased the expression of Bcl-$x_L$ protein in the hippocampal CA1 field. For example, red ginseng powder was administered orally in the dose of 200 mg/kg/day, once a day for 4 weeks before transient forebrain ischemia for 5 minute in gerbils, and immediately after 5 minute ischemia, red ginseng powder was further orally administered once (n=4). The hippocampal CA1 field was collected after 24 hours, and Western blotting by using anti-Bcl-$x_L$ protein antibody was performed in the same manner as shown in FIG. 8. The animals undergone sham operation and the control animals with transient forebrain ischemia for 5 minute (ischemic control animals) were administered orally with the equal amount of distilled water alone (n=4 in each group). In order to investigate whether oral administration of red ginseng powder at the dose of 200 mg/kg/day affects expression of Bcl-$x_L$ protein in peripheral organs or not, liver and spleen were collected and Western blotting was performed by the same procedures (n=4 in each group).

However, no significant increase in the expression of Bcl-$x_L$ protein in the hippocampal CA1 field was observed even in case of the oral administration of red ginseng powder in the dose of 200 mg/kg/day for 4 weeks. Further, red ginseng powder was administered orally in the dose of 200 mg/kg/day, once a day for 4 weeks before 5 minute ischemia, and the same dose of red ginseng powder was further administered orally for one week after 5 minute ischemia. However, the passive avoidance learning disability and nerve cell death in the hippocampal CA1 field of gerbils could not be ameliorated. This fact means that if increase in the expression of Bcl-$x_L$ protein is not induced by the oral administration of low dose of red ginseng powder, no protective effect on nerve cells is exhibited.

As described above, when red ginseng powder was administered orally for 4 weeks at the dose of 200 mg/kg/day in gerbils before cerebral ischemia, the expression of Bcl-$x_L$ protein in the hippocampal CA1 was not increased. However, when the same amount of red ginseng powder was administered orally in the same dosing schedule, the expression of Bcl-$x_L$ protein in the liver and the spleen was significantly increased as shown in FIG. 10 and FIG. 11. Statistical analyses were conducted by ANOVA+Scheffe's post hoc test.

Example 5 (Long Term Degeneration-Suppressing Effect of Oral Administration of High Dose of Red Ginseng Powder on Hippocampal CA1 Neurons)

One of the present inventors reported that when the brain temperature of gerbils was maintained at 37° C.±0.2° C. and blood flow of the bilateral common carotid arteries was clamped for 3 min and reperfused, about one half of nerve cells in the hippocampal CA1 field degenerated after one week (Sakanaka, M., et al., Proc. Natl. Acad. Sci. USA, 95, 4635-4640, 1998). Further, the present inventors (Sakanaka and Tanaka) demonstrated that fragmentation of nerve cell nuclei, an index of apoptosis-like cell death, was further in progress in the remaining nerve cells at this moment as revealed by TUNEL staining (Wen, T.-C., et al., J. Exp. Med., 188, 635-649, 1998; Peng, H., et al., J. Cereb. Blood Flow Metab., 18, 349-360, 1998). Consequently, it was demonstrated that in the hippocampal CA1 field of gerbils with transient forebrain ischemia for 3 min different from the case of 5 min ischemia, the degeneration of nerve cells also progressed even at one week and later after ischemia. We investigated the effect of oral administration of red ginseng powder for 4 weeks after ischemia using 3-min transient forebrain ischemia model in which nerve cell death continued for relatively long term.

According to the method of the present inventors (Sakanaka, M., et al., Proc. Natl. Acad. Sci. USA, 95, 4635-4640, 1998; Wen, T.-C., et al., J. Exp. Med., 188, 635-649, 1998; Peng, H., et al., J. Cereb. Blood Flow Metab., 18, 349-360, 1998), blood flow of the bilateral common carotid arteries was clamped for 3 min while maintaining the brain temperature of gerbils at 37° C.±0.2° C. under inhalation anesthesia. After awakening from anesthesia, red ginseng powder was administered orally at the dose of 1.5 g/kg/day once a day for 28 days (n=11). The animals undergone sham operation (n=12) and the control animals with 3-min forebrain ischemia (ischemic control animals) (n=8) were orally administered with the equal amount of distilled water alone. Thereafter, the step-down passive avoidance task experiments were performed, and the animals were anesthetized with pentobarbital, and they were perfused and fixed transcardially with phosphate buffer containing 4% paraformaldehyde and 2.5% glutaraldehyde. The brains were dissected out, embedded in paraffin and paraffin sections with 5 μm thickness were prepared. The neuronal density in 1 mm of the hippocampal CA1 field in each animal was measured according to the method of the inventors (Sakanaka, M., et al., Proc. Natl. Acad. Sci. USA, 95, 4635-4640, 1998; Wen, T.-C., et al., J. Exp. Med., 188, 635-649, 1998; Peng, H., et al., J. Cereb. Blood Flow Metab., 18, 349-360, 1998). Hereinafter, outlines of the step-down passive avoidance task experiment described in the above reference are described.

On 28 days after 3-min ischemia, the gerbil was placed on the safe platform of a conventional step-down passive avoidance apparatus, but at the beginning, the gerbil stepped down onto the lower grid floor several times, and it received electric shock, then returned back to the safe platform. During 5-minute training, most of the gerbils eventually stayed on the safe platform. 24 hours later, the gerbil was again placed on the safe platform while the shock generator was turned off, and the time until it stepped down onto the grid floor (the response latency) was measured to define as the learning ability of animal.

Results are shown in FIG. 12 and FIG. 13. FIG. 12 (A) shows the response latency in the passive avoidance task experiments and FIG. 12 (B) shows the neuronal density per 1 mm of the hippocampal CA1 field. As shown in FIG. 12 (A), when red ginseng powder was administered orally for 4 weeks after 3-min ischemia, the response latency of the passive avoidance task experiment was significantly prolonged as compared with that in the group of ischemic animals administered with distilled water. Further, as shown in FIG. 12 (B), when red ginseng powder was administered orally, the neuronal density in the hippocampal CA1 field was significantly increased as compared with the group of ischemic animals administered with distilled water.

FIG. 13 shows light microscopic photographs of the hippocampal CA1 field of (A) a sham-operated animal, (B) an ischemic animal administered with distilled water, and (C) an ischemic animals administered with red ginseng powder. As shown in FIG. 13, in the 3-min ischemic animals administered with distilled water (B), nerve cells (neurons) further degenerated (to die) on the later days after 1 week and the surviving neurons in the hippocampal CA1 field at one week after ischemia which were about ½ of the normal neurons in number, were decreased up to about ¼ of the normal neurons at the 28th day after ischemia, as compared with the sham-operated animals (A). However, when red ginseng powder was administered orally for 28 days after 3-min ischemia, the neuron death that occurred from the 1st week to 28th day after ischemia was significantly suppressed.

Example 6 (Treatment, Prevention or Therapy of Chorea by Red Ginseng Powder)

Chorea (Huntington's chorea) is known to be the representative single gene disease in neurodegenerative diseases and was suspected to be caused by the repeated sequence of CAG coding polyglutamine, but no methods for therapy have been developed. Transfection of the causal gene of chorea, mutant huntingtin, into cultured neural cells (neurons) originating in the striatum makes the cells enter apoptosis-like neuronal death. However, it has been reported that if Bcl-$x_L$ protein is forcibly expressed in the cultured nerve cells together with the mutant huntingitin, the neuron death can be almost completely suppressed (Saudou, F., et al., Cell, 95, 55-66, 1988). Consequently, if red ginseng powder, which has the promoting action on the expression of Bcl-$x_L$ protein in the brain and nervous tissues, is administered orally before or after onset of chorea, the effectiveness and efficacy are highly expected. The oral administration of red ginseng powder appears to be also effective for other polyglutamine diseases (Machedo-Jaseph disease, dentatorubral-pallidoluysian atrophy, etc.) besides chorea.

To human subjects (estimated body weight 60 kg), who have been ascertained to onset chorea or other polyglutamine diseases in future by gene diagnosis, or to patients (estimated body weight 60 kg), who have already developed polyglutamine diseases, red ginseng powder is administered orally in doses of 2.0 g-90 g a day, preferably 5.625 g-36 g a day, more preferably 11.25 g-18 g a day. When red ginseng powder is administered before onset of chorea or other polyglutamine diseases, even if the diseases are developed unluckily, it is desirable to continue the oral administration of red ginseng powder until the pathologic conditions are ameliorated or stabilized. Further, when red ginseng powder is administered orally to the patients who developed chorea or other polyglutamine diseases, the oral administration of red ginseng powder is continued until the pathologic conditions are ameliorated or stabilized.

Example 7 (Treatment, Prevention or Therapy of Dilated Cardiomyopathy by Oral Administration of Red Ginseng Powder)

Dilated cardiomyopathy is a disease which shows decreased heat function and cardiac dilation as a result of myocardial cell death (myocardial cell degeneration) from an unknown cause. The decreased heart function is deteriorated progressively and develops cardiac failure to death. When cardiac failure is deteriorated, it has been thought that no other methods for therapy except heart transplantation are present. Perhaps, when myocardial cells of patients with dilated cardiomyopathy are going to death, the cell death-suppressing gene product Bcl-$x_L$ protein, which is contained abundantly in myocardial cells, is considered to decrease. Consequently, as a result that the decrease in Bcl-$x_L$ protein is prevented by oral administration of red ginseng powder, the myocardial cell death of patients can be delayed, and then the heart function of patients may be preserved for long time.

For patients (estimated body weight 60 kg), who have been diagnosed as dilated cardiomyopathy, red ginseng powder is promptly administered orally in doses of 0.6 g-15 g a day, preferably 1.5 g-6 g a day, more preferably 2 g-4 g a day, every day. The oral administration is preferably continued until the pathologic conditions of patients are ameliorated or the progress of the pathologic conditions is arrested. Red ginseng powder and the other drugs for the circulatory system such as β-blockers, calcium antagonists, ACE-inhibitors, angiotensin receptor inhibitors, etc. can be administered orally in combination.

Example 8 (Treatment or Therapy of Brain Edema by Repetitive or Continuous Intravenous Administration of Low Doses of Ginsenoside $Rb_1$)

After the experiments with oral administration of red ginseng powder, the present inventors investigated whether brain edema after cerebral infarction (cerebral embolism) is improved by repetitive or continuous intravenous administration of low doses of ginsenoside $Rb_1$ or not.

Male SH-SP rats (weighing 250-300 g), at the age of 12-13 weeks, were used. Animals were bred in a room furnished with 12 hours light and dark cycles and water and feeds were supplied ad libitum. The cortical branch of the left middle cerebral artery (MCA) of each animal was coagulated and cut under inhalation anesthesia. Immediately after MCA permanent occlusion, ginsenoside $Rb_1$ dissolved in physiological saline was infused once intravenously (6 μg or 60 μg), and subsequently intravenously infused in a continuous manner for 28 days by using an Alza osmotic minipump (6 μg/day or 60 μg/day).

Control animals with MCA permanent occlusion (ischemic control animals) and sham-operated animals received the same amount of physiological saline.

At 32 days after the MCA permanent occlusion, the SH-SP rats were anesthetized with chloral hydrate, and they were perfused and fixed transcardially with 0.1 M phosphate buffer containing 4% paraformaldehyde. The brains of the animals were dissected out and cerebrocortical infarcted lesions were photographed.

Results are shown in FIG. 14.

In FIG. 14, the upper photographs are stereomicroscopic photographs of brains of 8 animals with cerebral infarction (cerebral embolism) administered with physiological saline, which were taken from the dorsal side. In FIG. 14, the lower photographs are stereomicroscopic photographs of brains of 8 animals with cerebral infarction (cerebral embolism) administered with ginsenoside $Rb_1$ (6 μg/day), which were taken from the dorsal side. Since the frontal edge of the brain is arranged toward the direction of right side, the left cerebral hemisphere with darkened cerebral infarct lesion is observed on the upper side of the longitudinal cerebral fissure. Normal right cerebral hemisphere observed on the lower side of the longitudinal cerebral fissure was included, in part, in the stereomicroscopic photographs. As shown in the upper photographs of FIG. 14, in case of cerebral infarction administered with physiological saline, darkened cerebral infarct lesion of the left cerebral hemisphere expanded largely, and the left cerebral hemisphere is larger than the right cerebral hemisphere in all cases, though some difference is observed among the cases. Especially, among the cases of cerebral infarction administered with physiological saline, in the brain of the right end on the first row and in the second brain from the left on the second row, the left cerebral hemisphere is obviously larger than the right cerebral hemisphere. This indicates that brain edema appears in the left cerebral hemisphere with MCA occlusion and the brain pressure or intracranial pressure is increased.

On the other hand, as shown in the lower photographs of FIG. 14, in the cases of cerebral infarction (cerebral embolism) administered intravenously with ginsenoside $Rb_1$ (6 μg/day), cerebral infarcted lesions are obviously reduced in all cases and no difference in size between the left cerebral hemisphere and the right cerebral hemisphere is observed. Namely, cerebral edema is not observed by repetitive or continuous intravenous administration of ginsenoside $Rb_1$.

Example 9 (Treatment or Therapy of Spinal Cord Injury by Repetitive or Continuous Intravenous Administration of Ginsenoside $Rb_1$)

Wistar rats (body weight about 300 g) loaded with 20 g of compression on the lower thoracic cord for 20 minutes were used as a spinal cord-injured model.

The rats were anesthetized with inhalation of halothane and nitrous oxide and were loaded with 20 g of compression on the lower thoracic cord for 20 minutes. After more than 30 minutes passed, ginsenoside $Rb_1$ (12 µg or 60 µg) dissolved in physiological saline was infused once into the left femoral vein, thereafter continuous or repetitive intravenous administration of ginsenoside $Rb_1$ (12 µg/day or 60 µg/day) was performed for 7 days by using an Alza osmotic mini pump. Control animals and sham-operated animals were administered with the same amount of physiological saline (vehicle) in the same schedule. The open field locomotor scores [Basso, Bettie and Bresnakan (BBB) scores] as an index of motor functions (Basso D. M. et al., J. Neurotrauma, 13, 343-359, 1996) were measured before loading spinal cord injury, on the day of spinal cord injury and from 1st day to 7th day after the spinal cord injury. The BBB scores of the sham-operated rats (normal rats) were 20-21. Results are shown in FIG. 16 and FIG. 17.

FIG. 16 shows a control rat administered with physiological saline and a rat administered with ginsenoside $Rb_1$ (60 µg/day) on the day of spinal cord injury and on the next day after spinal cord injury. As shown in FIG. 16, the rats, to which 20 g of compression was loaded on the lower thoracic cord for 20 minutes, obviously exhibited paraplegia in both hindlimbs immediately after the compression loading. However, when ginsenoside $Rb_1$ (60 µg/day) was intravenously administered after passing more than 30 minutes from loading 20 g of compression on the lower thoracic cord for 20 minutes, the paraplegia of both hindlimbs was significantly ameliorated 1-2 days later, and the rat could stand up with the aid of a holding bar as shown in FIG. 16. However, paraplegia of the hindlimbs of the rat administered with physiological saline was not ameliorated at all.

FIG. 17 shows a graph in which the motor ability of rats is quantified at the 7th day after spinal cord injuries by using the BBB scores. As shown in FIG. 17, the motor ability of rats with spinal cord injuries was significantly ameliorated in a dose-dependent manner by intravenously administered ginsenoside $Rb_1$. Data are represented as mean±SE. Statistical analyses were performed by Mann-Whitney U-test.

Example 10 (Treatment or Therapy of Spinal Cord Injury by Repetitive or Continuous Intravenous Administration of Low Dose of Crude Saponin Fraction of Ginseng)

Wistar rats (body weight about 300 g) loaded with 20 g of compression on the lower thoracic cord for 20 minutes were used as the spinal cord-injured model.

The rats were anesthetized with inhalation of halothane and nitrous oxide and were loaded with 20 g of compression on the lower thoracic cord for 20 minutes. After more than 30 minutes passed, a crude saponin fraction of medicinal ginseng (870 µg) dissolved in physiological saline was infused once into the left femoral vein, thereafter continuous or repetitive intravenous administration of the crude saponin fraction (870 µg/day) was performed for 7 days by using an Alza osmotic mini pump. Control animals with spinal cord injury were administered with the same amount of physiological saline (vehicle) in the same schedule. Results are shown in FIG. 18 and FIG. 19. FIG. 18 shows a rat administered with the crude saponin fraction and FIG. 19 shows a control rat administered with physiological saline (vehicle).

As shown in FIG. 18, on the day of loading spinal cord injury, the rat exhibited paraplegia in both hindlimbs and could not stand up in spite of the intravenous administration of the crude saponin fraction. However, the paraplegia of both hindlimbs of the rat was significantly ameliorated thereafter, and the rat at the 7th day after spinal cord injury could stand up by holding the outer wall of the open field (height 8 cm). On the other hand, as shown in FIG. 19, in the rat administered with physiological saline alone after loading spinal cord injury, paraplegia of the hindlimbs was not ameliorated at all in spite that 1 week passed after spinal cord injury.

According to the present experimental results using rats with spinal cord injuries, the therapeutic effects of the preparations comprising low doses of the crude saponin fraction(s) for intravenous repetitive administration on spinal cord injury are thought to be as excellent as those of ginsenoside $Rb_1$.

Example 11 (Treatment or Therapy of Spinal Cord Injury and Bedsore by Repetitive or Continuous Intravenous Administration of Low Dose of Ginsenoside $Rb_1$)

Wistar rats (body weight about 300 g) were anesthetized with inhalation of halothane and nitrous oxide and were loaded with 20 g of compression on the lower thoracic cord for 20 minutes. After they were awakened from anesthesia, the rats with paraplegia in both hindlimbs were allowed to stay for 1 hour and 40 minutes in the cage. Namely, the rats with spinal cord injury were allowed to leave for about 2 hours without any management and treatment from the time when 20 g of compression to the lower thoracic cord was loaded. Immediately thereafter, ginsenoside $Rb_1$ (60 µg) was infused once into the left femoral vein, and further, continuous or repetitive intravenous administration of ginsenoside $Rb_1$ (60 µg/day) was performed for 7 days by using an Alza osmotic minipump. Control animals with spinal cord injury were administered with the same amount of physiological saline (vehicle). Results are shown in FIG. 21.

As shown in FIG. 21, the rats administered intravenously with ginsenoside $Rb_1$ from 2 hours after initiation of the compression loading on the lower thoracic cord exhibited paraplegia in both hindlimbs on the day subjected to spinal cord injury and could not stand up, and on the next day, they could not still stand up, although the paraplegia in both hindlimbs was slightly improved. However, the paraplegia of both hindlimbs of the rats was gradually ameliorated from 3-4 days after the onset of spinal cord injury, and as shown in FIG. 21, the rats could stand up by holding the outer wall of the open field (height 8 cm). On the other hand, as shown in FIG. 21, in the rats administered with physiological saline (vehicle) alone since 2 hours passed after loading compression on the lower thoracic cord, paraplegia of the hindlimbs was not ameliorated at all in spite that 1 week passed after spinal cord injury. In addition, in the rats administered with physiological saline alone, as shown in FIG. 21, bedsore was frequently observed in the lower abdomen though individual differences were noted. However, bedsore (decubitus) was hardly observed in the animals administered with ginsenoside $Rb_1$.

Example 12 (Protective Action of Ginsenoside $Rb_1$ on Oligodendrocyte)

Nerve cells (neurons) and oligodendrocytes were cocultured and the investigation of whether or not ginsenoside $Rb_1$ promotes survival of both cells was performed. For that purpose, nerve cells were isolated from cerebral cortices of fetal rats at gestational day 17. The mixed brain cell culture of the forebrain of newborn rats was initiated to isolate oligodendrocytes. Fifty thousands of oligodendrocytes to 500,000 nerve cells were cocultured. To this culture system was added 1 fg/ml to 10 pg/ml ginsenoside $Rb_1$ in DMEM containing 1% fetal bovine serum and the mixed cells were cultured for 5 days. Subsequently, samples for electrophoresis were prepared and contents of the neuron-specific protein MAP2 (microtubule-associated protein 2) and the oligodendrocyte specific-protein CNPase in the culture well were assayed by means of Western blotting. Results are shown in FIG. 22.

In FIG. 22, the upper photograph shows Western blotting of MAP2 and the lower photograph shows that of CNPase. When ginsenoside $Rb_1$ at the concentrations of 1 fg/ml to 100 fg/ml was added to the coculture system of nerve cells and oligodendrocytes, the band of MAP 2 and the band of CNPase were obviously intense as compared with non-ginsenoside $Rb_1$-added and $10^4$ fg/ml ginsenoside $Rb_1$-added groups. This indicates that when low concentrations of ginsenoside $Rb_1$ were added to the coculture system at the concentrations of 1 fg/ml to 100 fg/ml, amounts of MAP2 and CNPase were obviously increased. Namely, the survival of nerve cells and oligodendrocytes were promoted by ginsenoside $Rb_1$. This fact strongly supports the effectiveness of low concentrations and low doses of ginsenoside $Rb_1$ for preventing, treating or curing diseases accompanied by oligodendrocyte cell death (multiple sclerosis, Binswanger's disease and brain and nervous diseases causing demyelination such as leukoencephalitis).

Example 13 (Upregulation of Bcl-$x_L$ Expression in Oligodendrocytes by Ginsenoside $Rb_1$)

In order to investigate whether ginsenoside $Rb_1$ enhances the expression of Bcl-$x_L$ in oligodendrocytes or not, for example, ginsenoside $Rb_1$ at the concentration from 1 fg/ml to 10 pg/ml was added to the primary cultured rat oligodendrocytes. After culture for 6 hours, Total RNA was extracted and Bcl-$x_L$ mRNA was assayed by RT-PCR. β-actin mRNA was used as an internal standard of RT-PCR. Further, a part of oligodendrocytes was used as a sample for SDS electrophoresis after treating with ginsenoside $Rb_1$, and the amount of anti-apoptotic factor Bcl-$x_L$ in the culture well was examined by immunoblotting (Western blotting). The mixed brain cell culture was initiated to isolate oligodendrocytes by using the forebrain of newborn rats. Results are shown in FIG. 23. In FIG. 23, the upper photographs show results of RT-PCR and the lower photograph shows results of the immunoblotting (Western blotting); $Rb_1$ (–) indicates no addition of ginsenoside $Rb_1$ and $Rb_1$(+) indicates addition of ginsenoside $Rb_1$ at 100 fg/ml.

The RT-PCR indicates that when ginsenoside $Rb_1$ was added at the concentration of 100 fg/ml, expression of Bcl-$x_L$ mRNA in the oligodendrocytes was obviously enhanced. Further, results of immunoblotting (Western blotting) indicate that Bcl-$x_L$ protein was also increased by the addition of ginsenoside $Rb_1$. The present experimental results strongly support that in spinal cord injuries and brain and nervous diseases accompanied by demyelination, intravenous administration of small doses of ginsenoside $Rb_1$ exhibits a protective action on oligodendrocytes.

Example 14 (Enhancement of Bcl-$x_L$ Expression by Intravenous Administration of Ginsenoside $Rb_1$)

We (the present inventors) investigated whether intravenous administration of ginsenoside $Rb_1$ increases the expression of Bcl-$x_L$ mRNA in brain tissues or not. For that purpose, for example, SH-SP rats (body weight 250-300 g) at the age of 12 weeks were used. Immediately after permanent occlusion of the MCA in SH-SP rats under inhalation anesthesia, ginsenoside $Rb_1$ dissolved in physiological saline was infused once intravenously (60 µg), and subsequently ginsenoside $Rb_1$ was intravenously infused continuously at the dose of 60 µg/day. Control animals with MCA permanent occlusion and sham-operated animals were administered with the same amount of physiological saline after MCA permanent occlusion. Results are shown in FIG. 24. Group 1 shows a sham-operated animal, an animal with MCA permanent occlusion administered with physiological saline (after MCA permanent occlusion, i.e. at the 4th hour after cerebral infarction); an animal with cerebral infarction administered with ginsenoside $Rb_1$ (at the 4th hour after MCA permanent occlusion); and an animal with cerebral infarction administered with ginsenoside $Rb_1$ (at the 6th hour after MCA permanent occlusion). Group 2 consists of animals under the same experimental conditions. Sham indicates sham-operated animals; $Rb_1$(–) indicates animals with cerebral infarction administered with physiological saline alone; and $Rb_1$(+) indicates animals with cerebral infarction administered intravenously with ginsenoside $Rb_1$. After the sham operation and at the 4th hour or the 6th hour after MCA permanent occlusion, the rats were anesthetized with chloral hydrate, and the left cerebral cortex (i.e. the cerebral cortex on the MCA permanent occluded side) was dissected out and total RNA was prepared for RT-PCR. The mRNA of β-actin was used as the internal standard.

As shown in FIG. 24, in Group 1 and Group 2, the expressions of Bcl-$x_L$ mRNA in the cerebral cortex were obviously increased both at the 4th hour and the 6th hour after the MCA permanent occlusion in the animals administered intravenously with ginsenoside $Rb_1$ as compared with the animals with sham operation and the cerebral infarcted animals administered with physiological saline.

Example 15 (Enhancement of Bcl-$x_L$ Expression in Myocardial Cells by Low Concentrations of Ginsenoside $Rb_1$)

We (the present inventors) have studied the effectiveness and efficacy of medicinal ginseng (red ginseng powder), crude saponin fraction(s) and ginsenoside $Rb_1$ using nervous tissues or constituent cells in nervous tissues (nerve cells and oligodendrocytes). Subsequently we studied the effectiveness of ginsenoside $Rb_1$ on heart. For that purpose, for example, changes in the expressions of Bcl-$x_L$ mRNA and Bcl-$x_L$ protein were examined with the use of RT-PCR and immunoblotting, when the primary cultured myocardial cells were cultured for 18 hours in the presence of ginsenoside $Rb_1$. Myocardial cells were prepared as follows. The hearts of fetal rats at gestational day 17 were treated with trypsin EDTA to prepare the dispersed cells, which were cultured for several days in DMEM containing 10% FCS (fetal calf serum). In RT-PCR, β-actin mRNA was used as the internal standard. In the immunoblotting, troponin T, a striated muscle-specific protein, was used as the internal standard, and expression of Bcl-$x_L$ protein was examined. In the immunoblotting, the same experiments were repeated 10 times by using different lots of myocardial cells, and Bcl-$x_L$ immunoreaction-positive bands were analyzed by densitometry and statistical analysis was performed. Results are shown in FIG. 25. In FIG. 25, the upper photographs show results of RT-PCR, and the middle photographs show results of immunoblotting (Western blotting), and the lower graph shows results of densitometric analysis of the data of Western blotting.

As shown in FIG. 25, the expression of Bcl-$x_L$ mRNA was obviously increased in the presence of ginsenoside $Rb_1$ at concentrations of 1 fg/ml-100 fg/ml. With regard to the Bcl-$x_L$ protein level, ginsenoside $Rb_1$ in the concentration range between 1 fg/ml and $10^4$ fg/ml significantly enhanced the expression of Bcl-$x_L$ protein. In the present experiments, although a mismatch between the expression of Bcl-$x_L$ mRNA and that of Bcl-$x_L$ protein was noted at $10^4$ fg/ml of ginsenoside $Rb_1$, it is speculated that the expression of Bcl-$x_L$ mRNA was already down-regulated at 18 hours after administration of such a high concentration of ginsenoside $Rb_1$ ($10^4$ fg/ml). Statistical analyses were conducted by ANOVA+Fisher's PLSD.

Example 16 (Protective Action of Low Concentrations of Ginsenoside $Rb_1$ on Myocardial Cells)

We (the present inventors) investigated whether ginsenoside $Rb_1$ could actually suppress myocardial cell death in the concentration range for increasing the expression of Bcl-$x_L$ protein or not. For that purpose, for example, the protective effect of ginsenoside $Rb_1$ on myocardial cells was examined when the primary cultured myocardial cells were cultured without addition of glucose. Ginsenoside $Rb_1$ in the concentration range from 0 to 1 ng/ml was added to serum-free DMEM without containing glucose, and myocardial cells were cultured for 4 or 5 days. Subsequently, the sample for electrophoresis was prepared, and immunoblotting (Western blotting) was performed by using anti-striated muscle specific α-actinin antibody. Results are shown in FIG. 26. In FIG. 26, the upper photographs show results of Western blotting of α-actinin, and the lower graph shows results of densitometric analysis of the Western blotting. Statistical analyses were conducted by ANOVA+Scheffe's post hoc test.

As shown in FIG. 26, when the culture was conducted only with the glucose-free and serum-free medium, the myocardial cells disappeared already at 4-5 days after culture, and when ginsenoside $Rb_1$ was added to the culture medium at the concentrations from 1 fg/ml to $10^4$ fg/ml, large numbers of pulsating myocardial cells were observed even at 4-5 days after culture, and the striated muscle specific α-actinin was significantly detected by immunoblotting. According to the above results, it was found that ginsenoside $Rb_1$ could increase the expression of myocardial cell Bcl-$x_L$ in a slightly broader concentration range (1-$10^4$ fg/ml) than the effective concentration range of ginsenoside $Rb_1$ for nerve cells and had the protective action on myocardial cells.

Example 17 (Therapeutic Effect of Dihydroginsenoside $Rb_1$ on Cerebral Infarction)

In the prior patent application (Japanese Patent Application No. Hei 11-243378, Brain cell or nerve cell-protective agents comprising ginseng), we, the present inventors, have described that compounds having brain cell or nerve cell-protective action can be newly explored by using candidate substances of the active components contained in ginseng as a leading compound(s). We attempted to demonstrate this fact in the present invention. For that purpose, for example, dihydroginsenoside $Rb_1$ represented by the above chemical formula (II) was used. As far as we know, dihydroginsenoside $Rb_1$ is considered to be a novel compound and can be produced by reducing ginsenoside $Rb_1$.

A process for production of dihydroginsenoside $Rb_1$ and NMR data thereof are shown as follows.

10.2 mg of 10% Pd/c (as a catalyst) was weighed and was poured into a two-neck flask with stopper cocks. One ml methanol (GR) was added to suspend. Balloon filled with hydrogen gas (about 1.1 atm.) was attached to the flask and the catalyst was activated at 0° C. for 30 minutes. 19.9 mg ginsenoside $Rb_1$ dissolved in 1 ml methanol was put into the flask by using a syringe. The mixture was vigorously stirred at 0° C. for 10 hours and 30 minutes (with a magnetic stirrer). The reaction mixture was filtered through filter paper and membrane filter with pores 0.45 μm in diameter. Methanol was removed off under reduction of pressure. The residue was dissolved in 10 ml pure water, and lyophilized to obtain 19.1 mg dihydroginsenoside $Rb_1$ (yield 97%) as white powder. The melting point was 193-195° C. Incidentally, the melting point of ginsenoside $Rb_1$ is 197-198° C. (Reference value).

Figure 29:
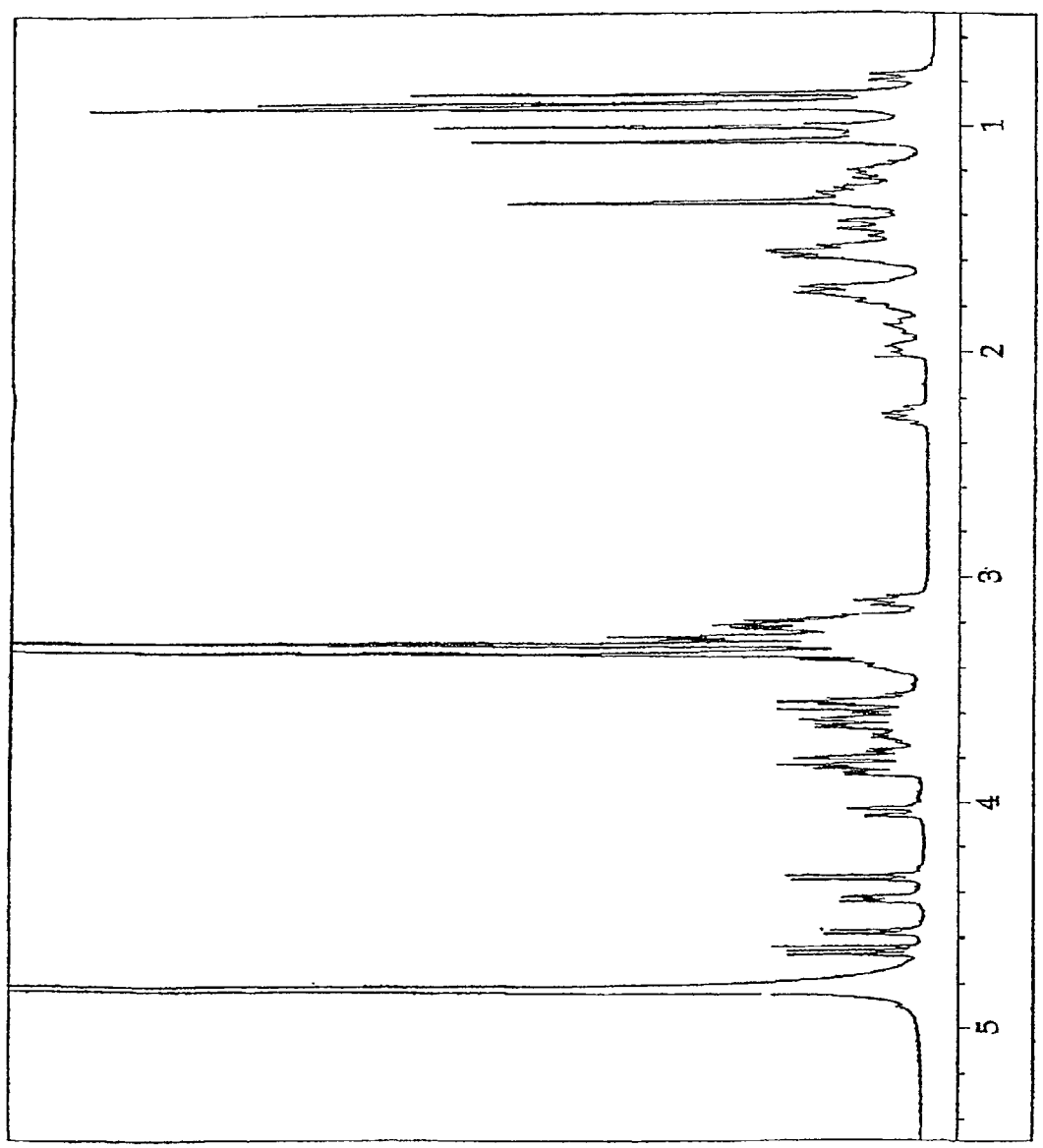
FIG. 29 shows the chart of NMR of dihydroginsenoside $Rb_1$.

In FIG. 29, the NMR chart (400 MHz, $CD_3OD$) is shown.

Male SH-SP rats, at the age of 16 weeks, weighing 300-320 g, were used. Animals were bred in a room furnished with 12 hours light and dark cycles and water and feeds were supplied ad libitum. The cortical branch of the left middle cerebral artery (MCA) of each animal was coagulated and cut under inhalation anesthesia. Immediately after MCA permanent occlusion, dihydroginsenoside $Rb_1$ dissolved in physiological saline was infused once intravenously (6 μg), and subsequently it was intravenously infused continuously for 24 hours by using an Alza osmotic minipump (6 μg/day).

Control animals with MCA permanent occlusion (ischemic control animals) were administered with the same amount of physiological saline (vehicle). At 24 hours after MCA permanent occlusion, a lethal dose of pentobarbital was injected intraperitoneally into rats. Immediately after death of animals, the brains were dissected out and frontal sections 2 mm thick were prepared. The sections were immersed in 1% 2,3,5-triphenyl-tetrazolium chloride (TTC) solution for 30 minutes at 37° C. and fixed with 10% formalin for more than 12 hours. Results are shown in FIG. 27 and FIG. 28. In FIG. 27, 2 cases administered with physiological saline, and in FIG. 28, 2 cases administered intravenously with dihydroginsenoside $Rb_1$ are shown.

As shown in FIG. 27, in the rats administered with physiological saline alone after MCA permanent occlusion, cerebral infarct lesions, which were not stained with TTC, were observed with white color in the cerebral cortex on the left side. On the other hand, as shown in FIG. 28, in the rats administered intravenously with dihydroginsenoside $Rb_1$ after MCA permanent occlusion, cerebral infarct lesions were markedly reduced. This effectiveness is thought to be equal to the therapeutic action of ginsenoside $Rb_1$ on cerebral infarction.

Example 18 (Prevention, Treatment and/or Therapy of Bedsore by Dihydroginsenoside $Rb_1$)

Bedsore (decubitus) of the bedridden patients and aged people is a cutaneous disease being a cause for deteriorating general condition and significantly damaging QOL (quality of life). In the early stage of bedsore, flare of the lesioned skin is observed. At this stage, there are few agents for external use which can be applied to the local lesion and penumbra thereof or few agents for intravenous administration to exhibit effectiveness and efficacy. This is a great problem in the dermatological field. Of course, the treatment or therapy of bedsore lesion deficient in cutaneous tissues is extremely difficult.

The external preparation(s) for skin (cream or ointment) is prepared by mixing dihydroginsenoside $Rb_1$ with any water-soluble base or any fat-soluble base with glucose or without containing glucose. The preparation(s) is applied at any time to the local lesion of bedsore and penumbra thereof until the bedsore lesion is cured, reduced or not deteriorated. At that time, the amount of dihydroginsenoside $Rb_1$ added to the base is adjusted to keep the extracellular fluid concentrations of dihydroginsenoside $Rb_1$ in the local lesion at 100 ng/ml or less, preferably 10 pg or less, more preferably 100 fg/ml or less. If necessary, intravenous administration of dihydroginsenoside $Rb_1$ is used together as described in example 17.

Example 19 (Prevention, Treatment or Therapy of Corneal Injury by Dihydroginsenoside $Rb_1$)

It is well known that corneal injuries occur at the application of contact lens or after corrective operation for myopia using excimer laser. However, eye drops, which can protect keratic or corneal tissues, are rarely known at present.

Ophthalmic lotions (eye drops) or ophthalmic ointments are prepared by mixing dihydroginsenoside $Rb_1$ with basal ophthalmic lotions or base, and they are applied for necessary times every day to the patients with keratic or corneal injuries, and the application is continued until ameliorating or healing keratic or corneal lesion. In that occasion, the amount of dihydroginsenoside $Rb_1$ in the base is adjusted to keep the extracellular fluid concentrations of dihydroginsenoside $Rb_1$ in the keratic or corneal lesioned tissues at 100 ng/ml or less, preferably 10 pg/ml or less, more preferably 100 fg/ml or less. Of course, dihydroginsenoside $Rb_1$ can be replaced by ginsenoside $Rb_1$.

Example 20 (Protection of Cornea for Transplantation by Dihydroginsenoside $Rb_1$)

The keratoplasty is frequently carried out in the opthalmological field as the remedy with the highest success rate in the transplantation medicine. However, since the cells composing corneal tissues for transplantation are certainly going to death during the term from collecting cornea from the dead body to performing keratoplasty, and thus such term is the greatest factor restricting the time from collecting cornea to grafting. After collecting the cornea for transplantation, dihydroginsenoside $Rb_1$ can be admixed to the conventional corneal preservative solution at concentrations of 100 ng/ml or less, preferably 10 pg/ml or less, and more preferably 100 fg/ml or less to protect cornea for transplantation.

Example 21 (Prevention, Therapy or Treatment of Chorea by Dihydroginsenoside $Rb_1$)

Chorea (Huntington's chorea) is known to be a representative single gene disease among the neurodegenerative diseases and is suspected to be caused by repetitive sequence of CAG coding polyglutamine. However, no methods for therapy have been developed. Transfection of the causal gene of chorea, mutant huntingtin, into cultured neurons originating in the striatum makes the neurons enter apoptosis-like death. However, it has been reported that if $Bcl-x_L$ is forcibly expressed in the cultured nerve cells together with the mutant huntingtin, the neuron death can be almost completely suppressed (Saudou, F., et al., Cell, 95, 55-66, 1988). Consequently, if dihydroginsenoside $Rb_1$, which has a $Bcl-x_L$ protein expression-promoting action in the brain and nervous tissues, is nasally, rectally or intravenously administered before or after onset of chorea, the effectiveness and efficacy is highly expected. For other polyglutamine diseases (Machedo-Jaseph disease, dentatorubral-pallidoluysian atrophy, etc.) besides chorea, nasal, rectal or intravenous administration of dihydroginsenoside $Rb_1$ appear to be effective. Further, dihydroginsenoside $Rb_1$ is expected to inhibit development of the secondary degeneration expanding from the primary lesion (striatal lesion) of chorea to the other cerebral regions having fiber connections with the striatum, as ginsenoside $Rb_1$ does.

To human subjects (estimated body weight 60 kg), who have been ascertained to onset chorea or other polyglutamine diseases in future by gene diagnosis, or to patients (estimated body weight 60 kg), who have already developed polyglutamine diseases (estimated body weight 60 kg), a preferable amount of dihydroginsenoside $Rb_1$ is administered nasally, rectally or intravenously until the pathologic conditions are ameliorated or stabilized. The amount of intravenous administration of dihydroginsenoside $Rb_1$ for treatment or therapy of polyglutamine diseases is equivalent to, or 5-10 times higher than that required for treatment or therapy of acute cerebral apoplexy. Dosage of nasal or rectal administration can be adjusted to maintain the blood concentrations of dihydroginsenoside $Rb_1$ equal to those of intravenously administered dihydroginsenoside $Rb_1$.

Example 22 (Prevention, Treatment or Therapy of Dilated Cardiomyopathy by Dihydroginsenoside $Rb_1$)

Dilated cardiomyopathy is a disease which shows decreased heat function and cardiac dilation as a result of myocardial cell death (myocardial cell degeneration) from an unknown cause(s). The decreased heart function is deteriorated progressively and develops cardiac failure to death. When cardiac failure is developed, it has been thought that no other methods for therapy except heart transplantation are present. Perhaps, when myocardial cells of patients with dilated cardiomyopathy is going to death, the cell death-suppressing gene product $Bcl-x_L$ protein, which is contained abundantly in myocardial cells, is considered to decrease. Consequently, decrease in $Bcl-x_L$ protein is prevented by intravenous, rectal or nasal administration of dihydroginsenoside $Rb_1$ and thereby myocardial cell death in the patients can be delayed, and then heart function of the patients can be preserved for a long time.

For patients (estimated body weight 60 kg), who have been diagnosed as dilated cardiomyopathy, a proper amount(s) of dihydroginsenoside $Rb_1$ is promptly administered nasally, rectally or intravenously until the pathologic conditions or symptoms are ameliorated or the progress of the pathologic conditions is arrested. Dihydroginsenoside $Rb_1$ and drugs for ingestion such as β-blockers, calcium antagonists, ACE-inhibitors, etc., can be administered in combination. When dihydroginsenoside $Rb_1$ is administered for therapy or treatment of diseases of peripheral organs and tissues such as cardiac diseases, the amount equal to the amount of dose to patients with central nervous diseases or $\frac{1}{10}$-$\frac{1}{10,000}$ of amount thereof can preferably be selected.

Example 23 (Prevention of Senescence of Skin by Ginsenoside $Rb_1$ as a Cosmetic Composition)

Senescence of skin accompanied by aging is mainly caused by ultraviolet irradiation, and it shows symptoms such as atrophy or shrink of skin, slackening of skin, white-hair, gray hair, exfoliation of the stratum corneum, exfoliation of cells in the stratum coneum, dandruff, scurf, dry skin, senile xerosis, asteatosis, oligosteatosis, asteatotic dermatitis, crack, itching, roughness, rhagade, ephelis, blotch, spots on the skin, furrows, lines, wrinkles, freckle, pigmentation, sunburn, dryess, etc. Ginsenoside $Rb_1$ exhibits protective actions on cells of skin including epidermal cells, keratinocytes, sebaceous gland cells, hair follicular cells, sweat gland cells, fibroblasts, stem cells, mesenchymal cells, adipose cells, etc, when its extracellular fluid concentrations in lesioned tissues are kept at 1 ng/ml or less, preferably 10 pg/ml or less, more preferably 100 fg/ml or less. Thus, excellent effects on the aging symptoms of skin can be exhibited by adding trace amounts of ginsenoside $Rb_1$ to any cosmetics, for example lotion (skin lotion), milky liquid (milky lotion), foundation, cold cream, cleansing cream, cleansing foam, night cream, beauty cream, face powder, lipstick, lip cream, foundation cream (make-up base), gargle, eye lotion, face lotion, UV liquid foundation, powder foundation, etc. if the local extracellular fluid concentrations of ginsenoside $Rb_1$ in skin are kept low as described above.

When ginsenoside $Rb_1$ is admixed with or added to the liquid cosmetics, for example conventional UV liquid foundation, its concentration is adjusted at 1000 ng/ml or less, preferably 10 ng/ml or less, more preferably 10 fg/ml-100 pg/ml or less, and the cosmetics is externally applied or externally sprayed every day on the skin. Then, the extracellular concentrations of ginsenoside $Rb_1$ in the local area of the skin can be maintained at low levels, and it is useful for improvement of aging symptoms of skin, prevention from the progress of aging symptoms of skin or prevention from the deterioration of aging symptoms of skin (shrink or atrophy of skin, white-hair, gray hair, scurf, dandruff, exfoliation of the stratum corneum, exfoliation of cells in the stratum corneum, senile xerosis, asteatosis, oligosteatosis, asteatotic dermatitis, dry skin, easiness to infect, vulnerability to infection, slackening or loosening of skin, itching, roughness, crack, dryness, blotch, spots on the skin, ephelis, wrinkles, furrows, lines, freckle, pigmentation and sunburn). Further, when ginsenoside $Rb_1$ is admixed or added to solid or gel cosmetics such as conventional foundation cream and night cream, the amount of admixing ginsenoside $Rb_1$ is adjusted at 1000 ng/g of cream or less, preferably 10 ng/g or less, more preferably about 10 fg-100 pg/g. The preparation(s) or cosmetics is applied externally on the skin every day and is useful for preventing, treating or managing the aging symptoms of skin (shrink, atrophy, slackening, loosening, itching, roughness, dryness, crack, rhagade, dry skin, ephelis, blotch, spot, wrinkle, furrow, line, freckle, pigmentation, sunburn, etc.). The upper limit for admixing or adding ginsenoside $Rb_1$ into the above cosmetics for the purpose of prevention, improvement or management of the aging symptoms of skin is less than 10 μg/ml in case of liquid cosmetics and less than 10 μg/g in case of solid or gel cosmetics. Namely, ginsenoside $Rb_1$ should be admixed with the above cosmetics at the concentrations less than 0.001%. Otherwise, the membrane of skin cells may be damaged. Of course, the cosmetics containing trace amounts of ginsenoside $Rb_1$ can be not only applied or sprayed externally to the face but also applied or sprayed externally to the other cutaneous tissues frequently irradiated with sun light (e.g. limbs or trunk). In this way, long term and continuous use of cosmetics or skin agents for external use containing low concentrations of ginsenoside $Rb_1$ can prevent or improve symptoms accompanied by the aging of the skin.

In addition, the various symptoms accompanied with the aging of skin can be prevented by admixing almost equal amounts of dihydroginsenoside $Rb_1$, crude saponin fraction of ginseng or components thereof in cosmetics or skin agents for external use, instead of ginsenoside $Rb_1$. Ginsenoside $Rb_1$, dihydroginsenoside $Rb_1$, extract(s) of ginseng, crude saponin fraction(s) and components thereof can be admixed in all ready-made conventional cosmetics and skin agents for external use, as long as they are used at low concentrations as described above. Of course, in case that cosmetic base containing any one of active ingredients is newly developed, the various symptoms caused by aging of the skin can be prevented, managed or improved by admixing any one of ginsenoside $Rb_1$, dihydroginsenoside $Rb_1$, extract(s) of ginseng, crude saponin fraction(s) and components thereof at low concentrations as described above. Further, as described above, any one of low concentrations of ginsenoside $Rb_1$, dihydroginsenoside $Rb_1$, extract(s) of ginseng, crude saponin fraction(s) and components thereof are combined together and they admixed with ready-made cosmetics or skin agents for external use or admixed with newly developed cosmetic base containing any other active ingredients, and, as the results, the cosmetics or the skin agents for external use for preventing, managing or improving the various symptoms caused by aging of the skin can be prepared. When admixing any one of ginsenoside $Rb_1$, dihydroginsenoside $Rb_1$, extract(s) of ginseng, crude saponin fraction(s) and components thereof with the cosmetics or skin agents for external use in the multiple combination, any concentration can be selected, as far as each concentration in the cosmetics or skin agents for external use is low level as described above. Further, in case that known cosmetic compositions other than the above ginseng components are admixed with the cosmetics for prevention of aging of the skin, the concentrations of the known cosmetic compositions should be preferably lower than previously reported.

In addition, any one of ginsenoside $Rb_1$, dihydroginsenoside $Rb_1$, extract(s) of ginseng, crude saponin fraction(s) and components thereof is admixed at low concentrations with ready-made hair-growing agents or hair-restoration agents, or with novel hair growers or hair restorers containing any other active ingredients, in the same manner as described in cases of cosmetics. These preparations or agents can be used for preventing deterioration of hair growing and hair restoration or hair loss, or for preventing progress of alopecia or depilation. Further, instead of the crude saponin fraction(s) of ginseng admixed in the cosmetics, hair growing agents or hair restoration agents, ginseng extract(s) can be used in an amount of 5 to 6 times excess or less. Of course, as far as low concentration of ginseng extract(s) is used, the crude saponin fraction(s) of ginseng and ginseng extract(s) are combined together and these can be admixed with the above cosmetics or with hair growing agents, hair restoration agents or agents for preventing progress of depilation or alopecia. Further, in case that any one of natural products or compositions thereof containing ginsenoside $Rb_1$ or other ginseng components are admixed with cosmetics, hair growing agents, hair restoration agents or agents for preventing progress of depilation or alopecia, and if the final content of ginsenoside $Rb_1$ and other ginseng components can be maintained at low concentrations as described above, the mixed preparation(s) or agent(s) can be used for improving, preventing or managing the aging symptoms of skin and loss of hair. Ginseng extract(s), crude saponin fraction(s), and constitutents of crude saponin fraction(s), ginsenoside $Rb_1$, dihydroginsenoside $Rb_1$ and chemical derivatives thereof can be also used for chemical peeling.

INDUSTRIAL APPLICABILITY

The present invention relates to (medicinal) ginseng, extracts thereof, ginseng components or metabolites thereof useful as cytoprotective agents. More particularly, the present invention relates to medicinal or pharmaceutical compositions for suppressing apoptosis or apoptosis-like cell death or for promoting the expression of a cell death-suppressing gene product $Bcl-x_L$ protein, comprising ginseng, its extracts, ginseng components, metabolites thereof or salts thereof.

Further, the present invention relates to the medicinal or pharmaceutical composition(s) for protecting cells, comprising ginsenoside $Rb_1$, metabolites thereof or salts thereof. More particularly, the present invention relates to the medicinal or pharmaceutical composition(s) for preventing, treating or curing brain edema, nervous tissue edema or spinal cord tissue edema, comprising ginsenoside $Rb_1$, metabolites thereof or salts thereof; the medicinal or pharmaceutical composition(s) for preventing, treating or curing bedsores caused by spinal cord injuries, comprising ginsenoside $Rb_1$, metabolites thereof or salts thereof; the medicinal or pharmaceutical composition(s) for promoting the expression of a cell death-suppressing gene $Bcl-x_L$ in nervous tissues, comprising ginsenoside $Rb_1$, metabolites thereof or salts thereof; the medicinal or pharmaceutical composition(s) for promoting the expression of a cell death-suppressing gene product $Bcl-x_L$ in oligodendrocytes, comprising ginsenoside $Rb_1$, metabolites thereof or salts thereof; protective agents for oligodendrocytes, comprising ginsenoside $Rb_1$, metabolites thereof or salts thereof; the medicinal or pharmaceutical composition(s) for promoting the expression of a cell death-suppressing gene product $Bcl-x_L$ in myocardial cells, comprising ginsenoside $Rb_1$, metabolites thereof or salts thereof; and the medicinal or pharmaceutical composition(s) for suppressing apoptosis or apoptosis-like cell death of myocardial cells, comprising ginsenoside $Rb_1$, metabolites thereof or salts thereof.

Further, the present invention relates to preparations for intravenous administration comprising ginseng, its extract(s), ginseng components, metabolites thereof or salts thereof. More particularly, the present invention relates to the preparations at low concentrations and low doses for intravenous administration.

Further, the present invention relates to the use of components of ginseng or metabolites thereof as leading compounds for exploring novel active ingredients or compounds for preventing, curing or treating the diseases or lesions hereinbefore, or for exploring protective agents for brain cells or protective agents for nerve cells.

Further, the present invention also relates to a novel chemical derivative prepared from ginsenoside $Rb_1$ as a leading compound, namely dihydroginsenoside $Rb_1$ which is useful as a cytoprotective agent. Further, the present invention relates to a medicinal or pharmaceutical composition(s) for preventing, treating or curing cerebral infarction or cerebral apoplexy or a medicinal or pharmaceutical composition(s) for suppressing necrosis, apoptosis or apoptosis-like cell death of nerve cells, comprising dihydroginsenoside $Rb_1$, metabolites thereof or salts thereof. The present invention further relates to a medicinal or pharmaceutical composition(s) that can be used as preparations for intravenous administration, comprising dihydroginsenoside $Rb_1$, metabolites thereof or salts thereof, namely, the medicinal or pharmaceutical composition(s) useful as the preparations for repetitive or continuous intravenous administration or the preparations for a single intravenous infusion at low concentrations and low doses.

The invention claimed is:

1. A method for treating a mammal suffering from or susceptible to a brain infarction, a cerebral infarction or cerebral apoplexy, comprising administering to the brain cells of the mammal a composition comprising ginsenoside Rb1 or salts thereof in a dosage form, wherein said dosage of ginsenoside Rb1 is adjusted to a dose range of 1.67 pg/kg/day to 1.67 mg/kg/day.

2. The method according to claim 1, wherein the brain cells are nerve cells or neurons.

3. The method according to any one of claims 1 and 2, wherein the composition is administered intravenously in a dose range of 0.167 μg/kg/day to 1.67 mg/kg/day.

4. The method according to any one of claims 1 and 2, wherein the composition is administered intravenously in a dose range of 1.67 pg/kg/day to 1.67 mg/kg/day.

* * * * *